US009657059B2

(12) United States Patent
Håkansson

(10) Patent No.: US 9,657,059 B2
(45) Date of Patent: May 23, 2017

(54) IMMUNE SYSTEM MODULATORS

(71) Applicant: Canimguide Therapeutics AB, Höllviken (SE)

(72) Inventor: Leif Håkansson, Höllviken (SE)

(73) Assignee: Canimguide Therapeutics AB, Höllviken (SE)

( * ) Notice: Subject to any disclaimer, the term of this patent is extended or adjusted under 35 U.S.C. 154(b) by 0 days.

(21) Appl. No.: 14/916,512

(22) PCT Filed: Sep. 8, 2014

(86) PCT No.: PCT/US2014/054612
§ 371 (c)(1),
(2) Date: Mar. 3, 2016

(87) PCT Pub. No.: WO2015/035332
PCT Pub. Date: Mar. 12, 2015

(65) Prior Publication Data
US 2016/0311854 A1    Oct. 27, 2016

Related U.S. Application Data

(60) Provisional application No. 61/875,598, filed on Sep. 9, 2013.

(51) Int. Cl.
| C07K 7/00 | (2006.01) |
| A61K 38/04 | (2006.01) |
| C07K 7/06 | (2006.01) |
| C07K 14/705 | (2006.01) |
| C07K 14/715 | (2006.01) |
| C07K 14/76 | (2006.01) |
| C07K 7/08 | (2006.01) |
| A61K 38/00 | (2006.01) |

(52) U.S. Cl.
CPC ............... *C07K 7/06* (2013.01); *C07K 7/08* (2013.01); *C07K 14/70546* (2013.01); *C07K 14/7155* (2013.01); *C07K 14/76* (2013.01); *A61K 38/00* (2013.01); *C07K 2319/00* (2013.01)

(58) Field of Classification Search
CPC ........ C07K 7/06; C07K 7/08; C07K 2319/00; C07K 14/70546; C07K 14/7155; C07K 14/76; A61K 38/00
See application file for complete search history.

(56) References Cited

U.S. PATENT DOCUMENTS

| 7,745,391 B2 | 6/2010 | Mintz et al. | |
| 7,960,126 B2 | 6/2011 | Håkansson et al. | |
| 8,133,688 B2 | 3/2012 | Håkansson et al. | |
| 9,120,874 B2 | 9/2015 | Håkansson et al. | |
| 2004/0031072 A1* | 2/2004 | La Rosa | C07K 14/415 800/278 |
| 2007/0031847 A1 | 2/2007 | Cargill et al. | |
| 2014/0161812 A1 | 6/2014 | Håkansson et al. | |
| 2016/0046702 A1 | 2/2016 | Håkansson et al. | |

FOREIGN PATENT DOCUMENTS

| EP | 1 806 364 A2 | 7/2007 |
| WO | WO 02/088307 | 11/2002 |
| WO | WO 03/106621 | 12/2003 |
| WO | WO 2004/022097 | 3/2004 |
| WO | WO 2004/046306 | 6/2004 |
| WO | WO 2006/013472 | 2/2006 |
| WO | WO 2007/133290 | 11/2007 |
| WO | WO 2008/136736 A2 | 11/2008 |
| WO | WO 2009/047360 | 4/2009 |
| WO | WO 2011/119484 | 9/2011 |
| WO | WO 2016/144650 | 9/2016 |

OTHER PUBLICATIONS

Genbank: AAU76211.1, "Sequence 57156 from U.S. Pat. No. 6,703,491" Submitted Mar. 9, 2004, in 1 page.
Genbank: AAU60963.1, "Sequence 41908 from U.S. Pat. No. 6,703,491" Submitted Mar. 9, 2004, in 1 page.
Genbank: EGQ19313.1, "hypothetical protein HMPREF9372_3709 [Sporosarcina newyorkensis 2681]" Submitted Apr. 29, 2011, in 2 pages.
Office Action dated Aug. 26, 2016 in Australian Application No. 2014317884.
International Preliminary Report on Patentability dated Mar. 15, 2016 in Application No. PCT/US2014/054612.
International Search Report and Written Opinion dated Dec. 17, 2014 in Application No. PCT/US2014/054612.
International Search Report and Written Opinion dated May 31, 2016 in Application No. PCT/US2016/020510.
Summary of BLAST searches for "FFVKL," "FFVKLS," "TFFVKL," "TFFVKLS," "KKLDTFFVKLSLFTER" and "KKLDTFFVKLSLFTER" for against database entries present in Apr. 2012, in 9 pages.
GenBank: AAD02558.1 "PGPS/NH17, partial [Petunia x hybrida]" Submitted Feb. 23, 1998, in 1 page.
GenBank: AAY03652.1. "Sequence 193 from U.S. Pat. No. 6,861,256" dated Mar. 1, 2005, in 1 page.
GenBank: ABH73247.1. "Sequence 193 from U.S. Pat. No. 7,041,437" dated May 9, 2006, in 1 page.

(Continued)

*Primary Examiner* — Julie Ha
*Assistant Examiner* — Li Ni Komatsu
(74) *Attorney, Agent, or Firm* — Knobbe, Martens, Olson & Bear, LLP

(57) ABSTRACT

The present invention described herein relates to compositions that interact with molecules that suppress the immune system. More specifically, embodiments described herein concern the discovery, manufacture, and use of compositions that remove immunosuppression the immune system by binding to immunoregulatory peptides that interact with receptors on immune cells, compositions the can stimulate immune cells, and compositions that are cytotoxic to tumor cells.

21 Claims, 53 Drawing Sheets

(56) References Cited

OTHER PUBLICATIONS

GenBank: ABT82318.1. Sequence 169788 from U.S. Pat. No. 7,214,786. dated May 8, 2007, in 1 page.
GenBank: ACC54912.1. "Sec61 gamma subunit alpha, partial [Xenopus borealis]" Submitted Feb. 4, 2008, in 1 page.
GenBank: AEE26217.1, "mechanosensitive ion channel family protein [Francisella cf. tularensis subsp. Novicida 3523]" Submitted Feb. 14, 2011, in 2 pages.
GenBank: AER13808.1, "NAD+-dependent glyceraldehyde-3-phosphate dehydrogenase, partial [Crepidomanes minutum]" Submitted Nov. 20, 2010, in 1 page.
GenBank: AER13809.1, "NAD+-dependent glyceraldehyde-3-phosphate dehydrogenase, partial [Crepidomanes minutum]" Submitted Nov. 20, 2010, in 1 page.
GenBank: AER13806.1, "NAD+-dependent glyceraldehyde-3-phosphate dehydrogenase, partial [Crepidomanes fallax]" Submitted Nov. 20, 2010, in 1 page.
GenBank: AEV00298.1. "Sequence 159416 from U.S. Pat. No. 8,067,671." dated Nov. 29, 2011, in 1 page.
GenBank: AEY43457.1, "Sequence 159416 from U.S. Pat. No. 8,088,976." dated Jan. 3, 2012, in 1 page.
GenBank: CBA05911.1. "hypothetical protein predicted by Glimmer/Critica [Neisseria meningitidis alpha275]" Submitted Sep. 13, 2007, in 1 page.
GenBank: CBA07448.1. "hypothetical protein predicted by Glimmer/Critica [Neisseria meningitidis alpha153]" Submitted Sep. 13, 2007, in 1 page.
GenBank: EDK23255.1. hypothetical protein RUMTOR_02533 [Ruminococcus torques ATCC 27756]. Submitted Feb. 3, 2007, in 2 pages.
GenBank: EDM02489.1. "rCG36896, partial [Rattus norvegicus]" Submitted Jul. 5, 2006, in 1 page.
GenBank: EEH01101.1. "conserved hypothetical protein [Borreliella finlandensis]" Submitted Jan. 30, 2008, in 1 page.
GenBank: EFV64484.1. "putative transposase [Neisseria meningitides H44/76]" Submitted Dec. 29, 2010, in 1 page.
GenBank: EGV62334.1. "hypothetical protein CANTEDRAFT_126106 [Candida tenuis ATCC 10573]" Submitted May 9, 2011, in 2 pages.
GenBank: GAA79446.1. "hypothetical protein P20495_1947 [Pseudoalteromonas sp. BSi20495]" Submitted Oct. 24, 2011, in 1 page.
NCBI Reference Sequence: YP_169980.1, corresponding to Gene ID: 3190887. FTT_0992 hypothetical protein [Francisella tularensissubsp. Tularensis SCHU S4] Submitted Aug. 13, 2009, in 2 pages.
NCBI Reference Sequence: ZP_01968952.1. "hypothetical protein RUMTOR_02533 {Ruminococcus torques ATCC 27756]" Submitted Mar. 26, 2007, in 2 pages.
NCBI Reference Sequence: ZP_03772822.1. "conserved hypothetical protein [Borrelia sp. SV1]" Submitted Nov. 20, 2010, in 1 page.
NCBI Reference Sequence: ZP_09243197.1. "hypothetical protein P20495_1947 [Pseudoalteromonas sp. BSi20495]" Submitted Dec. 6, 2011, in 1 page.
Genbank: YP_004444039, "hypothetical protein AGROH133_12330 [Agrobacterium sp. H133]" Submitted May 9, 2011, in 1 page.
Genbank: ADY66948.1, "hypothetical protein AGROH133_12330 [Agrobacterium sp. H133]" Submitted Oct. 1, 2010, in 1 page.
NCBI Reference Sequence: ZP_03783719, "hypothetical protein RUMHYD_03198 [Blautia hydrogenotrophica DSM 10507]" Submitted Jan. 14, 2009, in 2 pages.
Genbank: EEG47914.1, "TIGR00268 family protein [Blautia hydrogenotrophica DSM 10507]" Submitted Jan. 14, 2009, in 2 pages.
Genbank: YP_584917, "PepSYassociated TM helix [Cupriavidus metallidurans CH34]" Submitted Apr. 18, 2006, in 2 pages.
Genbank: ABF09648.1, "PepSYassociated TM helix [Cupriavidus metallidurans CH34]" Submitted Feb. 3, 2010, in 2 pages.
Genbank: ADT21006.1, "Sequence 42411 from U.S. Pat. No. 7,834,146" Submitted Nov. 16, 2010, in 1 page.
Genbank: AFA96582.1, "Sequence 42411 from U.S. Pat. No. 8,106,174" submitted Jan. 31, 2012, in 1 page.
Genbank: ABT54594.1, "Sequence 142064 from U.S. Pat. No. 7,214,786" submitted May 8, 2007, in 1 page.
Genbank: AAL69330.1, "inorganic pyrophosphatase, partial [Ochrobactrum anthropi ATCC 49188]" submitted Sep. 7, 2001, 1 page.
NCBI Reference Sequence: XP_009859504.1, corresponding to Genbank: LOC100181353, "Predicted: sodium/calcium exchanger 2-like [Ciona intestinalis]" dated Oct. 24, 2014, and to Applicant's knowledge, the indicated reference sequence was indexed on BLAST at least as of Apr. 2012, in 2 pages.
Genbank: YP_005416505, "pyrophosphateenergized proton pump [Rhodospirillum photometricum DSM 122]" submitted Feb. 2, 2012, in 2 pages.
Genbank: CCG07535.1, "Pyrophosphateenergized proton pump [Pararhodospirillum photometricum DSM 122]" submitted Feb. 2, 2012, in 2 pages.
NCBI Reference Sequence: ZP_04679926.1, "Vtype H(+)translocating pyrophosphatase [Ochrobactrum intermedium LMG 3301]" submitted Nov. 10, 2010, in 1 page.
Genbank: EEQ95432.1. "Vtype H(+)translocating pyrophosphatase [Ochrobactrum intermedium LMG 3301]" submitted in May 15, 2009, in 2 pages.
NCBI Reference Sequence: XP_003463117.1, corresponding to Gene ID: 100724157, "Predicted: origin recognition complex subunit 1 [Cavia porcellus]" , dated Jul. 14, 2015, and to Applicant's knowledge, the indicated reference sequence was indexed on BLAST at least as of Apr. 2012, in 2 pages.
NCBI Reference Sequence: XP_003128055.1, corresponding to Gene ID: 100520746, "Predicted: origin recognition complex subunit 1like isoformX1 [Sus scrofa]", dated Sep. 26, 2013, and to Applicant's knowledge, the indicated reference sequence was indexed on BLAST at least as of Apr. 2012, In 2 pages.
Genbank: EHB00695.1, "Origin recognition complex subunit 1 [Heterocephalus glaber]" submitted Jul. 11, 2011, in 2 pages.
Genbank: Q58DC8.2, "RecName: Full=Origin recognition complex subunit 1" submitted Feb. 2007, in 4 pages.
NCBI Reference Sequence: NP_001014918.1, corresponding to Gene ID: 513523, "origin recognition complex subunit 1 [ Bos taurus]" dated Apr. 11, 2005, in 3 pages.
Genbank: EGB09806.1, "hypothetical protein AURANDRAFT_71324 [Aureococcus anophagefferens]" submitted in Aug. 26, 2010, in 2 pages.
Genbank: EFY98846.1, "Ankyrin repeatcontaining domain protein [Metarhizium robertsii ARSEF 23]", this item lists a reference date of 2011, in 3 pages.
Genbank: EFY85297.1, "ankyrin repeat protein [Metarhizium acridum CQMa 102]" submitted in May 10, 2010, in 2 pages.
Genbank: CBY09431.1, "unnamed protein product [Oikopleura dioica]" submitted in Dec. 10, 2009, in 1 page.
NCBI Reference sequence Reference sequence YP_584917 , corresponding to Gene ID: 4039601, "Rmet_2775 PepSY-associated TM helix [ Cupriavidus metallidurans CH34 ]" submitted Jun. 7, 2011, 2 pages.
NCBI Reference sequence YP_005416505, corresponding to Gene ID: 12209565, "hppA pyrophosphate-energized proton pump [ Rhodospirillum photometricum DSM 122 ]", submitted Feb. 2, 2012, in 2 pages.

* cited by examiner

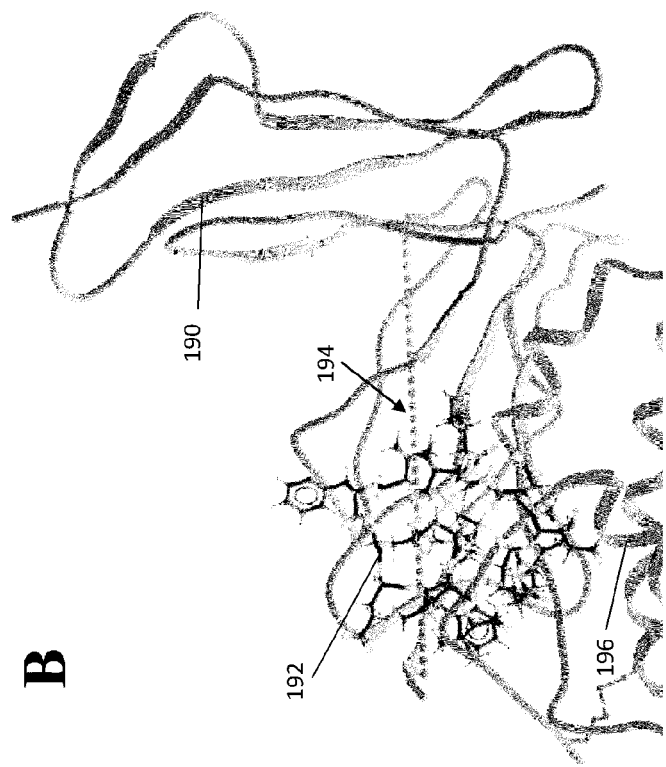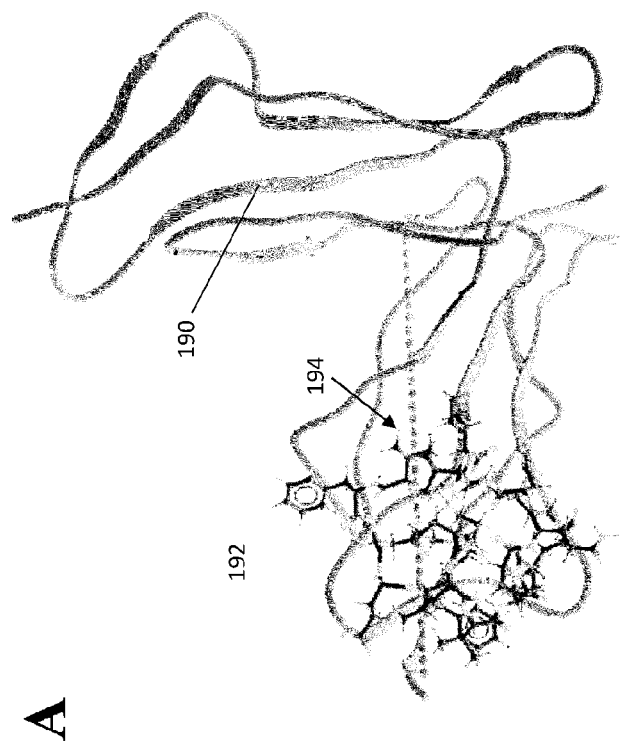
Fig 19

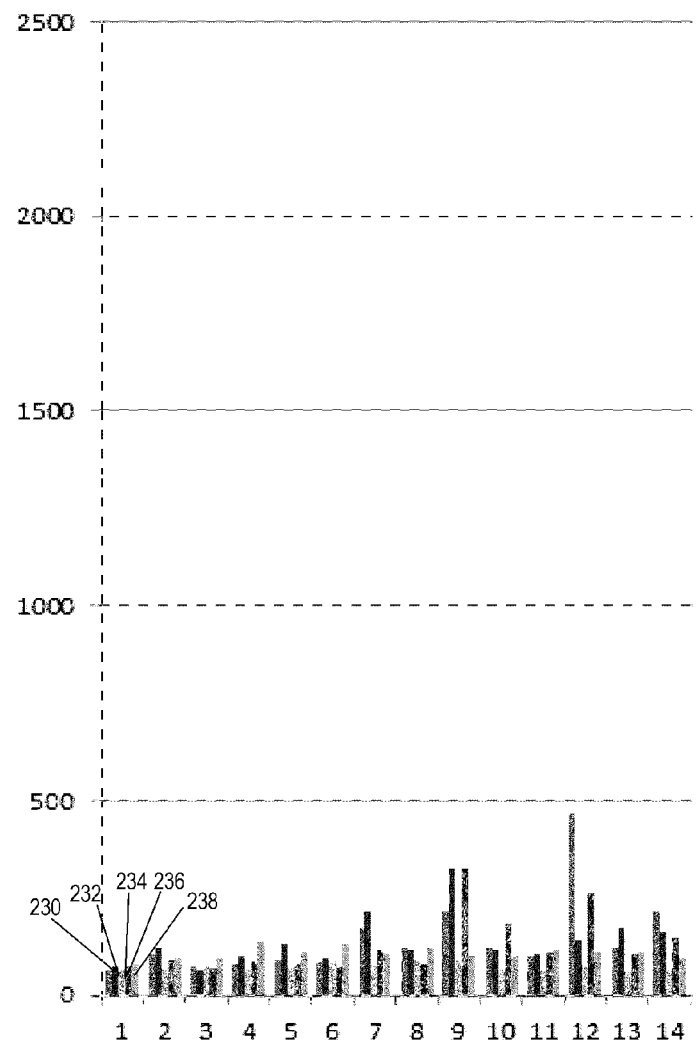

230 — Test : 16-2-2011 PGE73 10 ug/ml+anti-his(1/1000) no peptide added assay in PBS-buffer Rampo 1/1000

232 — Test : 17-2-2011 PGE73 10 ug/ml+anti-his(1/1000) also added: SCF027 (0,5 mg/ml) assay in PBS-buffer Rampo 1/1000

234 — Test : 18-2-2011 PGE73 10 ug/ml+anti-his(1/1000) also added: SCF029 (0,5 mg/ml) assay in PBS-buffer+10% DMSO Rampo 1/1000

236 — Test : 22-2-2011 PGE73 10 ug/ml+anti-his(1/1000) no peptide added assay in PBS-buffer+10% DMSO Rampo 1/1000

238 — Test : 23-2-2011 PGE73 10 ug/ml+anti-his(1/1000) also added: SCF028 (0,5 mg/ml) assay in PBS-buffer+10% DMSO Rampo 1/1000

Fig. 23A

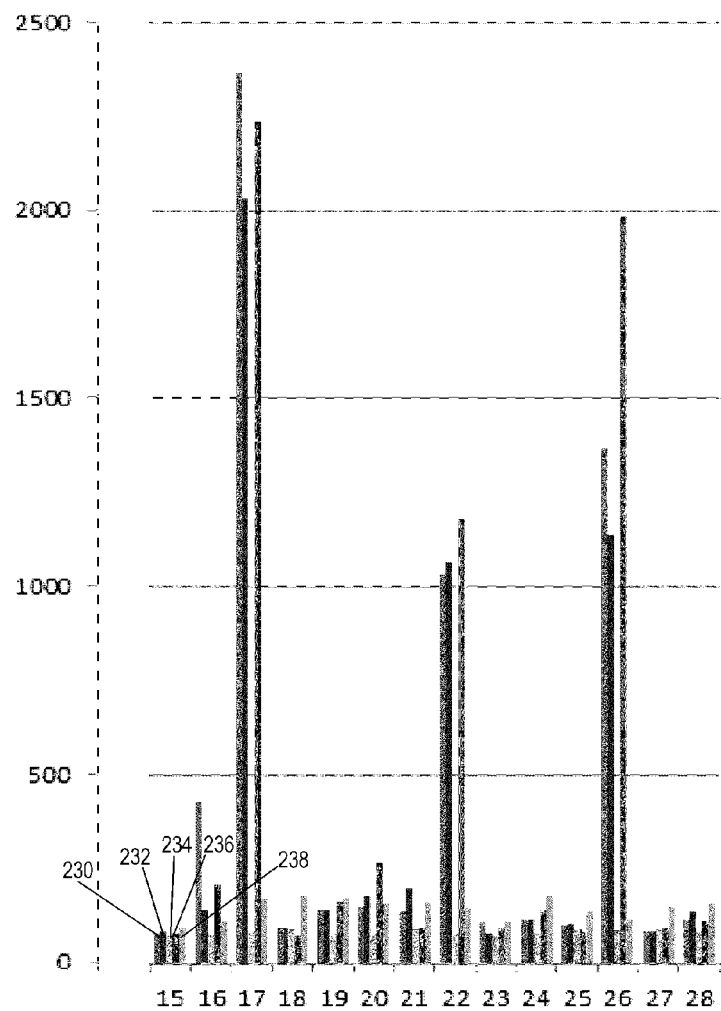

230 — Test : 16-2-2011 PGE73 10 ug/ml+anti-his(1/1000) no peptide added assay in PBS-buffer Rampo 1/1000

232 — Test : 17-2-2011 PGE73 10 ug/ml+anti-his(1/1000) also added: SCF027 (0,5 mg/ml) assay in PBS-buffer Rampo 1/1000

234 — Test : 18-2-2011 PGE73 10 ug/ml+anti-his(1/1000) also added: SCF029 (0,5 mg/ml) assay in PBS-buffer+10% DMSO Rampo 1/1000

236 — Test : 22-2-2011 PGE73 10 ug/ml+anti-his(1/1000) no peptide added assay in PBS-buffer+10% DMSO Rampo 1/1000

238 — Test : 23-2-2011 PGE73 10 ug/ml+anti-his(1/1000) also added: SCF028 (0,5 mg/ml) assay in PBS-buffer+10% DMSO Rampo 1/1000

Fig. 23B

All substitutions with rampo value over 500:

Substitutions >500

$$\begin{bmatrix} \text{KKLDTFFVKLSLFTER} & \text{(SEQ ID NO: 2)} \\ \text{R-G-QAM--VQQMN--} & \text{(largest)} \\ \phantom{xx}\text{E}\phantom{xx}\text{VS}\phantom{xxx}\text{MVQP} & \\ \phantom{xxxxxxx}\text{V}\phantom{xxxx}\text{TMHR} & \\ \phantom{xxxxxxx}\text{T}\phantom{xxxx}\text{H N} & \\ \phantom{xxxxxxx}\text{L}\phantom{xxxxxx}\text{P} & \\ \phantom{xxxxxxxxxxxxxx}\text{S} & \\ \phantom{xxxxxxxxxxxxxx}\text{G} & \\ \phantom{xxxxxxxxxxxxxx}\text{A} & \\ \phantom{xxxxxxxxxxxxxx}\text{R} & \text{(lowest)} \end{bmatrix}$$

The sequence options described here are shown in the formula of SEQ ID NO: 816.

Fig 28

```
                                           SEQ
                                           ID
                                           NO:
CIG3028      VFDEFKPLVEEPQNLIK 185
             | |*|***||*  **|
KKL15        KKLDTFFKKLSLFTE   819
```

| = Favorable electrostatic interaction
\* = Favorable hydrophobic interaction

Fig 31

SEQ ID NO: 820

| C | L | A | L | N | - | V | M | C | G |   |   |   |   |
|---|---|---|---|---|---|---|---|---|---|---|---|---|---|
|   |   | R |   | I |   |   | F |   |   |   |   |   |   |

SEQ ID NO: 821

|   |   |   |   |   |   |   | C | L | A | L | N | V | M | C | G |   |
|---|---|---|---|---|---|---|---|---|---|---|---|---|---|---|---|---|
|   |   |   |   |   |   |   |   |   |   | R |   | I |   | F |   |   |

SEQ ID NO: 822

|   | K | K | L | D | T | F | F | V | K | L | S | L | F | T | E | R |
|---|---|---|---|---|---|---|---|---|---|---|---|---|---|---|---|---|
|   | A |   | A | A | C | A | L | F | R | A | H | A | A | F | D | F |
|   | D |   | C | E | M | I | M | G |   | F | M | H | C | G |   | K |
|   | E |   | D | I | N | M | Q | L |   | G | N | I | G | H |   | N |
|   | G |   | E | V | P | N | S | P |   | I | Q | M | H | I |   | R |
|   | H |   | F | W | Q | P | T | R |   | M | T | N | I | L |   | T |
|   | I |   | G | Y | R | T | V |   |   | N |   | Q | L | M |   | Y |
|   | L |   | H |   | S | V |   |   |   | P |   | R | M | N |   |   |
|   | M |   | I |   | W |   |   |   |   | Q |   | S | N | P |   |   |
|   | N |   | K |   | Y |   |   |   |   | R |   | T | P | S |   |   |
|   | P |   | M |   |   |   |   |   |   | S |   | V | Q | V |   |   |
|   | Q |   | N |   |   |   |   |   |   | T |   | W | R | W |   |   |
|   | R |   | Q |   |   |   |   |   |   | V |   |   | S |   |   |   |
|   | T |   | R |   |   |   |   |   |   | Y |   |   | T |   |   |   |
|   | V |   | S |   |   |   |   |   |   |   |   |   | V |   |   |   |
|   | K |   | T |   |   |   |   |   |   |   |   |   | W |   |   |   |
|   |   |   | V |   |   |   |   |   |   |   |   |   |   |   |   |   |

Fig. 32

```
                           SEQUENCE LISTING

<160> NUMBER OF SEQ ID NOS: 822

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Lys Lys Leu Asp Thr Phe Phe Lys Lys Leu Ser Leu Phe Thr Glu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 2

Lys Lys Leu Asp Thr Phe Phe Val Lys Leu Ser Leu Phe Thr Glu Arg
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 3

Arg Lys Leu Asp Thr Phe Phe Val Lys Leu Ser Leu Phe Thr Glu Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 4

Lys Lys Gly Asp Thr Phe Phe Val Lys Leu Ser Leu Phe Thr Glu Arg
1               5                   10                  15

<210> SEQ ID NO 5
<211> LENGTH: 16
<212> TYPE: PRT
<213> ORGANISM: Artificial Sequence
```

-continued

```
<220> FEATURE:
<223> OTHER INFORMATION: Synthetic polypeptide

<400> SEQUENCE: 5

Lys Lys Glu Asp Thr Phe Phe Val Lys Leu Ser Leu Phe Thr Glu Arg
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Lys Lys Leu Asp Gln Phe Phe Val Lys Leu Ser Leu Phe Thr Glu Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

Lys Lys Leu Asp Thr Ala Phe Val Lys Leu Ser Leu Phe Thr Glu Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 8

Lys Lys Leu Asp Thr Val Phe Val Lys Leu Ser Leu Phe Thr Glu Arg
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 9

Lys Lys Leu Asp Thr Phe Met Val Lys Leu Ser Leu Phe Thr Glu Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 10

Lys Lys Leu Asp Thr Phe Ser Val Lys Leu Ser Leu Phe Thr Glu Arg
1               5                   10                  15

<210> SEQ ID NO 11
<211> LENGTH: 16
<212> TYPE: PRT
<213> ORGANISM: Artificial Sequence
<220> FEATURE:
```

<223> OTHER INFORMATION: Synthetic polypeptide

<400> SEQUENCE: 11

Lys Lys Leu Asp Thr Phe Val Val Lys Leu Ser Leu Phe Thr Glu Arg
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 12

Lys Lys Leu Asp Thr Phe Thr Val Lys Leu Ser Leu Phe Thr Glu Arg
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Lys Lys Leu Asp Thr Phe Leu Val Lys Leu Ser Leu Phe Thr Glu Arg
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 14

Lys Lys Leu Asp Thr Phe Phe Val Lys Val Ser Leu Phe Thr Glu Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 15

Lys Lys Leu Asp Thr Phe Phe Val Lys Leu Gln Leu Phe Thr Glu Arg
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 16

Lys Lys Leu Asp Thr Phe Phe Val Lys Leu Met Leu Phe Thr Glu Arg
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic polypeptide

```
<400> SEQUENCE: 17

Lys Lys Leu Asp Thr Phe Phe Val Lys Leu Thr Leu Phe Thr Glu Arg
 1               5                  10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 18

Lys Lys Leu Asp Thr Phe Phe Val Lys Leu His Leu Phe Thr Glu Arg
 1               5                  10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 19

Lys Lys Leu Asp Thr Phe Phe Val Lys Leu Ser Gln Phe Thr Glu Arg
 1               5                  10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 20

Lys Lys Leu Asp Thr Phe Phe Val Lys Leu Ser Val Phe Thr Glu Arg
 1               5                  10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 21

Lys Lys Leu Asp Thr Phe Phe Val Lys Leu Ser Met Phe Thr Glu Arg
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 22

Lys Lys Leu Asp Thr Phe Phe Val Lys Leu Ser Leu Met Thr Glu Arg
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic polypeptide
```

```
<400> SEQUENCE: 23

Lys Lys Leu Asp Thr Phe Phe Val Lys Leu Ser Leu Gln Thr Glu Arg
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 24

Lys Lys Leu Asp Thr Phe Phe Val Lys Leu Ser Leu His Thr Glu Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 25

Lys Lys Leu Asp Thr Phe Phe Val Lys Leu Ser Leu Asn Thr Glu Arg
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 26

Lys Lys Leu Asp Thr Phe Phe Val Lys Leu Ser Leu Pro Thr Glu Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 27

Lys Lys Leu Asp Thr Phe Phe Val Lys Leu Ser Leu Ser Thr Glu Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 28

Lys Lys Leu Asp Thr Phe Phe Val Lys Leu Ser Leu Gly Thr Glu Arg
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 29
```

Lys Lys Leu Asp Thr Phe Phe Val Lys Leu Ser Leu Ala Thr Glu Arg
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 30

Lys Lys Leu Asp Thr Phe Phe Val Lys Leu Ser Leu Arg Thr Glu Arg
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 31

Lys Lys Leu Asp Thr Phe Phe Val Lys Leu Ser Leu Phe Asn Glu Arg
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 32

Lys Lys Leu Asp Thr Phe Phe Val Lys Leu Ser Leu Phe Pro Glu Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 33

Lys Lys Leu Asp Thr Phe Phe Val Lys Leu Ser Leu Phe Arg Glu Arg
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Lys Lys Leu Asp Thr Phe Phe Val Lys Leu Ser Leu Phe Thr Glu
1               5                   10                  15

<210> SEQ ID NO 35
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 35

Lys Lys Leu Asp Thr Phe Phe Val Lys Leu Ser Leu Phe Thr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 36

Lys Lys Leu Asp Thr Phe Phe Val Lys Leu Ser Leu Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 37

Lys Lys Leu Asp Thr Phe Phe Val Lys Leu Ser Leu
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 38

Lys Lys Leu Asp Thr Phe Phe Val Lys Leu Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 39

Lys Lys Leu Asp Thr Phe Phe Val Lys Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 40

Lys Lys Leu Asp Thr Phe Phe Val Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 41

Lys Lys Leu Asp Thr Phe Phe Val

```
                1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 42

Lys Lys Leu Asp Thr Phe Phe
 1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 43

Lys Lys Leu Asp Thr Phe
 1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 44

Lys Lys Leu Asp Thr
 1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 45

Lys Lys Leu Asp
 1

<210> SEQ ID NO 46
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 46

Lys Leu Asp Thr Phe Phe Val Lys Leu Ser Leu Phe Thr Glu Arg
 1               5                  10                  15

<210> SEQ ID NO 47
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 47

Leu Asp Thr Phe Phe Val Lys Leu Ser Leu Phe Thr Glu Arg
 1               5                  10
```

<210> SEQ ID NO 48
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 48

Asp Thr Phe Phe Val Lys Leu Ser Leu Phe Thr Glu Arg
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 49

Thr Phe Phe Val Lys Leu Ser Leu Phe Thr Glu Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 50

Phe Phe Val Lys Leu Ser Leu Phe Thr Glu Arg
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 51

Phe Val Lys Leu Ser Leu Phe Thr Glu Arg
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 52

Val Lys Leu Ser Leu Phe Thr Glu Arg
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 53

Lys Leu Ser Leu Phe Thr Glu Arg
1               5

```
<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Leu Ser Leu Phe Thr Glu Arg
 1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 55

Ser Leu Phe Thr Glu Arg
 1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 56

Leu Phe Thr Glu Arg
 1               5

<210> SEQ ID NO 57
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 57

Phe Thr Glu Arg
 1

<210> SEQ ID NO 58
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 58

Lys Leu Asp Thr Phe Phe Val Lys Leu Ser Leu Phe Thr Glu
 1               5                  10

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 59

Leu Asp Thr Phe Phe Val Lys Leu Ser Leu Phe Thr
 1               5                  10
```

```
<210> SEQ ID NO 60
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 60

Asp Thr Phe Phe Val Lys Leu Ser Leu Phe
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 61

Thr Phe Phe Val Lys Leu Ser Leu
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 62

Phe Phe Val Lys Leu Ser
1               5

<210> SEQ ID NO 63
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 63

Phe Val Lys Leu
1

<210> SEQ ID NO 64
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 64

Lys Lys Leu Thr Phe Phe Val Lys Leu Ser Leu Phe Thr Glu Arg
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 65

Lys Lys Leu Asp Thr Phe Val Lys Leu Ser Leu Phe Thr Glu Arg
1               5                   10                  15

<210> SEQ ID NO 66
```

```
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 66

Lys Lys Leu Asp Thr Phe Phe Lys Leu Ser Leu Phe Thr Glu Arg
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 67

Lys Lys Leu Asp Thr Phe Phe Val Lys Ser Leu Phe Thr Glu Arg
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 68

Lys Lys Leu Asp Thr Phe Phe Val Lys Leu Ser Phe Thr Glu Arg
1               5                   10                  15

<210> SEQ ID NO 69
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 69

Lys Leu Asp Thr Phe Phe Val Lys Leu Ser Leu Phe Glu Arg
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 70

Lys Lys Thr Phe Phe Val Lys Leu Ser Leu Phe Thr Glu Arg
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 71

Lys Lys Leu Asp Phe Val Lys Leu Ser Leu Phe Thr Glu Arg
1               5                   10

<210> SEQ ID NO 72
<211> LENGTH: 14
```

```
<212> TYPE: PRT
<213> ORGANISM: Artificial Sequence
<220> FEATURE:
<223> OTHER INFORMATION: Synthetic polypeptide

<400> SEQUENCE: 72

Lys Lys Leu Asp Thr Glu Lys Leu Ser Leu Phe Thr Glu Arg
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 73

Lys Lys Leu Asp Thr Phe Phe Val Ser Leu Phe Thr Glu Arg
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 74

Lys Lys Leu Asp Thr Phe Phe Val Lys Leu Phe Thr Glu Arg
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 75

Lys Lys Leu Asp Thr Phe Phe Val Lys Leu Ser Leu Glu Arg
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 76

Lys Lys Phe Phe Val Lys Leu Ser Leu Phe Thr Glu Arg
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 77

Lys Lys Leu Asp Val Lys Leu Ser Leu Phe Thr Glu Arg
1               5                   10

<210> SEQ ID NO 78
<211> LENGTH: 13
<212> TYPE: PRT
```

```
<213> ORGANISM: Artificial Sequence
<220> FEATURE:
<223> OTHER INFORMATION: Synthetic polypeptide

<400> SEQUENCE: 78

Lys Lys Leu Asp Thr Phe Leu Ser Leu Phe Thr Glu Arg
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 79

Lys Lys Leu Asp Thr Phe Phe Val Leu Phe Thr Glu Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 80

Lys Lys Leu Asp Thr Phe Phe Val Lys Leu Thr Glu Arg
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 81

Lys Lys Leu Asp Thr Phe Phe Val Lys Leu Ser Leu Arg
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 82

Lys Phe Phe Val Lys Leu Ser Leu Phe Thr Glu Arg
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 83

Lys Lys Leu Val Lys Leu Ser Leu Phe Thr Glu Arg
1               5                   10

<210> SEQ ID NO 84
<211> LENGTH: 12
<212> TYPE: PRT
<213> ORGANISM: Artificial Sequence
```

```
<220> FEATURE:
<223> OTHER INFORMATION: Synthetic polypeptide

<400> SEQUENCE: 84

Lys Lys Leu Asp Thr Leu Ser Leu Phe Thr Glu Arg
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 85

Lys Lys Leu Asp Thr Phe Phe Leu Phe Thr Glu Arg
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 86

Lys Lys Leu Asp Thr Phe Phe Val Lys Thr Glu Arg
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 87

Lys Lys Leu Asp Thr Phe Phe Val Lys Leu Ser Arg
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 88

Lys Phe Val Lys Leu Ser Leu Phe Thr Glu Arg
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 89

Lys Lys Leu Lys Leu Ser Leu Phe Thr Glu Arg
1               5                   10

<210> SEQ ID NO 90
<211> LENGTH: 11
<212> TYPE: PRT
<213> ORGANISM: Artificial Sequence
<220> FEATURE:
```

```
<223> OTHER INFORMATION: Synthetic polypeptide

<400> SEQUENCE: 90

Lys Lys Leu Asp Thr Ser Leu Phe Thr Glu Arg
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 91

Lys Lys Leu Asp Thr Phe Phe Phe Thr Glu Arg
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 92

Lys Lys Leu Asp Thr Phe Phe Val Lys Glu Arg
1               5                   10

<210> SEQ ID NO 93
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 93

Gly Lys Leu Asp Thr Phe Phe Val Lys Leu Ser Leu Phe Thr Glu Arg
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 94

Lys Lys Gly Asp Thr Phe Phe Val Lys Leu Ser Leu Phe Thr Glu Arg
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 95

Lys Lys Leu Asp Gly Phe Phe Val Lys Leu Ser Leu Phe Thr Glu Arg
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic polypeptide
```

```
<400> SEQUENCE: 96

Lys Lys Leu Asp Thr Phe Gly Val Lys Leu Ser Leu Phe Thr Glu Arg
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 97

Lys Lys Leu Asp Thr Phe Phe Val Gly Leu Ser Leu Phe Thr Glu Arg
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 98

Lys Lys Leu Asp Thr Phe Phe Val Gly Leu Ser Leu Phe Thr Glu Arg
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 99

Lys Lys Leu Asp Thr Phe Phe Val Lys Leu Gly Leu Phe Thr Glu Arg
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 100

Lys Lys Leu Asp Thr Phe Phe Val Lys Leu Ser Leu Gly Thr Glu Arg
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 101

Lys Lys Leu Asp Thr Phe Phe Val Lys Leu Ser Leu Phe Thr Gly Arg
1               5                   10                  15

<210> SEQ ID NO 102
<211> LENGTH: 48
<212> TYPE: DNA
<213> ORGANISM: Artificial Sequence
<220> FEATURE:
<223> OTHER INFORMATION: Consensus polynucleotide encoding P28R (SEQ ID
      NO:2)
```

```
<220> FEATURE:
<221> NAME/KEY: misc_feature
<222> LOCATION: 9,15,24,30,33,36,42,48
<223> OTHER INFORMATION: N=A,G,C,or T

<400> SEQUENCE: 102
aaraarytng ayacnttytt ygtnaarytn wsnytnttya cngarmgn            48

<210> SEQ ID NO 103
<211> LENGTH: 48
<212> TYPE: DNA
<213> ORGANISM: Artificial Sequence
<220> FEATURE:
<223> OTHER INFORMATION: Exemplary polynucleotide encoding P28R (SEQ ID
      NO:2)

<400> SEQUENCE: 103
aaaaaactgg atacctttt tgtgaaactg agcctgttta ccgaacgc             48

<210> SEQ ID NO 104
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:3
<220> FEATURE:
<221> NAME/KEY: misc_feature
<222> LOCATION: 3,9,15,24,30,33,36,42,48
<223> OTHER INFORMATION: N=A,G,C,or T

<400> SEQUENCE: 104
mgnaarytng ayacnttytt ygtnaarytn wsnytnttya cngarmgn            48

<210> SEQ ID NO 105
<211> LENGTH: 48
<212> TYPE: DNA
<213> ORGANISM: Artificial Sequence
<220> FEATURE:
<223> OTHER INFORMATION: Exemplary NT encoding SEQ ID NO: 3

<400> SEQUENCE: 105
cgcaaactgg atacctttt tgtgaaactg agcctgttta ccgaacgc             48

<210> SEQ ID NO 106
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:4
<220> FEATURE:
<221> NAME/KEY: misc_feature
<222> LOCATION: 9,15,24,30,33,36,42,48
<223> OTHER INFORMATION: N=A,G,C,or T

<400> SEQUENCE: 106
aaraarggng ayacnttytt ygtnaarytn wsnytnttya cngarmgn            48

<210> SEQ ID NO 107
<211> LENGTH: 48
<212> TYPE: DNA
<213> ORGANISM: Artificial Sequence
<220> FEATURE:
<223> OTHER INFORMATION: Exemplary NT encoding  SEQ ID NO: 4

<400> SEQUENCE: 107
aaaaaaggcg atacctttt tgtgaaactg agcctgttta ccgaacgc             48
```

```
<210> SEQ ID NO 108
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:5
<220> FEATURE:
<221> NAME/KEY: misc_feature
<222> LOCATION: 15,24,30,33,36,42,48
<223> OTHER INFORMATION: N=A,G,C,or T

<400> SEQUENCE: 108
aaraargarg ayacnttytt ygtnaarytn wsnytnttya cngarmgn                48

<210> SEQ ID NO 109
<211> LENGTH: 48
<212> TYPE: DNA
<213> ORGANISM: Artificial Sequence
<220> FEATURE:
<223> OTHER INFORMATION: Exemplary NT encoding SEQ ID NO: 5

<400> SEQUENCE: 109
aaaaaagaag atacctttt tgtgaaactg agcctgttta ccgaacgc                 48

<210> SEQ ID NO 110
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:6
<220> FEATURE:
<221> NAME/KEY: misc_feature
<222> LOCATION: 9,24,30,33,36,42,48
<223> OTHER INFORMATION: N=A,G,C,or T

<400> SEQUENCE: 110
aaraarytng aycarttytt ygtnaarytn wsnytnttya cngarmgn                48

<210> SEQ ID NO 111
<211> LENGTH: 48
<212> TYPE: DNA
<213> ORGANISM: Artificial Sequence
<220> FEATURE:
<223> OTHER INFORMATION: Exemplary NT encoding SEQ ID NO: 6

<400> SEQUENCE: 111
aaaaaactgg atcagttttt tgtgaaactg agcctgttta ccgaacgc                48

<210> SEQ ID NO 112
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:7
<220> FEATURE:
<221> NAME/KEY: misc_feature
<222> LOCATION: 9, 15, 18, 24, 30, 33, 36, 42, 48
<223> OTHER INFORMATION: N=A,G,C,or T

<400> SEQUENCE: 112
aaraarytng ayacngcntt ygtnaarytn wsnytnttya cngarmgn                48

<210> SEQ ID NO 113
<211> LENGTH: 48
<212> TYPE: DNA
<213> ORGANISM: Artificial Sequence
<220> FEATURE:
<223> OTHER INFORMATION: Exemplary NT encoding SEQ ID NO: 7
```

<400> SEQUENCE: 113
aaaaaactgg ataccgcgtt tgtgaaactg agcctgttta ccgaacgc          48

<210> SEQ ID NO 114
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:8
<220> FEATURE:
<221> NAME/KEY: misc_feature
<222> LOCATION: 9, 15, 18, 24, 30, 33, 36, 42, 48
<223> OTHER INFORMATION: N=A,G,C,or T

<400> SEQUENCE: 114
aaraarytng ayacngtntt ygtnaarytn wsnytnttya cngarmgn          48

<210> SEQ ID NO 115
<211> LENGTH: 48
<212> TYPE: DNA
<213> ORGANISM: Artificial Sequence
<220> FEATURE:
<223> OTHER INFORMATION: Exemplary NT encoding SEQ ID NO: 8

<400> SEQUENCE: 115
aaaaaactgg ataccgtgtt tgtgaaactg agcctgttta ccgaacgc          48

<210> SEQ ID NO 116
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:9
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 116
aaraarytng ayacnttyat ggtnaarytn wsnytnttya cngarmgn          48

<210> SEQ ID NO 117
<211> LENGTH: 48
<212> TYPE: DNA
<213> ORGANISM: Artificial Sequence
<220> FEATURE:
<223> OTHER INFORMATION: Exemplary NT encoding SEQ ID NO: 9

<400> SEQUENCE: 117
aaaaaactgg ataccttat ggtgaaactg agcctgttta ccgaacgc           48

<210> SEQ ID NO 118
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:10
<220> FEATURE:
<221> NAME/KEY: misc_feature
<222> LOCATION: 9 15, 21, 24, 30, 33, 36, 42, 48
<223> OTHER INFORMATION: N=A,G,C,or T

<400> SEQUENCE: 118
aaraarytng ayacnttyws ngtnaarytn wsnytnttya cngarmgn          48

<210> SEQ ID NO 119
<211> LENGTH: 48

-continued

```
<212> TYPE: DNA
<213> ORGANISM: Artificial Sequence
<220> FEATURE:
<223> OTHER INFORMATION: Exemplary NT encoding SEQ ID NO: 10

<400> SEQUENCE: 119
aaaaaactgg atacctttag cgtgaaactg agcctgttta ccgaacgc        48

<210> SEQ ID NO 120
<211> LENGTH: 48
<212> TYPE: DNA
<213> ORGANISM: Artificial Sequence
<220> FEATURE:
<223> OTHER INFORMATION: Consensus polynucleotide encoding  SEQ ID NO:11

<400> SEQUENCE: 120
aaaaaactgg atacctttgt ggtgaaactg agcctgttta ccgaacgc        48

<210> SEQ ID NO 121
<211> LENGTH: 48
<212> TYPE: DNA
<213> ORGANISM: Artificial Sequence
<220> FEATURE:
<223> OTHER INFORMATION: Exemplary NT encoding SEQ ID NO:11
<220> FEATURE:
<221> NAME/KEY: misc_feature
<222> LOCATION: 9, 15, 21, 24, 30, 33, 36, 42, 48
<223> OTHER INFORMATION: N=A,G,C,or T

<400> SEQUENCE: 121
aaraarytng ayacnttygt ngtnaarytn wsnytnttya cngarmgn        48

<210> SEQ ID NO 122
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:12
<220> FEATURE:
<221> NAME/KEY: misc_feature
<222> LOCATION: 9, 15, 21, 24, 30, 33, 36, 42, 48
<223> OTHER INFORMATION: N=A,G,C,or T

<400> SEQUENCE: 122
aaraarytng ayacnttyac ngtnaarytn wsnytnttya cngarmgn        48

<210> SEQ ID NO 123
<211> LENGTH: 48
<212> TYPE: DNA
<213> ORGANISM: Artificial Sequence
<220> FEATURE:
<223> OTHER INFORMATION: Exemplary NT encoding SEQ ID NO: 12

<400> SEQUENCE: 123
aaaaaactgg atacctttac cgtgaaactg agcctgttta ccgaacgc        48

<210> SEQ ID NO 124
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:13
<220> FEATURE:
<221> NAME/KEY: misc_feature
<222> LOCATION: 9, 15, 21, 24, 30, 33, 36, 42, 48
<223> OTHER INFORMATION: N=A,G,C,or T

<400> SEQUENCE: 124
```
aaraarytng ayacnttyyt ngtnaarytn wsnytnttya cngarmgn        48

<210> SEQ ID NO 125
<211> LENGTH: 48
<212> TYPE: DNA
<213> ORGANISM: Artificial Sequence
<220> FEATURE:
<223> OTHER INFORMATION: Exemplary NT encoding SEQ ID NO: 13

<400> SEQUENCE: 125
aaaaaactgg atacctttct ggtgaaactg agcctgttta ccgaacgc        48

<210> SEQ ID NO 126
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:14
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 126
aaraarytng ayacnttytt ygtnaargtn wsnytnttya cngarmgn        48

<210> SEQ ID NO 127
<211> LENGTH: 48
<212> TYPE: DNA
<213> ORGANISM: Artificial Sequence
<220> FEATURE:
<223> OTHER INFORMATION: Exemplary NT encoding SEQ ID NO: 14

<400> SEQUENCE: 127
aaaaaactgg atacctttt tgtgaaagtg agcctgttta ccgaacgc        48

<210> SEQ ID NO 128
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:15
<220> FEATURE:
<221> NAME/KEY: misc_feature
<222> LOCATION: 9, 15, 24, 30, 36, 42, 48
<223> OTHER INFORMATION: N=A,G,C,or T

<400> SEQUENCE: 128
aaraarytng ayacnttytt ygtnaarytn carytnttya cngarmgn        48

<210> SEQ ID NO 129
<211> LENGTH: 48
<212> TYPE: DNA
<213> ORGANISM: Artificial Sequence
<220> FEATURE:
<223> OTHER INFORMATION: Exemplary NT encoding SEQ ID NO: 15

<400> SEQUENCE: 129
aaaaaactgg atacctttt tgtgaaactg cagctgttta ccgaacgc        48

<210> SEQ ID NO 130
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:16
<220> FEATURE:
<221> NAME/KEY: misc_feature
<222> LOCATION: 9, 15, 24, 30, 36, 42, 48
<223> OTHER INFORMATION: N=A,G,C,or T

<400> SEQUENCE: 130
aaraarytng ayacnttytt ygtnaarytn atgytnttya cngarmgn                48

<210> SEQ ID NO 131
<211> LENGTH: 48
<212> TYPE: DNA
<213> ORGANISM: Artificial Sequence
<220> FEATURE:
<223> OTHER INFORMATION: Exemplary NT encoding SEQ ID NO: 16

<400> SEQUENCE: 131
aaaaaactgg atacctttt tgtgaaactg atgctgttta ccgaacgc                 48

<210> SEQ ID NO 132
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:17
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 132
aaraarytng ayacnttytt ygtnaarytn acnytnttya cngarmgn                48

<210> SEQ ID NO 133
<211> LENGTH: 48
<212> TYPE: DNA
<213> ORGANISM: Artificial Sequence
<220> FEATURE:
<223> OTHER INFORMATION: Exemplary NT encoding SEQ ID NO: 17

<400> SEQUENCE: 133
aaaaaactgg atacctttt tgtgaaactg accctgttta ccgaacgc                 48

<210> SEQ ID NO 134
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:18
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 134
aaraarytng ayacnttytt ygtnaarytn cayytnttya cngarmgn                48

<210> SEQ ID NO 135
<211> LENGTH: 48
<212> TYPE: DNA
<213> ORGANISM: Artificial Sequence
<220> FEATURE:
<223> OTHER INFORMATION: Exemplary NT encoding SEQ ID NO: 18

<400> SEQUENCE: 135
aaaaaactgg atacctttt tgtgaaactg catctgttta ccgaacgc                 48

<210> SEQ ID NO 136
<211> LENGTH: 48
<212> TYPE: DNA

```
<213> ORGANISM: Artificial Sequence
<220> FEATURE:
<223> OTHER INFORMATION: Consensus polynucleotide encoding SEQ ID NO:19
<220> FEATURE:
<221> NAME/KEY: misc_feature
<222> LOCATION: 9, 15, 24, 30, 33, 42, 48
<223> OTHER INFORMATION: N=A,G,C,or T

<400> SEQUENCE: 136
aaraarytng ayacnttytt ygtnaarytn wsncarttya cngarmgn                48

<210> SEQ ID NO 137
<211> LENGTH: 48
<212> TYPE: DNA
<213> ORGANISM: Artificial Sequence
<220> FEATURE:
<223> OTHER INFORMATION: Exemplary NT encoding SEQ ID NO: 19

<400> SEQUENCE: 137
aaaaaactgg atacctttt tgtgaaactg agccagttta ccgaacgc                 48

<210> SEQ ID NO 138
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:20
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 138
aaraarytng ayacnttytt ygtnaarytn wsngtnttya cngarmgn                48

<210> SEQ ID NO 139
<211> LENGTH: 48
<212> TYPE: DNA
<213> ORGANISM: Artificial Sequence
<220> FEATURE:
<223> OTHER INFORMATION: Exemplary NT encoding SEQ ID NO: 20

<400> SEQUENCE: 139
aaaaaactgg atacctttt tgtgaaactg agcgtgttta ccgaacgc                 48

<210> SEQ ID NO 140
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:21
<220> FEATURE:
<221> NAME/KEY: misc_feature
<222> LOCATION: 9, 15, 24, 30, 33, 42, 48
<223> OTHER INFORMATION: N=A,G,C,or T

<400> SEQUENCE: 140
aaraarytng ayacnttytt ygtnaarytn wsnatgttya cngarmgn                48

<210> SEQ ID NO 141
<211> LENGTH: 48
<212> TYPE: DNA
<213> ORGANISM: Artificial Sequence
<220> FEATURE:
<223> OTHER INFORMATION: Exemplary NT encoding SEQ ID NO: 21

<400> SEQUENCE: 141
aaaaaactgg atacctttt tgtgaaactg agcatgttta ccgaacgc                 48
```

<210> SEQ ID NO 142
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:22
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 142
aaraarytng ayacnttytt ygtnaarytn wsnytnatga cngarmgn                48

<210> SEQ ID NO 143
<211> LENGTH: 48
<212> TYPE: DNA
<213> ORGANISM: Artificial Sequence
<220> FEATURE:
<223> OTHER INFORMATION: Exemplary NT encoding SEQ ID NO: 22

<400> SEQUENCE: 143
aaaaaactgg atacctttt tgtgaaactg agcctgatga ccgaacgc                 48

<210> SEQ ID NO 144
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:23
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 144
aaraarytng ayacnttytt ygtnaarytn wsnytncara cngarmgn                48

<210> SEQ ID NO 145
<211> LENGTH: 48
<212> TYPE: DNA
<213> ORGANISM: Artificial Sequence
<220> FEATURE:
<223> OTHER INFORMATION: Exemplary NT encoding SEQ ID NO: 23

<400> SEQUENCE: 145
aaaaaactgg atacctttt tgtgaaactg agcctgcaga ccgaacgc                 48

<210> SEQ ID NO 146
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:24
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 146
aaraarytng ayacnttytt ygtnaarytn wsnytncaya cngarmgn                48

<210> SEQ ID NO 147
<211> LENGTH: 48
<212> TYPE: DNA
<213> ORGANISM: Artificial Sequence
<220> FEATURE:

```
<223> OTHER INFORMATION: Exemplary NT encoding  SEQ ID NO: 24

<400> SEQUENCE: 147
aaaaaactgg atacctttt tgtgaaactg agcctgcata ccgaacgc          48

<210> SEQ ID NO 148
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:25
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 148
aaraarytng ayacnttytt ygtnaarytn wsnytnaaya cngarmgn          48

<210> SEQ ID NO 149
<211> LENGTH: 48
<212> TYPE: DNA
<213> ORGANISM: Artificial Sequence
<220> FEATURE:
<223> OTHER INFORMATION: Exemplary NT encoding SEQ ID NO: 25

<400> SEQUENCE: 149
aaaaaactgg atacctttt tgtgaaactg agcctgaaca ccgaacgc          48

<210> SEQ ID NO 150
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:26
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 150
aaraarytng ayacnttytt ygtnaarytn wsnytnccna cngarmgn          48

<210> SEQ ID NO 151
<211> LENGTH: 48
<212> TYPE: DNA
<213> ORGANISM: Artificial Sequence
<220> FEATURE:
<223> OTHER INFORMATION: Exemplary NT encoding SEQ ID NO: 26

<400> SEQUENCE: 151
aaaaaactgg atacctttt tgtgaaactg agcctgccga ccgaacgc          48

<210> SEQ ID NO 152
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:27
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 152
aaraarytng ayacnttytt ygtnaarytn wsnytnwsna cngarmgn          48
```

-continued

```
<210> SEQ ID NO 153
<211> LENGTH: 48
<212> TYPE: DNA
<213> ORGANISM: Artificial Sequence
<220> FEATURE:
<223> OTHER INFORMATION: Exemplary NT encoding SEQ ID NO: 27

<400> SEQUENCE: 153
aaaaaactgg atacctttt tgtgaaactg agcctgagca ccgaacgc                48

<210> SEQ ID NO 154
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:28
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 154
aaraarytng ayacnttytt ygtnaarytn wsnytnggna cngarmgn                48

<210> SEQ ID NO 155
<211> LENGTH: 48
<212> TYPE: DNA
<213> ORGANISM: Artificial Sequence
<220> FEATURE:
<223> OTHER INFORMATION: Exemplary NT encoding SEQ ID NO: 28

<400> SEQUENCE: 155
aaaaaactgg atacctttt tgtgaaactg agcctgggca ccgaacgc                48

<210> SEQ ID NO 156
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:29
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 156
aaraarytng ayacnttytt ygtnaarytn wsnytngcna cngarmgn                48

<210> SEQ ID NO 157
<211> LENGTH: 48
<212> TYPE: DNA
<213> ORGANISM: Artificial Sequence
<220> FEATURE:
<223> OTHER INFORMATION: Exemplary NT encoding SEQ ID NO: 29

<400> SEQUENCE: 157
aaaaaactgg atacctttt tgtgaaactg agcctggcga ccgaacgc                48

<210> SEQ ID NO 158
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:30
<220> FEATURE:
<221> NAME/KEY: misc_feature
<222> LOCATION: 9, 15, 24, 30, 33, 36, 39, 42, 48
<223> OTHER INFORMATION: N=A,G,C,or T
```

<400> SEQUENCE: 158
aaraarytng ayacnttytt ygtnaarytn wsnytnmgna cngarmgn                48

<210> SEQ ID NO 159
<211> LENGTH: 48
<212> TYPE: DNA
<213> ORGANISM: Artificial Sequence
<220> FEATURE:
<223> OTHER INFORMATION: Exemplary NT encoding SEQ ID NO: 30

<400> SEQUENCE: 159
aaaaaactgg atacctttt tgtgaaactg agcctgcgca ccgaacgc                 48

<210> SEQ ID NO 160
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:31
<220> FEATURE:
<221> NAME/KEY: misc_feature
<222> LOCATION: 9, 15, 24, 30, 33, 36, 48
<223> OTHER INFORMATION: N=A,G,C,or T

<400> SEQUENCE: 160
aaaaaactgg atacctttt tgtgaaactg agcctgttta acgaacgc                 48

<210> SEQ ID NO 161
<211> LENGTH: 48
<212> TYPE: DNA
<213> ORGANISM: Artificial Sequence
<220> FEATURE:
<223> OTHER INFORMATION: Exemplary NT encoding SEQ ID NO: 31

<400> SEQUENCE: 161
aaaaaactgg atacctttt tgtgaaactg agcctgttta acgaacgc                 48

<210> SEQ ID NO 162
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:32
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 162
aaraarytng ayacnttytt ygtnaarytn wsnytnttyc cngarmgn                48

<210> SEQ ID NO 163
<211> LENGTH: 48
<212> TYPE: DNA
<213> ORGANISM: Artificial Sequence
<220> FEATURE:
<223> OTHER INFORMATION: Exemplary NT encoding SEQ ID NO: 32

<400> SEQUENCE: 163
aaaaaactgg atacctttt tgtgaaactg agcctgtttc cggaacgc                 48

<210> SEQ ID NO 164
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:33

```
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 164
aaraarytng ayacnttytt ygtnaarytn wsnytnttym gngarmgn                48

<210> SEQ ID NO 165
<211> LENGTH: 48
<212> TYPE: DNA
<213> ORGANISM: Artificial Sequence
<220> FEATURE:
<223> OTHER INFORMATION: Exemplary NT encoding SEQ ID NO: 33

<400> SEQUENCE: 165
aaaaaactgg ataccttttt tgtgaaactg agcctgtttc gcgaacgc                48

<210> SEQ ID NO 166
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1-5
<223> OTHER INFORMATION: Variable length region= KKLDT RKLDT, KKGDT,
      KKEDT, KKLDQ, KKGDQ, KKEDQ, RKLDQ, RKGDQ, RKEDQ, RKGTD,
      RKEDT, KLDT, KGDT, KEDT, KLDQ, KGDQ, KEDQ, LDT,
      LDQ, GDT, GDQ, EDT, EDQ, DT, DQ, T, Q,
<220> FEATURE:
<221> NAME/KEY: VARIANT
<222> LOCATION: 1-5
<223> OTHER INFORMATION: Variable length region= or no amino acid
<220> FEATURE:
<221> NAME/KEY: VARIANT
<222> LOCATION: 6-7
<223> OTHER INFORMATION: Xaa Xaa= FF, FM, FS, FV, FT, FL, AF, AM, AS,
      AV, AT, AL, VF, VM, VS, VV, VT, or VL
<220> FEATURE:
<221> NAME/KEY: VARIANT
<222> LOCATION: 10-11
<223> OTHER INFORMATION: Xaa Xaa= LS, LQ, LM, LT, LH, VS, VQ, VM, VT, or
      VH
<220> FEATURE:
<221> NAME/KEY: VARIANT
<222> LOCATION: 12-14
<223> OTHER INFORMATION: Xaa Xaa Xaa=LFT, LMT, LQT, LHT, LNT, LPT, LST,
      LGT, LAT, LRT, QFT, QMT, QQT, QHT, QNT, QPT, QST,
      QGT, QAT, QRT, VFT, VMT, VQT, VHT, VNT, VPT, VST,
      VGT, VAT, VRT, MFT, MMT, MQT, MHT, MNT, MPT, MST,
<220> FEATURE:
<221> NAME/KEY: VARIANT
<222> LOCATION: (12)...(14)
<223> OTHER INFORMATION: Xaa Xaa Xaa=MGT, MAT, MRT, LFN, LMN, LQN, LHN,
      LNN, LPN, LSN, LGN, LAN, LRN, QFN, QMN, QQN, QHN,
      QNN, QPN, QSN, QGN, QAN, QRN, VFN, VMN, VQN, VHN,
      VNN, VPN, VSN, VGN, VAN, VRN, MFN, MMN, MQN, MHN,
<220> FEATURE:
<221> NAME/KEY: VARIANT
<222> LOCATION: (12)...(14)
<223> OTHER INFORMATION: Xaa Xaa Xaa=MNN, MPN, MSN, MGN, MAN, MRN, LFP,
      LMP, LQP, LHP, LNP, LPP, LSP, LGP, LAP, LRP, QFP,
      QMP, QQP, QHP, QNP, QPP, QSP, QGP, QAP, QRP, VFP,
      VMP, VQP, VHP, VNP, VPP, VSP, VGP, VAP, VRP, MFP,
<220> FEATURE:
<221> NAME/KEY: VARIANT
<222> LOCATION: (12)...(14)
<223> OTHER INFORMATION: Xaa Xaa Xaa=MMP, MQP, MHP, MNP, MPP, MSP, MGP,
      MAP, MRPR, LFR, LMR, LQR, LHR, LNR, LPR, LSR, LGR,
      LAR, LRR, QFR, QMR, QQR, QHR, QNR, QPR, QSR, QGR,
      QAR, QRR, VFR, VMR, VQR, VHR, VNR, VPR, VSR, VGR,
<220> FEATURE:
<221> NAME/KEY: VARIANT
```

```
<222> LOCATION: (12)...(14)
<223> OTHER INFORMATION: Xaa Xaa Xaa=VAR, VRR, MFR, MMR, MQR, MHR, MNR,
      MPR, MSR, MGR, MAR, or MRR
<220> FEATURE:
<221> NAME/KEY: VARIANT
<222> LOCATION: (15)...(16)
<223> OTHER INFORMATION: Variable length region=ER, R, or no amino acid

<400> SEQUENCE: 166

Xaa Xaa Xaa Xaa Xaa Xaa Xaa Val Lys Xaa Xaa Xaa Xaa Xaa Xaa Xaa
1               5                   10                  15

<210> SEQ ID NO 167
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 167

Lys Lys Leu Asp Thr
1               5

<210> SEQ ID NO 168
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 168

Arg Lys Leu Asp Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 169

Lys Lys Gly Asp Thr
1               5

<210> SEQ ID NO 170
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 170

Lys Lys Glu Asp Thr
1               5

<210> SEQ ID NO 171
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 171

Lys Lys Leu Asp Gln
1               5
```

```
<210> SEQ ID NO 172
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 172

Lys Leu Asp Thr
 1

<210> SEQ ID NO 173
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1-4
<223> OTHER INFORMATION: Variable length region=KKLD, RKLD, KKGD, KKED,
      KLD, KGD, KED, LD, GD, ED, D, or no amino acid
<220> FEATURE:
<221> NAME/KEY: VARIANT
<222> LOCATION: 12-14
<223> OTHER INFORMATION: Xaa Xaa Xaa= LFT, LMT, LQT, LHT, LNT, LPT, LST,
      LGT, LAT, LRT, QFT, QMT, QQT, QHT, QNT, QPT, QST,
      QGT, QAT, QRT, VFT, VMT, VQT, VHT, VNT, VPT, VST,
      VGT, VAT, VRT, MFT, MMT, MQT, MHT, MNT, MPT, MST,
<220> FEATURE:
<221> NAME/KEY: VARIANT
<222> LOCATION: 12-14
<223> OTHER INFORMATION: Xaa Xaa Xaa= MGT, MAT, MRT, LFN, LMN, LQN, LHN,
      LNN, LPN, LSN, LGN, LAN, LRN, QFN, QMN, QQN, QHN,
      QNN, QPN, QSN, QGN, QAN, QRN, VFN, VMN, VQN, VHN,
      VNN, VPN, VSN, VGN, VAN, VRN, MFN, MMN, MQN, MHN,
<220> FEATURE:
<221> NAME/KEY: VARIANT
<222> LOCATION: 12-14
<223> OTHER INFORMATION: Xaa Xaa Xaa= MNN, MPN, MSN, MGN, MAN, MRN, LFP,
      LMP, LQP, LHP, LNP, LPP, LSP, LGP, LAP, LRP, QFP,
      QMP, QQP, QHP, QNP, QPP, QSP, QGP, QAP, QRP, VFP,
      VMP, VQP, VHP, VNP, VPP, VSP, VGP, VAP, VRP, MFP,
<220> FEATURE:
<221> NAME/KEY: VARIANT
<222> LOCATION: 12-14
<223> OTHER INFORMATION: Xaa Xaa Xaa= MMP, MQP, MHP, MNP, MPP, MSP, MGP,
      MAP, MRPR, LFR, LMR, LQR, LHR, LNR, LPR, LSR, LGR,
      LAR, LRR, QFR, QMR, QQR, QHR, QNR, QPR, QSR, QGR,
      QAR, QRR, VFR, VMR, VQR, VHR, VNR, VPR, VSR, VGR,
<220> FEATURE:
<221> NAME/KEY: VARIANT
<222> LOCATION: (12)...(14)
<223> OTHER INFORMATION: Xaa Xaa Xaa= VAR, VRR, MFR, MMR, MQR, MHR, MNR,
      MPR, MSR, MGR, MAR, MRR, or no amino acid
<220> FEATURE:
<221> NAME/KEY: VARIANT
<222> LOCATION: (15)...(16)
<223> OTHER INFORMATION: Variable length region=ER, R, or no amino acid

<400> SEQUENCE: 173

Xaa Xaa Xaa Xaa Thr Phe Phe Val Lys Leu Ser Xaa Xaa Xaa Xaa Xaa
 1               5                  10                  15

<210> SEQ ID NO 174
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 174

Lys Lys Leu Asp
 1
```

<210> SEQ ID NO 175
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 175

Arg Lys Leu Asp
 1

<210> SEQ ID NO 176
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 176

Lys Lys Gly Asp
 1

<210> SEQ ID NO 177
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 177

Lys Lys Glu Asp
 1

<210> SEQ ID NO 178
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1-6
<223> OTHER INFORMATION: The sequence may be deleted at the N terminus
      by 1, 2, 3, 4, 5, or 6 amino acids
<220> FEATURE:
<221> NAME/KEY: VARIANT
<222> LOCATION: 7
<223> OTHER INFORMATION: Xaa= F, S, M, V, T, L, or no amino acid
<220> FEATURE:
<221> NAME/KEY: VARIANT
<222> LOCATION: 11
<223> OTHER INFORMATION: Xaa= S, Q, M, T, or H
<220> FEATURE:
<221> NAME/KEY: VARIANT
<222> LOCATION: 13
<223> OTHER INFORMATION: Xaa= F, M, Q, H, N, P, S, G, A, or R
<220> FEATURE:
<221> NAME/KEY: VARIANT
<222> LOCATION: 16
<223> OTHER INFORMATION: Xaa= R, or no amino acid

<400> SEQUENCE: 178

Lys Lys Leu Asp Thr Phe Xaa Val Lys Leu Xaa Leu Xaa Thr Glu Xaa
 1               5                  10                  15

<210> SEQ ID NO 179
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 179

Lys Lys Leu Asp Thr Phe
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 180

Lys Leu Asp Thr Phe
1               5

<210> SEQ ID NO 181
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 181

Leu Asp Thr Phe
1

<210> SEQ ID NO 182
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 182

Phe Phe Val Lys
1

<210> SEQ ID NO 183
<211> LENGTH: 23
<212> TYPE: PRT
<213> ORGANISM: Homo sapiens

<400> SEQUENCE: 183

Asn Glu Glu Thr Phe Leu Lys Lys Tyr Leu Tyr Glu Ile Ala Arg Arg
1               5                   10                  15

His Pro Tyr Phe Tyr Ala Pro
            20

<210> SEQ ID NO 184
<211> LENGTH: 18
<212> TYPE: PRT
<213> ORGANISM: Homo sapiens

<400> SEQUENCE: 184

Glu Leu Phe Glu Gln Leu Gly Glu Tyr Lys Phe Gln Asn Ala Leu Leu
1               5                   10                  15

Val Arg

<210> SEQ ID NO 185
<211> LENGTH: 17
<212> TYPE: PRT
<213> ORGANISM: Homo sapiens

```
<400> SEQUENCE: 185

Val Phe Asp Glu Phe Lys Pro Leu Val Glu Pro Gln Asn Leu Ile
1               5                   10                  15

Lys

<210> SEQ ID NO 186
<211> LENGTH: 10
<212> TYPE: PRT
<213> ORGANISM: Homo sapiens

<400> SEQUENCE: 186

Val Phe Asp Glu Phe Lys Pro Leu Val Glu
1               5                   10

<210> SEQ ID NO 187
<211> LENGTH: 7
<212> TYPE: PRT
<213> ORGANISM: Homo sapiens

<400> SEQUENCE: 187

Glu Pro Gln Asn Leu Ile Lys
1               5

<210> SEQ ID NO 188
<211> LENGTH: 15
<212> TYPE: PRT
<213> ORGANISM: Homo sapiens

<400> SEQUENCE: 188

Lys Val Pro Gln Val Ser Thr Pro Thr Leu Val Glu Val Ser Arg
1               5                   10                  15

<210> SEQ ID NO 189
<211> LENGTH: 12
<212> TYPE: PRT
<213> ORGANISM: Homo sapiens

<400> SEQUENCE: 189

Lys Leu Val Asn Glu Val Thr Glu Phe Ala Lys Thr
1               5                   10

<210> SEQ ID NO 190
<211> LENGTH: 12
<212> TYPE: PRT
<213> ORGANISM: Homo sapiens

<400> SEQUENCE: 190

Asn Glu Glu Thr Phe Leu Lys Lys Tyr Leu Tyr Glu
1               5                   10

<210> SEQ ID NO 191
<211> LENGTH: 11
<212> TYPE: PRT
<213> ORGANISM: Homo sapiens

<400> SEQUENCE: 191

Leu Asp Glu Leu Arg Asp Glu Gly Lys Ala Ser
1               5                   10

<210> SEQ ID NO 192
<211> LENGTH: 12
<212> TYPE: PRT
<213> ORGANISM: Homo sapiens
```

<400> SEQUENCE: 192

Glu Met Ala Asp Cys Cys Ala Lys Gln Glu Pro Glu
1               5                   10

<210> SEQ ID NO 193
<211> LENGTH: 11
<212> TYPE: PRT
<213> ORGANISM: Homo sapiens

<400> SEQUENCE: 193

Glu Leu Phe Glu Gln Leu Gly Glu Tyr Lys Phe
1               5                   10

<210> SEQ ID NO 194
<211> LENGTH: 8
<212> TYPE: PRT
<213> ORGANISM: Homo sapiens

<400> SEQUENCE: 194

Lys Tyr Leu Tyr Glu Ile Ala Arg
1               5

<210> SEQ ID NO 195
<211> LENGTH: 15
<212> TYPE: PRT
<213> ORGANISM: Homo sapiens

<400> SEQUENCE: 195

Lys Val Pro Gln Val Ser Thr Pro Thr Leu Val Glu Val Ser Arg
1               5                   10                  15

<210> SEQ ID NO 196
<211> LENGTH: 17
<212> TYPE: PRT
<213> ORGANISM: Homo sapiens

<400> SEQUENCE: 196

Val Phe Asp Glu Phe Lys Pro Leu Val Glu Glu Pro Gln Asn Leu Ile
1               5                   10                  15

Lys

<210> SEQ ID NO 197
<211> LENGTH: 14
<212> TYPE: PRT
<213> ORGANISM: Homo sapiens

<400> SEQUENCE: 197

Val Pro Gln Val Ser Thr Pro Thr Leu Val Glu Val Ser Arg
1               5                   10

<210> SEQ ID NO 198
<211> LENGTH: 16
<212> TYPE: PRT
<213> ORGANISM: Homo sapiens

<400> SEQUENCE: 198

Arg Pro Cys Phe Ser Ala Leu Glu Val Asp Glu Thr Tyr Val Pro Lys
1               5                   10                  15

<210> SEQ ID NO 199
<211> LENGTH: 8
<212> TYPE: PRT
<213> ORGANISM: Homo sapiens

```
<400> SEQUENCE: 199

Phe Gln Asn Ala Leu Leu Val Arg
1               5

<210> SEQ ID NO 200
<211> LENGTH: 9
<212> TYPE: PRT
<213> ORGANISM: Homo sapiens

<400> SEQUENCE: 200

Ser Leu His Thr Leu Phe Gly Asp Lys
1               5

<210> SEQ ID NO 201
<211> LENGTH: 12
<212> TYPE: PRT
<213> ORGANISM: Homo sapiens

<400> SEQUENCE: 201

Leu Lys Glu Cys Cys Glu Lys Pro Leu Leu Glu Lys
1               5                   10

<210> SEQ ID NO 202
<211> LENGTH: 8
<212> TYPE: PRT
<213> ORGANISM: Homo sapiens

<400> SEQUENCE: 202

Leu Cys Thr Val Ala Thr Leu Arg
1               5

<210> SEQ ID NO 203
<211> LENGTH: 7
<212> TYPE: PRT
<213> ORGANISM: Homo sapiens

<400> SEQUENCE: 203

Tyr Leu Tyr Glu Ile Ala Arg
1               5

<210> SEQ ID NO 204
<211> LENGTH: 13
<212> TYPE: PRT
<213> ORGANISM: Homo sapiens

<400> SEQUENCE: 204

Cys Cys Ala Ala Ala Asp Pro His Glu Cys Tyr Ala Lys
1               5                   10

<210> SEQ ID NO 205
<211> LENGTH: 12
<212> TYPE: PRT
<213> ORGANISM: Homo sapiens

<400> SEQUENCE: 205

Ala Ala Phe Thr Glu Cys Cys Gln Ala Ala Asp Lys
1               5                   10

<210> SEQ ID NO 206
<211> LENGTH: 9
<212> TYPE: PRT
<213> ORGANISM: Homo sapiens

<400> SEQUENCE: 206
```

```
Cys Cys Thr Glu Ser Leu Val Asn Arg
  1               5

<210> SEQ ID NO 207
<211> LENGTH: 13
<212> TYPE: PRT
<213> ORGANISM: Homo sapiens

<400> SEQUENCE: 207

Gln Glu Pro Glu Arg Asn Glu Cys Phe Leu Gln His Lys
  1               5                  10

<210> SEQ ID NO 208
<211> LENGTH: 12
<212> TYPE: PRT
<213> ORGANISM: Homo sapiens

<400> SEQUENCE: 208

Ala Val Met Asp Asp Phe Ala Ala Phe Val Glu Lys
  1               5                  10

<210> SEQ ID NO 209
<211> LENGTH: 8
<212> TYPE: PRT
<213> ORGANISM: Homo sapiens

<400> SEQUENCE: 209

Asn Glu Cys Phe Leu Gln His Lys
  1               5

<210> SEQ ID NO 210
<211> LENGTH: 13
<212> TYPE: PRT
<213> ORGANISM: Homo sapiens

<400> SEQUENCE: 210

Gln Asn Cys Glu Leu Phe Glu Gln Leu Gly Glu Tyr Lys
  1               5                  10

<210> SEQ ID NO 211
<211> LENGTH: 13
<212> TYPE: PRT
<213> ORGANISM: Homo sapiens

<400> SEQUENCE: 211

Gln Glu Pro Glu Arg Asn Glu Cys Phe Leu Gln His Lys
  1               5                  10

<210> SEQ ID NO 212
<211> LENGTH: 17
<212> TYPE: PRT
<213> ORGANISM: Homo sapiens

<400> SEQUENCE: 212

Val His Thr Glu Cys Cys His Gly Asp Leu Leu Glu Cys Ala Asp Asp
  1               5                  10                  15

Arg

<210> SEQ ID NO 213
<211> LENGTH: 10
<212> TYPE: PRT
<213> ORGANISM: Homo sapiens

<400> SEQUENCE: 213
```

```
Phe Lys Asp Leu Gly Glu Glu Asn Phe Lys
 1               5                  10

<210> SEQ ID NO 214
<211> LENGTH: 12
<212> TYPE: PRT
<213> ORGANISM: Homo sapiens

<400> SEQUENCE: 214

Tyr Ile Cys Glu Asn Gln Asp Ser Ile Ser Ser Lys
 1               5                  10

<210> SEQ ID NO 215
<211> LENGTH: 9
<212> TYPE: PRT
<213> ORGANISM: Homo sapiens

<400> SEQUENCE: 215

Leu Asp Glu Leu Arg Asp Glu Gly Lys
 1               5

<210> SEQ ID NO 216
<211> LENGTH: 8
<212> TYPE: PRT
<213> ORGANISM: Homo sapiens

<400> SEQUENCE: 216

Asp Asp Asn Pro Asn Leu Pro Arg
 1               5

<210> SEQ ID NO 217
<211> LENGTH: 18
<212> TYPE: PRT
<213> ORGANISM: Homo sapiens

<400> SEQUENCE: 217

Asp His Val Lys Leu Val Asn Glu Val Thr Glu Phe Ala Lys Thr Cys
 1               5                  10                  15

Val Ala

<210> SEQ ID NO 218
<211> LENGTH: 24
<212> TYPE: PRT
<213> ORGANISM: Homo sapiens

<400> SEQUENCE: 218

Asp Asp Lys Glu Thr Cys Phe Ala Glu Glu Gly Lys Lys Leu Val Ala
 1               5                  10                  15

Ala Ser Gln Ala Ala Leu Gly Leu
          20

<210> SEQ ID NO 219
<211> LENGTH: 23
<212> TYPE: PRT
<213> ORGANISM: Homo sapiens

<400> SEQUENCE: 219

Asp Arg Val Thr Lys Cys Cys Thr Glu Ser Leu Val Asn Arg Arg Pro
 1               5                  10                  15

Cys Phe Ser Ala Leu Glu Val
          20
```

```
<210> SEQ ID NO 220
<211> LENGTH: 17
<212> TYPE: PRT
<213> ORGANISM: Homo sapiens

<400> SEQUENCE: 220

Asp Glu Thr Tyr Val Pro Lys Glu Phe Asn Ala Glu Thr Phe Thr His
1               5                   10                  15

Ala

<210> SEQ ID NO 221
<211> LENGTH: 27
<212> TYPE: PRT
<213> ORGANISM: Homo sapiens

<400> SEQUENCE: 221

Asp Ser Ile Ser Ser Lys Leu Lys Glu Cys Cys Glu Lys Pro Leu Leu
1               5                   10                  15

Glu Lys Ser His Cys Ile Ala Glu Val Glu Asn
            20                  25

<210> SEQ ID NO 222
<211> LENGTH: 16
<212> TYPE: PRT
<213> ORGANISM: Homo sapiens

<400> SEQUENCE: 222

Asp Lys Leu Cys Thr Val Ala Thr Leu Arg Glu Thr Tyr Gly Glu Met
1               5                   10                  15

<210> SEQ ID NO 223
<211> LENGTH: 34
<212> TYPE: PRT
<213> ORGANISM: Homo sapiens

<400> SEQUENCE: 223

Tyr Ser Val Val Leu Leu Leu Arg Leu Ala Lys Thr Tyr Glu Thr Thr
1               5                   10                  15

Leu Glu Lys Cys Cys Ala Ala Ala Asp Pro His Glu Cys Tyr Ala Lys
            20                  25                  30

Val Phe

<210> SEQ ID NO 224
<211> LENGTH: 34
<212> TYPE: PRT
<213> ORGANISM: Homo sapiens

<400> SEQUENCE: 224

Lys Leu Cys Thr Val Ala Thr Leu Arg Glu Thr Tyr Gly Glu Met Ala
1               5                   10                  15

Asp Cys Cys Ala Lys Gln Glu Pro Glu Arg Asn Glu Cys Phe Leu Gln
            20                  25                  30

His Lys

<210> SEQ ID NO 225
<211> LENGTH: 36
<212> TYPE: PRT
<213> ORGANISM: Homo sapiens

<400> SEQUENCE: 225

Ile Cys Thr Leu Ser Glu Lys Glu Arg Gln Ile Lys Lys Gln Thr Ala
1               5                   10                  15
```

-continued

Leu Val Glu Leu Val Lys His Lys Pro Lys Ala Thr Lys Glu Gln Leu
            20                  25                  30

Lys Ala Val Met
        35

<210> SEQ ID NO 226
<211> LENGTH: 35
<212> TYPE: PRT
<213> ORGANISM: Homo sapiens

<400> SEQUENCE: 226

Leu Ala Lys Tyr Ile Cys Glu Asn Gln Asp Ser Ile Ser Ser Lys Leu
1               5                   10                  15

Lys Glu Cys Cys Glu Lys Pro Leu Leu Glu Lys His Cys Ile Ala Glu
            20                  25                  30

Val Glu Asn
        35

<210> SEQ ID NO 227
<211> LENGTH: 40
<212> TYPE: PRT
<213> ORGANISM: Homo sapiens

<400> SEQUENCE: 227

Val Phe Leu Gly Met Phe Leu Tyr Glu Tyr Ala Arg Arg His Pro Asp
1               5                   10                  15

Tyr Ser Val Val Leu Leu Leu Arg Leu Ala Lys Thr Tyr Glu Thr Thr
            20                  25                  30

Leu Glu Lys Cys Cys Ala Ala Ala
        35                  40

<210> SEQ ID NO 228
<211> LENGTH: 42
<212> TYPE: PRT
<213> ORGANISM: Homo sapiens

<400> SEQUENCE: 228

Leu Gly Glu Glu Asn Phe Lys Ala Leu Val Leu Ile Ala Phe Ala Gln
1               5                   10                  15

Tyr Leu Gln Gln Cys Pro Phe Glu Asp His Val Lys Leu Val Asn Glu
            20                  25                  30

Val Thr Glu Phe Ala Lys Thr Cys Val Ala
        35                  40

<210> SEQ ID NO 229
<211> LENGTH: 40
<212> TYPE: PRT
<213> ORGANISM: Homo sapiens

<400> SEQUENCE: 229

Arg Val Thr Lys Cys Cys Thr Glu Ser Leu Val Asn Arg Arg Pro Cys
1               5                   10                  15

Phe Ser Ala Leu Glu Val Asp Glu Thr Tyr Val Pro Lys Glu Phe Asn
            20                  25                  30

Ala Glu Thr Phe Thr Phe His Ala
        35                  40

<210> SEQ ID NO 230
<211> LENGTH: 42
<212> TYPE: PRT

```
<213> ORGANISM: Homo sapiens

<400> SEQUENCE: 230

Tyr Leu Ser Val Val Leu Asn Gln Leu Cys Val Leu His Glu Lys Thr
 1               5                  10                  15

Pro Val Ser Asp Arg Val Thr Lys Cys Cys Cys Thr Glu Ser Leu Val
            20                  25                  30

Asn Arg Arg Pro Phe Ser Ala Leu Glu Val
        35                  40

<210> SEQ ID NO 231
<211> LENGTH: 10
<212> TYPE: PRT
<213> ORGANISM: Homo sapiens

<400> SEQUENCE: 231

Leu Val Asn Glu Val Thr Glu Phe Ala Lys
 1               5                  10

<210> SEQ ID NO 232
<211> LENGTH: 9
<212> TYPE: PRT
<213> ORGANISM: Homo sapiens

<400> SEQUENCE: 232

Ser Leu His Thr Leu Phe Gly Asp Lys
 1               5

<210> SEQ ID NO 233
<211> LENGTH: 8
<212> TYPE: PRT
<213> ORGANISM: Homo sapiens

<400> SEQUENCE: 233

Leu Cys Thr Val Ala Thr Leu Arg
 1               5

<210> SEQ ID NO 234
<211> LENGTH: 12
<212> TYPE: PRT
<213> ORGANISM: Artificial Sequence
<220> FEATURE:
<223> OTHER INFORMATION: P28R truncation

<400> SEQUENCE: 234

Glu Thr Tyr Gly Glu Met Ala Asp Cys Cys Ala Lys
 1               5                  10

<210> SEQ ID NO 235
<211> LENGTH: 7
<212> TYPE: PRT
<213> ORGANISM: Artificial Sequence
<220> FEATURE:
<223> OTHER INFORMATION: P28R truncation

<400> SEQUENCE: 235

Tyr Leu Tyr Glu Ile Ala Arg
 1               5

<210> SEQ ID NO 236
<211> LENGTH: 9
<212> TYPE: PRT
<213> ORGANISM: Homo sapiens

<400> SEQUENCE: 236
```

Leu Asp Glu Leu Arg Asp Glu Gly Lys
1               5

<210> SEQ ID NO 237
<211> LENGTH: 12
<212> TYPE: PRT
<213> ORGANISM: Homo sapiens

<400> SEQUENCE: 237

Tyr Ile Cys Glu Asn Gln Asp Ser Ile Ser Ser Lys
1               5                   10

<210> SEQ ID NO 238
<211> LENGTH: 12
<212> TYPE: PRT
<213> ORGANISM: Homo sapiens

<400> SEQUENCE: 238

Leu Lys Glu Cys Cys Glu Lys Pro Leu Leu Glu Lys
1               5                   10

<210> SEQ ID NO 239
<211> LENGTH: 11
<212> TYPE: PRT
<213> ORGANISM: Homo sapiens

<400> SEQUENCE: 239

His Pro Asp Tyr Ser Val Val Leu Leu Leu Arg
1               5                   10

<210> SEQ ID NO 240
<211> LENGTH: 13
<212> TYPE: PRT
<213> ORGANISM: Homo sapiens

<400> SEQUENCE: 240

Cys Cys Ala Ala Ala Asp Pro His Glu Cys Tyr Ala Lys
1               5                   10

<210> SEQ ID NO 241
<211> LENGTH: 13
<212> TYPE: PRT
<213> ORGANISM: Homo sapiens

<400> SEQUENCE: 241

Gln Asn Cys Glu Leu Phe Glu Gln Leu Gly Glu Tyr Lys
1               5                   10

<210> SEQ ID NO 242
<211> LENGTH: 8
<212> TYPE: PRT
<213> ORGANISM: Homo sapiens

<400> SEQUENCE: 242

Phe Gln Asn Ala Leu Leu Val Arg
1               5

<210> SEQ ID NO 243
<211> LENGTH: 9
<212> TYPE: PRT
<213> ORGANISM: Homo sapiens

<400> SEQUENCE: 243

Cys Cys Thr Glu Ser Leu Val Asn Arg

```
            1               5

<210> SEQ ID NO 244
<211> LENGTH: 12
<212> TYPE: PRT
<213> ORGANISM: Homo sapiens

<400> SEQUENCE: 244

Ala Val Met Asp Asp Phe Ala Ala Phe Val Glu Lys
  1               5                  10

<210> SEQ ID NO 245
<211> LENGTH: 7
<212> TYPE: PRT
<213> ORGANISM: Homo sapiens

<400> SEQUENCE: 245

Leu Ser Gln Arg Phe Pro Lys
  1               5

<210> SEQ ID NO 246
<211> LENGTH: 8
<212> TYPE: PRT
<213> ORGANISM: Homo sapiens

<400> SEQUENCE: 246

Asp Asp Asn Pro Asn Leu Pro Arg
  1               5

<210> SEQ ID NO 247
<211> LENGTH: 272
<212> TYPE: PRT
<213> ORGANISM: Homo sapiens

<400> SEQUENCE: 247

Met Asp Ser Tyr Leu Leu Met Trp Gly Leu Leu Thr Phe Ile Met Val
  1               5                  10                  15

Pro Gly Cys Gln Ala Glu Leu Cys Asp Asp Asp Pro Pro Glu Ile Pro
                 20                  25                  30

His Ala Thr Phe Lys Ala Met Ala Tyr Lys Glu Gly Thr Met Leu Asn
             35                  40                  45

Cys Glu Cys Lys Arg Gly Phe Arg Arg Ile Lys Ser Gly Ser Leu Tyr
         50                  55                  60

Met Leu Cys Thr Gly Asn Ser Ser His Ser Ser Trp Asp Asn Gln Cys
 65                  70                  75                  80

Gln Cys Thr Ser Ser Ala Thr Arg Asn Thr Thr Lys Gln Val Thr Pro
                 85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190
```

```
Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Thr Ile
            260                 265                 270
```

<210> SEQ ID NO 248
<211> LENGTH: 1170
<212> TYPE: PRT
<213> ORGANISM: Homo sapiens

<400> SEQUENCE: 248

```
Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
                20                  25                  30

Ala Arg Ser Phe Ser Pro Pro Arg Ala Gly Arg His Phe Gly Tyr Arg
            35                  40                  45

Val Leu Gln Val Gly Asn Gly Val Ile Val Gly Ala Pro Gly Glu Gly
        50                  55                  60

Asn Ser Thr Gly Ser Leu Tyr Gln Cys Gln Ser Gly Thr Gly His Cys
65                  70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Ala Cys Asp
            100                 105                 110

Pro Gly Leu Ser Arg Thr Cys Asp Gln Asn Thr Tyr Leu Ser Gly Leu
        115                 120                 125

Cys Tyr Leu Phe Arg Gln Asn Leu Gln Gly Pro Met Leu Gln Gly Arg
    130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Arg Lys Asp Pro Asp Ala Leu Leu Lys His Val
    210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Ile Thr Asp Gly Glu Ala Thr Asp Ser Gly Asn
            260                 265                 270

Ile Asp Ala Ala Lys Asp Ile Ile Arg Tyr Ile Ile Gly Ile Gly Lys
        275                 280                 285

His Phe Gln Thr Lys Glu Ser Gln Glu Thr Leu His Lys Phe Ala Ser
    290                 295                 300
```

```
Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
        355                 360                 365

Gly Ala Lys Asp Trp Ala Gly Gly Phe Leu Asp Leu Lys Ala Asp Leu
    370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly His Trp Ser Gln Val
        435                 440                 445

Gln Thr Ile His Gly Thr Gln Ile Gly Ser Tyr Phe Gly Gly Glu Leu
    450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Val Ser Glu Leu Gln Gly
            500                 505                 510

Asp Pro Gly Tyr Pro Leu Gly Arg Phe Gly Glu Ala Ile Thr Ala Leu
        515                 520                 525

Thr Asp Ile Asn Gly Asp Gly Leu Val Asp Val Ala Val Gly Ala Pro
530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
                565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
        595                 600                 605

Val Leu Ser Ser Arg Pro Val Val Asp Met Val Thr Leu Met Ser Phe
610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
                645                 650                 655

Lys Ser Leu Ile Pro Gln Phe Gln Gly Arg Leu Val Ala Asn Leu Thr
            660                 665                 670

Tyr Thr Leu Gln Leu Asp Gly His Arg Thr Arg Arg Arg Gly Leu Phe
        675                 680                 685

Pro Gly Gly Arg His Glu Leu Arg Arg Asn Ile Ala Val Thr Thr Ser
    690                 695                 700

Met Ser Cys Thr Asp Phe Ser Phe His Phe Pro Val Cys Val Gln Asp
705                 710                 715                 720
```

```
Leu Ile Ser Pro Ile Asn Val Ser Leu Asn Phe Ser Leu Trp Glu Glu
            725                 730                 735

Glu Gly Thr Pro Arg Asp Gln Arg Ala Gln Gly Lys Asp Ile Pro Pro
        740                 745                 750

Ile Leu Arg Pro Ser Leu His Ser Glu Thr Trp Glu Ile Pro Phe Glu
            755                 760                 765

Lys Asn Cys Gly Glu Asp Lys Lys Cys Glu Ala Asn Leu Arg Val Ser
770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
            820                 825                 830

Glu Met Leu Lys Pro His Ser Gln Ile Pro Val Ser Cys Glu Glu Leu
            835                 840                 845

Pro Glu Glu Ser Arg Leu Leu Ser Arg Ala Leu Ser Cys Asn Val Ser
            850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Glu Asp Asn Ser
                900                 905                 910

Ala Thr Thr Ile Ile Pro Ile Leu Tyr Pro Ile Asn Ile Leu Ile Gln
            915                 920                 925

Asp Gln Glu Asp Ser Thr Leu Tyr Val Ser Phe Thr Pro Lys Gly Pro
            930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
            995                 1000                1005

Ala Ala Glu Pro Cys Leu Pro Gly Ala Leu Phe Arg Cys Pro Val Val
            1010                1015                1020

Phe Arg Gln Glu Ile Leu Val Gln Val Ile Gly Thr Leu Glu Leu Val
1025                1030                1035                1040

Gly Glu Ile Glu Ala Ser Ser Met Phe Ser Leu Cys Ser Ser Leu Ser
                1045                1050                1055

Ile Ser Phe Asn Ser Ser Lys His Phe His Leu Tyr Gly Ser Asn Ala
            1060                1065                1070

Ser Leu Ala Gln Val Val Met Lys Val Asp Val Val Tyr Glu Lys Gln
            1075                1080                1085

Met Leu Tyr Leu Tyr Val Leu Ser Gly Ile Gly Gly Leu Leu Leu Leu
            1090                1095                1100

Leu Leu Ile Phe Ile Val Leu Tyr Lys Val Gly Phe Phe Lys Arg Asn
1105                1110                1115                1120

Leu Lys Glu Lys Met Glu Ala Gly Arg Gly Val Pro Asn Gly Ile Pro
            1125                1130                1135

Ala Glu Asp Ser Glu Gln Leu Ala Ser Gly Gln Glu Ala Gly Asp Pro
```

```
                    1140                1145                1150
Gly Cys Leu Lys Pro Leu His Glu Lys Asp Ser Glu Ser Gly Gly Gly
            1155                1160                1165

Lys Asp
    1170

<210> SEQ ID NO 249
<211> LENGTH: 600
<212> TYPE: PRT
<213> ORGANISM: Homo sapiens

<400> SEQUENCE: 249

Met Leu Gly Leu Arg Pro Pro Leu Leu Ala Leu Val Gly Leu Leu Ser
  1               5                  10                  15

Leu Gly Cys Val Leu Ser Gln Glu Cys Thr Lys Phe Lys Val Ser Ser
                 20                  25                  30

Cys Arg Glu Cys Ile Glu Ser Gly Pro Gly Cys Thr Trp Cys Gln Lys
             35                  40                  45

Leu Asn Phe Thr Gly Pro Gly Asp Pro Asp Ser Ile Arg Cys Asp Thr
 50                  55                  60

Arg Pro Gln Leu Leu Met Arg Gly Cys Ala Ala Asp Asp Ile Met Asp
 65                  70                  75                  80

Pro Thr Ser Leu Ala Glu Thr Gln Glu Asp His Asn Gly Gly Gln Lys
                 85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Leu Asp Asp Leu Arg
130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
            195                 200                 205

Lys Leu Thr Asn Asn Ser Asn Gln Phe Gln Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
            275                 280                 285

Glu Asp Asn Leu Tyr Lys Arg Ser Asn Glu Phe Asp Tyr Pro Ser Val
290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335
```

```
Ile Pro Lys Ser Ala Val Gly Glu Leu Ser Glu Asp Ser Ser Asn Val
                340                 345                 350

Val His Leu Ile Lys Asn Ala Tyr Asn Lys Leu Ser Ser Arg Val Phe
            355                 360                 365

Leu Asp His Asn Ala Leu Pro Asp Thr Leu Lys Val Thr Tyr Asp Ser
        370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val
        595                 600

<210> SEQ ID NO 250
<211> LENGTH: 12
<212> TYPE: PRT
<213> ORGANISM: Artificial Sequence
<220> FEATURE:
<223> OTHER INFORMATION: P28R truncation

<400> SEQUENCE: 250

Thr Phe Phe Val Lys Leu Ser Leu Phe Thr Glu Arg
1               5                   10

<210> SEQ ID NO 251
<211> LENGTH: 8
<212> TYPE: PRT
<213> ORGANISM: Artificial Sequence
<220> FEATURE:
<223> OTHER INFORMATION: P28R truncation

<400> SEQUENCE: 251

Val Lys Leu Ser Leu Phe Thr Glu
1               5

<210> SEQ ID NO 252
```

<211> LENGTH: 5
<212> TYPE: PRT
<213> ORGANISM: Artificial Sequence
<220> FEATURE:
<223> OTHER INFORMATION: Synthetic peptide

<400> SEQUENCE: 252

Lys Lys Gly Asp Gln
1               5

<210> SEQ ID NO 253
<211> LENGTH: 5
<212> TYPE: PRT
<213> ORGANISM: Artificial Sequence
<220> FEATURE:
<223> OTHER INFORMATION: Synthetic peptide

<400> SEQUENCE: 253

Lys Lys Glu Asp Gln
1               5

<210> SEQ ID NO 254
<211> LENGTH: 5
<212> TYPE: PRT
<213> ORGANISM: Artificial Sequence
<220> FEATURE:
<223> OTHER INFORMATION: Synthetic peptide

<400> SEQUENCE: 254

Arg Lys Leu Asp Gln
1               5

<210> SEQ ID NO 255
<211> LENGTH: 5
<212> TYPE: PRT
<213> ORGANISM: Artificial Sequence
<220> FEATURE:
<223> OTHER INFORMATION: Synthetic peptide

<400> SEQUENCE: 255

Arg Lys Gly Asp Gln
1               5

<210> SEQ ID NO 256
<211> LENGTH: 5
<212> TYPE: PRT
<213> ORGANISM: Artificial Sequence
<220> FEATURE:
<223> OTHER INFORMATION: Synthetic peptide

<400> SEQUENCE: 256

Arg Lys Glu Asp Gln
1               5

<210> SEQ ID NO 257
<211> LENGTH: 5
<212> TYPE: PRT
<213> ORGANISM: Artificial Sequence
<220> FEATURE:
<223> OTHER INFORMATION: Synthetic peptide

<400> SEQUENCE: 257

Arg Lys Gly Thr Asp
1               5

<210> SEQ ID NO 258
<211> LENGTH: 5

```
<212> TYPE: PRT
<213> ORGANISM: Artificial Sequence
<220> FEATURE:
<223> OTHER INFORMATION: Synthetic peptide

<400> SEQUENCE: 258

Arg Lys Glu Asp Thr
 1               5

<210> SEQ ID NO 259
<211> LENGTH: 4
<212> TYPE: PRT
<213> ORGANISM: Artificial Sequence
<220> FEATURE:
<223> OTHER INFORMATION: Synthetic peptide

<400> SEQUENCE: 259

Lys Gly Asp Thr
 1

<210> SEQ ID NO 260
<211> LENGTH: 4
<212> TYPE: PRT
<213> ORGANISM: Artificial Sequence
<220> FEATURE:
<223> OTHER INFORMATION: Synthetic peptide

<400> SEQUENCE: 260

Lys Glu Asp Thr
 1

<210> SEQ ID NO 261
<211> LENGTH: 4
<212> TYPE: PRT
<213> ORGANISM: Artificial Sequence
<220> FEATURE:
<223> OTHER INFORMATION: Synthetic peptide

<400> SEQUENCE: 261

Lys Leu Asp Gln
 1

<210> SEQ ID NO 262
<211> LENGTH: 4
<212> TYPE: PRT
<213> ORGANISM: Artificial Sequence
<220> FEATURE:
<223> OTHER INFORMATION: Synthetic peptide

<400> SEQUENCE: 262

Lys Gly Asp Gln
 1

<210> SEQ ID NO 263
<211> LENGTH: 4
<212> TYPE: PRT
<213> ORGANISM: Artificial Sequence
<220> FEATURE:
<223> OTHER INFORMATION: Synthetic peptide

<400> SEQUENCE: 263

Lys Glu Asp Gln
 1

<210> SEQ ID NO 264
<211> LENGTH: 16
<212> TYPE: PRT
```

```
<213> ORGANISM: Artificial Sequence
<220> FEATURE:
<223> OTHER INFORMATION: Synthetic peptide

<400> SEQUENCE: 264

Lys Lys Leu Asp Thr Phe Phe Lys Lys Leu Ser Leu Phe Thr Glu Arg
 1               5                  10                  15

<210> SEQ ID NO 265
<211> LENGTH: 9
<212> TYPE: PRT
<213> ORGANISM: Artificial Sequence
<220> FEATURE:
<223> OTHER INFORMATION: Synthetic peptide

<400> SEQUENCE: 265

Cys Leu Ala Leu Asn Val Met Cys Gly
 1               5

<210> SEQ ID NO 266
<211> LENGTH: 9
<212> TYPE: PRT
<213> ORGANISM: Artificial Sequence
<220> FEATURE:
<223> OTHER INFORMATION: Synthetic peptide

<400> SEQUENCE: 266

Cys Leu Arg Leu Asn Val Phe Cys Gly
 1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic peptide

<400> SEQUENCE: 267

Cys Leu Arg Leu Ile Val Met Cys Gly
 1               5

<210> SEQ ID NO 268
<211> LENGTH: 16
<212> TYPE: PRT
<213> ORGANISM: Artificial Sequence
<220> FEATURE:
<223> OTHER INFORMATION: Synthetic peptide

<400> SEQUENCE: 268

Ala Lys Leu Asp Thr Phe Phe Val Lys Leu Ser Leu Phe Thr Glu Arg
 1               5                  10                  15

<210> SEQ ID NO 269
<211> LENGTH: 16
<212> TYPE: PRT
<213> ORGANISM: Artificial Sequence
<220> FEATURE:
<223> OTHER INFORMATION: Synthetic peptide

<400> SEQUENCE: 269

Asp Lys Leu Asp Thr Phe Phe Val Lys Leu Ser Leu Phe Thr Glu Arg
 1               5                  10                  15

<210> SEQ ID NO 270
<211> LENGTH: 16
<212> TYPE: PRT
<213> ORGANISM: Artificial Sequence
```

```
<220> FEATURE:
<223> OTHER INFORMATION: Synthetic peptide

<400> SEQUENCE: 270

Glu Lys Leu Asp Thr Phe Phe Val Lys Leu Ser Leu Phe Thr Glu Arg
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Synthetic peptide

<400> SEQUENCE: 271

Gly Lys Leu Asp Thr Phe Phe Val Lys Leu Ser Leu Phe Thr Glu Arg
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Synthetic peptide

<400> SEQUENCE: 272

His Lys Leu Asp Thr Phe Phe Val Lys Leu Ser Leu Phe Thr Glu Arg
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Synthetic peptide

<400> SEQUENCE: 273

Ile Lys Leu Asp Thr Phe Phe Val Lys Leu Ser Leu Phe Thr Glu Arg
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Synthetic peptide

<400> SEQUENCE: 274

Leu Lys Leu Asp Thr Phe Phe Val Lys Leu Ser Leu Phe Thr Glu Arg
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: Synthetic peptide

<400> SEQUENCE: 275

Met Lys Leu Asp Thr Phe Phe Val Lys Leu Ser Leu Phe Thr Glu Arg
1               5                   10                  15

<210> SEQ ID NO 276
<211> LENGTH: 16
<212> TYPE: PRT
<213> ORGANISM: Artificial Sequence
<220> FEATURE:
```

<223> OTHER INFORMATION: Synthetic peptide

<400> SEQUENCE: 276

Asn Lys Leu Asp Thr Phe Phe Val Lys Leu Ser Leu Phe Thr Glu Arg
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Synthetic peptide

<400> SEQUENCE: 277

Pro Lys Leu Asp Thr Phe Phe Val Lys Leu Ser Leu Phe Thr Glu Arg
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Synthetic peptide

<400> SEQUENCE: 278

Gln Lys Leu Asp Thr Phe Phe Val Lys Leu Ser Leu Phe Thr Glu Arg
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Synthetic peptide

<400> SEQUENCE: 279

Arg Lys Leu Asp Thr Phe Phe Val Lys Leu Ser Leu Phe Thr Glu Arg
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Synthetic peptide

<400> SEQUENCE: 280

Thr Lys Leu Asp Thr Phe Phe Val Lys Leu Ser Leu Phe Thr Glu Arg
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Synthetic peptide

<400> SEQUENCE: 281

Val Lys Leu Asp Thr Phe Phe Val Lys Leu Ser Leu Phe Thr Glu Arg
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Synthetic peptide

<400> SEQUENCE: 282

Lys Lys Ala Asp Thr Phe Phe Val Lys Leu Ser Leu Phe Thr Glu Arg
1               5                   10                  15

<210> SEQ ID NO 283
<211> LENGTH: 16
<212> TYPE: PRT
<213> ORGANISM: Artificial Sequence
<220> FEATURE:
<223> OTHER INFORMATION: Synthetic peptide

<400> SEQUENCE: 283

Lys Lys Cys Asp Thr Phe Phe Val Lys Leu Ser Leu Phe Thr Glu Arg
1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Synthetic peptide

<400> SEQUENCE: 284

Lys Lys Asp Asp Thr Phe Phe Val Lys Leu Ser Leu Phe Thr Glu Arg
1               5                   10                  15

<210> SEQ ID NO 285
<211> LENGTH: 16
<212> TYPE: PRT
<213> ORGANISM: Artificial Sequence
<220> FEATURE:
<223> OTHER INFORMATION: Synthetic peptide

<400> SEQUENCE: 285

Lys Lys Glu Asp Thr Phe Phe Val Lys Leu Ser Leu Phe Thr Glu Arg
1               5                   10                  15

<210> SEQ ID NO 286
<211> LENGTH: 16
<212> TYPE: PRT
<213> ORGANISM: Artificial Sequence
<220> FEATURE:
<223> OTHER INFORMATION: Synthetic peptide

<400> SEQUENCE: 286

Lys Lys Phe Asp Thr Phe Phe Val Lys Leu Ser Leu Phe Thr Glu Arg
1               5                   10                  15

<210> SEQ ID NO 287
<211> LENGTH: 16
<212> TYPE: PRT
<213> ORGANISM: Artificial Sequence
<220> FEATURE:
<223> OTHER INFORMATION: Synthetic peptide

<400> SEQUENCE: 287

Lys Lys Gly Asp Thr Phe Phe Val Lys Leu Ser Leu Phe Thr Glu Arg
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Synthetic peptide

<400> SEQUENCE: 288

Lys Lys His Asp Thr Phe Phe Val Lys Leu Ser Leu Phe Thr Glu Arg
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Synthetic peptide

<400> SEQUENCE: 289

Lys Lys Ile Asp Thr Phe Phe Val Lys Leu Ser Leu Phe Thr Glu Arg
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Synthetic peptide

<400> SEQUENCE: 290

Lys Lys Lys Asp Thr Phe Phe Val Lys Leu Ser Leu Phe Thr Glu Arg
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Synthetic peptide

<400> SEQUENCE: 291

Lys Lys Met Asp Thr Phe Phe Val Lys Leu Ser Leu Phe Thr Glu Arg
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Synthetic peptide

<400> SEQUENCE: 292

Lys Lys Asn Asp Thr Phe Phe Val Lys Leu Ser Leu Phe Thr Glu Arg
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Synthetic peptide

<400> SEQUENCE: 293

Lys Lys Gln Asp Thr Phe Phe Val Lys Leu Ser Leu Phe Thr Glu Arg
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Synthetic peptide

<400> SEQUENCE: 294

```
Lys Lys Arg Asp Thr Phe Phe Val Lys Leu Ser Leu Phe Thr Glu Arg
  1               5                  10                  15

<210> SEQ ID NO 295
<211> LENGTH: 16
<212> TYPE: PRT
<213> ORGANISM: Artificial Sequence
<220> FEATURE:
<223> OTHER INFORMATION: Synthetic peptide

<400> SEQUENCE: 295

Lys Lys Ser Asp Thr Phe Phe Val Lys Leu Ser Leu Phe Thr Glu Arg
  1               5                  10                  15

<210> SEQ ID NO 296
<211> LENGTH: 16
<212> TYPE: PRT
<213> ORGANISM: Artificial Sequence
<220> FEATURE:
<223> OTHER INFORMATION: Synthetic peptide

<400> SEQUENCE: 296

Lys Lys Thr Asp Thr Phe Phe Val Lys Leu Ser Leu Phe Thr Glu Arg
  1               5                  10                  15

<210> SEQ ID NO 297
<211> LENGTH: 16
<212> TYPE: PRT
<213> ORGANISM: Artificial Sequence
<220> FEATURE:
<223> OTHER INFORMATION: Synthetic peptide

<400> SEQUENCE: 297

Lys Lys Val Asp Thr Phe Phe Val Lys Leu Ser Leu Phe Thr Glu Arg
  1               5                  10                  15

<210> SEQ ID NO 298
<211> LENGTH: 16
<212> TYPE: PRT
<213> ORGANISM: Artificial Sequence
<220> FEATURE:
<223> OTHER INFORMATION: Synthetic peptide

<400> SEQUENCE: 298

Lys Lys Leu Ala Thr Phe Phe Val Lys Leu Ser Leu Phe Thr Glu Arg
  1               5                  10                  15

<210> SEQ ID NO 299
<211> LENGTH: 16
<212> TYPE: PRT
<213> ORGANISM: Artificial Sequence
<220> FEATURE:
<223> OTHER INFORMATION: Synthetic peptide

<400> SEQUENCE: 299

Lys Lys Leu Glu Thr Phe Phe Val Lys Leu Ser Leu Phe Thr Glu Arg
  1               5                  10                  15

<210> SEQ ID NO 300
<211> LENGTH: 16
<212> TYPE: PRT
<213> ORGANISM: Artificial Sequence
<220> FEATURE:
<223> OTHER INFORMATION: Synthetic peptide

<400> SEQUENCE: 300
```

```
Lys Lys Leu Ile Thr Phe Phe Val Lys Leu Ser Leu Phe Thr Glu Arg
1               5                   10                  15
```

<210> SEQ ID NO 301
<211> LENGTH: 16
<212> TYPE: PRT
<213> ORGANISM: Artificial Sequence
<220> FEATURE:
<223> OTHER INFORMATION: Synthetic peptide

<400> SEQUENCE: 301

```
Lys Lys Leu Val Thr Phe Phe Val Lys Leu Ser Leu Phe Thr Glu Arg
1               5                   10                  15
```

<210> SEQ ID NO 302
<211> LENGTH: 16
<212> TYPE: PRT
<213> ORGANISM: Artificial Sequence
<220> FEATURE:
<223> OTHER INFORMATION: Synthetic peptide

<400> SEQUENCE: 302

```
Lys Lys Leu Trp Thr Phe Phe Val Lys Leu Ser Leu Phe Thr Glu Arg
1               5                   10                  15
```

<210> SEQ ID NO 303
<211> LENGTH: 16
<212> TYPE: PRT
<213> ORGANISM: Artificial Sequence
<220> FEATURE:
<223> OTHER INFORMATION: Synthetic peptide

<400> SEQUENCE: 303

```
Lys Lys Leu Tyr Thr Phe Phe Val Lys Leu Ser Leu Phe Thr Glu Arg
1               5                   10                  15
```

<210> SEQ ID NO 304
<211> LENGTH: 16
<212> TYPE: PRT
<213> ORGANISM: Artificial Sequence
<220> FEATURE:
<223> OTHER INFORMATION: Synthetic peptide

<400> SEQUENCE: 304

```
Lys Lys Leu Asp Cys Phe Phe Val Lys Leu Ser Leu Phe Thr Glu Arg
1               5                   10                  15
```

<210> SEQ ID NO 305
<211> LENGTH: 16
<212> TYPE: PRT
<213> ORGANISM: Artificial Sequence
<220> FEATURE:
<223> OTHER INFORMATION: Synthetic peptide

<400> SEQUENCE: 305

```
Lys Lys Leu Asp Met Phe Phe Val Lys Leu Ser Leu Phe Thr Glu Arg
1               5                   10                  15
```

<210> SEQ ID NO 306
<211> LENGTH: 16
<212> TYPE: PRT
<213> ORGANISM: Artificial Sequence
<220> FEATURE:
<223> OTHER INFORMATION: Synthetic peptide

<400> SEQUENCE: 306

```
Lys Lys Leu Asp Asn Phe Phe Val Lys Leu Ser Leu Phe Thr Glu Arg
```

```
1               5                   10                  15
```

<210> SEQ ID NO 307
<211> LENGTH: 16
<212> TYPE: PRT
<213> ORGANISM: Artificial Sequence
<220> FEATURE:
<223> OTHER INFORMATION: Synthetic peptide

<400> SEQUENCE: 307

```
Lys Lys Leu Asp Pro Phe Phe Val Lys Leu Ser Leu Phe Thr Glu Arg
 1               5                   10                  15
```

<210> SEQ ID NO 308
<211> LENGTH: 16
<212> TYPE: PRT
<213> ORGANISM: Artificial Sequence
<220> FEATURE:
<223> OTHER INFORMATION: Synthetic peptide

<400> SEQUENCE: 308

```
Lys Lys Leu Asp Gln Phe Phe Val Lys Leu Ser Leu Phe Thr Glu Arg
 1               5                   10                  15
```

<210> SEQ ID NO 309
<211> LENGTH: 16
<212> TYPE: PRT
<213> ORGANISM: Artificial Sequence
<220> FEATURE:
<223> OTHER INFORMATION: Synthetic peptide

<400> SEQUENCE: 309

```
Lys Lys Leu Asp Arg Phe Phe Val Lys Leu Ser Leu Phe Thr Glu Arg
 1               5                   10                  15
```

<210> SEQ ID NO 310
<211> LENGTH: 16
<212> TYPE: PRT
<213> ORGANISM: Artificial Sequence
<220> FEATURE:
<223> OTHER INFORMATION: Synthetic peptide

<400> SEQUENCE: 310

```
Lys Lys Leu Asp Ser Phe Phe Val Lys Leu Ser Leu Phe Thr Glu Arg
 1               5                   10                  15
```

<210> SEQ ID NO 311
<211> LENGTH: 16
<212> TYPE: PRT
<213> ORGANISM: Artificial Sequence
<220> FEATURE:
<223> OTHER INFORMATION: Synthetic peptide

<400> SEQUENCE: 311

```
Lys Lys Leu Asp Trp Phe Phe Val Lys Leu Ser Leu Phe Thr Glu Arg
 1               5                   10                  15
```

<210> SEQ ID NO 312
<211> LENGTH: 16
<212> TYPE: PRT
<213> ORGANISM: Artificial Sequence
<220> FEATURE:
<223> OTHER INFORMATION: Synthetic peptide

<400> SEQUENCE: 312

```
Lys Lys Leu Asp Tyr Phe Phe Val Lys Leu Ser Leu Phe Thr Glu Arg
 1               5                   10                  15
```

<210> SEQ ID NO 313
<211> LENGTH: 16
<212> TYPE: PRT
<213> ORGANISM: Artificial Sequence
<220> FEATURE:
<223> OTHER INFORMATION: Synthetic peptide

<400> SEQUENCE: 313

Lys Lys Leu Asp Thr Ala Phe Val Lys Leu Ser Leu Phe Thr Glu Arg
 1               5                  10                  15

<210> SEQ ID NO 314
<211> LENGTH: 16
<212> TYPE: PRT
<213> ORGANISM: Artificial Sequence
<220> FEATURE:
<223> OTHER INFORMATION: Synthetic peptide

<400> SEQUENCE: 314

Lys Lys Leu Asp Thr Ile Phe Val Lys Leu Ser Leu Phe Thr Glu Arg
 1               5                  10                  15

<210> SEQ ID NO 315
<211> LENGTH: 16
<212> TYPE: PRT
<213> ORGANISM: Artificial Sequence
<220> FEATURE:
<223> OTHER INFORMATION: Synthetic peptide

<400> SEQUENCE: 315

Lys Lys Leu Asp Thr Met Phe Val Lys Leu Ser Leu Phe Thr Glu Arg
 1               5                  10                  15

<210> SEQ ID NO 316
<211> LENGTH: 16
<212> TYPE: PRT
<213> ORGANISM: Artificial Sequence
<220> FEATURE:
<223> OTHER INFORMATION: Synthetic peptide

<400> SEQUENCE: 316

Lys Lys Leu Asp Thr Asn Phe Val Lys Leu Ser Leu Phe Thr Glu Arg
 1               5                  10                  15

<210> SEQ ID NO 317
<211> LENGTH: 16
<212> TYPE: PRT
<213> ORGANISM: Artificial Sequence
<220> FEATURE:
<223> OTHER INFORMATION: Synthetic peptide

<400> SEQUENCE: 317

Lys Lys Leu Asp Thr Pro Phe Val Lys Leu Ser Leu Phe Thr Glu Arg
 1               5                  10                  15

<210> SEQ ID NO 318
<211> LENGTH: 16
<212> TYPE: PRT
<213> ORGANISM: Artificial Sequence
<220> FEATURE:
<223> OTHER INFORMATION: Synthetic peptide

<400> SEQUENCE: 318

Lys Lys Leu Asp Thr Thr Phe Val Lys Leu Ser Leu Phe Thr Glu Arg
 1               5                  10                  15

<210> SEQ ID NO 319
<211> LENGTH: 16
<212> TYPE: PRT
<213> ORGANISM: Artificial Sequence
<220> FEATURE:
<223> OTHER INFORMATION: Synthetic peptide

<400> SEQUENCE: 319

Lys Lys Leu Asp Thr Val Phe Val Lys Leu Ser Leu Phe Thr Glu Arg
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Synthetic peptide

<400> SEQUENCE: 320

Lys Lys Leu Asp Thr Phe Leu Val Lys Leu Ser Leu Phe Thr Glu Arg
1               5                   10                  15

<210> SEQ ID NO 321
<211> LENGTH: 16
<212> TYPE: PRT
<213> ORGANISM: Artificial Sequence
<220> FEATURE:
<223> OTHER INFORMATION: Synthetic peptide

<400> SEQUENCE: 321

Lys Lys Leu Asp Thr Phe Met Val Lys Leu Ser Leu Phe Thr Glu Arg
1               5                   10                  15

<210> SEQ ID NO 322
<211> LENGTH: 16
<212> TYPE: PRT
<213> ORGANISM: Artificial Sequence
<220> FEATURE:
<223> OTHER INFORMATION: Synthetic peptide

<400> SEQUENCE: 322

Lys Lys Leu Asp Thr Phe Gln Val Lys Leu Ser Leu Phe Thr Glu Arg
1               5                   10                  15

<210> SEQ ID NO 323
<211> LENGTH: 16
<212> TYPE: PRT
<213> ORGANISM: Artificial Sequence
<220> FEATURE:
<223> OTHER INFORMATION: Synthetic peptide

<400> SEQUENCE: 323

Lys Lys Leu Asp Thr Phe Ser Val Lys Leu Ser Leu Phe Thr Glu Arg
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Synthetic peptide

<400> SEQUENCE: 324

Lys Lys Leu Asp Thr Phe Thr Val Lys Leu Ser Leu Phe Thr Glu Arg
1               5                   10                  15

```
<210> SEQ ID NO 325
<211> LENGTH: 16
<212> TYPE: PRT
<213> ORGANISM: Artificial Sequence
<220> FEATURE:
<223> OTHER INFORMATION: Synthetic peptide

<400> SEQUENCE: 325

Lys Lys Leu Asp Thr Phe Val Val Lys Leu Ser Leu Phe Thr Glu Arg
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Synthetic peptide

<400> SEQUENCE: 326

Lys Lys Leu Asp Thr Phe Phe Phe Lys Leu Ser Leu Phe Thr Glu Arg
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Synthetic peptide

<400> SEQUENCE: 327

Lys Lys Leu Asp Thr Phe Phe Gly Lys Leu Ser Leu Phe Thr Glu Arg
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Synthetic peptide

<400> SEQUENCE: 328

Lys Lys Leu Asp Thr Phe Phe Leu Lys Leu Ser Leu Phe Thr Glu Arg
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Synthetic peptide

<400> SEQUENCE: 329

Lys Lys Leu Asp Thr Phe Phe Pro Lys Leu Ser Leu Phe Thr Glu Arg
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Synthetic peptide

<400> SEQUENCE: 330

Lys Lys Leu Asp Thr Phe Phe Arg Lys Leu Ser Leu Phe Thr Glu Arg
1               5                   10                  15

<210> SEQ ID NO 331
```

```
<211> LENGTH: 16
<212> TYPE: PRT
<213> ORGANISM: Artificial Sequence
<220> FEATURE:
<223> OTHER INFORMATION: Synthetic peptide

<400> SEQUENCE: 331

Lys Lys Leu Asp Thr Phe Phe Val Arg Leu Ser Leu Phe Thr Glu Arg
 1               5                  10                  15

<210> SEQ ID NO 332
<211> LENGTH: 16
<212> TYPE: PRT
<213> ORGANISM: Artificial Sequence
<220> FEATURE:
<223> OTHER INFORMATION: Synthetic peptide

<400> SEQUENCE: 332

Lys Lys Leu Asp Thr Phe Phe Val Lys Ala Ser Leu Phe Thr Glu Arg
 1               5                  10                  15

<210> SEQ ID NO 333
<211> LENGTH: 16
<212> TYPE: PRT
<213> ORGANISM: Artificial Sequence
<220> FEATURE:
<223> OTHER INFORMATION: Synthetic peptide

<400> SEQUENCE: 333

Lys Lys Leu Asp Thr Phe Phe Val Lys Phe Ser Leu Phe Thr Glu Arg
 1               5                  10                  15

<210> SEQ ID NO 334
<211> LENGTH: 16
<212> TYPE: PRT
<213> ORGANISM: Artificial Sequence
<220> FEATURE:
<223> OTHER INFORMATION: Synthetic peptide

<400> SEQUENCE: 334

Lys Lys Leu Asp Thr Phe Phe Val Lys Gly Ser Leu Phe Thr Glu Arg
 1               5                  10                  15

<210> SEQ ID NO 335
<211> LENGTH: 16
<212> TYPE: PRT
<213> ORGANISM: Artificial Sequence
<220> FEATURE:
<223> OTHER INFORMATION: Synthetic peptide

<400> SEQUENCE: 335

Lys Lys Leu Asp Thr Phe Phe Val Lys Ile Ser Leu Phe Thr Glu Arg
 1               5                  10                  15

<210> SEQ ID NO 336
<211> LENGTH: 16
<212> TYPE: PRT
<213> ORGANISM: Artificial Sequence
<220> FEATURE:
<223> OTHER INFORMATION: Synthetic peptide

<400> SEQUENCE: 336

Lys Lys Leu Asp Thr Phe Phe Val Lys Met Ser Leu Phe Thr Glu Arg
 1               5                  10                  15

<210> SEQ ID NO 337
<211> LENGTH: 16
```

<212> TYPE: PRT
<213> ORGANISM: Artificial Sequence
<220> FEATURE:
<223> OTHER INFORMATION: Synthetic peptide

<400> SEQUENCE: 337

Lys Lys Leu Asp Thr Phe Phe Val Lys Asn Ser Leu Phe Thr Glu Arg
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Synthetic peptide

<400> SEQUENCE: 338

Lys Lys Leu Asp Thr Phe Phe Val Lys Pro Ser Leu Phe Thr Glu Arg
1               5                   10                  15

<210> SEQ ID NO 339
<211> LENGTH: 16
<212> TYPE: PRT
<213> ORGANISM: Artificial Sequence
<220> FEATURE:
<223> OTHER INFORMATION: Synthetic peptide

<400> SEQUENCE: 339

Lys Lys Leu Asp Thr Phe Phe Val Lys Gln Ser Leu Phe Thr Glu Arg
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Synthetic peptide

<400> SEQUENCE: 340

Lys Lys Leu Asp Thr Phe Phe Val Lys Arg Ser Leu Phe Thr Glu Arg
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Synthetic peptide

<400> SEQUENCE: 341

Lys Lys Leu Asp Thr Phe Phe Val Lys Ser Ser Leu Phe Thr Glu Arg
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Synthetic peptide

<400> SEQUENCE: 342

Lys Lys Leu Asp Thr Phe Phe Val Lys Thr Ser Leu Phe Thr Glu Arg
1               5                   10                  15

<210> SEQ ID NO 343
<211> LENGTH: 16
<212> TYPE: PRT

```
<213> ORGANISM: Artificial Sequence
<220> FEATURE:
<223> OTHER INFORMATION: Synthetic peptide

<400> SEQUENCE: 343

Lys Lys Leu Asp Thr Phe Phe Val Lys Val Ser Leu Phe Thr Glu Arg
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Synthetic peptide

<400> SEQUENCE: 344

Lys Lys Leu Asp Thr Phe Phe Val Lys Tyr Ser Leu Phe Thr Glu Arg
1               5                   10                  15

<210> SEQ ID NO 345
<211> LENGTH: 16
<212> TYPE: PRT
<213> ORGANISM: Artificial Sequence
<220> FEATURE:
<223> OTHER INFORMATION: Synthetic peptide

<400> SEQUENCE: 345

Lys Lys Leu Asp Thr Phe Phe Val Lys Leu His Leu Phe Thr Glu Arg
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Synthetic peptide

<400> SEQUENCE: 346

Lys Lys Leu Asp Thr Phe Phe Val Lys Leu Met Leu Phe Thr Glu Arg
1               5                   10                  15

<210> SEQ ID NO 347
<211> LENGTH: 16
<212> TYPE: PRT
<213> ORGANISM: Artificial Sequence
<220> FEATURE:
<223> OTHER INFORMATION: Synthetic peptide

<400> SEQUENCE: 347

Lys Lys Leu Asp Thr Phe Phe Val Lys Leu Asn Leu Phe Thr Glu Arg
1               5                   10                  15

<210> SEQ ID NO 348
<211> LENGTH: 16
<212> TYPE: PRT
<213> ORGANISM: Artificial Sequence
<220> FEATURE:
<223> OTHER INFORMATION: Synthetic peptide

<400> SEQUENCE: 348

Lys Lys Leu Asp Thr Phe Phe Val Lys Leu Gln Leu Phe Thr Glu Arg
1               5                   10                  15

<210> SEQ ID NO 349
<211> LENGTH: 16
<212> TYPE: PRT
<213> ORGANISM: Artificial Sequence
```

```
<220> FEATURE:
<223> OTHER INFORMATION: Synthetic peptide

<400> SEQUENCE: 349

Lys Lys Leu Asp Thr Phe Phe Val Lys Leu Thr Leu Phe Thr Glu Arg
 1               5                  10                  15

<210> SEQ ID NO 350
<211> LENGTH: 16
<212> TYPE: PRT
<213> ORGANISM: Artificial Sequence
<220> FEATURE:
<223> OTHER INFORMATION: Synthetic peptide

<400> SEQUENCE: 350

Lys Lys Leu Asp Thr Phe Phe Val Lys Leu Ser Ala Phe Thr Glu Arg
 1               5                  10                  15

<210> SEQ ID NO 351
<211> LENGTH: 16
<212> TYPE: PRT
<213> ORGANISM: Artificial Sequence
<220> FEATURE:
<223> OTHER INFORMATION: Synthetic peptide

<400> SEQUENCE: 351

Lys Lys Leu Asp Thr Phe Phe Val Lys Leu Ser His Phe Thr Glu Arg
 1               5                  10                  15

<210> SEQ ID NO 352
<211> LENGTH: 16
<212> TYPE: PRT
<213> ORGANISM: Artificial Sequence
<220> FEATURE:
<223> OTHER INFORMATION: Synthetic peptide

<400> SEQUENCE: 352

Lys Lys Leu Asp Thr Phe Phe Val Lys Leu Ser Ile Phe Thr Glu Arg
 1               5                  10                  15

<210> SEQ ID NO 353
<211> LENGTH: 16
<212> TYPE: PRT
<213> ORGANISM: Artificial Sequence
<220> FEATURE:
<223> OTHER INFORMATION: Synthetic peptide

<400> SEQUENCE: 353

Lys Lys Leu Asp Thr Phe Phe Val Lys Leu Ser Met Phe Thr Glu Arg
 1               5                  10                  15

<210> SEQ ID NO 354
<211> LENGTH: 16
<212> TYPE: PRT
<213> ORGANISM: Artificial Sequence
<220> FEATURE:
<223> OTHER INFORMATION: Synthetic peptide

<400> SEQUENCE: 354

Lys Lys Leu Asp Thr Phe Phe Val Lys Leu Ser Asn Phe Thr Glu Arg
 1               5                  10                  15

<210> SEQ ID NO 355
<211> LENGTH: 16
<212> TYPE: PRT
<213> ORGANISM: Artificial Sequence
<220> FEATURE:
```

<223> OTHER INFORMATION: Synthetic peptide

<400> SEQUENCE: 355

Lys Lys Leu Asp Thr Phe Phe Val Lys Leu Ser Gln Phe Thr Glu Arg
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Synthetic peptide

<400> SEQUENCE: 356

Lys Lys Leu Asp Thr Phe Phe Val Lys Leu Ser Arg Phe Thr Glu Arg
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Synthetic peptide

<400> SEQUENCE: 357

Lys Lys Leu Asp Thr Phe Phe Val Lys Leu Ser Ser Phe Thr Glu Arg
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Synthetic peptide

<400> SEQUENCE: 358

Lys Lys Leu Asp Thr Phe Phe Val Lys Leu Ser Thr Phe Thr Glu Arg
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Synthetic peptide

<400> SEQUENCE: 359

Lys Lys Leu Asp Thr Phe Phe Val Lys Leu Ser Val Phe Thr Glu Arg
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Synthetic peptide

<400> SEQUENCE: 360

Lys Lys Leu Asp Thr Phe Phe Val Lys Leu Ser Trp Phe Thr Glu Arg
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Synthetic peptide

<400> SEQUENCE: 361

Lys Lys Leu Asp Thr Phe Phe Val Lys Leu Ser Leu Ala Thr Glu Arg
1               5                   10                  15

<210> SEQ ID NO 362
<211> LENGTH: 16
<212> TYPE: PRT
<213> ORGANISM: Artificial Sequence
<220> FEATURE:
<223> OTHER INFORMATION: Synthetic peptide

<400> SEQUENCE: 362

Lys Lys Leu Asp Thr Phe Phe Val Lys Leu Ser Leu Cys Thr Glu Arg
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Synthetic peptide

<400> SEQUENCE: 363

Lys Lys Leu Asp Thr Phe Phe Val Lys Leu Ser Leu Gly Thr Glu Arg
1               5                   10                  15

<210> SEQ ID NO 364
<211> LENGTH: 16
<212> TYPE: PRT
<213> ORGANISM: Artificial Sequence
<220> FEATURE:
<223> OTHER INFORMATION: Synthetic peptide

<400> SEQUENCE: 364

Lys Lys Leu Asp Thr Phe Phe Val Lys Leu Ser Leu His Thr Glu Arg
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Synthetic peptide

<400> SEQUENCE: 365

Lys Lys Leu Asp Thr Phe Phe Val Lys Leu Ser Leu Ile Thr Glu Arg
1               5                   10                  15

<210> SEQ ID NO 366
<211> LENGTH: 16
<212> TYPE: PRT
<213> ORGANISM: Artificial Sequence
<220> FEATURE:
<223> OTHER INFORMATION: Synthetic peptide

<400> SEQUENCE: 366

Lys Lys Leu Asp Thr Phe Phe Val Lys Leu Ser Leu Leu Thr Glu Arg
1               5                   10                  15

<210> SEQ ID NO 367
<211> LENGTH: 16
<212> TYPE: PRT
<213> ORGANISM: Artificial Sequence
<220> FEATURE:
<223> OTHER INFORMATION: Synthetic peptide

```
<400> SEQUENCE: 367

Lys Lys Leu Asp Thr Phe Phe Val Lys Leu Ser Leu Met Thr Glu Arg
1               5                   10                  15

<210> SEQ ID NO 368
<211> LENGTH: 16
<212> TYPE: PRT
<213> ORGANISM: Artificial Sequence
<220> FEATURE:
<223> OTHER INFORMATION: Synthetic peptide

<400> SEQUENCE: 368

Lys Lys Leu Asp Thr Phe Phe Val Lys Leu Ser Leu Asn Thr Glu Arg
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Synthetic peptide

<400> SEQUENCE: 369

Lys Lys Leu Asp Thr Phe Phe Val Lys Leu Ser Leu Pro Thr Glu Arg
1               5                   10                  15

<210> SEQ ID NO 370
<211> LENGTH: 16
<212> TYPE: PRT
<213> ORGANISM: Artificial Sequence
<220> FEATURE:
<223> OTHER INFORMATION: Synthetic peptide

<400> SEQUENCE: 370

Lys Lys Leu Asp Thr Phe Phe Val Lys Leu Ser Leu Gln Thr Glu Arg
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Synthetic peptide

<400> SEQUENCE: 371

Lys Lys Leu Asp Thr Phe Phe Val Lys Leu Ser Leu Arg Thr Glu Arg
1               5                   10                  15

<210> SEQ ID NO 372
<211> LENGTH: 16
<212> TYPE: PRT
<213> ORGANISM: Artificial Sequence
<220> FEATURE:
<223> OTHER INFORMATION: Synthetic peptide

<400> SEQUENCE: 372

Lys Lys Leu Asp Thr Phe Phe Val Lys Leu Ser Leu Ser Thr Glu Arg
1               5                   10                  15

<210> SEQ ID NO 373
<211> LENGTH: 16
<212> TYPE: PRT
<213> ORGANISM: Artificial Sequence
<220> FEATURE:
<223> OTHER INFORMATION: Synthetic peptide

<400> SEQUENCE: 373
```

```
Lys Lys Leu Asp Thr Phe Phe Val Lys Leu Ser Leu Thr Thr Glu Arg
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Synthetic peptide

<400> SEQUENCE: 374

Lys Lys Leu Asp Thr Phe Phe Val Lys Leu Ser Leu Val Thr Glu Arg
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: Synthetic peptide

<400> SEQUENCE: 375

Lys Lys Leu Asp Thr Phe Phe Val Lys Leu Ser Leu Trp Thr Glu Arg
1               5                   10                  15

<210> SEQ ID NO 376
<211> LENGTH: 16
<212> TYPE: PRT
<213> ORGANISM: Artificial Sequence
<220> FEATURE:
<223> OTHER INFORMATION: Synthetic peptide

<400> SEQUENCE: 376

Lys Lys Leu Asp Thr Phe Phe Val Lys Leu Ser Leu Phe Phe Glu Arg
1               5                   10                  15

<210> SEQ ID NO 377
<211> LENGTH: 16
<212> TYPE: PRT
<213> ORGANISM: Artificial Sequence
<220> FEATURE:
<223> OTHER INFORMATION: Synthetic peptide

<400> SEQUENCE: 377

Lys Lys Leu Asp Thr Phe Phe Val Lys Leu Ser Leu Phe Gly Glu Arg
1               5                   10                  15

<210> SEQ ID NO 378
<211> LENGTH: 16
<212> TYPE: PRT
<213> ORGANISM: Artificial Sequence
<220> FEATURE:
<223> OTHER INFORMATION: Synthetic peptide

<400> SEQUENCE: 378

Lys Lys Leu Asp Thr Phe Phe Val Lys Leu Ser Leu Phe His Glu Arg
1               5                   10                  15

<210> SEQ ID NO 379
<211> LENGTH: 16
<212> TYPE: PRT
<213> ORGANISM: Artificial Sequence
<220> FEATURE:
<223> OTHER INFORMATION: Synthetic peptide

<400> SEQUENCE: 379
```

```
Lys Lys Leu Asp Thr Phe Phe Val Lys Leu Ser Leu Phe Ile Glu Arg
1               5                   10                  15
```

<210> SEQ ID NO 380
<211> LENGTH: 16
<212> TYPE: PRT
<213> ORGANISM: Artificial Sequence
<220> FEATURE:
<223> OTHER INFORMATION: Synthetic peptide

<400> SEQUENCE: 380

```
Lys Lys Leu Asp Thr Phe Phe Val Lys Leu Ser Leu Phe Leu Glu Arg
1               5                   10                  15
```

<210> SEQ ID NO 381
<211> LENGTH: 16
<212> TYPE: PRT
<213> ORGANISM: Artificial Sequence
<220> FEATURE:
<223> OTHER INFORMATION: Synthetic peptide

<400> SEQUENCE: 381

```
Lys Lys Leu Asp Thr Phe Phe Val Lys Leu Ser Leu Phe Met Glu Arg
1               5                   10                  15
```

<210> SEQ ID NO 382
<211> LENGTH: 16
<212> TYPE: PRT
<213> ORGANISM: Artificial Sequence
<220> FEATURE:
<223> OTHER INFORMATION: Synthetic peptide

<400> SEQUENCE: 382

```
Lys Lys Leu Asp Thr Phe Phe Val Lys Leu Ser Leu Phe Asn Glu Arg
1               5                   10                  15
```

<210> SEQ ID NO 383
<211> LENGTH: 16
<212> TYPE: PRT
<213> ORGANISM: Artificial Sequence
<220> FEATURE:
<223> OTHER INFORMATION: Synthetic peptide

<400> SEQUENCE: 383

```
Lys Lys Leu Asp Thr Phe Phe Val Lys Leu Ser Leu Phe Pro Glu Arg
1               5                   10                  15
```

<210> SEQ ID NO 384
<211> LENGTH: 16
<212> TYPE: PRT
<213> ORGANISM: Artificial Sequence
<220> FEATURE:
<223> OTHER INFORMATION: Synthetic peptide

<400> SEQUENCE: 384

```
Lys Lys Leu Asp Thr Phe Phe Val Lys Leu Ser Leu Phe Ser Glu Arg
1               5                   10                  15
```

<210> SEQ ID NO 385
<211> LENGTH: 16
<212> TYPE: PRT
<213> ORGANISM: Artificial Sequence
<220> FEATURE:
<223> OTHER INFORMATION: Synthetic peptide

<400> SEQUENCE: 385

```
Lys Lys Leu Asp Thr Phe Phe Val Lys Leu Ser Leu Phe Val Glu Arg
```

```
1               5                   10                  15
```

<210> SEQ ID NO 386
<211> LENGTH: 16
<212> TYPE: PRT
<213> ORGANISM: Artificial Sequence
<220> FEATURE:
<223> OTHER INFORMATION: Synthetic peptide

<400> SEQUENCE: 386

```
Lys Lys Leu Asp Thr Phe Phe Val Lys Leu Ser Leu Phe Trp Glu Arg
 1               5                   10                  15
```

<210> SEQ ID NO 387
<211> LENGTH: 16
<212> TYPE: PRT
<213> ORGANISM: Artificial Sequence
<220> FEATURE:
<223> OTHER INFORMATION: Synthetic peptide

<400> SEQUENCE: 387

```
Lys Lys Leu Asp Thr Phe Phe Val Lys Leu Ser Leu Phe Thr Asp Arg
 1               5                   10                  15
```

<210> SEQ ID NO 388
<211> LENGTH: 16
<212> TYPE: PRT
<213> ORGANISM: Artificial Sequence
<220> FEATURE:
<223> OTHER INFORMATION: Synthetic peptide

<400> SEQUENCE: 388

```
Lys Lys Leu Asp Thr Phe Phe Val Lys Leu Ser Leu Phe Thr Glu Phe
 1               5                   10                  15
```

<210> SEQ ID NO 389
<211> LENGTH: 16
<212> TYPE: PRT
<213> ORGANISM: Artificial Sequence
<220> FEATURE:
<223> OTHER INFORMATION: Synthetic peptide

<400> SEQUENCE: 389

```
Lys Lys Leu Asp Thr Phe Phe Val Lys Leu Ser Leu Phe Thr Glu Lys
 1               5                   10                  15
```

<210> SEQ ID NO 390
<211> LENGTH: 16
<212> TYPE: PRT
<213> ORGANISM: Artificial Sequence
<220> FEATURE:
<223> OTHER INFORMATION: Synthetic peptide

<400> SEQUENCE: 390

```
Lys Lys Leu Asp Thr Phe Phe Val Lys Leu Ser Leu Phe Thr Glu Asn
 1               5                   10                  15
```

<210> SEQ ID NO 391
<211> LENGTH: 16
<212> TYPE: PRT
<213> ORGANISM: Artificial Sequence
<220> FEATURE:
<223> OTHER INFORMATION: Synthetic peptide

<400> SEQUENCE: 391

```
Lys Lys Leu Asp Thr Phe Phe Val Lys Leu Ser Leu Phe Thr Glu Arg
 1               5                   10                  15
```

<210> SEQ ID NO 392
<211> LENGTH: 16
<212> TYPE: PRT
<213> ORGANISM: Artificial Sequence
<220> FEATURE:
<223> OTHER INFORMATION: Synthetic peptide

<400> SEQUENCE: 392

Lys Lys Leu Asp Thr Phe Phe Val Lys Leu Ser Leu Phe Thr Glu Thr
 1               5                  10                  15

<210> SEQ ID NO 393
<211> LENGTH: 16
<212> TYPE: PRT
<213> ORGANISM: Artificial Sequence
<220> FEATURE:
<223> OTHER INFORMATION: Synthetic peptide

<400> SEQUENCE: 393

Lys Lys Leu Asp Thr Phe Phe Val Lys Leu Ser Leu Phe Thr Glu Tyr
 1               5                  10                  15

<210> SEQ ID NO 394
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = K, A, D, E, G, H, I, L, M, N, P, Q, R, T,
     V, or absent
<220> FEATURE:
<221> NAME/KEY: VARIANT
<222> LOCATION: 3
<223> OTHER INFORMATION: Xaa = L, A, C, D, E, F, G, H, I, K, M, N, Q, R,
     S, T, V, or absent
<220> FEATURE:
<221> NAME/KEY: VARIANT
<222> LOCATION: 4
<223> OTHER INFORMATION: Xaa = D, A, E, I, V, W, Y, or absent
<220> FEATURE:
<221> NAME/KEY: VARIANT
<222> LOCATION: 5
<223> OTHER INFORMATION: Xaa = T, C, M, N, P, Q, R, S, W, Y, or absent
<220> FEATURE:
<221> NAME/KEY: VARIANT
<222> LOCATION: 6
<223> OTHER INFORMATION: Xaa = F, A, I, M, N, P, T, V, or absent
<220> FEATURE:
<221> NAME/KEY: VARIANT
<222> LOCATION: (7)...(7)
<223> OTHER INFORMATION: Xaa = F, L, M, Q, S, T, V, or absent
<220> FEATURE:
<221> NAME/KEY: VARIANT
<222> LOCATION: (8)...(8)
<223> OTHER INFORMATION: Xaa = V, F, G, L, P, R, or absent
<220> FEATURE:
<221> NAME/KEY: VARIANT
<222> LOCATION: (10)...(10)
<223> OTHER INFORMATION: Xaa = L,A,F,G,I,M,N,P,Q,R,S,T,V,Y, or absent
<220> FEATURE:
<221> NAME/KEY: VARIANT
<222> LOCATION: (11)...(11)
<223> OTHER INFORMATION: Xaa = S, H, M, N, Q, T, or absent
<220> FEATURE:
<221> NAME/KEY: VARIANT
<222> LOCATION: (12)...(12)
<223> OTHER INFORMATION: Xaa = L, A, H, I, M, N, Q, R, S, T, V, W, or
     absent
<220> FEATURE:
<221> NAME/KEY: VARIANT

```
<222> LOCATION: (13)...(13)
<223> OTHER INFORMATION: XAa = F, A, C, G, H, I, L, M, N, P, Q, R, S, T,
      V, W, or absent
<220> FEATURE:
<221> NAME/KEY: VARIANT
<222> LOCATION: (14)...(14)
<223> OTHER INFORMATION: Xaa = T, F, G, H, I, L, M, N, P, S, V, W or
      absent
<220> FEATURE:
<221> NAME/KEY: VARIANT
<222> LOCATION: (16)...(16)
<223> OTHER INFORMATION: Xaa = R, F, K, N, R, T, Y or absent

<400> SEQUENCE: 394

Xaa Lys Xaa Xaa Xaa Xaa Xaa Xaa Lys Xaa Xaa Xaa Xaa Xaa Glu Xaa
 1               5                  10                  15

<210> SEQ ID NO 395
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = K, A, D, E, G, H, I, L, M, N, P, Q, R, T,
      V, or absent
<220> FEATURE:
<221> NAME/KEY: VARIANT
<222> LOCATION: 3
<223> OTHER INFORMATION: Xaa = LDTFFV, GDTFFV, EDTFFV, LDQFFV, LDTAFV,
      LDTVFV, LDTFMV, LDTFSV, LDTFVV, LDTFTV, LDTFLV,
      LDGFFV, LDTFGV, ADTFFV, CDTFFV, DDTFFV,
      FDTFFV, HDTFFV, IDTFFV, KDTFFV, MDTFFV, NDTFFV,
<220> FEATURE:
<221> NAME/KEY: VARIANT
<222> LOCATION: 3
<223> OTHER INFORMATION: Xaa = QDTFFV, RDTFFV, SDTFFV, TDTFFV, VDTFFV,
      LATFFV, LETFFV, LITFFV, LVTFFV, LWTFFV, LYTFFV,
      LDCFFV, LDMFFV, LDNFFV, LDPFFV, LDRFFV, LDSFFV,
      LDWFFV, LDYFFV, LDTIFV, LDTMFV, LDTNFV, LDTPFV,
<220> FEATURE:
<221> NAME/KEY: VARIANT
<222> LOCATION: 3
<223> OTHER INFORMATION: Xaa = LDTTFV, LDTFQV, LDTFFF, LDTFFG, LDTFFL,
      LDTFFP, LDTFFR, LDTFIV, LDTSFV, LDTFAV, LDTFCV,
      LDTQFV, LDTLFV, LTTFFV, LDTFFI, LDHFFV, LMTFFV,
      LDTFEV, LDTFWV, LFTFFV, LDVFFV, LDTFRV, LDTFHV,
<220> FEATURE:
<221> NAME/KEY: VARIANT
<222> LOCATION: 3
<223> OTHER INFORMATION: Xaa = LDTYFV, LPTFFV, PDTFFV, LDTFPV, LDTFNV,
      LDTWFV, LDTGFV, LDAFFV, LQTFFV, LCTFFV, LSTFFV,
      YDTFFV, LDEFFV, WDTFFV, LDTKFV, LDTCFV, LDTFYV,
      LDTHFV, LHTFFV, LRTFFV, LDLFFV, LDTRFV, LLTFFV,
<220> FEATURE:
<221> NAME/KEY: VARIANT
<222> LOCATION: (3)...(3)
<223> OTHER INFORMATION: Xaa = LDTFDV, LDTFFA, LDTFFT, LNTFFV, LDDFFV,
      LDIFFV, LDFFFV, LKTFFV, LDTFFQ, LGTFFV, LDTFFC,
      LDKFFV, LDTFKV, LDTEFV, LDTFFW, LDTFFM, LDTFFS,
      LDTFFH, LDTFFY, LDTFFN, LDTDFV, LDTFFE, LDTFFD,
<220> FEATURE:
<221> NAME/KEY: VARIANT
<222> LOCATION: (3)...(3)
<223> OTHER INFORMATION: Xaa = LTFFV, LDTFF, TFFV, LDF, LDTE, FFV, LDV,
      LV, L, or absent
<220> FEATURE:
<221> NAME/KEY: VARIANT
<222> LOCATION: (5)...(5)
<223> OTHER INFORMATION: Xaa = LSLFT, VSLFT, LQLFT, LMLFT, LTLFT, LHLFT,
      LSQFT, LSVFT, LSMFT, LSLMT, LSLQT, LSLHT, LSLNT,
      LSLPT, LSLST, LSLGT, LSLAT, LSLRT, LSLFN, LSLFP,
      LSLFR, LGLFT, ASLFT, FSLFT, GSLFT, ISLFT, MSLFT,
<220> FEATURE:
<221> NAME/KEY: VARIANT
```

```
<222> LOCATION: (5)...(5)
<223> OTHER INFORMATION: Xaa = NSLFT, PSLFT, QSLFT, RSLFT, SSLFT, TSLFT,
      YSLFT, LNLFT, LSAFT, LSHFT, LSIFT, LSNFT, LSRFT,
      LSSFT, LSTFT, LSWFT, LSLCT, LSLIT, LSLLT, LSLTT,
      LSLVT, LSLWT, LSLFF, LSLFG, LSLFH, LSLFI, LSLFL,
<220> FEATURE:
<221> NAME/KEY: VARIANT
<222> LOCATION: (5)...(5)
<223> OTHER INFORMATION: Xaa = LSLFM, LSLFS, LSLFV, LSLFW, LYLFT, LVLFT,
      LSFFT, LSGFT, LSKFT, LSCFT, LCLFT, LRLFT, LPLFT,
      LWLFT, LKLFT, LDLFT, LSYFT, LALFT, WSLFT, LSLFA,
      LSLFQ, LSPFT, HSLFT, LSLYT, LILFT, KSLFT, CSLFT,
<220> FEATURE:
<221> NAME/KEY: VARIANT
<222> LOCATION: (5)...(5)
<223> OTHER INFORMATION: Xaa = LSLFY, LSLFK, LSLFC, LFLFT, LELFT, LSLKT,
      LLLFT, LSLFD, LSLDT, LSLFE, DSLFT, LSLET, LSDFT,
      LSEFT, ESLFT, SLFT, LSFT, LFT, LSL, LT, T, or
      absent
<220> FEATURE:
<221> NAME/KEY: VARIANT
<222> LOCATION: (7)...(7)
<223> OTHER INFORMATION: Xaa = R, F, K, N, R, T, Y, or absent

<400> SEQUENCE: 395

Xaa Lys Xaa Lys Xaa Glu Xaa
 1               5

<210> SEQ ID NO 396
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 396

Lys Lys Leu Asp Thr Phe Phe Val Lys Leu Ser Leu Phe Thr Glu Arg
 1               5                  10                  15

<210> SEQ ID NO 397
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 397

Lys Lys Leu Asp Thr Phe Ile Val Lys Leu Ser Leu Phe Thr Glu Arg
 1               5                  10                  15

<210> SEQ ID NO 398
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 398

Lys Lys Leu Asp Thr Phe Phe Val Lys Leu Ser Leu Phe Thr Glu Arg
 1               5                  10                  15

<210> SEQ ID NO 399
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 399

Lys Lys Leu Asp Thr Phe Phe Val Lys Leu Ser Leu Phe Thr Glu Arg
```

```
1               5                   10                  15
```

<210> SEQ ID NO 400
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 400

```
Lys Lys Leu Asp Thr Phe Phe Val Lys Leu Ser Leu Phe Thr Glu Arg
1               5                   10                  15
```

<210> SEQ ID NO 401
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 401

```
Lys Lys Leu Asp Thr Ser Phe Val Lys Leu Ser Leu Phe Thr Glu Arg
1               5                   10                  15
```

<210> SEQ ID NO 402
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 402

```
Lys Asn Leu Asp Thr Phe Phe Val Lys Leu Ser Leu Phe Thr Glu Arg
1               5                   10                  15
```

<210> SEQ ID NO 403
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 403

```
Lys Lys Leu Asp Thr Phe Phe Val Lys Leu Ser Leu Phe Thr Glu Arg
1               5                   10                  15
```

<210> SEQ ID NO 404
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 404

```
Lys Lys Leu Asp Thr Phe Ala Val Lys Leu Ser Leu Phe Thr Glu Arg
1               5                   10                  15
```

<210> SEQ ID NO 405
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 405

```
Lys Pro Leu Asp Thr Phe Phe Val Lys Leu Ser Leu Phe Thr Glu Arg
1               5                   10                  15
```

<210> SEQ ID NO 406
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 406

Lys Lys Leu Asp Thr Phe Phe Val Lys Leu Ser Leu Phe Thr Glu Arg
 1               5                  10                  15

<210> SEQ ID NO 407
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 407

Lys Arg Leu Asp Thr Phe Phe Val Lys Leu Ser Leu Phe Thr Glu Arg
 1               5                  10                  15

<210> SEQ ID NO 408
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 408

Lys Lys Leu Asp Thr Phe Phe Val Lys Leu Ser Leu Phe Thr Glu Arg
 1               5                  10                  15

<210> SEQ ID NO 409
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 409

Lys Lys Leu Asp Thr Phe Cys Val Lys Leu Ser Leu Phe Thr Glu Arg
 1               5                  10                  15

<210> SEQ ID NO 410
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 410

Lys Lys Leu Asp Thr Gln Phe Val Lys Leu Ser Leu Phe Thr Glu Arg
 1               5                  10                  15

<210> SEQ ID NO 411
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 411

Lys Lys Leu Asp Thr Leu Phe Val Lys Leu Ser Leu Phe Thr Glu Arg
 1               5                  10                  15

<210> SEQ ID NO 412
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 412

Lys Gly Leu Asp Thr Phe Phe Val Lys Leu Ser Leu Phe Thr Glu Arg
 1               5                  10                  15

<210> SEQ ID NO 413
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 413

Lys Lys Leu Thr Thr Phe Phe Val Lys Leu Ser Leu Phe Thr Glu Arg
 1               5                  10                  15

<210> SEQ ID NO 414
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 414

Lys Lys Leu Asp Thr Phe Phe Val Lys Leu Ser Leu Phe Thr Glu Arg
 1               5                  10                  15

<210> SEQ ID NO 415
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 415

Lys Lys Leu Asp Thr Phe Phe Val Lys Leu Tyr Leu Phe Thr Glu Arg
 1               5                  10                  15

<210> SEQ ID NO 416
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 416

Lys Lys Leu Asp Thr Phe Phe Ile Lys Leu Ser Leu Phe Thr Glu Arg
 1               5                  10                  15

<210> SEQ ID NO 417
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 417

Lys Met Leu Asp Thr Phe Phe Val Lys Leu Ser Leu Phe Thr Glu Arg
 1               5                  10                  15

```
<210> SEQ ID NO 418
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 418

Lys His Leu Asp Thr Phe Phe Val Lys Leu Ser Leu Phe Thr Glu Arg
 1               5                  10                  15

<210> SEQ ID NO 419
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 419

Lys Lys Leu Asp Thr Phe Phe Val Lys Leu Val Leu Phe Thr Glu Arg
 1               5                  10                  15

<210> SEQ ID NO 420
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 420

Lys Lys Leu Asp His Phe Phe Val Lys Leu Ser Leu Phe Thr Glu Arg
 1               5                  10                  15

<210> SEQ ID NO 421
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 421

Lys Phe Leu Asp Thr Phe Phe Val Lys Leu Ser Leu Phe Thr Glu Arg
 1               5                  10                  15

<210> SEQ ID NO 422
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 422

Lys Lys Leu Asp Thr Phe Phe Val Lys Leu Ser Phe Phe Thr Glu Arg
 1               5                  10                  15

<210> SEQ ID NO 423
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 423

Lys Lys Leu Met Thr Phe Phe Val Lys Leu Ser Leu Phe Thr Glu Arg
 1               5                  10                  15

<210> SEQ ID NO 424
```

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 424

Lys Lys Leu Asp Thr Phe Glu Val Lys Leu Ser Leu Phe Thr Glu Arg
1               5                   10                  15

<210> SEQ ID NO 425
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 425

Lys Lys Leu Asp Thr Phe Trp Val Lys Leu Ser Leu Phe Thr Glu Arg
1               5                   10                  15

<210> SEQ ID NO 426
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 426

Lys Lys Leu Phe Thr Phe Phe Val Lys Leu Ser Leu Phe Thr Glu Arg
1               5                   10                  15

<210> SEQ ID NO 427
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 427

Lys Lys Leu Asp Thr Phe Phe Val Lys Leu Ser Leu Phe Thr Glu Arg
1               5                   10                  15

<210> SEQ ID NO 428
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 428

Lys Lys Leu Asp Thr Phe Phe Val Lys Leu Ser Leu Phe Thr Glu Arg
1               5                   10                  15

<210> SEQ ID NO 429
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 429

Lys Lys Leu Asp Val Phe Phe Val Lys Leu Ser Leu Phe Thr Glu Arg
1               5                   10                  15

<210> SEQ ID NO 430
<211> LENGTH: 16
```

<212> TYPE: PRT
<213> ORGANISM: Artificial Sequence
<220> FEATURE:
<223> OTHER INFORMATION: Synthetic polypeptide

<400> SEQUENCE: 430

Lys Lys Leu Asp Thr Phe Phe Val Lys Leu Ser Leu Phe Thr Glu Arg
1               5                   10                  15

<210> SEQ ID NO 431
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 431

Lys Lys Leu Asp Thr Phe Phe Val Lys Leu Ser Gly Phe Thr Glu Arg
1               5                   10                  15

<210> SEQ ID NO 432
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 432

Lys Lys Leu Asp Thr Phe Arg Val Lys Leu Ser Leu Phe Thr Glu Arg
1               5                   10                  15

<210> SEQ ID NO 433
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 433

Lys Lys Leu Asp Thr Phe His Val Lys Leu Ser Leu Phe Thr Glu Arg
1               5                   10                  15

<210> SEQ ID NO 434
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 434

Lys Lys Leu Asp Thr Tyr Phe Val Lys Leu Ser Leu Phe Thr Glu Arg
1               5                   10                  15

<210> SEQ ID NO 435
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 435

Lys Lys Leu Pro Thr Phe Phe Val Lys Leu Ser Leu Phe Thr Glu Arg
1               5                   10                  15

<210> SEQ ID NO 436
<211> LENGTH: 16
<212> TYPE: PRT

```
<213> ORGANISM: Artificial Sequence
<220> FEATURE:
<223> OTHER INFORMATION: Synthetic polypeptide

<400> SEQUENCE: 436

Lys Lys Pro Asp Thr Phe Phe Val Lys Leu Ser Leu Phe Thr Glu Arg
1               5                   10                  15

<210> SEQ ID NO 437
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 437

Lys Lys Leu Asp Thr Phe Pro Val Lys Leu Ser Leu Phe Thr Glu Arg
1               5                   10                  15

<210> SEQ ID NO 438
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 438

Lys Lys Leu Asp Thr Phe Phe Val Lys Leu Ser Lys Phe Thr Glu Arg
1               5                   10                  15

<210> SEQ ID NO 439
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 439

Lys Lys Leu Asp Thr Phe Phe Val Lys Leu Ser Leu Phe Thr Pro Arg
1               5                   10                  15

<210> SEQ ID NO 440
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 440

Lys Gln Leu Asp Thr Phe Phe Val Lys Leu Ser Leu Phe Thr Glu Arg
1               5                   10                  15

<210> SEQ ID NO 441
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 441

Lys Glu Leu Asp Thr Phe Phe Val Lys Leu Ser Leu Phe Thr Glu Arg
1               5                   10                  15

<210> SEQ ID NO 442
<211> LENGTH: 16
<212> TYPE: PRT
<213> ORGANISM: Artificial Sequence
```

```
<220> FEATURE:
<223> OTHER INFORMATION: Synthetic polypeptide

<400> SEQUENCE: 442

Lys Lys Leu Asp Thr Phe Phe Val Lys Leu Ser Leu Phe Thr Glu Arg
 1               5                  10                  15

<210> SEQ ID NO 443
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 443

Lys Lys Leu Asp Thr Phe Asn Val Lys Leu Ser Leu Phe Thr Glu Arg
 1               5                  10                  15

<210> SEQ ID NO 444
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 444

Lys Lys Leu Asp Thr Trp Phe Val Lys Leu Ser Leu Phe Thr Glu Arg
 1               5                  10                  15

<210> SEQ ID NO 445
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 445

Lys Lys Leu Asp Thr Phe Phe Val Thr Leu Ser Leu Phe Thr Glu Arg
 1               5                  10                  15

<210> SEQ ID NO 446
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 446

Lys Lys Leu Asp Thr Gly Phe Val Lys Leu Ser Leu Phe Thr Glu Arg
 1               5                  10                  15

<210> SEQ ID NO 447
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 447

Lys Lys Leu Asp Ala Phe Phe Val Lys Leu Ser Leu Phe Thr Glu Arg
 1               5                  10                  15

<210> SEQ ID NO 448
<211> LENGTH: 16
<212> TYPE: PRT
<213> ORGANISM: Artificial Sequence
<220> FEATURE:
```

<223> OTHER INFORMATION: Synthetic polypeptide

<400> SEQUENCE: 448

Lys Lys Leu Gln Thr Phe Phe Val Lys Leu Ser Leu Phe Thr Glu Arg
1               5                   10                  15

<210> SEQ ID NO 449
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 449

Lys Lys Leu Cys Thr Phe Phe Val Lys Leu Ser Leu Phe Thr Glu Arg
1               5                   10                  15

<210> SEQ ID NO 450
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 450

Lys Lys Leu Asp Thr Phe Phe Val Lys Leu Ser Leu Phe Thr Gln Arg
1               5                   10                  15

<210> SEQ ID NO 451
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 451

Lys Lys Leu Ser Thr Phe Phe Val Lys Leu Ser Leu Phe Thr Glu Arg
1               5                   10                  15

<210> SEQ ID NO 452
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 452

Lys Lys Tyr Asp Thr Phe Phe Val Lys Leu Ser Leu Phe Thr Glu Arg
1               5                   10                  15

<210> SEQ ID NO 453
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 453

Ser Lys Leu Asp Thr Phe Phe Val Lys Leu Ser Leu Phe Thr Glu Arg
1               5                   10                  15

<210> SEQ ID NO 454
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 454

Lys Leu Leu Asp Thr Phe Phe Val Lys Leu Ser Leu Phe Thr Glu Arg
1               5                   10                  15

<210> SEQ ID NO 455
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 455

Lys Lys Leu Asp Thr Phe Phe Val Lys Leu Ser Cys Phe Thr Glu Arg
1               5                   10                  15

<210> SEQ ID NO 456
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 456

Lys Lys Leu Asp Glu Phe Phe Val Lys Leu Ser Leu Phe Thr Glu Arg
1               5                   10                  15

<210> SEQ ID NO 457
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 457

Lys Lys Leu Asp Thr Phe Phe Val Lys Leu Cys Leu Phe Thr Glu Arg
1               5                   10                  15

<210> SEQ ID NO 458
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 458

Lys Lys Trp Asp Thr Phe Phe Val Lys Leu Ser Leu Phe Thr Glu Arg
1               5                   10                  15

<210> SEQ ID NO 459
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 459

Lys Lys Leu Asp Thr Phe Phe Val Lys Leu Ser Leu Phe Thr Tyr Arg
1               5                   10                  15

<210> SEQ ID NO 460
<211> LENGTH: 16
<212> TYPE: PRT
<213> ORGANISM: Artificial Sequence
<220> FEATURE:
<223> OTHER INFORMATION: Synthetic polypeptide

```
<400> SEQUENCE: 460

Lys Lys Leu Asp Thr Lys Phe Val Lys Leu Ser Leu Phe Thr Glu Arg
1               5                   10                  15

<210> SEQ ID NO 461
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 461

Lys Asp Leu Asp Thr Phe Phe Val Lys Leu Ser Leu Phe Thr Glu Arg
1               5                   10                  15

<210> SEQ ID NO 462
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 462

Lys Lys Leu Asp Thr Cys Phe Val Lys Leu Ser Leu Phe Thr Glu Arg
1               5                   10                  15

<210> SEQ ID NO 463
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 463

Lys Lys Leu Asp Thr Phe Tyr Val Lys Leu Ser Leu Phe Thr Glu Arg
1               5                   10                  15

<210> SEQ ID NO 464
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 464

Lys Lys Leu Asp Thr Phe Phe Val Lys Leu Arg Leu Phe Thr Glu Arg
1               5                   10                  15

<210> SEQ ID NO 465
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 465

Phe Lys Leu Asp Thr Phe Phe Val Lys Leu Ser Leu Phe Thr Glu Arg
1               5                   10                  15

<210> SEQ ID NO 466
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 466
```

Lys Lys Leu Asp Thr His Phe Val Lys Leu Ser Leu Phe Thr Glu Arg
1               5                   10                  15

<210> SEQ ID NO 467
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 467

Lys Ile Leu Asp Thr Phe Phe Val Lys Leu Ser Leu Phe Thr Glu Arg
1               5                   10                  15

<210> SEQ ID NO 468
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 468

Lys Thr Leu Asp Thr Phe Phe Val Lys Leu Ser Leu Phe Thr Glu Arg
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 469

Lys Lys Leu Asp Thr Phe Phe Val Gln Leu Ser Leu Phe Thr Glu Arg
1               5                   10                  15

<210> SEQ ID NO 470
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 470

Lys Lys Leu Asp Thr Phe Phe Val Lys Leu Pro Leu Phe Thr Glu Arg
1               5                   10                  15

<210> SEQ ID NO 471
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 471

Lys Lys Leu Asp Thr Phe Phe Val Lys Leu Ser Leu Phe Thr Lys Arg
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 472

Lys Lys Leu Asp Thr Phe Phe Val Lys Leu Trp Leu Phe Thr Glu Arg
1               5                   10                  15

<210> SEQ ID NO 473
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 473

Lys Lys Leu Asp Thr Phe Phe Val Lys Leu Lys Leu Phe Thr Glu Arg
1               5                   10                  15

<210> SEQ ID NO 474
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 474

Lys Lys Leu Asp Thr Phe Phe Val Lys Leu Asp Leu Phe Thr Glu Arg
1               5                   10                  15

<210> SEQ ID NO 475
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 475

Lys Lys Leu Asp Thr Phe Phe Val Lys Leu Ser Tyr Phe Thr Glu Arg
1               5                   10                  15

<210> SEQ ID NO 476
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 476

Lys Lys Leu Asp Thr Phe Phe Val Lys Leu Ser Leu Phe Thr Glu Arg
1               5                   10                  15

<210> SEQ ID NO 477
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 477

Lys Lys Leu Asp Thr Phe Phe Val Lys Leu Ala Leu Phe Thr Glu Arg
1               5                   10                  15

<210> SEQ ID NO 478
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 478

Lys Lys Leu Asp Thr Phe Phe Val Lys Leu Ser Leu Phe Thr His Arg

```
                    1               5                   10                  15
```

<210> SEQ ID NO 479
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 479

```
Lys Lys Leu His Thr Phe Phe Val Lys Leu Ser Leu Phe Thr Glu Arg
 1               5                   10                  15
```

<210> SEQ ID NO 480
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 480

```
Lys Lys Leu Arg Thr Phe Phe Val Lys Leu Ser Leu Phe Thr Glu Arg
 1               5                   10                  15
```

<210> SEQ ID NO 481
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 481

```
Lys Val Leu Asp Thr Phe Phe Val Lys Leu Ser Leu Phe Thr Glu Arg
 1               5                   10                  15
```

<210> SEQ ID NO 482
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 482

```
Lys Lys Leu Asp Thr Phe Phe Val Lys Trp Ser Leu Phe Thr Glu Arg
 1               5                   10                  15
```

<210> SEQ ID NO 483
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 483

```
Tyr Lys Leu Asp Thr Phe Phe Val Lys Leu Ser Leu Phe Thr Glu Arg
 1               5                   10                  15
```

<210> SEQ ID NO 484
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 484

```
Lys Lys Leu Asp Leu Phe Phe Val Lys Leu Ser Leu Phe Thr Glu Arg
 1               5                   10                  15
```

<210> SEQ ID NO 485
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 485

Lys Ala Leu Asp Thr Phe Phe Val Lys Leu Ser Leu Phe Thr Glu Arg
1               5                   10                  15

<210> SEQ ID NO 486
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 486

Lys Lys Leu Asp Thr Arg Phe Val Lys Leu Ser Leu Phe Thr Glu Arg
1               5                   10                  15

<210> SEQ ID NO 487
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 487

Lys Lys Leu Asp Thr Phe Phe Val Lys Leu Ser Leu Phe Thr Glu Arg
1               5                   10                  15

<210> SEQ ID NO 488
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 488

Lys Lys Leu Asp Thr Phe Phe Val His Leu Ser Leu Phe Thr Glu Arg
1               5                   10                  15

<210> SEQ ID NO 489
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 489

Lys Lys Leu Asp Thr Phe Phe Val Lys Leu Ser Leu Phe Ala Glu Arg
1               5                   10                  15

<210> SEQ ID NO 490
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 490

Lys Trp Leu Asp Thr Phe Phe Val Lys Leu Ser Leu Phe Thr Glu Arg
1               5                   10                  15

<210> SEQ ID NO 491
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 491

Lys Lys Leu Leu Thr Phe Phe Val Lys Leu Ser Leu Phe Thr Glu Arg
 1               5                  10                  15

<210> SEQ ID NO 492
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 492

Lys Lys Leu Asp Thr Phe Asp Val Lys Leu Ser Leu Phe Thr Glu Arg
 1               5                  10                  15

<210> SEQ ID NO 493
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 493

Lys Lys Leu Asp Thr Phe Phe Val Lys Leu Ser Leu Phe Gln Glu Arg
 1               5                  10                  15

<210> SEQ ID NO 494
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 494

Lys Tyr Leu Asp Thr Phe Phe Val Lys Leu Ser Leu Phe Thr Glu Arg
 1               5                  10                  15

<210> SEQ ID NO 495
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 495

Lys Lys Leu Asp Thr Phe Phe Ala Lys Leu Ser Leu Phe Thr Glu Arg
 1               5                  10                  15

<210> SEQ ID NO 496
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 496

Lys Lys Leu Asp Thr Phe Phe Thr Lys Leu Ser Leu Phe Thr Glu Arg
 1               5                  10                  15

```
<210> SEQ ID NO 497
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 497

Lys Lys Leu Asp Thr Phe Phe Val Lys Leu Ser Pro Phe Thr Glu Arg
 1               5                  10                  15

<210> SEQ ID NO 498
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 498

Lys Lys Leu Asn Thr Phe Phe Val Lys Leu Ser Leu Phe Thr Glu Arg
 1               5                  10                  15

<210> SEQ ID NO 499
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 499

Lys Cys Leu Asp Thr Phe Phe Val Lys Leu Ser Leu Phe Thr Glu Arg
 1               5                  10                  15

<210> SEQ ID NO 500
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 500

Lys Lys Leu Asp Asp Phe Phe Val Lys Leu Ser Leu Phe Thr Glu Arg
 1               5                  10                  15

<210> SEQ ID NO 501
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 501

Lys Lys Leu Asp Ile Phe Phe Val Lys Leu Ser Leu Phe Thr Glu Arg
 1               5                  10                  15

<210> SEQ ID NO 502
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 502

Lys Lys Leu Asp Thr Phe Phe Val Lys His Ser Leu Phe Thr Glu Arg
 1               5                  10                  15

<210> SEQ ID NO 503
```

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 503

Lys Lys Leu Asp Thr Phe Phe Val Lys Leu Ser Leu Tyr Thr Glu Arg
 1               5                  10                  15

<210> SEQ ID NO 504
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 504

Lys Lys Leu Asp Phe Phe Phe Val Lys Leu Ser Leu Phe Thr Glu Arg
 1               5                  10                  15

<210> SEQ ID NO 505
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 505

Lys Lys Leu Asp Thr Phe Phe Val Lys Leu Ile Leu Phe Thr Glu Arg
 1               5                  10                  15

<210> SEQ ID NO 506
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 506

Lys Lys Leu Asp Thr Phe Phe Val Lys Lys Ser Leu Phe Thr Glu Arg
 1               5                  10                  15

<210> SEQ ID NO 507
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 507

Trp Lys Leu Asp Thr Phe Phe Val Lys Leu Ser Leu Phe Thr Glu Arg
 1               5                  10                  15

<210> SEQ ID NO 508
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 508

Lys Lys Leu Asp Thr Phe Phe Val Lys Cys Ser Leu Phe Thr Glu Arg
 1               5                  10                  15

<210> SEQ ID NO 509
<211> LENGTH: 16
```

<212> TYPE: PRT
<213> ORGANISM: Artificial Sequence
<220> FEATURE:
<223> OTHER INFORMATION: Synthetic polypeptide

<400> SEQUENCE: 509

Lys Lys Leu Asp Thr Phe Phe Val Met Leu Ser Leu Phe Thr Glu Arg
1               5                   10                  15

<210> SEQ ID NO 510
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 510

Lys Ser Leu Asp Thr Phe Phe Val Lys Leu Ser Leu Phe Thr Glu Arg
1               5                   10                  15

<210> SEQ ID NO 511
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 511

Lys Lys Leu Asp Thr Phe Phe Val Ser Leu Ser Leu Phe Thr Glu Arg
1               5                   10                  15

<210> SEQ ID NO 512
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 512

Lys Lys Leu Lys Thr Phe Phe Val Lys Leu Ser Leu Phe Thr Glu Arg
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 513

Lys Lys Leu Asp Thr Phe Phe Gln Lys Leu Ser Leu Phe Thr Glu Arg
1               5                   10                  15

<210> SEQ ID NO 514
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 514

Lys Lys Leu Asp Thr Phe Phe Val Lys Leu Ser Leu Phe Tyr Glu Arg
1               5                   10                  15

<210> SEQ ID NO 515
<211> LENGTH: 16
<212> TYPE: PRT

<213> ORGANISM: Artificial Sequence
<220> FEATURE:
<223> OTHER INFORMATION: Synthetic polypeptide

<400> SEQUENCE: 515

Lys Lys Leu Gly Thr Phe Phe Val Lys Leu Ser Leu Phe Thr Glu Arg
1               5                   10                  15

<210> SEQ ID NO 516
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 516

Lys Lys Leu Asp Thr Phe Phe Val Lys Leu Ser Leu Phe Thr Glu Arg
1               5                   10                  15

<210> SEQ ID NO 517
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 517

Lys Lys Leu Asp Thr Phe Phe Val Lys Leu Ser Leu Phe Lys Glu Arg
1               5                   10                  15

<210> SEQ ID NO 518
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 518

Lys Lys Leu Asp Thr Phe Phe Val Asn Leu Ser Leu Phe Thr Glu Arg
1               5                   10                  15

<210> SEQ ID NO 519
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 519

Lys Lys Leu Asp Thr Phe Phe Cys Lys Leu Ser Leu Phe Thr Glu Arg
1               5                   10                  15

<210> SEQ ID NO 520
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 520

Lys Lys Leu Asp Thr Phe Phe Val Lys Leu Ser Leu Phe Cys Glu Arg
1               5                   10                  15

<210> SEQ ID NO 521
<211> LENGTH: 16
<212> TYPE: PRT
<213> ORGANISM: Artificial Sequence

```
<220> FEATURE:
<223> OTHER INFORMATION: Synthetic polypeptide

<400> SEQUENCE: 521

Lys Lys Leu Asp Thr Phe Phe Val Lys Leu Ser Leu Phe Thr Glu Val
1               5                   10                  15

<210> SEQ ID NO 522
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 522

Lys Lys Leu Asp Thr Phe Phe Val Lys Leu Phe Leu Phe Thr Glu Arg
1               5                   10                  15

<210> SEQ ID NO 523
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 523

Lys Lys Leu Asp Thr Phe Phe Val Val Leu Ser Leu Phe Thr Glu Arg
1               5                   10                  15

<210> SEQ ID NO 524
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 524

Lys Lys Leu Asp Thr Phe Phe Val Lys Leu Ser Leu Phe Thr Met Arg
1               5                   10                  15

<210> SEQ ID NO 525
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 525

Lys Lys Leu Asp Thr Phe Phe Val Lys Leu Ser Leu Phe Thr Leu Arg
1               5                   10                  15

<210> SEQ ID NO 526
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 526

Lys Lys Leu Asp Thr Phe Phe Val Trp Leu Ser Leu Phe Thr Glu Arg
1               5                   10                  15

<210> SEQ ID NO 527
<211> LENGTH: 16
<212> TYPE: PRT
<213> ORGANISM: Artificial Sequence
<220> FEATURE:
```

```
<223> OTHER INFORMATION: Synthetic polypeptide

<400> SEQUENCE: 527

Lys Lys Leu Asp Thr Phe Phe Val Glu Leu Ser Leu Phe Thr Glu Arg
1               5                   10                  15

<210> SEQ ID NO 528
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 528

Lys Lys Leu Asp Thr Phe Phe Val Lys Leu Ser Leu Phe Thr Glu His
1               5                   10                  15

<210> SEQ ID NO 529
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 529

Lys Lys Leu Asp Thr Phe Phe Val Lys Leu Ser Leu Phe Thr Glu Met
1               5                   10                  15

<210> SEQ ID NO 530
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 530

Lys Lys Leu Asp Lys Phe Phe Val Lys Leu Ser Leu Phe Thr Glu Arg
1               5                   10                  15

<210> SEQ ID NO 531
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 531

Lys Lys Leu Asp Thr Phe Phe Val Lys Leu Ser Leu Phe Thr Arg Arg
1               5                   10                  15

<210> SEQ ID NO 532
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 532

Lys Lys Leu Asp Thr Phe Phe Val Lys Leu Glu Leu Phe Thr Glu Arg
1               5                   10                  15

<210> SEQ ID NO 533
<211> LENGTH: 16
<212> TYPE: PRT
<213> ORGANISM: Artificial Sequence
<220> FEATURE:
<223> OTHER INFORMATION: Synthetic polypeptide
```

<400> SEQUENCE: 533

Lys Lys Leu Asp Thr Phe Phe Val Lys Leu Ser Leu Phe Thr Glu Pro
1               5                   10                  15

<210> SEQ ID NO 534
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 534

Lys Lys Leu Asp Thr Phe Phe Val Pro Leu Ser Leu Phe Thr Glu Arg
1               5                   10                  15

<210> SEQ ID NO 535
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 535

Lys Lys Leu Asp Thr Phe Lys Val Lys Leu Ser Leu Phe Thr Glu Arg
1               5                   10                  15

<210> SEQ ID NO 536
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 536

Lys Lys Leu Asp Thr Glu Phe Val Lys Leu Ser Leu Phe Thr Glu Arg
1               5                   10                  15

<210> SEQ ID NO 537
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 537

Lys Lys Leu Asp Thr Phe Phe Trp Lys Leu Ser Leu Phe Thr Glu Arg
1               5                   10                  15

<210> SEQ ID NO 538
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 538

Lys Lys Leu Asp Thr Phe Phe Val Lys Leu Ser Leu Phe Thr Glu Ala
1               5                   10                  15

<210> SEQ ID NO 539
<211> LENGTH: 16
<212> TYPE: PRT
<213> ORGANISM: Artificial Sequence
<220> FEATURE:
<223> OTHER INFORMATION: Synthetic polypeptide

```
<400> SEQUENCE: 539

Lys Lys Leu Asp Thr Phe Phe Val Lys Leu Ser Leu Phe Thr Trp Arg
1               5                   10                  15

<210> SEQ ID NO 540
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 540

Lys Lys Leu Asp Thr Phe Phe Met Lys Leu Ser Leu Phe Thr Glu Arg
1               5                   10                  15

<210> SEQ ID NO 541
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 541

Lys Lys Leu Asp Thr Phe Phe Val Cys Leu Ser Leu Phe Thr Glu Arg
1               5                   10                  15

<210> SEQ ID NO 542
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 542

Lys Lys Leu Asp Thr Phe Phe Val Lys Leu Ser Leu Lys Thr Glu Arg
1               5                   10                  15

<210> SEQ ID NO 543
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 543

Lys Lys Leu Asp Thr Phe Phe Val Lys Leu Ser Leu Phe Thr Glu Gly
1               5                   10                  15

<210> SEQ ID NO 544
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 544

Lys Lys Leu Asp Thr Phe Phe Val Lys Leu Ser Leu Phe Thr Glu Leu
1               5                   10                  15

<210> SEQ ID NO 545
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 545
```

```
Lys Lys Leu Asp Thr Phe Phe Ser Lys Leu Ser Leu Phe Thr Glu Arg
1               5                   10                  15

<210> SEQ ID NO 546
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 546

Cys Lys Leu Asp Thr Phe Phe Val Lys Leu Ser Leu Phe Thr Glu Arg
1               5                   10                  15

<210> SEQ ID NO 547
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 547

Lys Lys Leu Asp Thr Phe Phe His Lys Leu Ser Leu Phe Thr Glu Arg
1               5                   10                  15

<210> SEQ ID NO 548
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 548

Lys Lys Leu Asp Thr Phe Phe Val Lys Leu Leu Leu Phe Thr Glu Arg
1               5                   10                  15

<210> SEQ ID NO 549
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 549

Lys Lys Leu Asp Thr Phe Phe Tyr Lys Leu Ser Leu Phe Thr Glu Arg
1               5                   10                  15

<210> SEQ ID NO 550
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 550

Lys Lys Leu Asp Thr Phe Phe Asn Lys Leu Ser Leu Phe Thr Glu Arg
1               5                   10                  15

<210> SEQ ID NO 551
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 551
```

Lys Lys Leu Asp Thr Phe Phe Val Lys Leu Ser Leu Phe Thr Glu Trp
1               5                   10                  15

<210> SEQ ID NO 552
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 552

Lys Lys Leu Asp Thr Phe Phe Val Tyr Leu Ser Leu Phe Thr Glu Arg
1               5                   10                  15

<210> SEQ ID NO 553
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 553

Lys Lys Leu Asp Thr Asp Phe Val Lys Leu Ser Leu Phe Thr Glu Arg
1               5                   10                  15

<210> SEQ ID NO 554
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 554

Lys Lys Leu Asp Thr Phe Phe Val Ala Leu Ser Leu Phe Thr Glu Arg
1               5                   10                  15

<210> SEQ ID NO 555
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 555

Lys Lys Leu Asp Thr Phe Phe Val Ile Leu Ser Leu Phe Thr Glu Arg
1               5                   10                  15

<210> SEQ ID NO 556
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 556

Lys Lys Leu Asp Thr Phe Phe Val Lys Leu Ser Leu Phe Thr Cys Arg
1               5                   10                  15

<210> SEQ ID NO 557
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 557

Lys Lys Leu Asp Thr Phe Phe Val Lys Leu Ser Leu Phe Thr Glu Ser

```
                1               5                   10                  15
```

<210> SEQ ID NO 558
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 558

```
Lys Lys Leu Asp Thr Phe Phe Val Lys Leu Ser Leu Phe Thr Glu Ile
  1               5                   10                  15
```

<210> SEQ ID NO 559
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 559

```
Lys Lys Leu Asp Thr Phe Phe Val Lys Leu Ser Leu Phe Thr Glu Cys
  1               5                   10                  15
```

<210> SEQ ID NO 560
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 560

```
Lys Lys Leu Asp Thr Phe Phe Val Phe Leu Ser Leu Phe Thr Glu Arg
  1               5                   10                  15
```

<210> SEQ ID NO 561
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 561

```
Lys Lys Leu Asp Thr Phe Phe Val Lys Leu Ser Leu Phe Thr Ala Arg
  1               5                   10                  15
```

<210> SEQ ID NO 562
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 562

```
Lys Lys Leu Asp Thr Phe Phe Val Leu Leu Ser Leu Phe Thr Glu Arg
  1               5                   10                  15
```

<210> SEQ ID NO 563
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 563

```
Lys Lys Leu Asp Thr Phe Phe Val Lys Leu Ser Leu Phe Thr Ser Arg
  1               5                   10                  15
```

<210> SEQ ID NO 564
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 564

Lys Lys Leu Asp Thr Phe Phe Val Lys Leu Ser Leu Phe Thr Ile Arg
1               5                   10                  15

<210> SEQ ID NO 565
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 565

Lys Lys Leu Asp Thr Phe Phe Val Lys Leu Ser Leu Phe Thr Val Arg
1               5                   10                  15

<210> SEQ ID NO 566
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 566

Lys Lys Leu Asp Thr Phe Phe Val Lys Leu Ser Leu Phe Thr Asn Arg
1               5                   10                  15

<210> SEQ ID NO 567
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 567

Lys Lys Leu Asp Thr Phe Phe Val Lys Leu Ser Leu Phe Asp Glu Arg
1               5                   10                  15

<210> SEQ ID NO 568
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 568

Lys Lys Leu Asp Thr Phe Phe Val Lys Leu Ser Leu Phe Thr Thr Arg
1               5                   10                  15

<210> SEQ ID NO 569
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 569

Lys Lys Leu Asp Thr Phe Phe Val Asp Leu Ser Leu Phe Thr Glu Arg
1               5                   10                  15

<210> SEQ ID NO 570
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 570

Lys Lys Leu Asp Thr Phe Phe Glu Lys Leu Ser Leu Phe Thr Glu Arg
1               5                   10                  15

<210> SEQ ID NO 571
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 571

Lys Lys Leu Asp Thr Phe Phe Val Lys Leu Ser Leu Phe Thr Phe Arg
1               5                   10                  15

<210> SEQ ID NO 572
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 572

Lys Lys Leu Asp Thr Phe Phe Val Lys Leu Ser Leu Phe Thr Glu Asp
1               5                   10                  15

<210> SEQ ID NO 573
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 573

Lys Lys Leu Asp Thr Phe Phe Val Lys Leu Ser Leu Phe Thr Glu Gln
1               5                   10                  15

<210> SEQ ID NO 574
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 574

Lys Lys Leu Asp Thr Phe Phe Asp Lys Leu Ser Leu Phe Thr Glu Arg
1               5                   10                  15

<210> SEQ ID NO 575
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 575

Lys Lys Leu Asp Thr Phe Phe Val Lys Leu Ser Leu Asp Thr Glu Arg
1               5                   10                  15

```
<210> SEQ ID NO 576
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 576

Lys Lys Leu Asp Thr Phe Phe Val Lys Leu Ser Leu Phe Glu Glu Arg
1               5                   10                  15

<210> SEQ ID NO 577
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 577

Lys Lys Leu Asp Thr Phe Phe Val Lys Leu Ser Leu Phe Thr Glu Glu
1               5                   10                  15

<210> SEQ ID NO 578
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 578

Lys Lys Leu Asp Thr Phe Phe Val Lys Asp Ser Leu Phe Thr Glu Arg
1               5                   10                  15

<210> SEQ ID NO 579
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 579

Lys Lys Leu Asp Thr Phe Phe Val Lys Leu Ser Leu Glu Thr Glu Arg
1               5                   10                  15

<210> SEQ ID NO 580
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 580

Lys Lys Leu Asp Thr Phe Phe Val Lys Leu Ser Asp Phe Thr Glu Arg
1               5                   10                  15

<210> SEQ ID NO 581
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 581

Lys Lys Leu Asp Thr Phe Phe Val Lys Leu Ser Glu Phe Thr Glu Arg
1               5                   10                  15

<210> SEQ ID NO 582
```

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 582

Lys Lys Leu Asp Thr Phe Phe Val Lys Glu Ser Leu Phe Thr Glu Arg
1               5                   10                  15

<210> SEQ ID NO 583
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 583

Lys Lys Leu Asp Thr Phe Phe Val Lys Leu Ser Leu Met Thr Glu Arg
1               5                   10                  15

<210> SEQ ID NO 584
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 584

Lys Lys Leu Asp Thr Phe Phe Val Lys Leu Gln Leu Phe Thr Glu Arg
1               5                   10                  15

<210> SEQ ID NO 585
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 585

Lys Lys Leu Asp Thr Val Met Val Lys Leu Gln Leu Met Thr Glu Arg
1               5                   10                  15

<210> SEQ ID NO 586
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 586

Arg Lys Leu Asp Thr Phe Phe Val Lys Leu Ser Leu Phe Thr Glu Arg
1               5                   10                  15

Arg Arg

<210> SEQ ID NO 587
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 587

Lys Ser Leu Asp Thr Phe Phe Val Lys Leu Ser Leu Phe Thr Glu Arg
1               5                   10                  15
```

```
<210> SEQ ID NO 588
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 588

Lys Lys Leu Asp Thr Phe Phe Val Lys Leu Ser Leu Phe Thr Phe Arg
1               5                   10                  15

<210> SEQ ID NO 589
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 589

Lys Lys Leu Asp Thr Phe Phe Val Tyr Leu Ser Leu Phe Thr Glu Arg
1               5                   10                  15

<210> SEQ ID NO 590
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 590

Lys Lys Leu Asp Thr Phe Phe Val Asn Leu Ser Leu Phe Thr Glu Arg
1               5                   10                  15

<210> SEQ ID NO 591
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 591

Lys Lys Leu Asp Thr Phe Phe Val Asp Leu Ser Leu Phe Thr Glu Arg
1               5                   10                  15

<210> SEQ ID NO 592
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 592

Lys Lys Leu Asp Thr Phe Phe Pro Lys Leu Ser Leu Phe Thr Glu Arg
1               5                   10                  15

<210> SEQ ID NO 593
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 593

Lys Lys Leu Asp Thr Phe Met Val Lys Leu Ser Gln His Thr Glu Arg
1               5                   10                  15

<210> SEQ ID NO 594
```

```
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: 17
<223> OTHER INFORMATION: Pegylation

<400> SEQUENCE: 594

Lys Lys Leu Asp Thr Phe Phe Val Lys Leu Ser Leu Phe Thr Glu Arg
 1               5                  10                  15

Cys

<210> SEQ ID NO 595
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 595

Lys Lys Leu Asp Gln Phe Phe Val Lys Leu Ser Gln His Asn Glu Arg
 1               5                  10                  15

<210> SEQ ID NO 596
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 596

Leu Asp Thr Phe Phe Val
 1               5

<210> SEQ ID NO 597
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 597

Gly Asp Thr Phe Phe Val
 1               5

<210> SEQ ID NO 598
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 598

Glu Asp Thr Phe Phe Val
 1               5

<210> SEQ ID NO 599
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 599
```

Leu Asp Gln Phe Phe Val
1               5

<210> SEQ ID NO 600
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 600

Leu Asp Thr Ala Phe Val
1               5

<210> SEQ ID NO 601
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 601

Leu Asp Thr Val Phe Val
1               5

<210> SEQ ID NO 602
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 602

Leu Asp Thr Phe Met Val
1               5

<210> SEQ ID NO 603
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 603

Leu Asp Thr Phe Ser Val
1               5

<210> SEQ ID NO 604
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 604

Leu Asp Thr Phe Val Val
1               5

<210> SEQ ID NO 605
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 605

Leu Asp Thr Phe Thr Val

```
1               5
```

<210> SEQ ID NO 606
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 606

```
Leu Asp Thr Phe Leu Val
1               5
```

<210> SEQ ID NO 607
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 607

```
Leu Asp Gly Phe Phe Val
1               5
```

<210> SEQ ID NO 608
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 608

```
Leu Asp Thr Phe Gly Val
1               5
```

<210> SEQ ID NO 609
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 609

```
Leu Asp Thr Phe Phe Lys
1               5
```

<210> SEQ ID NO 610
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 610

```
Ala Asp Thr Phe Phe Val
1               5
```

<210> SEQ ID NO 611
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 611

```
Cys Asp Thr Phe Phe Val
1               5
```

```
<210> SEQ ID NO 612
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 612

Asp Asp Thr Phe Phe Val
1               5

<210> SEQ ID NO 613
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 613

Phe Asp Thr Phe Phe Val
1               5

<210> SEQ ID NO 614
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 614

His Asp Thr Phe Phe Val
1               5

<210> SEQ ID NO 615
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 615

Ile Asp Thr Phe Phe Val
1               5

<210> SEQ ID NO 616
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 616

Lys Asp Thr Phe Phe Val
1               5

<210> SEQ ID NO 617
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 617

Met Asp Thr Phe Phe Val
1               5
```

```
<210> SEQ ID NO 618
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 618

Asn Asp Thr Phe Phe Val
1               5

<210> SEQ ID NO 619
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 619

Gln Asp Thr Phe Phe Val
1               5

<210> SEQ ID NO 620
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 620

Arg Asp Thr Phe Phe Val
1               5

<210> SEQ ID NO 621
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 621

Ser Asp Thr Phe Phe Val
1               5

<210> SEQ ID NO 622
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 622

Thr Asp Thr Phe Phe Val
1               5

<210> SEQ ID NO 623
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 623

Val Asp Thr Phe Phe Val
1               5
```

```
<210> SEQ ID NO 624
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 624

Leu Ala Thr Phe Phe Val
1               5

<210> SEQ ID NO 625
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 625

Leu Glu Thr Phe Phe Val
1               5

<210> SEQ ID NO 626
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 626

Leu Ile Thr Phe Phe Val
1               5

<210> SEQ ID NO 627
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 627

Leu Val Thr Phe Phe Val
1               5

<210> SEQ ID NO 628
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 628

Leu Trp Thr Phe Phe Val
1               5

<210> SEQ ID NO 629
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 629

Leu Tyr Thr Phe Phe Val
1               5

<210> SEQ ID NO 630
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 630

Leu Asp Cys Phe Phe Val
 1               5

<210> SEQ ID NO 631
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 631

Leu Asp Met Phe Phe Val
 1               5

<210> SEQ ID NO 632
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 632

Leu Asp Asn Phe Phe Val
 1               5

<210> SEQ ID NO 633
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 633

Leu Asp Pro Phe Phe Val
 1               5

<210> SEQ ID NO 634
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 634

Leu Asp Arg Phe Phe Val
 1               5

<210> SEQ ID NO 635
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 635

Leu Asp Ser Phe Phe Val
 1               5

<210> SEQ ID NO 636
<211> LENGTH: 6
```

```
<212> TYPE: PRT
<213> ORGANISM: Artificial Sequence
<220> FEATURE:
<223> OTHER INFORMATION: Synthetic polypeptide

<400> SEQUENCE: 636

Leu Asp Trp Phe Phe Val
1               5

<210> SEQ ID NO 637
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 637

Leu Asp Tyr Phe Phe Val
1               5

<210> SEQ ID NO 638
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 638

Leu Asp Thr Ile Phe Val
1               5

<210> SEQ ID NO 639
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 639

Leu Asp Thr Met Phe Val
1               5

<210> SEQ ID NO 640
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 640

Leu Asp Thr Asn Phe Val
1               5

<210> SEQ ID NO 641
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 641

Leu Asp Thr Pro Phe Val
1               5

<210> SEQ ID NO 642
<211> LENGTH: 6
<212> TYPE: PRT
```

```
<213> ORGANISM: Artificial Sequence
<220> FEATURE:
<223> OTHER INFORMATION: Synthetic polypeptide

<400> SEQUENCE: 642

Leu Asp Thr Thr Phe Val
 1               5

<210> SEQ ID NO 643
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 643

Leu Asp Thr Phe Gln Val
 1               5

<210> SEQ ID NO 644
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 644

Leu Asp Thr Phe Phe Phe
 1               5

<210> SEQ ID NO 645
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 645

Leu Asp Thr Phe Phe Gly
 1               5

<210> SEQ ID NO 646
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 646

Leu Asp Thr Phe Phe Leu
 1               5

<210> SEQ ID NO 647
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 647

Leu Asp Thr Phe Phe Pro
 1               5

<210> SEQ ID NO 648
<211> LENGTH: 6
<212> TYPE: PRT
<213> ORGANISM: Artificial Sequence
```

```
<220> FEATURE:
<223> OTHER INFORMATION: Synthetic polypeptide

<400> SEQUENCE: 648

Leu Asp Thr Phe Phe Arg
 1               5

<210> SEQ ID NO 649
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 649

Leu Asp Thr Phe Ile Val
 1               5

<210> SEQ ID NO 650
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 650

Leu Asp Thr Ser Phe Val
 1               5

<210> SEQ ID NO 651
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 651

Leu Asp Thr Phe Ala Val
 1               5

<210> SEQ ID NO 652
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 652

Leu Asp Thr Phe Cys Val
 1               5

<210> SEQ ID NO 653
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 653

Leu Asp Thr Gln Phe Val
 1               5

<210> SEQ ID NO 654
<211> LENGTH: 6
<212> TYPE: PRT
<213> ORGANISM: Artificial Sequence
<220> FEATURE:
```

<223> OTHER INFORMATION: Synthetic polypeptide

<400> SEQUENCE: 654

Leu Asp Thr Leu Phe Val
1               5

<210> SEQ ID NO 655
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 655

Leu Thr Thr Phe Phe Val
1               5

<210> SEQ ID NO 656
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 656

Leu Asp Thr Phe Phe Ile
1               5

<210> SEQ ID NO 657
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 657

Leu Asp His Phe Phe Val
1               5

<210> SEQ ID NO 658
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 658

Leu Met Thr Phe Phe Val
1               5

<210> SEQ ID NO 659
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 659

Leu Asp Thr Phe Glu Val
1               5

<210> SEQ ID NO 660
<211> LENGTH: 6
<212> TYPE: PRT
<213> ORGANISM: Artificial Sequence
<220> FEATURE:
<223> OTHER INFORMATION: Synthetic polypeptide

```
<400> SEQUENCE: 660

Leu Asp Thr Phe Trp Val
1               5

<210> SEQ ID NO 661
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 661

Leu Phe Thr Phe Phe Val
1               5

<210> SEQ ID NO 662
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 662

Leu Asp Val Phe Phe Val
1               5

<210> SEQ ID NO 663
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 663

Leu Asp Thr Phe Arg Val
1               5

<210> SEQ ID NO 664
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 664

Leu Asp Thr Phe His Val
1               5

<210> SEQ ID NO 665
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 665

Leu Asp Thr Tyr Phe Val
1               5

<210> SEQ ID NO 666
<211> LENGTH: 6
<212> TYPE: PRT
<213> ORGANISM: Artificial Sequence
<220> FEATURE:
<223> OTHER INFORMATION: Synthetic polypeptide
```

```
<400> SEQUENCE: 666

Leu Pro Thr Phe Phe Val
1               5

<210> SEQ ID NO 667
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 667

Pro Asp Thr Phe Phe Val
1               5

<210> SEQ ID NO 668
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 668

Leu Asp Thr Phe Pro Val
1               5

<210> SEQ ID NO 669
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 669

Leu Asp Thr Phe Asn Val
1               5

<210> SEQ ID NO 670
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 670

Leu Asp Thr Trp Phe Val
1               5

<210> SEQ ID NO 671
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 671

Leu Asp Thr Gly Phe Val
1               5

<210> SEQ ID NO 672
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 672
```

```
Leu Asp Ala Phe Phe Val
1               5

<210> SEQ ID NO 673
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 673

Leu Gln Thr Phe Phe Val
1               5

<210> SEQ ID NO 674
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 674

Leu Cys Thr Phe Phe Val
1               5

<210> SEQ ID NO 675
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 675

Leu Ser Thr Phe Phe Val
1               5

<210> SEQ ID NO 676
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 676

Tyr Asp Thr Phe Phe Val
1               5

<210> SEQ ID NO 677
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 677

Leu Asp Glu Phe Phe Val
1               5

<210> SEQ ID NO 678
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 678
```

Trp Asp Thr Phe Phe Val
1               5

<210> SEQ ID NO 679
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 679

Leu Asp Thr Lys Phe Val
1               5

<210> SEQ ID NO 680
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 680

Leu Asp Thr Cys Phe Val
1               5

<210> SEQ ID NO 681
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 681

Leu Asp Thr Phe Tyr Val
1               5

<210> SEQ ID NO 682
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 682

Leu Asp Thr His Phe Val
1               5

<210> SEQ ID NO 683
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 683

Leu His Thr Phe Phe Val
1               5

<210> SEQ ID NO 684
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 684

Leu Arg Thr Phe Phe Val

```
1               5
```

<210> SEQ ID NO 685
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 685

```
Leu Asp Leu Phe Phe Val
1               5
```

<210> SEQ ID NO 686
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 686

```
Leu Asp Thr Arg Phe Val
1               5
```

<210> SEQ ID NO 687
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 687

```
Leu Leu Thr Phe Phe Val
1               5
```

<210> SEQ ID NO 688
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 688

```
Leu Asp Thr Phe Asp Val
1               5
```

<210> SEQ ID NO 689
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 689

```
Leu Asp Thr Phe Phe Ala
1               5
```

<210> SEQ ID NO 690
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 690

```
Leu Asp Thr Phe Phe Thr
1               5
```

```
<210> SEQ ID NO 691
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 691

Leu Asn Thr Phe Phe Val
 1               5

<210> SEQ ID NO 692
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 692

Leu Asp Asp Phe Phe Val
 1               5

<210> SEQ ID NO 693
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 693

Leu Asp Ile Phe Phe Val
 1               5

<210> SEQ ID NO 694
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 694

Leu Asp Phe Phe Phe Val
 1               5

<210> SEQ ID NO 695
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 695

Leu Lys Thr Phe Phe Val
 1               5

<210> SEQ ID NO 696
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 696

Leu Asp Thr Phe Phe Gln
 1               5
```

```
<210> SEQ ID NO 697
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 697

Leu Gly Thr Phe Phe Val
1               5

<210> SEQ ID NO 698
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 698

Leu Asp Thr Phe Phe Cys
1               5

<210> SEQ ID NO 699
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 699

Leu Asp Lys Phe Phe Val
1               5

<210> SEQ ID NO 700
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 700

Leu Asp Thr Phe Lys Val
1               5

<210> SEQ ID NO 701
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 701

Leu Asp Thr Glu Phe Val
1               5

<210> SEQ ID NO 702
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 702

Leu Asp Thr Phe Phe Trp
1               5
```

```
<210> SEQ ID NO 703
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 703

Leu Asp Thr Phe Phe Met
1               5

<210> SEQ ID NO 704
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 704

Leu Asp Thr Phe Phe Ser
1               5

<210> SEQ ID NO 705
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 705

Leu Asp Thr Phe Phe His
1               5

<210> SEQ ID NO 706
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 706

Leu Asp Thr Phe Phe Tyr
1               5

<210> SEQ ID NO 707
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 707

Leu Asp Thr Phe Phe Asn
1               5

<210> SEQ ID NO 708
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 708

Leu Asp Thr Asp Phe Val
1               5

<210> SEQ ID NO 709
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 709

Leu Asp Thr Phe Phe Glu
 1               5

<210> SEQ ID NO 710
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 710

Leu Asp Thr Phe Phe Asp
 1               5

<210> SEQ ID NO 711
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 711

Leu Thr Phe Phe Val
 1               5

<210> SEQ ID NO 712
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 712

Leu Asp Thr Phe Phe
 1               5

<210> SEQ ID NO 713
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 713

Thr Phe Phe Val
 1

<210> SEQ ID NO 714
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 714

Leu Asp Thr Glu
 1

<210> SEQ ID NO 715
<211> LENGTH: 5
```

-continued

```
<212> TYPE: PRT
<213> ORGANISM: Artificial Sequence
<220> FEATURE:
<223> OTHER INFORMATION: Synthetic polypeptide

<400> SEQUENCE: 715

Leu Ser Leu Phe Thr
 1               5

<210> SEQ ID NO 716
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 716

Val Ser Leu Phe Thr
 1               5

<210> SEQ ID NO 717
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 717

Leu Gln Leu Phe Thr
 1               5

<210> SEQ ID NO 718
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 718

Leu Met Leu Phe Thr
 1               5

<210> SEQ ID NO 719
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 719

Leu Thr Leu Phe Thr
 1               5

<210> SEQ ID NO 720
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 720

Leu His Leu Phe Thr
 1               5

<210> SEQ ID NO 721
<211> LENGTH: 5
<212> TYPE: PRT
```

```
<213> ORGANISM: Artificial Sequence
<220> FEATURE:
<223> OTHER INFORMATION: Synthetic polypeptide

<400> SEQUENCE: 721

Leu Ser Gln Phe Thr
 1               5

<210> SEQ ID NO 722
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 722

Leu Ser Val Phe Thr
 1               5

<210> SEQ ID NO 723
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 723

Leu Ser Met Phe Thr
 1               5

<210> SEQ ID NO 724
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 724

Leu Ser Leu Met Thr
 1               5

<210> SEQ ID NO 725
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 725

Leu Ser Leu Gln Thr
 1               5

<210> SEQ ID NO 726
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 726

Leu Ser Leu His Thr
 1               5

<210> SEQ ID NO 727
<211> LENGTH: 5
<212> TYPE: PRT
<213> ORGANISM: Artificial Sequence
```

```
<220> FEATURE:
<223> OTHER INFORMATION: Synthetic polypeptide

<400> SEQUENCE: 727

Leu Ser Leu Asn Thr
1               5

<210> SEQ ID NO 728
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 728

Leu Ser Leu Pro Thr
1               5

<210> SEQ ID NO 729
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 729

Leu Ser Leu Ser Thr
1               5

<210> SEQ ID NO 730
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 730

Leu Ser Leu Gly Thr
1               5

<210> SEQ ID NO 731
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 731

Leu Ser Leu Ala Thr
1               5

<210> SEQ ID NO 732
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 732

Leu Ser Leu Arg Thr
1               5

<210> SEQ ID NO 733
<211> LENGTH: 5
<212> TYPE: PRT
<213> ORGANISM: Artificial Sequence
<220> FEATURE:
```

-continued

<223> OTHER INFORMATION: Synthetic polypeptide

<400> SEQUENCE: 733

Leu Ser Leu Phe Asn
1               5

<210> SEQ ID NO 734
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 734

Leu Ser Leu Phe Pro
1               5

<210> SEQ ID NO 735
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 735

Leu Ser Leu Phe Arg
1               5

<210> SEQ ID NO 736
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 736

Leu Gly Leu Phe Thr
1               5

<210> SEQ ID NO 737
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 737

Ala Ser Leu Phe Thr
1               5

<210> SEQ ID NO 738
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 738

Phe Ser Leu Phe Thr
1               5

<210> SEQ ID NO 739
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 739

Gly Ser Leu Phe Thr
1               5

<210> SEQ ID NO 740
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 740

Ile Ser Leu Phe Thr
1               5

<210> SEQ ID NO 741
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 741

Met Ser Leu Phe Thr
1               5

<210> SEQ ID NO 742
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 742

Asn Ser Leu Phe Thr
1               5

<210> SEQ ID NO 743
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 743

Pro Ser Leu Phe Thr
1               5

<210> SEQ ID NO 744
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 744

Gln Ser Leu Phe Thr
1               5

<210> SEQ ID NO 745
<211> LENGTH: 5
<212> TYPE: PRT
<213> ORGANISM: Artificial Sequence
<220> FEATURE:
<223> OTHER INFORMATION: Synthetic polypeptide

```
<400> SEQUENCE: 745

Arg Ser Leu Phe Thr
 1               5

<210> SEQ ID NO 746
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 746

Ser Ser Leu Phe Thr
 1               5

<210> SEQ ID NO 747
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 747

Thr Ser Leu Phe Thr
 1               5

<210> SEQ ID NO 748
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 748

Tyr Ser Leu Phe Thr
 1               5

<210> SEQ ID NO 749
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 749

Leu Asn Leu Phe Thr
 1               5

<210> SEQ ID NO 750
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 750

Leu Ser Ala Phe Thr
 1               5

<210> SEQ ID NO 751
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 751
```

Leu Ser His Phe Thr
1               5

<210> SEQ ID NO 752
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 752

Leu Ser Ile Phe Thr
1               5

<210> SEQ ID NO 753
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 753

Leu Ser Asn Phe Thr
1               5

<210> SEQ ID NO 754
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 754

Leu Ser Arg Phe Thr
1               5

<210> SEQ ID NO 755
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 755

Leu Ser Ser Phe Thr
1               5

<210> SEQ ID NO 756
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 756

Leu Ser Thr Phe Thr
1               5

<210> SEQ ID NO 757
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 757

```
Leu Ser Trp Phe Thr
1               5

<210> SEQ ID NO 758
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 758

Leu Ser Leu Cys Thr
1               5

<210> SEQ ID NO 759
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 759

Leu Ser Leu Ile Thr
1               5

<210> SEQ ID NO 760
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 760

Leu Ser Leu Leu Thr
1               5

<210> SEQ ID NO 761
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 761

Leu Ser Leu Thr Thr
1               5

<210> SEQ ID NO 762
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 762

Leu Ser Leu Val Thr
1               5

<210> SEQ ID NO 763
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 763

Leu Ser Leu Trp Thr
```

```
1               5

<210> SEQ ID NO 764
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 764

Leu Ser Leu Phe Phe
1               5

<210> SEQ ID NO 765
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 765

Leu Ser Leu Phe Gly
1               5

<210> SEQ ID NO 766
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 766

Leu Ser Leu Phe His
1               5

<210> SEQ ID NO 767
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 767

Leu Ser Leu Phe Ile
1               5

<210> SEQ ID NO 768
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 768

Leu Ser Leu Phe Leu
1               5

<210> SEQ ID NO 769
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 769

Leu Ser Leu Phe Met
1               5
```

```
<210> SEQ ID NO 770
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 770

Leu Ser Leu Phe Ser
 1               5

<210> SEQ ID NO 771
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 771

Leu Ser Leu Phe Val
 1               5

<210> SEQ ID NO 772
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 772

Leu Ser Leu Phe Trp
 1               5

<210> SEQ ID NO 773
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 773

Leu Tyr Leu Phe Thr
 1               5

<210> SEQ ID NO 774
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 774

Leu Val Leu Phe Thr
 1               5

<210> SEQ ID NO 775
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 775

Leu Ser Phe Phe Thr
 1               5
```

```
<210> SEQ ID NO 776
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 776

Leu Ser Gly Phe Thr
 1               5

<210> SEQ ID NO 777
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 777

Leu Ser Lys Phe Thr
 1               5

<210> SEQ ID NO 778
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 778

Leu Ser Cys Phe Thr
 1               5

<210> SEQ ID NO 779
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 779

Leu Cys Leu Phe Thr
 1               5

<210> SEQ ID NO 780
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 780

Leu Arg Leu Phe Thr
 1               5

<210> SEQ ID NO 781
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 781

Leu Pro Leu Phe Thr
 1               5
```

```
<210> SEQ ID NO 782
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 782

Leu Trp Leu Phe Thr
1               5

<210> SEQ ID NO 783
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 783

Leu Lys Leu Phe Thr
1               5

<210> SEQ ID NO 784
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 784

Leu Asp Leu Phe Thr
1               5

<210> SEQ ID NO 785
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 785

Leu Ser Tyr Phe Thr
1               5

<210> SEQ ID NO 786
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 786

Leu Ala Leu Phe Thr
1               5

<210> SEQ ID NO 787
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 787

Trp Ser Leu Phe Thr
1               5

<210> SEQ ID NO 788
```

-continued

```
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 788

Leu Ser Leu Phe Ala
1               5

<210> SEQ ID NO 789
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 789

Leu Ser Leu Phe Gln
1               5

<210> SEQ ID NO 790
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 790

Leu Ser Pro Phe Thr
1               5

<210> SEQ ID NO 791
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 791

His Ser Leu Phe Thr
1               5

<210> SEQ ID NO 792
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 792

Leu Ser Leu Tyr Thr
1               5

<210> SEQ ID NO 793
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 793

Leu Ile Leu Phe Thr
1               5

<210> SEQ ID NO 794
<211> LENGTH: 5
```

```
<212> TYPE: PRT
<213> ORGANISM: Artificial Sequence
<220> FEATURE:
<223> OTHER INFORMATION: Synthetic polypeptide

<400> SEQUENCE: 794

Lys Ser Leu Phe Thr
 1               5

<210> SEQ ID NO 795
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 795

Cys Ser Leu Phe Thr
 1               5

<210> SEQ ID NO 796
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 796

Leu Ser Leu Phe Tyr
 1               5

<210> SEQ ID NO 797
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 797

Leu Ser Leu Phe Lys
 1               5

<210> SEQ ID NO 798
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 798

Leu Ser Leu Phe Cys
 1               5

<210> SEQ ID NO 799
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 799

Leu Phe Leu Phe Thr
 1               5

<210> SEQ ID NO 800
<211> LENGTH: 5
<212> TYPE: PRT
```

```
<213> ORGANISM: Artificial Sequence
<220> FEATURE:
<223> OTHER INFORMATION: Synthetic polypeptide

<400> SEQUENCE: 800

Leu Glu Leu Phe Thr
 1               5

<210> SEQ ID NO 801
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 801

Leu Ser Leu Lys Thr
 1               5

<210> SEQ ID NO 802
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 802

Leu Leu Leu Phe Thr
 1               5

<210> SEQ ID NO 803
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 803

Leu Ser Leu Phe Asp
 1               5

<210> SEQ ID NO 804
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 804

Leu Ser Leu Asp Thr
 1               5

<210> SEQ ID NO 805
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 805

Leu Ser Leu Phe Glu
 1               5

<210> SEQ ID NO 806
<211> LENGTH: 5
<212> TYPE: PRT
<213> ORGANISM: Artificial Sequence
```

```
<220> FEATURE:
<223> OTHER INFORMATION: Synthetic polypeptide

<400> SEQUENCE: 806

Asp Ser Leu Phe Thr
 1               5

<210> SEQ ID NO 807
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 807

Leu Ser Leu Glu Thr
 1               5

<210> SEQ ID NO 808
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 808

Leu Ser Asp Phe Thr
 1               5

<210> SEQ ID NO 809
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 809

Leu Ser Glu Phe Thr
 1               5

<210> SEQ ID NO 810
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 810

Glu Ser Leu Phe Thr
 1               5

<210> SEQ ID NO 811
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 811

Ser Leu Phe Thr
 1

<210> SEQ ID NO 812
<211> LENGTH: 4
<212> TYPE: PRT
<213> ORGANISM: Artificial Sequence
<220> FEATURE:
```

```
<223> OTHER INFORMATION: Synthetic polypeptide

<400> SEQUENCE: 812

Leu Ser Phe Thr
1

<210> SEQ ID NO 813
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 813

Ala Val Ile Leu
1

<210> SEQ ID NO 814
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 814

Ser Thr Asn Gln
1

<210> SEQ ID NO 815
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 815

Met Arg Pro Arg
1

<210> SEQ ID NO 816
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X = K or R
<220> FEATURE:
<221> NAME/KEY: MISC_FEATURE
<222> LOCATION: (3)..(3)
<223> OTHER INFORMATION: X = L or G or E
<220> FEATURE:
<221> NAME/KEY: MISC_FEATURE
<222> LOCATION: (5)..(5)
<223> OTHER INFORMATION: X = T or Q
<220> FEATURE:
<221> NAME/KEY: MISC_FEATURE
<222> LOCATION: (6)..(6)
<223> OTHER INFORMATION: X = F or A or V
<220> FEATURE:
<221> NAME/KEY: MISC_FEATURE
<222> LOCATION: (7)..(7)
<223> OTHER INFORMATION: X = F or M or S or V or T or L
<220> FEATURE:
<221> NAME/KEY: MISC_FEATURE
<222> LOCATION: (10)..(10)
<223> OTHER INFORMATION: X = L or V
<220> FEATURE:
<221> NAME/KEY: MISC_FEATURE
```

```
<222> LOCATION: (11)..(11)
<223> OTHER INFORMATION: X = S or Q or M or T or H
<220> FEATURE:
<221> NAME/KEY: MISC_FEATURE
<222> LOCATION: (12)..(12)
<223> OTHER INFORMATION: X = L or Q or V or M
<220> FEATURE:
<221> NAME/KEY: MISC_FEATURE
<222> LOCATION: (13)..(13)
<223> OTHER INFORMATION: X = F or M or Q or H or N or P or S or G or A
      or R
<220> FEATURE:
<221> NAME/KEY: MISC_FEATURE
<222> LOCATION: (14)..(14)
<223> OTHER INFORMATION: X = T or N or P or R

<400> SEQUENCE: 816

Xaa Lys Xaa Asp Xaa Xaa Xaa Val Lys Xaa Xaa Xaa Xaa Xaa Glu Arg
 1               5                  10                  15

<210> SEQ ID NO 817
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 817

Lys Lys Leu Asp Thr Phe Phe Val Lys Leu Ser Leu Phe Glu Arg
 1               5                  10                  15

<210> SEQ ID NO 818
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 818

Lys Lys Leu Asp Thr Phe Lys Leu Ser Leu Phe Thr Glu Arg
 1               5                  10

<210> SEQ ID NO 819
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 819

Lys Lys Leu Asp Thr Phe Phe Lys Lys Leu Ser Leu Phe Thr Glu
 1               5                  10                  15

<210> SEQ ID NO 820
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: X = A or R
<220> FEATURE:
<221> NAME/KEY: MISC_FEATURE
<222> LOCATION: (5)..(5)
<223> OTHER INFORMATION: X = N or I
<220> FEATURE:
<221> NAME/KEY: MISC_FEATURE
<222> LOCATION: (6)..(6)
<223> OTHER INFORMATION: X = Absent
```

```
<220> FEATURE:
<221> NAME/KEY: MISC_FEATURE
<222> LOCATION: (8)..(8)
<223> OTHER INFORMATION: X = M or F

<400> SEQUENCE: 820

Cys Leu Xaa Leu Xaa Xaa Val Xaa Cys Gly
1               5                   10

<210> SEQ ID NO 821
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: X = A or R
<220> FEATURE:
<221> NAME/KEY: MISC_FEATURE
<222> LOCATION: (5)..(5)
<223> OTHER INFORMATION: X = N or I
<220> FEATURE:
<221> NAME/KEY: MISC_FEATURE
<222> LOCATION: (7)..(7)
<223> OTHER INFORMATION: X = M or F

<400> SEQUENCE: 821

Cys Leu Xaa Leu Xaa Val Xaa Cys Gly
1               5

<210> SEQ ID NO 822
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: X = K or A or D or E or G or H or I or L or M
     or N or P or Q or R or T or V or K
<220> FEATURE:
<221> NAME/KEY: MISC_FEATURE
<222> LOCATION: (3)..(3)
<223> OTHER INFORMATION: X = L or A or C or D or E or F or G or H or I
     or K or M or N or Q or R or S or T or V
<220> FEATURE:
<221> NAME/KEY: MISC_FEATURE
<222> LOCATION: (4)..(4)
<223> OTHER INFORMATION: X = D or A or E or I or V or W or Y
<220> FEATURE:
<221> NAME/KEY: MISC_FEATURE
<222> LOCATION: (5)..(5)
<223> OTHER INFORMATION: X = T or C or M or N or P or Q or R or S or W
     or Y
<220> FEATURE:
<221> NAME/KEY: MISC_FEATURE
<222> LOCATION: (6)..(6)
<223> OTHER INFORMATION: X = F or A or I or M or N or P or T or V
<220> FEATURE:
<221> NAME/KEY: MISC_FEATURE
<222> LOCATION: (7)..(7)
<223> OTHER INFORMATION: X = F or L or M or Q or S or T or V
<220> FEATURE:
<221> NAME/KEY: MISC_FEATURE
<222> LOCATION: (8)..(8)
<223> OTHER INFORMATION: X = V or F or G or L or P or R
<220> FEATURE:
<221> NAME/KEY: MISC_FEATURE
<222> LOCATION: (9)..(9)
<223> OTHER INFORMATION: X = K or R
<220> FEATURE:
<221> NAME/KEY: MISC_FEATURE
```

```
-continued

<222> LOCATION: (10)..(10)
<223> OTHER INFORMATION: X = L or A or F or G or I or M or N or P or Q
      or R or S or T or V or Y
<220> FEATURE:
<221> NAME/KEY: MISC_FEATURE
<222> LOCATION: (11)..(11)
<223> OTHER INFORMATION: X = S or H or M or N or Q or T
<220> FEATURE:
<221> NAME/KEY: MISC_FEATURE
<222> LOCATION: (12)..(12)
<223> OTHER INFORMATION: X = L or A or H or I or M or N or Q or R or S
      or T or V or W
<220> FEATURE:
<221> NAME/KEY: MISC_FEATURE
<222> LOCATION: (13)..(13)
<223> OTHER INFORMATION: X = F or A or C ro G or H or I or L or M or N
      or P or Q or R or S or T or V or W
<220> FEATURE:
<221> NAME/KEY: MISC_FEATURE
<222> LOCATION: (14)..(14)
<223> OTHER INFORMATION: X = T or F or G or H or I or L or M or N or P
      or S or V or W
<220> FEATURE:
<221> NAME/KEY: MISC_FEATURE
<222> LOCATION: (15)..(15)
<223> OTHER INFORMATION: X = E or D
<220> FEATURE:
<221> NAME/KEY: MISC_FEATURE
<222> LOCATION: (16)..(16)
<223> OTHER INFORMATION: X = R or F or K or N or R or T or Y

<400> SEQUENCE: 822

Xaa Lys Xaa Xaa Xaa Xaa Xaa Xaa Xaa Xaa Xaa Xaa Xaa Xaa Xaa Xaa
1               5                   10                  15
```

IMMUNE SYSTEM MODULATORS

RELATED APPLICATIONS

This application is a U.S. National Phase of PCT International App. No. PCT/US2014/054612, filed on Sep. 8, 2014, designating the United States of America and published in the English language, which claims the benefit of U.S. Provisional Application Ser. No. 61/875,598, filed Sep. 9, 2013, which is hereby incorporated by reference in its entirety.

SEQUENCE IN ELECTRONIC FORMAT

The present application is being filed along with a Sequence Listing as an ASCII text file via EFS-Web. The Sequence Listing is provided as a file entitled CANIG005NP.TXT, created and last saved on Mar. 3, 2016, which is 162,244 bytes in size, and updated by a file entitled CANIG005NPREPLACEMENT.TXT, created and last saved on Jun. 16, 2016, which is 162,299 bytes in size, and updated by a file entitled CANIG005NPREPLACEMENT2.TXT, created and last saved on Sep. 12, 2016, which is 203,947 bytes in size. The information in the electronic format of the Sequence Listing is incorporated herein by reference in its entirety in accordance with 35 U.S.C. §1.52(e).

FIELD OF THE INVENTION

Aspects of the present invention generally relate to compositions that interact with molecules, which suppress the immune system. More specifically, embodiments described herein concern the discovery, manufacture, and use of compositions that modulate the immune system.

BACKGROUND OF THE INVENTION

The immune system is finely tuned to detect and eradicate foreign molecules and, at the same time, avoid over reactivity, which could result in destruction of normal tissues resulting in autoimmune or chronic inflammatory diseases. The initiation of a specific immune response is a well-orchestrated chain of events culminating in the activation of effector functions, such as the release of cytokines, production of specific antibodies and/or cellular cytotoxic activity.

The role of the immune system in human cancer has been under debate for several years. It has been puzzling, for example, that an increased incidence of malignant tumors is not observed in immunocompromised animals, such as nude mice. These animals are not as profoundly immunocompromised as one would expect, since they are able to mount significant anti-tumor immune reactivity. When severely immunocompromised transgenic mice of the Stat 1 −/−, IFNγR −/−, or RAG2 −/− genotypes were studied, the tumor incidence and the immunogenicity of cancers growing in these animals strongly supported the existence of an immune mediated anti-cancer reactivity with the capacity to control cancer development. Based on these results, the immuno-editing model was developed (Dunn and Schreiber, Immunity, 21:137-148 (2004)).

Similarly, the modest increase in cancer incidence in therapeutically immunosuppressed, allo-organ transplanted patients seems to be explained by the early appearance of immunosuppression in epithelial cancers (Schüle J, et al., Breast Cancer Res Treat. 2002; 74:33-40; Wolfram R M, et al., Int J Cancer. 2000; 88:239-44, Petersen R P, et al., Cancer. 2006; 107:2866-72). The occurrence of spontaneous immune-mediated tumor regression, the correlation between tumor-infiltrating lymphocytes and prognosis, the occurrence of tumor specific cytotoxic T-lymphocytes and antibodies and the efficacy of immunostimulatory treatment all support a significant role of the immune system in the control or regulation of cancer progression.

These observations are also consistent with the results of Clinchy et al. (Clinchy B, et al., Cancer. 2007; 109:1742-9), showing that dysregulation of the immune system in cancer, with an enhanced capacity to produce IL-6, correlate to poor prognosis in radically resected colorectal cancer patients. Not even in the group of high risk patients with locally advance tumors, T3N1-2, did patients die from their cancer if their immune cells exhibited a normal production of IL-6. Similarly, Galon et al. (Galon J, et al., Science. 2006; 313:1960-4, Mlecnik B, et al., J Clin Oncol. 2011, 29:610-8) have shown that T-cell immune parameters strongly correlate to the prognosis in these patients.

The majority of human cancers of different origin induce immune mediated anti-tumor reactivity, but immunosuppressor mechanisms often appearing at an early stage, compromise the immune system. The existence of regional immunosuppression in the absence of systemic suppression (concomitant immunity), indicates a regional, systemic gradient of immunosuppression (Gorelik E., et al., Adv Cancer Res. 1983; 39:71-120). For instance, the function of immune cells can be more impaired near the tumor than in peripheral blood (Vose B M, et al., Int J Cancer 1977 20:895-902). Several factors may mediate this suppression (Ménétrier-Caux C, et al., Br J Cancer 1999 79: 119-130, Heimdal J H, et al., Scand J Immunol 2000 51: 271-278, Heimdal J H, et al., Scand J Immunol 2001 53: 162-170), but no fundamental mechanism has been identified (Kim R, et al., Cancer Res. 2006 Jun. 1; 66(11):5527-36, Mocellin S, et al., J Immunother 2001 24:392-407). The impact of the hostile intratumoral milieu has been described by several groups (Perdrizet G A, et al., J Exp Med. 1990; 171:1205-20, Yu P, et al., J Exp Med. 2005 201:779-91.) Immune reactivity against cancer can be suppressed at various levels, e.g., initiation, recruitment of effector cells to the tumor and migration of these cells within the tumor and their cytotoxic activity. Effector mechanisms present at the tumor site can also provide immune mediated cancer control.

Although data indicate that the immune system is of major importance for cancer control (Dunn G P, et al., Immunity. 2004 21:137-48, Galon J, et al., Science. 2006 313:1960-4, Koebel C M, et al., Nature. 2007 450:903-7, Clinchy B, et al., Cancer. 2007 109:1742-9, Teng M W, et al., J Leukoc Biol. 2008 84:988-93) malignant tumors continue to grow and the efficacy of immunotherapy is rather poor with an objective remission rate of 10-20%. There can be several reasons for this apparent paradox, e.g., tumors avoid recognition by the immune system due to tumor antigens being weak self-antigens, poor antigen presentation due to down-regulation of TAP and MHC I and II) or induction of tolerance or cancer related immunosuppression. The impact of an hostile intra-tumoral milieu is demonstrated by results from animal experiments (Perdrizet G A, et al., J Exp Med. 1990; 171:1205-20, Yu P, et al., J Exp Med. 2005 201:779-91.) and human tumors (Gajewski T F, et al., J Immunother. 2006 29:233-40, Whiteside T L, Oncogene. 2008 27:5904-12).

Different types of immunosuppressor cells, regulatory T-cells, immature dendritic cells (iDC), tumor associated macrophages (TAM) and myeloid derived suppressor cells (MDSC), can function substantially in cancer related immunosuppression. The immune balance is generally skewed to a Th2 dominance characterized by cytokines, such as IL-4, IL-10 and PGE2. Additionally, other immunosuppressor mechanisms, such as serum blocking factors, circulating immune complexes, enhanced IL-1Ra production and enhanced intra-tumoral proteolytic activity can function in cancer related immunosuppression.

While investigating mechanisms for induction of interleukin-6 (IL-6) in cancer patients, immunoregulatory peptide sequences derived from serum albumin were found (see e.g., U.S. Pat. Nos. 7,960,126; 8,110,347; and 8,110,347; as well as, US Publication No. 2010/0323370, each of which is hereby expressly incorporated by reference in their entireties. Interleukin-2 (IL-2) plays a major role in initiation and activation of the immune response and its capacity to induce lymphokine activated killer cells (LAK-cells), T-cell proliferation and cytotoxicity. Several reports have shown that peripheral blood mononuclear cells (PBMC) from cancer patients have a diminished capacity to both synthesize (Wanebo H J, et al., Cancer. 1986 57:656-62, Mantovani, G., et al., Diagn. Clin. Immunol. 1987 5: 104-111, Lauerova L, et al., Neoplasma 1999 46: 141-149) and respond to IL-2 (Tsubono M, et al., J Clin Lab Immunol 1990 33:107-115, Pellegrini P, et al., Cancer Immunol Immunother 1996 42:1-8). Soluble products from tumor explants or serum from cancer patients can inhibit cytokine production, inhibit IL-2 receptor expression (Botti C, et al., Intl J Biol Markers 1998 13:51-69, Lauerova L, et al., Neoplasma 1999 46:141-149) and/or reduce the proliferative capacity in normal T lymphocytes (Botti C, et al., Intl J Biol Markers 1998 13:51-69).

Integrins are a superfamily of transmembrane glycoproteins, found predominantly on leukocytes that mediate cell-cell and cell substratum interactions. Integrins play an important role in immune regulation, as well, in particular αLβ2, (Leukocyte Function Associated molecule-1, LFA-1) is of pivotal importance for the initiation and regulation of an immune response, tissue recruitment and migration of inflammatory cells and cytotoxic activity of lymphocytes (Hogg N, et al., J Cell Sci. 2003 116:4695-705, Giblin Pa., et al., Curr Pharm Des. 2006 12:2771-95, Evans R, et al., Cell Sci. 2009 122:215-25). In addition, LFA-1 is involved in the proliferative response to interleukin-2 (Vyth-Dreese F A, Eur J Immunol. 1993 12:3292-9) and some fragments of albumin bind to LFA-1 and/or the IL-2 receptor thereby modulating the functional properties mediated through these receptors including immune cell proliferation (see U.S. Publication No. 2011/0262470, which is hereby expressly incorporated by reference in its entirety). Despite these advancements, the need for more compositions to modulate the immune system, especially in individuals that have a compromised immune system and/or cancer, is manifest.

BRIEF SUMMARY OF THE INVENTION

Several molecules that regulate the immune system have been discovered. As described herein, many peptides (e.g., peptides obtained from enzymatically cleaved or denatured albumin and/or albumin fragments) bind to receptors (e.g., IL-2 and/or LFA-1 receptors) on human immune cells and thereby inhibit several immune cell functions or properties (e.g., lymphocyte proliferation, leukocyte spreading/migration, natural killer cell (NK-cell) cytotoxicity), which are central to maintaining a healthy immune system. Interestingly, a significantly enhanced degradation of albumin was found to occur when resistance to treatment developed in a mouse model (Culp W D, et al., J ProteomeRes. 2006; 5:1332-43). Accordingly, some embodiments include molecules that are or that structurally resemble or mimic albumin-derived immunoregulatory peptides or structures (e.g., synthetically derived mimics or analogs, or peptidomimetics), which bind to and/or interact with receptors on human immune cells and inhibit or suppress the immune system (e.g., reducing lymphocyte proliferation, leukocyte spreading/migration, and/or NK-cell cytotoxicity). Additionally, several molecules were developed that bind to and/or interact with albumin-derived immunoregulatory peptides or structures to inhibit the interaction of the albumin-derived immunoregulatory peptides or structures with receptors on human immune cells. For example, antibodies and peptides that bind to the albumin-derived immunoregulatory peptides or structures were made and these inhibitors of albumin-derived immunoregulatory peptides or structures were found to interfere with the ability of the albumin-derived immunoregulatory peptides or structures to inhibit or suppress immune cell function.

Preferred inhibitors of albumin-derived immunoregulatory peptides or structures, such as P28R (SEQ ID NO: 2) or P28 core (SEQ ID NO: 62), were identified using the methods and approaches described herein. The P28R and P28 core inhibitors, for instance, was found to de-block (e.g., displace bound immunoregulatory peptides or 3O28 structures from an immune cell receptor, such as LFA-1), remove or displace the albumin-derived immunoregulatory peptides or structures that were bound to or associated with immune cell receptors (e.g., LFA-1) and thereby restore normal immune cell function (e.g., immune cell proliferation in response to an inducer, such as IL-2, activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation). As such, it is contemplated herein that in accordance with some embodiments herein, P28R and P28 core can induce enhanced cytotoxicity, cytokine production, cell migration, and/or cell proliferation. P28R was also found to directly stimulate immune cells and induce cytotoxicity in tumor cells. It is contemplated that several other inhibitors of albumin-derived immunoregulatory peptides or structures can be developed using the teachings described herein. Accordingly, aspects of the invention include peptides, modified peptides, peptidomimetics, aptamers, antibodies, and fragments thereof, which bind to immunoregulatory structures, such as albumin-derived immunoregulatory peptides or structures, as well as, methods of manufacture, and methods of use thereof, in particular, methods to reduce immunosuppression in a subject in need thereof (e.g., immune suppression resulting from cancer or pathogenic, viral or bacterial, enduring or chronic infections, for example due to antibiotic resistance).

Some embodiments of the invention relates to a compositions that comprise an isolated peptide comprising Formula VII, wherein Formula VII is:

(SEQ ID NO: 394)
$X_{700}KX_{701}X_{702}X_{703}X_{704}X_{705}X_{706}KX_{707}X_{708}X_{709}X_{710}X_{711}$ $EX_{712}$ wherein X700 is K, A, D, E, G, H, I, L, M, N, P, Q, R, T, V, or K, or absent;

wherein X701 is L, A, C, D, E, F, G, H, I, K, M, N, Q, R, S, T, or V, or absent;

wherein X702 is D, A, E, I, V, W, or Y, or absent;

wherein X703 is T, C, M, N, P, Q, R, S, W, or Y, or absent;

wherein X704 is F, A, I, M, N, P, T, or V, or absent;

wherein X705 is F, L, M, Q, S, T or V, or absent;

wherein X706 is V, F, G, L, P, or R, or absent;

wherein X707 is L, A, F, G, I, M, N, P, Q, R, S, T, V, or Y, or absent;

wherein X708 is S, H, M, N, Q, or T, or absent;

wherein X709 is L, A, H, I, M, N, Q, R, S, T, V, or W, or absent;

wherein X710 is F, A, C, G, H, I, L, M, NP, Q, R, S, T, V, or W, or absent;

wherein X711 is T, F, G, H, I, L, M, N, P, S, V, or W, or absent; and wherein X712 is R, F, K, N, R, T, or Y, or absent.

Said formula VII may be one of SEQ ID NO: 1-101, 167-172, 174-177, 179-393, 396-581, or 582.

Some embodiments of the invention include compositions that comprise an isolated peptide comprising Formula VIII, wherein Formula VIII is:

$$X_{800}K\ X_{801}K\ X_{802}E\ X_{803} \quad \text{(SEQ ID NO: 395)}$$

wherein $X_{800}$ is K, A, D, E, G, H, I, L, M, N, P, Q, R, T, V, or K, or absent;

wherein $X_{801}$ is LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent;

wherein $X_{802}$ is LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent; and wherein $X_{803}$ is R, F, K, N, R, T, or Y, or absent.

Said formula VIII may be one of SEQ ID NOs: 1-34, 64-68, 70-72, 74-77, 80, 83, 86, 89, 92-96, 99-100, 264, 268-269, 270-386, 388-393, 396-401, 403, 404, 406, 408-411, 413-416, 419-420, 422-438, 442-444, 446-449, 451-453, 455-458, 460, 462-466, 470, 472-477, 479-480, 482-484, 486, 487, 489, 491-493, 495-498, 500-508, 512-517, 519-522, 528-530, 532, 533, 535-538, 540, 542-551, 553, 557-559, 567, 570, 572-581, or 582.

Some embodiments of the invention include compositions that comprise an isolated peptide comprising Formula I, wherein Formula I is:

$$XX_1VKX_2X_3X_4$$ (SEQ ID NO: 166)

wherein X is KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, Q, or absent.

wherein $X_1$ is FF, FM, FS, FV, FT, FL, AF, AM, AS, AV, AT, AL, VF, VM, VS, VV, VT, or VL, or absent;

wherein $X_2$ is LS, LQ, LM, LT, LH, VS, VQ, VM, VT, or VH, or absent;

wherein $X_3$ is LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR; and wherein $X_4$ is ER, E, or absent.

Said formula I may be one of SEQ ID NOs: 2-40, 46-52, 58-65, 67-71, 74-77, 80-83, 86-88, 92-96, 99-101, 166, 173, 178, 182, 268-325, 332-392-393, 396-415, 417-444, 446-468, 470-487, 489-494, 497-508, 510, 512, 514-517, 520-522, 524-525, 528-533, 535-536, 538-539, 542-544, 546, 548, 551, 553, 556-559, 561, 563-568, 571-573, 575-581 or 582, such as said formula I may be one of SEQ ID NOs: 2 to 33.

Some embodiments of the invention include compositions that comprise an isolated peptide comprising formula II, wherein formula II is $XTFFVKLSX_1X_2$ (SEQ ID NO: 173), wherein X is KKLD (SEQ ID NO: 174), RKLD (SEQ ID NO: 175), KKGD (SEQ ID NO: 176), KKED (SEQ ID NO: 177), KLD, LD, D, or absent wherein $X_1$ is LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent; and wherein $X_2$ is ER, or E, or absent, such as said formula II may be one of SEQ ID NO: 2-5, 19-38, 46-49, 58-61, 64, 68-70, 75, 81, 87, 93, 94, 100, 101, 173, 268-303, 350-393, 396, 398, 399, 400, 402, 403, 405, 406-408, 412-414, 417, 418, 421-423, 426-428, 430, 431, 435, 436, 438, 439, 440-442, 448-455, 458, 459, 461, 465, 467, 468, 471, 475, 476, 478-481, 483, 485, 487, 489-491, 493, 494, 497-499, 503, 507, 510, 512, 514-517, 520, 521, 524, 525, 528, 529, 531, 533, 538, 539, 542-, 544, 546, 551, 556-559, 561, 563-568, 571-573, 575-577, 579, 580, or 581. Other examples includes an isolated peptide, wherein X is KKLD (SEQ ID NO: 174) or wherein $X_2$ is ER or wherein said formula is TFFVKLSLFTER (SEQ ID NO: 49) or TFFVKLSLFTE (SEQ ID NO: 250) or wherein said formula is KKLDTFFVKLSLFTER (SEQ ID NO: 2) or KKLDTFFVKLSLFTE (SEQ ID NO: 34).

Some embodiments of the invention include compositions that comprise an isolated peptide comprising Formula III, wherein Formula III is:

$$XX_1VKLX_2LX_3TEX_4$$ (SEQ ID NO: 178)

wherein X is KKLDTF (SEQ ID NO: 179), KLDTF (SEQ ID NO: 180), LDTF (SEQ ID NO: 181), DTF, TF, or F, or absent;

wherein $X_1$ is F, M, S, V, T, or L, or absent;

wherein $X_2$ is S, Q, M, T, or H, or absent;

wherein X₃ is F, M, Q, H, N, P, S, G, A, or R, or absent; and wherein X₄ is R or absent.

Said formula III may be one of SEQ ID NO: 2-13, 15-18, 22-30, 34, 46-52, 58, 64, 65, 70, 71, 76, 77, 82, 83, 88, 93-96, 99, 100, 178, 268-325. Examples includes wherein X is KKLDTF (SEQ ID NO: 178) or wherein X4 is R or wherein said formula is VKLSLFTER (SEQ ID NO: 52) or VKLSLFTE (SEQ ID NO: 251) or wherein said formula is KKLDTFFVKLSLFTER (SEQ ID NO: 2) or KKLDTFFVKLSLFTE (SEQ ID NO: 34).

Other examples includes isolated peptides comprising at least one of SEQ ID NOs: 1-101, 167-172, 174-177, 179-393, 396-581 and 582 or at least one of SEQ ID NOs: 1-32, 34, 64-66, 68, 76, 94-96, 98, and 264-393 or at least one of the sequences of Table 5.1.

The above mentioned isolated peptides, may have at least one amino acid being a D amino acid, artificial amino acid, or chemically modified amino acid and/or comprise an N-terminal acetyl group and/or comprise a C-terminal amide group and/or be glycosylated or nitrosylated.

The above mentioned isolated peptides may be joined to at least one of polyethylene glycol, a fatty acid, or a pharmacokinetic modifier and/or comprises a cyclic peptide.

The above mentioned isolated peptides may comprise at least one modification, for example at least one of a D amino acid and/or a N-terminal acetyl group and/or a C-terminal amide group and/or glycosylation and/or nitrosylation and/or carbonylation and/or oxidation and/or a linked pharmacokinetic modifier and/or a linked polyethylene glycol or any combination thereof.

The above mentioned isolated peptides can be less than or equal to 1100 amino acids in length, such as between 7 amino acids and 20 amino acids in length.

The above mentioned isolated peptides may be joined to at least one of a support, a carrier, and/or a fusion protein.

The above mentioned isolated peptides may be multimerized.

The above mentioned peptides may comprise a detectable label joined thereto, such as a biotinylated label, a radioactive label, a fluorescent label, or a colloidal gold label and/or comprise a cytotoxic agent joined thereto, such as a radiochemical, or a toxin.

The above defined peptides may be less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 16, 15, 14, 13, 12, 11, 10, 9, 8, 7, 6 or 5 amino acids in length or any length in between any of these numbers.

Some embodiments of the invention relates to an isolated polynucleotide comprising a sequence encoding any of the peptides disclosed above, such as SEQ ID NOs: 2, 62, 102-165, 583-586, or 589. The invention also relates to a vector comprising the isolated polynucleotides. The peptides encoded by the isolated polynucleotide which may be present in a vector is less than or equal to 1100 amino acids in length, such as between 7 amino acids and 20 amino acids in length.

Some embodiments of the invention relates to a protein complex comprising any of the isolated peptides mentioned above bound to at least one of albumin, a fragment of albumin, a support, a carrier or a fusion protein. The invention also relates to a method of making the protein complex comprising:

contacting any of the above defined peptides with a biological sample obtained from a human subject, wherein said biological sample comprises albumin or a fragment thereof; and detecting the presence of said protein complex.

Said peptides may for examples be attached to a support.

Some embodiments of the invention relates to a method of detecting the presence of an albumin or an albumin fragment in a biological sample comprising:

contacting any of the above defined peptides with a biological sample that comprises albumin or a fragment thereof and detecting the binding of said peptide to said albumin or said albumin fragment.

In some embodiments, the invention relates to a binding means specific for the above defined peptides, wherein the binding means is an antibody, polyclonal or monoclonal or binding fragment thereof, such as functional fragments such as a single domain antibody such as the antibody may be a monoclonal antibody and the binding fragment may be a monoclonal antibody binding fragment.

In some embodiments, the invention relates to an aptamer that is specific for a peptide which comprises at least one of the sequences of Tables 1-4 (SEQ ID NOs: 183-184, and 188-246), such as the aptamer is specific for the peptide of the sequence VFDEFKPLVEEPQNLIK (SEQ ID NO: 185). The aptamer may for example be a DNA or a peptide aptamer.

In some embodiments, the invention relates to a method of inhibiting immunosuppression in a patient in need thereof, said method comprising:

identifying a patient having a condition associated with immunosuppression;

administering to the patient any of the above defined peptides and detecting an increase in leukocyte spreading in the patient. The peptide may be less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 16, 15, 14, 13, 12, 11, 10, 9, 8, 7, 6 or 5 amino acids in length or any length in between any of these numbers and the peptide may be synthetic. Administering of said peptide may comprise administering a composition consisting of at least 0.1% of the peptide by weight, for example, at least 0.1%, 0.2%, 0.5%, 1%, 2%, 3%, 4%, 5%, 6%, 7%, 8%, 9%, 10%, 20%, or 30% of the peptide by weight, including ranges between any two of the listed values. Said patient may suffer from cancer, a viral infection, or a bacterial infection, such as said cancer may be colorectal cancer, renal cancer, breast cancer, skin cancer, ovarian cancer, prostate cancer, pancreatic, lung, or hematopoietic cell cancer. The method may further comprise detecting an increase in lymphocyte migration.

In some embodiments the invention relates to a method of inhibiting binding of an albumin fragment to a receptor, the method comprising:

identifying a human suffering from immunosuppression;

contacting an immune cell with any of the peptides defined above; and detecting an increase in proliferation of the immune cell after contact with said peptide. The immune cell may for example be a lymphocyte or PBMC. The human may suffer from cancer, a viral infection, or a bacterial infection, such as said cancer may be colorectal cancer, renal cancer, breast cancer, skin cancer, ovarian cancer, prostate cancer, pancreatic, lung, or hematopoietic cell cancer.

In some embodiments the invention relates to a method of increasing NK-cell cytotoxicity comprising:
  identifying a human suffering from immunosuppression;
  contacting NK-cells with the any of the above defied peptides; and
  detecting an increase in cytotoxicity of said NK-cells after contact with said peptide as compared to a control sample, such as the cytotoxicity of NK-cells in the absence of said peptide or the cytotoxicity of NK-cells and an unrelated peptide. The human may suffer from cancer, a viral infection, or a bacterial infection, such as said cancer may be colorectal cancer, renal cancer, breast cancer, skin cancer, ovarian cancer, prostate cancer, pancreatic, lung, or hematopoietic cell cancer.

In some embodiments, the invention relates to a method of increasing human lymphocyte migration comprising:
  identifying a human suffering from immunosuppression;
  contacting human lymphocytes with any of the above defined peptides; and
  detecting an increase in migration of said human lymphocytes after contact with said peptide as compared to a control sample, such as the migration of human lymphocytes in the absence of said peptide or the migration of human lymphocytes and an unrelated peptide. The human may suffer from cancer, a viral infection, or a bacterial infection, such as said cancer may be colorectal cancer, renal cancer, breast cancer, skin cancer, ovarian cancer, prostate cancer, pancreatic, lung, or hematopoietic cell cancer.

In some embodiments the invention relates to a method of inhibiting the binding of a human albumin or a human albumin fragment to the LFA-1 receptor or the IL-2 receptor or both on human lymphocytes comprising:
  contacting human lymphocytes with any of the above defined peptides in the presence of human albumin or a human albumin fragment; and
  detecting an inhibition of binding of a human albumin or a human albumin fragment to the LFA-1 receptor or the IL-2 receptor or both on human lymphocytes as compared to a control sample, such as the binding of a human albumin or a human albumin fragment to the LFA-1 receptor or the IL-2 receptor or both on human lymphocytes in the absence of said peptide or the binding of a human albumin or a human albumin fragment to the LFA-1 receptor or the IL-2 receptor or both on human lymphocytes in the presence of an unrelated peptide. The human albumin fragment comprises a sequence with at least 95% identity to SEQ ID NO: 185, such as the human albumin fragment comprise the sequence of SEQ ID NO: 185.

In some embodiments the invention relates to a method of inhibiting the binding of a human albumin or a human albumin fragment to the LFA-1 receptor or the IL-2 receptor or both on human lymphocytes comprising:
  providing human lymphocytes, wherein at least one of the LFA-1 receptor and IL-2 receptor is bound to a human albumin of albumin fragment;
  specifically binding a molecule to the human albumin or albumin fragment; and
  detecting an decrease of inhibition of stimulation of the human lymphocytes via the LFA-1 receptor, IL-2 receptor. The human albumin fragment comprises a sequence with at least 95% identity to SEQ ID NO: 185, such as the human albumin fragment comprise the sequence of SEQ ID NO: 185.

In some embodiments, the invention relates to a method of binding cancer cells with a peptide comprising:
  contacting cancer cells with any of the above defined peptides; and
  detecting the binding of said peptide to said cancer cells. Said cancer may be colorectal cancer cells, renal cancer cells, breast cancer cells, skin cancer cells, ovarian cancer cells, prostate cancer cells, pancreatic cancer cells, lung cancer cells, renal cancer cells, malignant melanoma cells, or hematopoietic cancer cells. Said peptide may comprise a detectable label joined thereto, such as a biotinylated label, a radioactive label, a fluorescent label, or a colloidal gold label and/or comprises a cytotoxic agent joined thereto, such as a radiochemical, or a toxin and/or an antibody or antibody fragment or functional fragment thereof.

In some embodiments, the invention relates to a method of inhibiting the proliferation of human cancer cells comprising:
  identifying a human cancer patient;
  contacting immune cells of the human cancer patient with any of the above defined peptides; and
  detecting an inhibition of proliferation of cancer cells of the patient or an induction of cell death of cancer cells of the patient. An inhibition of proliferation of cancer cells of the patient may for example be detected and/or an induction of cell death of cancer cells of the patient may be detected. The cancer may for example be colorectal cancer cells, renal cancer cells, breast cancer cells, skin cancer cells, ovarian cancer cells, prostate cancer cells, pancreatic cancer cells, lung cancer cells, renal cancer cells, malignant melanoma cells, or hematopoietic cancer cells. For example an increase in the proliferation of immune cells of the human may be detected. The immune cells may be lymphocytes or PBMC. The peptide use in the method may be synthetic.

In some embodiments the invention relates to a method of removing a ligand bound to the LFA-1 receptor of human lymphocytes comprising:
  contacting human lymphocytes with any of the above defined peptides; and
  detecting a reduced binding of a ligand for the LFA-1 receptor. Said human lymphocytes may be from a patient with cancer, a bacterial infection or a viral infection such as a patient suffering from breast cancer, renal cell carcinoma, skin cancer, ovarian cancer, prostate cancer, pancreatic, lung, or hematopoietic cell cancer.

In some embodiments, the invention relates to a method of removing a ligand bound to the IL-2 receptor of human lymphocytes comprising:
  contacting human lymphocytes with any of the above defined peptides; and
  detecting a reduced binding of a ligand for the IL-2 receptor. Said human lymphocytes may be from a patient with cancer, a bacterial infection or a viral infection such as a patient suffering from breast cancer, renal cell carcinoma, skin cancer, ovarian cancer, prostate cancer, pancreatic, lung, or hematopoietic cell cancer.

In some embodiments, the invention relates to a method of reducing immunosuppression in a human that is immunosuppressed comprising:
  providing to a human, a peptide as defined above; and
  detecting a reduction of immunosupression in said human such as by detecting an activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation. Said human may have cancer, a bacterial infection or a viral infection, such as said cancer is breast cancer, renal cell carcinoma, skin cancer, ovarian cancer, prostate cancer, pancreatic, lung, or hematopoietic cell cancer. Said peptide may be administered to said human as a composition consisting of at least at least 0.1% of the peptide by weight, for example, at least 0.1%, 0.2%, 0.5%, 1%, 2%, 3%, 4%, 5%, 6%, 7%, 8%, 9%, 10%, 20%, or 30% of the peptide by weight, including ranges between any two of the listed values. In some embodiments, detection in immunosuppression comprises detecting one or more of enhanced cytotoxicity, cytokine production, cell migration, and/or cell proliferation.

In some embodiments the invention relates to a method of inhibiting the binding of a human albumin or a human albumin fragment to the LFA-1 receptor or the IL-2 receptor or both on human lymphocytes comprising:
  providing a human the polynucleotide or vector as defined above; and
  detecting an inhibition of binding of a human albumin or a human albumin fragment to the LFA-1 receptor or the IL-2 receptor or both.

In some embodiments, the invention relates to a method of inhibiting the proliferation of human cancer cells comprising:
  providing the polynucleotide or vector as defined above to a human that has cancer cells; and
  detecting an inhibition of proliferation of said cancer cells.

In some embodiments, the invention relates to a method of removing a ligand bound to the LFA-1 receptor or IL-2 receptor or both of human lymphocytes comprising:
  contacting human lymphocytes with the polynucleotide or vector as defined above; and
  detecting a reduced binding of a ligand for the LFA-1 receptor or the IL-2 receptor or both.

In some embodiments, the invention relates to a method of reducing immunosuppression in a human that is immunosuppressed comprising:
  providing the polynucleotide or vector as defined above to said human; and
  detecting a reduction of immunosupression in said human such as by detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. In some embodiments, detecting a reduction of immunosuppression comprises detecting one or more of enhanced cytotoxicity, cytokine production, cell migration, and/or cell proliferation.

In some embodiments, the invention relates to a pharmaceutical composition comprising:
  any of the above defined peptides; and
  a pharmaceutically acceptable carrier, excipient, or diluent. The peptide comprises at least one of SEQ ID NOs: 1-33, 34, 46-53, 62, 64-66, 68, 76, 94-96, 98, 583-586 or 589.

In some embodiments, the invention relates to a method for identifying a patient in need of treatment with an inhibitor of immunoregulatory peptides or structures, the method comprising:
  contacting immune cells of the patient in vitro with any of the above defined peptides;
  detecting an inhibition of proliferation of said immune cells;
  classifying the patient as likely to respond to treatment with the inhibitor of immunoregulatory peptides or structures if said peptide inhibits proliferation of said immune cells. The method may for example further comprise reducing immunosuppression in the patient in need, wherein reducing immunosuppression comprises providing to the patient in need, a peptide as defined above and/or further comprise detecting a reduction of immunosupression in said human and/or further comprising reducing immunosuppression in the patient in need, wherein reducing immunosuppression comprises providing to the patient in need, a vector or polynucleotide as defined above and/or further comprising detecting a reduction of immunosupression in said human.

In another embodiment the invention relates to an isolated peptide, wherein said peptide comprises an amino acid residue homologous to amino acid residue K2 of SEQ ID NO: 2 and/or, wherein said peptide comprises an amino acid residue homologous to amino acid residue K9 of SEQ ID NO: 2 and/or, wherein said peptide comprises an amino acid residue homologous to amino acid residue E15 of SEQ ID NO: 2.

The above defined peptides may comprise at least one modification, for example at least one non-naturally occurring amino acid and/or comprises at least one D amino acid, an N-terminal acetyl group, a C-terminal amide group, glycosylation, nitrosylation, a linked pharmacokinetic modifier, or a linked polyethylene glycol Any of the above defined peptides may have a length being less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 16, 15, 14, 13, 12, 11, 10, 9, 8, 7, 6 or 5 amino acids in length or a length between any two of these numbers, such as between 6 amino acids and 20 amino acids in length, between 7 amino acids and 20 amino acids in length preferably between 8-16 amino acids in length, and most preferably between 9 and 15 amino acids in length. Any of the above defined peptides may be joined to a support as well as multimerized.

In another embodiment the invention relates to an isolated polynucleotide comprising a sequence encoding any of the above defined peptides as well as vectors comprising the isolated polynucleotide as well as a protein complex comprising albumin or a fragment of albumin bound to any of the above defined peptides. The protein complex may be bound to a support.

Some embodiments of the invention include compositions that comprise an isolated peptide comprising, consisting of or consisting essentially of Formula (I), $XX_1VKX_2X_3X_4$ (SEQ ID NO: 166). In some embodiments, this isolated peptide has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ can be one of LS, LQ, LM, LT, LH, VS, VQ, VM, VT, or VH. In some embodiments, $X_3$ can be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, E, or absent. In some embodiments, if X is absent, $X_1$ is FF, and $X_2$ is LS. In some embodiments, the peptide comprises one of SEQ ID NOs: 2-33.

Some embodiments of the invention include compositions that comprise an isolated peptide comprising, consisting of or consisting essentially of formula (II), $X_{20}$TFFVKLSX$_{21}$X$_{22}$ (SEQ ID NO: 173). In some embodiments, this isolated peptide has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, MRR, or absent. In some embodiments, $X_{22}$ is an optional sequence, and can be ER, E, or absent.

Some embodiments of the invention include compositions that comprise an isolated peptide comprising, consisting of or consisting essentially of Formula (III), $X_{30}X_{31}$VKLX$_{32}$LX$_{33}$TEX$_{34}$ (SEQ ID NO: 178). In some embodiments, this isolated peptide has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, $X_{30}$ is an optional sequence, and can be KKLDTF (SEQ ID NO: 179), KLDTF (SEQ ID NO: 180), LDTF (SEQ ID NO: 181), DTF, TF, F, or absent. In some embodiments, $X_{31}$ is an optional sequence, and can be F, S, M, V, T, L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R, or absent.

Some embodiments of the invention include compositions that comprise an isolated peptide comprising, consisting of or consisting essentially of Formula (VII), $X_{700}$K $X_{701}$ $X_{702}X_{703}$ $X_{704}X_{705}X_{706}$K $X_{707}$ $X_{708}$ $X_{709}$ $X_{710}$ $X_{711}$E $X_{712}$ (SEQ ID NO: 394). In some embodiments, this isolated peptide has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T or V, or absent. In some embodiments, $X_{706}$ is an optional sequence, and can be V, F, G, L, P, R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent.

Some embodiments of the invention include compositions that comprise an isolated peptide comprising, consisting of or consisting essentially of Formula (VIII), $X_{800}K\ X_{801}K\ X_{802}E\ X_{803}$ (SEQ ID NO: 395). In some embodiments, this isolated peptide has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTYFV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent.

Some embodiments of the invention include compositions that comprise an isolated peptide comprising, consisting of or consisting essentially of any one or more of the peptides set forth in Table 5.1. In some embodiments, this isolated peptide has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments of the invention include compositions that comprise an isolated polynucleotide comprising, consisting of or consisting essentially of isolated polynucleotides encoding a peptide inhibitor (e.g., any one or more of the peptides described above) of an albumin-derived immunoregulatory peptide or structure, as described herein. Some embodiments include vectors that include such isolated polynucleotides. Some embodiments also include protein complexes, which comprise an albumin or albumin fragment bound to an inhibitor of one or more albumin-derived immunoregulatory peptides or structures, as described herein.

In some embodiments, any of the compositions described above comprises a buffer selected from the group consisting of: Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

Some embodiments include methods of making the protein complexes as described herein. The methods can include contacting a peptide as describe herein with a biological sample from a human. In some embodiments, the biological sample includes an albumin or an albumin fragment. The methods can include detecting the presence of the protein complex.

Some embodiments of the invention include methods of detecting the presence of an albumin or an albumin fragment in a biological sample. The methods can include contacting a peptide inhibitor (e.g., an inhibitor of one or more albumin-derived immunoregulatory peptides or structures, as described herein) with a biological sample that includes an albumin or an albumin fragment. The methods can include detecting the binding of the albumin or albumin fragment to the inhibitor of one or more albumin-derived immunoregulatory peptides or structures, as described herein. Some embodiments of the invention include antibodies or binding fragment thereof that are specific for one or more albumin-derived immunoregulatory peptides or structures, as described herein.

Some embodiments of the invention include aptamers that are specific for and bind to a peptide having the sequence VFDEFKPLVEEPQNLIK (SEQ ID NO: 185) or a fragment thereof. Some embodiments of the invention include aptamers that are specific for and bind to any of the immunoregulatory peptides described herein (e.g., any one of the peptides described in the tables provided herein). In some embodiments, the aptamers are oligonucleotide aptamers. In some embodiments, the aptamers are peptide aptamers.

Some embodiments of the invention include methods of addressing a patient suffering from immunosuppression, such as immunosupression resulting from cancer, or infection by a pathogenic, viral or bacterial, enduring or chronic infections, for example due to antibiotic resistance. Such approaches include methods of treating immunosuppression or inhibiting an aspect of or marker for immunosuppression, such as a reduced immune cell proliferation, reduced NK-cell cytotoxicity, or reduced leukocyte migration or methods of treating a viral or bacterial disease (e.g., methods of treating or inhibiting a chronic viral infection such as hepatitis or a bacterial infection such as that caused by *Staphylococcus, Streptococcus, Psuedomonas*, or other pathogenic bacteria. The methods can include identifying a patient having a condition associated with immunosuppression such as cancer or a bacterial or viral infection or an enduring or chronic bacterial or viral infection. The methods can include administering to the identified patient one or more of the peptide inhibitors (e.g., an inhibitor of one or more albumin-derived immunoregulatory peptides or structures), as described herein and, optionally, detecting activation or stimulation of an immune cell, as evidenced by an increase in CD69 or CD71 expression, induction of the secretion of a signal substance, as evidenced by interferon gamma or IL-12 production, stimulation of the release of a cytolytic substance, as evidenced by the release of granzyme B or perforin, enhanced cytotoxicity, cytokine production, cell migration, and/or cell proliferation. The methods can also include detecting an increase in leukocyte spreading in the patient. Some of these methods can include, for example, compositions that comprise an isolated peptide comprising, consisting of or consisting essentially of any one or more of the peptides set forth in Table 5.1 or 5.4, or a peptide comprising, consisting of, or consisting essentially of SEQ ID NO: 2, 62, 584, or 589. In some embodiments, the isolated peptide from Table 5.1 or 5.4 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments of the invention include methods of inhibiting binding of an albumin fragment to a receptor. The methods can include identifying a human that has immunosuppression. The methods can include contacting an immune cell with a peptide (e.g., an inhibitor of one or more albumin-derived immunoregulatory peptides or structures), as described herein. Serum of the human can be present when the immune cell is contacted with the inhibitor. The methods can include detecting an increase in proliferation of the immune cell or activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin after contact with the inhibitor of one or more albumin-derived immunoregulatory peptides or structures, as described herein. In some embodiments, the methods comprise detecting one or more of enhanced cytotoxicity, cytokine production, cell migration, and/or cell proliferation.

Some embodiments of the invention include methods of increasing NK-cell or lymphocyte cytotoxicity in the presence of autologous human serum. The methods can include identifying a human that has immunosuppression. The methods can include contacting NK-cells with a peptide as described herein (e.g., an inhibitor of one or more albumin-derived immunoregulatory peptides or structures) in the presence of serum of the human. The methods can include detecting an increase in cytotoxicity of said NK-cells after contact with the inhibitor, as compared to a control sample. Control samples can include the cytotoxicity of NK-cells in the presence of autologous human serum in the absence of said inhibitor or the cytotoxicity of NK-cells in the presence of autologous human serum and an unrelated peptide.

Some embodiments of the invention include methods of increasing human lymphocyte functions, such as migration in the presence of autologous human serum or activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation. The methods can include identifying a human suffering from immunosuppression. The methods can include contacting human lymphocytes with a peptide as described herein (e.g., an inhibitor of one or more albumin-derived immunoregulatory peptides or structures) in the presence of serum of the human. The methods can include detecting an increase in migration of said human lymphocytes or activation or stimulation of an immune cell, as evidenced by an increase in CD69 or CD71 expression, induction of the secretion of a signal substance, as evidenced by interferon gamma or IL-12 production, stimulation of the release of a cytolytic substance, as evidenced by the release of granzyme B or perforin, enhanced cytotoxicity, cytokine production, cell migration, and/or cell proliferation after contact with the inhibitor, as compared to a control sample. Control samples can include the migration of human lymphocytes in the presence of autologous human serum in the absence of the inhibitor or the migration of human lymphocytes in the presence of autologous human serum and an unrelated peptide. In some embodiments, the methods comprise As detecting enhanced cytotoxicity, cytokine production, cell migration, and/or cell proliferation.

Some embodiments of the invention include methods of inhibiting the binding of a human albumin or a human albumin fragment to cell receptors, such as the LFA-1 receptor or the IL-2 receptor or both, on human lymphocytes. The methods can include contacting human lymphocytes with a peptide as describe herein (e.g., an inhibitor of one or more albumin-derived immunoregulatory peptides or structures) in the presence of human albumin or a human albumin fragment. The methods can include detecting an inhibition of binding of a human albumin or a human albumin fragment to the LFA-1 receptor or the IL-2 receptor or both on human lymphocytes, as compared to a control sample. Control samples can include the binding of a human albumin or a human albumin fragment to the LFA-1 receptor or the IL-2 receptor or both on human lymphocytes in the absence of said inhibitor or the binding of a human albumin or a human albumin fragment to the LFA-1 receptor or the IL-2 receptor or both on human lymphocytes in the presence of an unrelated peptide.

Some embodiments of the invention include methods of inhibiting the binding of a human albumin or a human albumin fragment to the LFA-1 receptor or the IL-2 receptor or both on human lymphocytes. The methods can include providing human lymphocytes. In some embodiments, at least one of the LFA-1 receptor or IL-2 receptor is bound to a human albumin of albumin fragment. The methods can include specifically binding an inhibitor (e.g., an inhibitor of one or more albumin-derived immunoregulatory peptides or structures, as described herein) to the human albumin or albumin fragment. The methods can include detecting a decrease of inhibition of stimulation of the human lymphocytes via the LFA-1 receptor, IL-2 receptor or activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. In some embodiments, the methods detecting enhanced cytotoxicity, cytokine production, cell migration, and/or cell proliferation.

Some embodiments of the invention include methods of binding cancer cells with a molecule that specifically interacts with said cancer cells (e.g., an inhibitor of one or more albumin-derived immunoregulatory peptides or structures, as described herein). The methods can include contacting cancer cells with one or more of the inhibitors, as described herein. In some embodiments, the method comprises an ex vivo or in vitro method. In some embodiments, the method comprises an in vivo method. In some embodiments, the inhibitor is administered peri-tumorally, or near a tumor of a patient, for example within 10 cm, 9, 8, 7, 6, 5, 4, 3, 2, 1, or 0.5 cm of the tumor. In some embodiments, the inhibitor is administered systemically. In some embodiments, the inhibitor is administered in conjunction with a second therapeutic agent, for example a therapeutic agent selected to stimulate an immune cell after an LFA-1 receptor of the immune cell has been de-blocked, or a therapeutic agent selected to stimulate an immune cell after an IL-2 receptor of the immune cell has been de-blocked. The methods can include detecting the binding of said inhibitor to said cancer cells.

Some embodiments of the invention include methods of inhibiting the proliferation of human cancer cells. The methods can include identifying a human cancer patient. The methods can include contacting immune cells of the human cancer patient with an inhibitor (e.g., an inhibitor of one or more albumin-derived immunoregulatory peptides or structures, as described herein). In some embodiments, the inhibitor is administered peri-tumorally, or near a tumor of the patient, for example within 10 cm, 9, 8, 7, 6, 5, 4, 3, 2, 1, or 0.5 cm of the tumor. In some embodiments, the inhibitor is administered systemically. In some embodiments, the inhibitor is administered in conjunction with a second therapeutic agent, for example a therapeutic agent selected to stimulate an immune cell after an LFA-1 receptor of the immune cell has been de-blocked. The methods can include detecting an inhibition of proliferation of cancer cells of the patient or an induction of apoptosis or cell death of cancer cells of the patient. Optionally, the method can include co-administering at least one additional therapeutic agent, for example a therapeutic agent that stimulates the activation of immune cells (e.g. enhanced expression of CD69 and/or CD71, secretion of IL-12 of IFNγ, or secretion of perforin or granzyme B, enhanced cytotoxicity, cytokine production, cell migration, and/or cell proliferation) directly or indirectly through the LFA-1 receptor. In some embodiments, the additional therapeutic agent stimulates one or more of enhanced cytotoxicity, cytokine production, cell migration, and/or cell proliferation.

Some embodiments of the invention include methods of removing a ligand bound to the LFA-1 receptor of human lymphocytes. The methods can include contacting human lymphocytes with an inhibitor (e.g., an inhibitor of one or more albumin-derived immunoregulatory peptides or structures, as described herein). The methods can include detecting a reduced binding of a ligand for the LFA-1 receptor.

Some embodiments of the invention include methods of removing a ligand bound to the IL-2 receptor of human lymphocytes. The methods can include contacting human lymphocytes with an inhibitor (e.g., an inhibitor of one or more albumin-derived immunoregulatory peptides or structures, as described herein). The methods can include detecting a reduced binding of a ligand for the IL-2 receptor or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. In some embodiments, the methods comprise detecting one or more of enhanced cytotoxicity, cytokine production, cell migration, and/or cell proliferation.

Some embodiments of the invention include methods of reducing immunosuppression in a human that is immunosuppressed. The methods can include providing to a human, a an inhibitor, as described herein (e.g., an inhibitor of one or more albumin-derived immunoregulatory peptides or structures). The methods can include detecting a reduction of immunosuppression in the human or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. In some embodiments, the methods comprise detecting one or more of enhanced cytotoxicity, cytokine production, cell migration, and/or cell proliferation.

Some embodiments of the invention include methods of inhibiting the binding of a human albumin or a human albumin fragment to the LFA-1 receptor or the IL-2 receptor or both on human lymphocytes. The methods can include providing a human with one or more of the polynucleotides and/or vector as described herein (e.g., a polynucleotide or vector having a sequence encoding one or more of the inhibitors of the albumin-derived immunoregulatory peptides or structures). The methods can include detecting an inhibition of binding of a human albumin or a human albumin fragment to the LFA-1 receptor or the IL-2 receptor or both or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. Optionally, the method can include detecting one or more of enhanced cytotoxicity, cytokine production, cell migration, and/or cell proliferation. Optionally, the method can include co-administering at least one additional therapeutic agent, for example a therapeutic agent that stimulates the activation of immune cells (e.g. enhanced expression of CD69 and/or CD71, secretion of IL-12 of IFNγ, secretion of perforin or granzyme B, enhanced cytotoxicity, cytokine production, cell migration, and/or cell proliferation) directly or indirectly through the LFA-1 receptor. The additional therapeutic agent can be administered concurrently with, or after the inhibitor. In some embodiments, the second therapeutic agent stimulates one or more of enhanced cytotoxicity, cytokine production, cell migration, and/or cell proliferation.

Some embodiments of the invention include methods of inhibiting the proliferation of human cancer cells. The methods can include providing a human that has cancer with one or more of the polynucleotides or vector as described herein (e.g., a polynucleotide or vector having a sequence encoding one or more of the inhibitors of the albumin-derived immunoregulatory peptides or structures). In some embodiments, the inhibitor is administered peri-tumorally, or near a tumor of the patient, for example within 10 cm, 9, 8, 7, 6, 5, 4, 3, 2, 1, or 0.5 cm of the tumor. In some embodiments, the inhibitor is administered systemically. In some embodiments, the inhibitor is administered in conjunction with a second therapeutic agent, for example a therapeutic agent selected to stimulate an immune cell after an LFA-1 receptor of the immune cell has been de-blocked. The methods can include detecting an inhibition of proliferation of said cancer cells or detecting activation or stimulation of an immune cell, as evidenced by an increase in CD69 or CD71 expression, induction of the secretion of a signal substance, as evidenced by interferon gamma or IL-12 production, stimulation of the release of a cytolytic substance, as evidenced by the release of granzyme B or perforin, enhanced cytotoxicity, cytokine production, cell migration, or cell proliferation. In some embodiments, the methods comprise detecting one or more of enhanced cytotoxicity, cytokine production, cell migration, and/or cell proliferation.

Some embodiments of the invention include inducing infiltration of a cancer by immune cells. The methods can include administering a peptide inhibitor as described herein peri-tumorally, or near a tumor of a patient, for example within 10 cm, 9, 8, 7, 6, 5, 4, 3, 2, 1, or 0.5 cm of the tumor. The methods can include detecting an infiltration of the cancer by immune cells.

Some embodiments of the invention include methods of removing a ligand bound to the LFA-1 receptor or IL-2 receptor or both of human lymphocytes. The methods can include providing a human with one or more of the polynucleotides or vector as described herein (e.g., a polynucleotide or vector having a sequence encoding one or more of the inhibitors of the albumin-derived immunoregulatory peptides or structures). The methods can include detecting a reduced binding of a ligand for the LFA-1 receptor or the IL-2 receptor or both.

Some embodiments of the invention include methods of reducing immunosuppression in a human that is immunosuppressed. The methods can include providing a human with one or more of the polynucleotides or vector as described herein (e.g., a polynucleotide or vector having a sequence encoding one or more of the inhibitors of the albumin-derived immunoregulatory peptides or structures). The methods can include detecting a reduction of immunosuppression in the human such as detecting activation or stimulation of an immune cell, as evidenced by an increase in CD69 or CD71 expression, induction of the secretion of a signal substance, as evidenced by interferon gamma or IL-12 production, stimulation of the release of a cytolytic substance, as evidenced by the release of granzyme B or perforin, enhanced cytotoxicity, cytokine production, cell migration, and/or cell proliferation. In some embodiments, the methods comprise detecting one or more of enhanced cytotoxicity, cytokine production, cell migration, and/or cell proliferation.

Some embodiments of the invention include pharmaceutical compositions. The pharmaceutical compositions can include one or more of the polynucleotides or vector as described herein (e.g., a polynucleotide or vector having a sequence encoding one or more of the inhibitors of the albumin-derived immunoregulatory peptides or structures) and/or one or more of the inhibitors described herein (e.g., a peptide inhibitor of one or more albumin-derived immunoregulatory peptides or structures, as described herein). The pharmaceutical compositions can include a pharmaceutically acceptable carrier or diluent.

Some embodiments of the invention include methods for identifying a patient in need of inhibition of immunoregulatory peptides. The patient can have albumin-derived immunoregulatory peptides or structures bound to his or her immune cells, and/or can be likely to respond to treatment with an inhibitor of the albumin-derived immunoregulatory peptides or structures. The diagnostic method can include contacting immune cells of the patient in vitro with at least one inhibitor of immunoregulatory peptides or structures. The diagnostic method can include classifying the patient as having immunoregulatory peptides or structures, and/or as likely to respond to treatment with an inhibitor of immunoregulatory peptides or structures when the block of immunoregulatory peptides or structures increases restoration of immune parameters or improves immune response, for example, proliferation or response by the PBMCs of said subject. The method can include determining which inhibitor or inhibitors of immunoregulatory peptides have immunomodulatory activity in the patient.

Some embodiments of the invention include an isolated peptide comprising the amino acid sequence FFVKLS (SEQ ID NO: 62), wherein the isolated peptide comprises no more than 30 amino acid residues. In some embodiments, the isolated peptide comprises no more than 29 amino acid residues, for example, no more than 28 amino acids residues, 27, 26, 25, 24, 23, 22, 21, 20, 19, 18, 17, 16, 15, 14, 13, 12, 11, 10, 9, 8, 7, or 6 amino acid residues or a range defined by any two of these numbers. In some embodiments, the isolated peptide comprises no more than 16 amino acid residues. In some embodiments, the isolated peptide comprises no more than 8 amino acid residues. In some embodiments, the isolated peptide consists of or consists essentially of the amino acid sequence FFVKLS (SEQ ID NO: 62).

Some embodiments of the invention include an isolated peptide comprising the amino acid sequence KKLDTFFVKLSLFTER (SEQ ID NO: 2). In some embodiments, the isolated peptide comprises no more than 100 amino acid residues, for example no more than 99, 90, 80, 70, 60, 50, 40, 30, or 20 amino acid residues or a range defined by any two of these numbers. In some embodiments, the isolated peptide comprises no more than 30 amino acid residues. In some embodiments, the isolated peptide consists of the amino acid sequence of SEQ ID NO: 2.

Some embodiments of the invention include an isolated peptide comprising the amino acid sequence RKLDTFFVKLSLFTERRR (SEQ ID NO: 586). In some embodiments, the isolated peptide comprises no more than 100 amino acid residues, for example no more than 99, 90, 80, 70, 60, 50, 40, 30, or 20 amino acid residues or a range defined by any two of these numbers. In some embodiments, the isolated peptide comprises no more than 30 amino acid residues. In some embodiments, the isolated peptide consists of the amino acid sequence of SEQ ID NO: 586.

Some embodiments of the invention include an isolated peptide comprising the formula $X_1X_2X_3X_4X_5X_6X_7X_8X_9X_{10}X_{11}X_{12}X_{13}X_{14}X_{15}X_{16}X_{17}$; in which $X_1$ is any amino acid or is absent; $X_2$ is a positively charged amino acid, F, or N; $X_3$ is any amino acid; $X_4$ is any amino acid; $X_5$ is a polar uncharged amino acid, R, Y, or W; $X_6$ is a hydrophobic or uncharged polar amino acid; $X_7$ is a hydrophobic or uncharged polar amino acid; $X_8$ is a hydrophobic, non-aromatic carbon chain amino acid that is not M or F; $X_9$ is a positively charged amino acid, T, Q, or Y; $X_{10}$ is any amino acid that is not negatively charged; $X_{11}$ is a polar uncharged amino acid or H; $X_{12}$ is any amino acid that is not negatively charged; $X_{13}$ is any amino acid that is not negatively charged; $X_{14}$ is any amino acid that is not negatively charged; $X_{15}$ is a negatively charged amino acid, Y, or Q; $X_{16}$ is any amino acid that is not negatively charged; and $X_{17}$ is one or more positively charged amino acids or is absent. Optionally $X_1$ comprises a positively charged amino acid. In some embodiments, $X_1$ is R or K. In some embodiments, $X_{17}$ is RR. In some embodiments, $X_1$ is R and $X_{17}$ is RR. In some embodiments, $X_1$ comprises R, and $X_{17}$ comprises RR. In some embodiments, the peptide is soluble in an aqueous solution. In some embodiments, the peptide is soluble in an aqueous solution. In some embodiments, at least one of: $X_1$ is K; $X_2$ is K; $X_3$ is L; $X_4$ is D; $X_5$ is T; $X_6$ is F; $X_7$ is F; $X_8$ is V; $X_9$ is K; $X_{10}$ is L; $X_{11}$ is S; $X_{12}$ is L; $X_{13}$ is F; $X_{14}$ is T; $X_{15}$ is E; or $X_{16}$ is R. In some embodiments, the isolated peptide comprises the amino acid sequence KKLDTFFVKLSLFTER (SEQ ID NO: 2). In some embodiments, the isolated peptide comprises the amino acid sequence RKLDTFFVKLSLFTERRR (SEQ ID NO: 586). In some embodiments, the isolated peptide has a length of 30 amino acid residues or less, for example no more than about 30, 29, 28, 27, 26, 25, 24, 23, 22, 21, 20, 19, 18, 17, 16, 15, 14, 13, 12, 11, 10, 9, 8, 7, or 6 amino acid residues or a range defined by any two of these numbers. In some embodiments, the isolated peptide consists of the formula $X_0X_1X_2X_3X_4X_5X_6X_7X_8X_9X_{10}X_{11}X_{12}X_{13}X_{14}X_{15}X_{16}X_{17}$. In some embodiments, the isolated peptide comprises the amino acid sequence KKLDTFFVKLSLFTER (SEQ ID NO: 2). In some embodiments, the isolated peptide comprises the amino acid sequence RKLDTFFVKLSLFTERRR (SEQ ID NO: 586).

In some embodiments, any of the above isolated peptides comprises a synthetic peptide.

In some embodiments, any of the above isolated peptides comprises at least one modification, for example at least one of a D amino acid, an N-terminal acetyl group, a C-terminal amide group, glycosylation, nitrosylation, carbonylation, oxidation, a linked pharmacokinetic modifier, and a linked polyethylene glycol or any combination thereof.

In some embodiments, any of the above isolated peptides activates an immune cell. By way of example, activation of an immune cell can include proliferation of the immune cell, increased expression of CD69 or CD71, secretion of a signal substance such as IFNγ of IL-12, secretion of a cytolytic molecule such as perforin or granzyme B, enhanced cytotoxicity, cytokine production, and/or cell migration.

In some embodiments, any of the above isolated peptides activates an immune cell, if a solution comprising the immune cell comprises a second peptide having the sequence VFDEFKPLVEEPQNLIK (SEQ ID NO: 185), or if an LFA-1 receptor of the immune cell is bound to the second peptide.

In some embodiments, if any of the above isolated peptides is contacted with a second peptide consisting of the amino acid sequence VFDEFKPLVEEPQNLIK (SEQ ID NO: 185), the isolated peptide specifically binds to the second peptide.

In some embodiments, if any of the above isolated peptides is contacted with an immune cell comprising an LFA-1 receptor and a second peptide consisting of the amino acid sequence VFDEFKPLVEEPQNLIK (SEQ ID NO: 185), the isolated peptide inhibits binding of the second peptide to the LFA-1 receptor.

Some embodiments of the invention include a composition comprising any of the isolated peptides described above and a pharmaceutically acceptable carrier or diluent. In some embodiments, the pharmaceutically acceptable carrier or diluent comprises a degradable particle. In some embodiments, the composition comprises an amount of the peptide that is at least about 1 ng of the peptide, for example at least about 1 ng, 2 ng, 3 ng, 4 ng, 5 ng, 10 ng, 20 ng, 50 ng, 60 ng, 70 ng, 80 ng, 90 ng, 100 ng, 200 ng, 300 ng, 400 ng, 500 ng, 600 ng, 700 ng, 800 ng, 900 ng, about 1 µg, 2 µg, 3 µg, 4 µg, 5 µg, 6 µg, 7 µg, 8 µg, 9 µg, 10 µg, 20 µg, 30 µg, 40 µg, 50 µg, 60 µg, 70 µg, 80 µg, 90 µg, 100 µg, or 200 µg or a range defined by any two of these numbers. In some embodiments, the composition comprises a buffer selected from the group consisting of: Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES. In some embodiments, if contacted with a cancer cell, the composition induces cytotoxicity of the cancer cell. In some embodiments, the cancer cell comprises a prostate cancer cell. In some embodiments, the composition comprises a gel. In some embodiments, the composition will remain in a gel format for at least 72 hours under physiological conditions.

Some embodiments of the invention include a method comprising administering to an individual having a cancer, and in need of treatment therefor, an effective amount of any of the compositions described above, thereby inducing at least one of the following: (a) activation of an immune cell (e.g. enhanced expression of CD69 and/or CD71, secretion of IL-12 of IFNγ, or secretion of perforin or granzyme B, enhanced cytotoxicity, cytokine production, cell migration, and/or cell proliferation); (b) inhibition of binding of a damaged albumin, an aggregate of albumins, an albumin fragment, or a second peptide to an LFA-1 receptor or IL-2 receptor, wherein the second peptide or albumin fragment, if present, comprises at least one of SEQ ID NOs: 183-246; or (c) cytotoxicity to the tumor cell. In some embodiments, (a) and (b) are induced. In some embodiments, (a), (b), and (c) are induced. In some embodiments, the receptor comprises an LFA-1 receptor. In some embodiments, the receptor comprises an IL-2 receptor. In some embodiments, the albumin fragment or second peptide comprises no more than 100 amino acid residues. In some embodiments, the albumin fragment or second peptide comprises SEQ ID NO: 185. In some embodiments, the albumin fragment or second peptide consists of SEQ ID NO: 185. In some embodiments, the LFA-1 receptor is available for stimulation following inhibition of binding of the albumin, albumin fragment, or second peptide. In some embodiments, the immune cell is stimulated following inhibition of binding of the albumin, albumin fragment, or second peptide. In some embodiments, the immune cell is stimulated by a second therapeutic agent. In some embodiments, the second therapeutic agent is administered concurrently with the composition. In some embodiments, the composition comprises the second therapeutic agent. In some embodiments, the second therapeutic agent is administered prior to administering the composition. In some embodiments, the second therapeutic agent is administered subsequent to administering the composition. In some embodiments, the peptide of the composition is administered to the individual at a dose of at least about 0.1 mg/kg, for example at least about 0.2 mg/kg, 0.3 mg/kg, 0.4 mg/kg, 0.5 mg/kg, 0.9 mg/kg, 1 mg/kg, 2 mg/kg, 3 mg/kg, 5 mg/kg, of 10 mg/kg or a range defined by any two of these values. In some embodiments, the peptide of the composition is administered in at least a first administration and a second administration at least five days after the first administration. In some embodiments, the peptide is administered to a tissue within about 10 cm of a tumor of the cancer. In some embodiments, the peptide is administered peri-tumorally to a tumor of the cancer. In some embodiments, the cancer comprises at least one of colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer. In some embodiments, the individual comprises serum comprising a damaged albumin, an aggregate of albumins, an albumin fragment, or a second peptide, wherein the albumin fragment or second peptide comprises at least one of SEQ ID NOs: 183-246. In some embodiments, the a second peptide or albumin fragment comprising the amino acid sequence VFDEFKPLVEEPQNLIK (SEQ ID NO: 185). In some embodiments, the second peptide or albumin fragment comprises no more than 100 amino acid residues.

Some embodiments of the invention include a method of activating an immune cell (e.g. enhanced expression of CD69 and/or CD71, secretion of IL-12 of IFNγ, or secretion of perforin or granzyme B, enhanced cytotoxicity, cytokine production, and/or cell migration) in a cancer patient, the method comprising contacting the immune cell with an isolated peptide comprising the amino acid sequence FFVKLS (SEQ ID NO: 62), wherein the peptide consists of about six to thirty amino acids. In some embodiments, contacting the immune cell with the isolated peptide inhibits binding of a damaged albumin, an aggregate of albumins, an albumin fragment, or a second peptide to an LFA-1 receptor, wherein the albumin fragment or second peptide comprises at least one of SEQ ID NOs: 183-246. In some embodiments, the albumin fragment or second peptide comprises no more than 100 amino acids. In some embodiments, the albumin fragment or second peptide comprises SEQ ID NO: 185. In some embodiments, the albumin fragment or second peptide consists of SEQ ID NO: 185. In some embodiments, the LFA-1 receptor is available for stimulation following inhibition of binding of the albumin, albumin fragment, or second peptide. In some embodiments, the immune cell is stimulated following inhibition of binding of the albumin, albumin fragment, or second peptide. In some embodiments, the immune cell is stimulated by a second therapeutic agent. In some embodiments, the second therapeutic agent is administered concurrently with the composition. In some embodiments, the composition comprises the second therapeutic agent. In some embodiments, the second therapeutic agent is administered prior to administration of the composition. In some embodiments, the second therapeutic agent is administered subsequent to administration of the composition.

Some embodiments of the invention include a method of binding cancer cells with a peptide. The method can comprise contacting a cancer cell with any of the peptides described above, and detecting the binding of said peptide to said cancer cell. In some embodiments, the peptide comprises a detectable moiety. In some embodiments, the detectable moiety comprises a biotinylated label, a radioactive label, a fluorescent label, an enzyme, or a colloidal gold label. In some embodiments, the cancer cell is a colorectal cancer cell, a renal cancer cell, a breast cancer cell, a skin cancer cell, an ovarian cancer cell, a prostate cancer cell, a pancreatic cancer cell, a lung cancer cell, a malignant melanoma cell, a small cell lung cancer cell, a non-small lung cancer (adenocarcinoma) cell, a squamous cell carcinoma cell, a bladder cancer cell, an osteosarcoma cell, a bronchial cancer cell, or a hematopoietic cell cancer cell. In some embodiments, said peptide comprises an antibody or antibody fragment.

Some embodiments of the invention include a method of ameliorating immunosuppression in a subject in need thereof, the method comprising administering to the subject an effective amount of the composition of any of claims 29-36, thereby inducing at least one of the following: (a) activation of an immune cell (e.g. enhanced expression of CD69 and/or CD71, secretion of IL-12 of IFNγ, or secretion of perforin or granzyme B, enhanced cytotoxicity, cytokine production, and/or cell migration); or (b) inhibition of binding of a damaged albumin, an aggregate of albumins, an albumin fragment, or a second peptide to an LFA-1 receptor, wherein the second peptide or albumin fragment, if present, comprises at least one of SEQ ID NOs: 183-246. In some embodiments, the albumin fragment or second peptide comprises no more than 100 amino acid residues. In some embodiments, the albumin fragment or second peptide comprises SEQ ID NO: 185. In some embodiments, the albumin fragment or second peptide consists of SEQ ID NO: 185. In some embodiments, the LFA-1 receptor is available for stimulation following inhibition of binding of the albumin, albumin fragment, or second peptide.

Some embodiments include a kit comprising the isolated peptide of any one of claims 1-26; and a detectable label. In some embodiments, the label comprises a biotinylated label, a radioactive label, a fluorescent label, an enzyme, or a colloidal gold label.

Some embodiments include an isolated nucleic acid encoding any of the isolated peptides described above. Some embodiments include an isolated vector comprising this nucleic acid.

Some embodiments of the invention include use of any of the isolated peptides described above for the preparation of a medicament for the treatment of cancer.

Some embodiments of the invention include use of any of the isolated peptides described above for the preparation of a medicament for stimulating an immune cell in a cancer patient.

Some embodiments of the invention include use of any of the compositions described above for the preparation of a medicament for the treatment of cancer.

Some embodiments of the invention include use of any of the compositions described above for the preparation of a medicament for stimulating an immune cell in a cancer patient.

In some embodiments, for any of the uses described above, the cancer comprises at least one of colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer.

Some embodiments of the invention include use of any of the isolated peptides described above for the preparation of a medicament for the treatment of immunosuppression.

Some embodiments of the invention include use of any of the compositions described above for the preparation of a medicament for the treatment of immunosuppression.

A number of Alternatives are also provided herein:

Alternative 1 includes an isolated peptide comprising Formula VII wherein Formula VII is: $X_{700}K\ X_{701}\ X_{702}X_{703}\ X_{704}X_{705}\ X_{706}\ KX_{707}\ X_{708}\ X_{709}\ X_{710}X_{711}EX_{712}$ (SEQ ID NO: 394), wherein $X_{700}$ is K, A, D, E, G, H, I, L, M, N, P, Q, R, T, V, or K, or absent; wherein $X_{701}$ is L, A, C, D, E, F, G, H, I, K, M, N, Q, R, S, T, or V, or absent; wherein $X_{702}$ is D, A, E, I, V, W, or Y, or absent; wherein $X_{703}$ is T, C, M, N, P, Q, R, S, W, or Y, or absent; wherein $X_{704}$ is F, A, I, M, N, P, T, or V, or absent; wherein $X_{705}$ is F, L, M, Q, S, T or V, or absent; wherein $X_{706}$ is V, F, G, L, P, or R, or absent; wherein $X_{707}$ is L, A, F, G, I, M, N, P, Q, R, S, T, V, or Y, or absent; wherein $X_{708}$ is S, H, M, N, Q, or T, or absent; wherein $X_{709}$ is L, A, H, I, M, N, Q, R, S, T, V, or W, or absent; wherein $X_{710}$ is F, A, C, G, H, I, L, M, NP, Q, R, S, T, V, or W, or absent; wherein $X_{711}$ is T, F, G, H, I, L, M, N, P, S, V, or W, or absent; and wherein $X_{712}$ is R, F, K, N, R, T, or Y, or absent.

Alternative 2 includes the isolated peptide of Alternative 1, wherein said Formula VII is one of SEQ ID NO: 1-101, 167-172, 174-177, 179-393, 396-581, or 582.

Alternative 3 includes an isolated peptide comprising Formula VIII, wherein Formula VIII is: $X_{800}K\ X_{801}K\ X_{802}E\ X_{803}$ (SEQ ID NO: 395), wherein $X_{800}$ is K, A, D, E, G, H, I, L, M, N, P, Q, R, T, V, or K, or absent; wherein $X_{801}$ is LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent; wherein $X_{802}$ is LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLGT (SEQ ID NO: 729), LSLAT (SEQ ID NO: 730), LSLRT (SEQ ID NO: 731), LSLFN (SEQ ID NO: 732), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent.

Alternative 4 includes the isolated peptide of Alternative 3, wherein said formula VIII is one of SEQ ID NOs: 1-34, 64-68, 70-72, 74-77, 80, 83, 86, 89, 92-96, 99-100, 264, 268-269, 270-386, 388-393, 396-401, 403, 404, 406, 408-411, 413-416, 419-420, 422-438, 442-444, 446-449, 451-453, 455-458, 460, 462-466, 470, 472-477, 479-480, 482-484, 486, 487, 489, 491-493, 495-498, 500-508, 512-517, 519-522, 528-530, 532, 533, 535-538, 540, 542-551, 553, 557-559, 567, 570, 572-581, or 582.

Alternative 5 includes an isolated peptide comprising Formula I, wherein Formula I is: $XX_1VKX_2X_3X_4$ (SEQ ID NO: 166), wherein X is KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, Q, or absent, wherein $X_1$ is FF, FM, FS, FV, FT, FL, AF, AM, AS, AV, AT, AL, VF, VM, VS, VV, VT, or VL, or absent, wherein X2 is LS, LQ, LM, LT, LH, VS, VQ, VM, VT, or VH, or absent, wherein $X_3$ is LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR; and wherein $X_4$ is ER, E, or absent.

Alternative 6 includes the isolated peptide of Alternative 5, wherein said Formula I is one of SEQ ID NOs: 2-40, 46-52, 58-65, 67-71, 74-77, 80-83, 86-88, 92-96, 99-101, 166, 173, 178, 182, 268-325, 332-392-393, 396-415, 417-444, 446-468, 470-487, 489-494, 497-508, 510, 512, 514-517, 520-522, 524-525, 528-533, 535-536, 538-539, 542-544, 546, 548, 551, 553, 556-559, 561, 563-568, 571-573, 575-581 or 582.

Alternative 7 includes the isolated peptide of Alternative 5, wherein said Formula I is one of SEQ ID NOs: 2 to 33.

Alternative 8 an isolated peptide comprising Formula II, wherein Formula II is XTFFVKLSX$_1$X$_2$ (SEQ ID NO: 173), wherein X is KKLD (SEQ ID NO: 174), RKLD (SEQ ID NO: 175), KKGD (SEQ ID NO: 176), KKED (SEQ ID NO: 177), KLD, LD, D, or absent, wherein $X_1$ is LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent, and wherein $X_2$ is ER, or E, or absent.

Alternative 9 includes the isolated peptide of Alternative 8, wherein said Formula II is one of SEQ ID No: 2-5, 19-38, 46-49, 58-61, 64, 68-70, 75, 81, 87, 93, 94, 100, 101, 173, 268-303, 350-393, 396, 398, 399, 400, 402, 403, 405, 406-408, 412-414, 417, 418, 421-423, 426-428, 430, 431, 435, 436, 438, 439, 440-442, 448-455, 458, 459, 461, 465, 467, 468, 471, 475, 476, 478-481, 483, 485, 487, 489-491, 493, 494, 497-499, 503, 507, 510, 512, 514-517, 520, 521, 524, 525, 528, 529, 531, 533, 538, 539, 542-, 544, 546, 551, 556-559, 561, 563-568, 571-573, 575-577, 579, 580, or 581.

Alternative 10 includes the isolated peptide of Alternative 8, wherein X is KKLD (SEQ ID NO: 174).

Alternative 11 includes the isolated peptide of Alternative 8, wherein $X_2$ is ER.

Alternative 12 includes the isolated peptide of Alternative 8, wherein said formula is TFFVKLSLFTER (SEQ ID NO: 49) or TFFVKLSLFTE (SEQ ID NO: 250).

Alternative 13 includes the isolated peptide of Alternative 8, wherein said formula is KKLDTFFVKLSLFTER (SEQ ID NO: 2) or KKLDTFFVKLSLFTE (SEQ ID NO: 34).

Alternative 14 includes an isolated peptide comprising Formula III, wherein Formula III is: XX$_1$VKLX$_2$LX$_3$TEX$_4$ (SEQ ID NO: 178), wherein X is KKLDTF (SEQ ID NO: 179), KLDTF (SEQ ID NO: 180), LDTF (SEQ ID NO: 181), DTF, TF, or F, or absent, wherein $X_1$ is F, M, S, V, T, or L, or absent, wherein $X_2$ is S, Q, M, T, or H, or absent, wherein $X_3$ is F, M, Q, H, N, P, S, G, A, or R, or absent, and wherein $X_4$ is R or absent.

Alternative 15 includes the isolated peptide of Alternative 14, wherein said Formula III is one of SEQ ID No: 2-13, 15-18, 22-30, 34, 46-52, 58, 64, 65, 70, 71, 76, 77, 82, 83, 88, 93-96, 99, 100, 178, 268-325.

Alternative 16 includes the isolated peptide of Alternative 14, wherein X is KKLDTF (SEQ ID NO: 178).

Alternative 17 includes the isolated peptide of Alternative 14, wherein $X_4$ is R.

Alternative 18 includes the isolated peptide of Alternative 14, wherein said formula is VKLSLFTER (SEQ ID NO: 52) or VKLSLFTE (SEQ ID NO: 251).

Alternative 19 includes the isolated peptide of Alternative 14, wherein said formula is KKLDTFFVKLSLFTER (SEQ ID NO: 2) or KKLDTFFVKLSLFTE (SEQ ID NO: 34).

Alternative 20 includes an isolated peptide comprising at least one of SEQ ID NOs: 1-101, 167-172, 174-177, 179-393, 396-581 and 582.

Alternative 21 includes the isolated peptide of Alternative 20, comprising at least one of SEQ ID NOs: 1-32, 34, 64-66, 68, 76, 94-96, 98, and 264-393.

Alternative 22 includes the isolated peptide of any one of Alternatives 1 to 21, wherein the isolated peptide comprises at least one of the sequences of Table 5.1.

Alternative 23 includes the isolated peptide of anyone of Alternatives 1 to 22, wherein at least one amino acid is a D amino acid, artificial amino acid, and chemically modified amino acid.

Alternative 24 includes the isolated peptide of anyone of Alternatives 1 to 23, further comprising an N-terminal acetyl group.

Alternative 25 includes the isolated peptide of anyone of Alternatives 1 to 24, further comprising a C-terminal amide group.

Alternative 26 includes the isolated peptide of anyone of Alternatives 1 to 25, wherein said isolated peptide is chemically modified.

Alternative 27 includes the isolated peptide of anyone of Alternatives 1 to 26, wherein said peptide comprises at least one modification, for example wherein the peptide is glycosylated, nitrosylated, carbonylated, oxidized, or joined to at least one of polyethylene glycol, a fatty acid, or a pharmacokinetic modifier.

Alternative 28 includes the isolated polypeptide of anyone of Alternative 1 to 23 wherein the polypeptide comprises a cyclic peptide.

Alternative 29 includes the isolated peptide of any one of Alternatives 1 to 28, wherein said peptide comprises at least one modification, for example at least one of a D amino acid, an N-terminal acetyl group, a C-terminal amide group, glycosylation, nitrosylation, carbonylation, oxidation, a linked pharmacokinetic modifier, and a linked polyethylene glycol or any combination thereof.

Alternative 30 includes the isolated peptide of any one of Alternatives 1 to 29, wherein said peptide is less than or equal to 1100 amino acids in length.

Alternative 31 includes the isolated peptide of anyone of Alternatives 1 to 29, wherein said peptide is between 6 amino acids and 20 amino acids in length.

Alternative 32 includes the isolated peptide of anyone of Alternatives 1 to 31, wherein the isolated peptide does not have an N-terminal acetyl group.

Alternative 33 includes the isolated peptide of anyone of Alternatives 1 to 31, wherein the isolated peptide does not have a C-terminal amide group.

Alternative 34 includes the isolated peptide of anyone of Alternatives 1 to 33, wherein said peptide is joined to at least one of a support, a carrier, and a fusion protein.

Alternative 35 includes the isolated peptide of anyone of Alternatives 1 to 34, wherein said peptide is multimerized.

Alternative 36 includes an isolated polynucleotide comprising a sequence encoding the peptide of any one of Alternatives 1 to 22.

Alternative 37 includes the isolated polynucleotide of Alternative 36 comprising one of SEQ ID NOs: 102 to 165.

Alternative 38 includes a vector comprising the isolated polynucleotide of Alternative 36.

Alternative 39 includes a vector comprising the isolated polynucleotide of Alternative 37.

Alternative 40 includes the isolated polynucleotide of Alternative 36 or 37 or the vector of Alternative 38 or 39, wherein said peptide is less than or equal to 1100 amino acids in length.

Alternative 41 includes the isolated polynucleotide of Alternative 36 or 37 or the vector of Alternative 38 or 39, wherein said peptide is between 6 amino acids and 20 amino acids in length.

Alternative 42 includes a protein complex comprising the peptide of anyone of Alternatives 1 to 35 bound to at least one of albumin, a fragment of albumin, an immunoglobulin, a support, a carrier, and a fusion protein.

Alternative 43 includes a method of making a protein complex according to Alternative 42, comprising: contacting the peptide of anyone of Alternatives 1 to 35 with a biological sample obtained from a human subject, wherein said biological sample comprises immunoglobulin, albumin, or a fragment thereof; and detecting the presence of said protein complex.

Alternative 44 includes the method of Alternative 43, wherein said peptide of anyone of Alternatives 1 to 35 is attached to a support.

Alternative 45 includes a method of detecting the presence of an albumin or an albumin fragment in a biological sample, the method comprising: contacting the peptide of anyone of Alternatives 1 to 35 with a biological sample that comprises albumin or a fragment thereof and detecting the binding of said peptide to said albumin or said albumin fragment.

Alternative 46 includes a binding means specific for the peptide of any one of Alternatives 1 to 35, wherein the binding means is an antibody or binding fragment thereof.

Alternative 47 includes the binding means of Alternative 46, wherein the antibody is a monoclonal antibody and the binding fragment is a monoclonal antibody binding fragment.

Alternative 48 includes an aptamer that is specific for a peptide comprising at least one of the sequences of Tables 1-4 (SEQ ID NOs: 183-184, and 188-246).

Alternative 49 includes the aptamer of Alternative 48, wherein the aptamer is specific for the peptide of the sequence VFDEFKPLVEEPQNLIK (SEQ ID NO: 185).

Alternative 50 includes the aptamer of Alternative 48 or 49, wherein said aptamer is a DNA aptamer.

Alternative 51 includes the aptamer of Alternative 48 or 49, wherein said aptamer is a peptide aptamer.

Alternative 52 includes a method of inhibiting immunosuppression in a patient in need thereof, said method comprising: identifying a patient having a condition associated with immunosuppression; administering to the patient a peptide of any of Alternatives 1-35; and detecting an increase in leukocyte spreading in the patient or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. Optionally the method includes detecting one or more of enhanced cytotoxicity, cytokine production, cell migration, and/or cell proliferation.

Alternative 53 includes the method of Alternative 52, wherein said peptide is less than or equal to 30, 29, 28, 27, 26, 25, 24, 23, 22, 21, 20, 19, 16, 15, 14, 13, 12, 11, 10, 9, 8, 7, or 6 amino acids in length or a length that is between any two of these numbers.

Alternative 54 includes the method of Alternative 52, wherein said peptide is a synthetic peptide.

Alternative 55 includes the method of Alternative 52, wherein administering said peptide comprises administering a composition consisting of at least 0.1% of the peptide by weight, for example, at least 0.1%, 0.2%, 0.5%, 1%, 2%, 3%, 4%, 5%, 6%, 7%, 8%, 9%, 10%, 20%, or 30% of the peptide by weight, including ranges between any two of the listed values Alternative 56 includes the method of Alternative 52, wherein said patient has cancer, a viral infection, or a bacterial infection.

Alternative 57 includes the method of Alternative 56, wherein the cancer is colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer.

Alternative 58 includes the method of Alternative 52, further comprising detecting an increase in lymphocyte migration.

Alternative 59 includes a method of inhibiting binding of an albumin fragment to a receptor, the method comprising: identifying a human suffering from immunosuppression; contacting an immune cell with a peptide of any of Alternatives 1 to 35; and detecting an increase in proliferation of the immune cell after contact with said peptide or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. Optionally, the method includes one or more of enhanced cytotoxicity, cytokine production, cell migration, and/or cell proliferation.

Alternative 60 includes the method of Alternative 59, wherein the immune cells is a lymphocyte, monocyte, macrophage, or NK-cell.

Alternative 61 includes the method of Alternative 59, wherein the immune cell is a PBMC, monocyte, macrophage, or NK-cell.

Alternative 62 includes the method of Alternative 59, wherein the human has cancer, a viral infection, or a bacterial infection.

Alternative 63 includes the method of Alternative 62, wherein said human has colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer.

Alternative 64 includes a method of increasing NK-cell cytotoxicity comprising: identifying a human suffering from immunosuppression; contacting NK-cells with the peptide comprising the sequence of any of Alternatives 1 to 35; and detecting an increase in cytotoxicity of said NK-cells after contact with said peptide as compared to a control sample, such as the cytotoxicity of NK-cells in the absence of said peptide or the cytotoxicity of NK-cells and an unrelated peptide.

Alternative 65 includes the method of Alternative 64, wherein said human is a patient with cancer, a bacterial infection, or a viral infection.

Alternative 66 includes the method of Alternative 64, wherein said patient with cancer has colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer.

Alternative 67 includes a method of increasing human lymphocyte migration comprising: identifying a human suffering from immunosuppression; contacting human lymphocytes with a peptide of any of Alternatives 1-35; and detecting an increase in migration of said human lymphocytes after contact with said peptide as compared to a control sample, such as the migration of human lymphocytes in the absence of said peptide or the migration of human lymphocytes and an unrelated peptide.

Alternative 68 includes the method of Alternative 67, wherein said human has cancer, a bacterial infection or a viral infection.

Alternative 69 includes the method of Alternative 68, wherein said human has at least one of colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, and hematopoietic cell cancer.

Alternative 70 includes a method of inhibiting the binding of a human albumin or a human albumin fragment to the LFA-1 receptor or the IL-2 receptor or both on human lymphocytes, the method comprising: contacting human lymphocytes with a peptide of any of Alternatives 1-35 in the presence of human albumin or a human albumin fragment; and detecting an inhibition of binding of the human albumin or human albumin fragment to the LFA-1 receptor or the IL-2 receptor or both on human lymphocytes as compared to a control sample, wherein the control sample comprises binding of a human albumin or a human albumin fragment to an LFA-1 receptor or IL-2 receptor or both on a human lymphocyte in the absence of said peptide, or binding of a human albumin or a human albumin fragment to an LFA-1 receptor or IL-2 receptor or both on a human lymphocyte in the presence of an unrelated peptide.

Alternative 71 includes the method of Alternative 70 wherein the human albumin fragment comprises a sequence with at least 95% identity to SEQ ID NO: 185.

Alternative 72 includes the method of Alternative 71, wherein the human albumin fragment comprises the sequence of SEQ ID NO: 185.

Alternative 73 includes a method of inhibiting the binding of a human albumin or a human albumin fragment to the LFA-1 receptor or the IL-2 receptor or both on human lymphocytes comprising: providing human lymphocytes, wherein at least one of the LFA-1 receptor and IL-2 receptor is bound to a human albumin of albumin fragment; specifically binding a molecule to the human albumin or albumin fragment; and detecting an decrease of inhibition of stimulation of the human lymphocytes via the LFA-1 receptor, IL-2 receptor.

Alternative 74 includes the method of Alternative 73 wherein the human albumin fragment comprises a sequence with at least 95% identity to SEQ ID NO: 185.

Alternative 75 includes the method of Alternative 74, wherein the human albumin fragment comprises the sequence of SEQ ID NO: 185.

Alternative 76 includes a method of binding cancer cells with a peptide comprising: contacting a cancer cell with the peptide of any of Alternatives 1-35; and detecting the binding of said peptide to said cancer cell.

Alternative 77 includes the method of Alternative 76, wherein the cancer cell is a colorectal cancer cell, a renal cancer cell, a breast cancer cell, a skin cancer cell, an ovarian cancer cell, a prostate cancer cell, a pancreatic cancer cell, a lung cancer cell, a malignant melanoma cell, a small cell lung cancer cell, a non-small lung cancer (adenocarcinoma) cell, a squamous cell carcinoma cell, a bladder cancer cell, an osteosarcoma cell, a bronchial cancer cell, or a hematopoietic cell cancer cell.

Alternative 78 includes the method of Alternative 76, wherein said peptide comprises a detectable label joined thereto, such as a biotinylated label, a radioactive label, a fluorescent label, or a colloidal gold label.

Alternative 79 includes the method of Alternative 76, wherein said peptide comprises a cytotoxic agent joined thereto, such as a radiochemical, or a toxin.

Alternative 80 includes the method of Alternative 76, wherein said peptide comprises an antibody or antibody fragment.

Alternative 81 includes the peptide of anyone of Alternatives 1 to 35, further comprising a detectable label joined thereto, such as a biotinylated label, a radioactive label, a fluorescent label, or a colloidal gold label.

Alternative 82 includes the peptide of anyone of Alternatives 1 to 36, further comprising a cytotoxic agent joined thereto, such as a radiochemical, or a toxin.

Alternative 83 includes a method of inhibiting the proliferation of human cancer cells comprising: identifying a human cancer patient; contacting immune cells of the human cancer patient with a peptide of any of Alternatives 1 to 35; and detecting an inhibition of proliferation of cancer cells of the patient or an induction of cell death of cancer cells of the patient.

Alternative 84 includes the method of Alternative 83, wherein an inhibition of proliferation of cancer cells of the patient is detected.

Alternative 85 includes the method of Alternative 83, wherein at least one of an induction of cell death of cancer cells or tumor regressive changes is detected.

Alternative 86 includes the method of Alternative 83, wherein the cancer cells are at least one colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, and hematopoietic cell cancer.

Alternative 87 includes the method of Alternative 83, further comprising detecting an increase in at least one of the proliferation, migration, endothelial transmigration, and cytotoxicity of immune cells of the human.

Alternative 88 includes the method of Alternative 83 wherein the immune cells are PBMCs.

Alternative 89 includes the method of Alternative 88, wherein the immune cells are lymphocytes.

Alternative 90 includes the method of Alternative 83, wherein said peptide is synthetic Alternative 91 includes a method of removing a ligand bound to the LFA-1 receptor of human lymphocytes comprising: contacting human lymphocytes with a peptide of any of Alternatives 1-31; and detecting a reduced binding of a ligand for the LFA-1 receptor.

Alternative 92 includes the =method of Alternative 91, wherein said human lymphocytes are from a patient with cancer, a bacterial infection or a viral infection.

Alternative 93 includes the method of Alternative 92, wherein said patient has at least one of colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, and hematopoietic cell cancer.

Alternative 94 includes a method of removing a ligand bound to the IL-2 receptor of human lymphocytes comprising: contacting human lymphocytes with a peptide of any of Alternatives 1 to 35; and detecting a reduced binding of a ligand for the IL-2 receptor.

Alternative 95 includes the method of Alternative 94, wherein said human lymphocytes are from a patient with cancer, a bacterial infection or a viral infection.

Alternative 96 includes the method of Alternative 95, wherein said patient has at least one of colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, and hematopoietic cell cancer.

Alternative 97 includes a method of reducing immunosuppression in a human that is immunosuppressed comprising: providing to a human, a peptide of any of Alternatives 1 to 35; and detecting a reduction of immunosuppression in said human or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. Optionally, the method includes detecting one or more of enhanced cytotoxicity, cytokine production, cell migration, and/or cell proliferation.

Alternative 98 includes the method of Alternative 97, wherein said human has cancer, a bacterial infection or a viral infection.

Alternative 99 includes the method of Alternative 98, wherein said cancer is colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer.

Alternative 100 includes the method of Alternative 99, wherein providing said peptide comprises administering to said human a composition consisting of at least 0.1% of the peptide by weight, for example, at least 0.1%, 0.2%, 0.5%, 1%, 2%, 3%, 4%, 5%, 6%, 7%, 8%, 9%, 10%, 20%, or 30% of the peptide by weight, including ranges between any two of the listed values Alternative 101 includes a method of inhibiting the binding of a human albumin or a human albumin fragment to the LFA-1 receptor or the IL-2 receptor or both on human lymphocytes comprising: providing a human the polynucleotide or vector of anyone of Alternatives 36-41; and detecting an inhibition of binding of a human albumin or a human albumin fragment to the LFA-1 receptor or the IL-2 receptor or both.

Alternative 102 includes a method of inhibiting the proliferation of human cancer cells comprising: providing the polynucleotide or vector of anyone of Alternatives 36-41 to a human that has cancer cells; and detecting an inhibition of proliferation of said cancer cells.

Alternative 103 includes a method of removing a ligand bound to the LFA-1 receptor or IL-2 receptor or both of human lymphocytes comprising: contacting human lymphocytes with the polynucleotide or vector of anyone of Alternatives 36 to 41; and detecting a reduced binding of a ligand for the LFA-1 receptor or the IL-2 receptor or both.

Alternative 104 includes a method of reducing immunosuppression in a human that is immunosuppressed comprising: providing the polynucleotide or vector of anyone of Alternatives 36 to 41 to said human; and detecting a reduction of immunosuppression or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin in said human. Optionally the method includes detecting one or more of enhanced cytotoxicity, cytokine production, cell migration, and/or cell proliferation.

Alternative 105 includes a modified peptide of Alternatives 1 to 35, wherein said peptide comprises at least one modification, for example at least one of a D amino acid, an N-terminal acetyl group, a C-terminal amide group, a glycosylated amino acid, a nitrosylated amino acid, a carbonylated amino acid, an oxidized amino acid, or wherein said peptide is joined to polyethylene glycol, a fatty acid, or a pharmacokinetic modifier.

Alternative 106 includes the modified peptide of Alternative 103, wherein said peptide is less than or equal to 30, 29, 28, 27, 26, 25, 24, 23, 22, 21, 20, 19, 16, 15, 14, 13, 12, 11, 10, 9, 8, 7, or 6 amino acids in length.

Alternative 107 includes a pharmaceutical composition comprising: the peptide of any of Alternatives 1 to 35 or Alternatives 103 to 104; and a pharmaceutically acceptable carrier, excipient, or diluent.

Alternative 108 includes the pharmaceutical composition of Alternative 107, wherein the peptide comprises at least one of SEQ ID NOs: 1-33, 34, 46-53, 62, 64-66, 68, 76, 94-96, 98, and 586.

Alternative 109 includes a method for identifying a patient in need of treatment with an inhibitor of immunoregulatory peptides or structures, the method comprising: contacting immune cells of the patient in vitro with a peptide of any of Alternatives 1-35; detecting a restoration of reactivity of said immune cells; and classifying the patient as likely to respond to treatment with the inhibitor of immunoregulatory peptides or structures if said peptide inhibits proliferation of said immune cells.

Alternative 110 includes the method of Alternative 109, further comprising reducing immunosuppression in the patient in need, wherein reducing immunosuppression comprises providing to the patient in need, a peptide of any of Alternatives 1 to 35.

Alternative 111 includes the method of Alternative 110, further comprising detecting a reduction of immunosuppression in said human.

Alternative 112 includes the method of Alternative 109, further comprising reducing immunosuppression in the patient in need, wherein reducing immunosuppression comprises providing to the patient in need, a vector or polynucleotide of any of Alternatives 36-41.

Alternative 113 includes the method of Alternative 112, further comprising detecting a reduction of immunosuppression or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin in said human. Optionally, the method includes detecting one or more of enhanced cytotoxicity, cytokine production, cell migration, and/or cell proliferation.

Alternative 114 includes the isolated peptide of any of Alternatives 1 to 23, wherein said peptide comprises an amino acid residue homologous to amino acid residue K2 of SEQ ID NO: 2.

Alternative 115 includes the isolated peptide of any of Alternatives 1 to 23, wherein said peptide comprises an amino acid residue homologous to amino acid residue K9 of SEQ ID NO: 2.

Alternative 116 includes the isolated peptide of any of Alternatives 1 to 23, wherein said peptide comprises an amino acid residue homologous to amino acid residue E15 of SEQ ID NO: 2.

Alternative 117 includes the isolated peptide of Alternative 114, wherein said peptide comprises an amino acid residue homologous to amino acid residue K9 of SEQ ID NO: 2.

Alternative 118 includes the isolated peptide of Alternative 114, wherein said peptide comprises an amino acid residue homologous to amino acid residue E15 of SEQ ID NO: 2.

Alternative includes the isolated peptide of Alternative 115, wherein said peptide comprises an amino acid residue homologous to amino acid residue E15 of SEQ ID NO: 2.

Alternative 120 includes the isolated peptide of Alternative 114, wherein said peptide comprises an amino acid residue homologous to amino acid residue K9 of SEQ ID NO: 2, and wherein said peptide comprises an amino acid residue homologous to amino acid residue E15 of SEQ ID NO: 2.

Alternative 121 includes the isolated peptide of any of Alternatives 1 to 23 or Alternatives 114 to 120, wherein said peptide comprises at least one non-naturally occurring amino acid.

Alternative 122 includes the isolated peptide of any of Alternatives 114 to 120, wherein said peptide comprises at least one modification, for example at least one of a D amino acid, an N-terminal acetyl group, a C-terminal amide group, a glycosylated amino acid, a nitrosylated amino acid, a carbonylated amino acid, an oxidized amino acid, or wherein said peptide is joined to polyethylene glycol, a fatty acid, or a pharmacokinetic modifier.

Alternative 123 includes the isolated peptide of anyone of Alternatives 114 to 120, wherein said peptide is less than or equal to 30, 29, 28, 27, 26, 25, 24, 23, 22, 21, 20, 19, 16, 15, 14, 13, 12, 11, 10, 9, 8, 7, or 6 amino acids in length or a length defined by a range that is between any two of these numbers.

Alternative 124 includes the isolated peptide of anyone of Alternatives 114 to 120, wherein said peptide is between 6 amino acids and 20 amino acids in length, preferably between 8-16 amino acids in length, and most preferably between 9 and 15 amino acids in length.

Alternative 125 includes the isolated peptide of anyone of Alternatives 114 to 120, wherein said peptide is joined to a support.

Alternative 126 includes the isolated peptide of anyone of Alternatives 114 to 120, wherein said peptide is multimerized.

Alternative 127 includes an isolated polynucleotide comprising a sequence encoding the peptide of any one of Alternatives 114-120.

Alternative 128 includes a vector comprising the isolated polynucleotide of Alternative 127.

Alternative 129 includes a vector comprising the isolated polynucleotide of Alternative 128.

Alternative 130 includes the isolated polynucleotide of Alternative 127 or the vector of Alternative 128, wherein said peptide is less than or equal to 30, 29, 28, 27, 26, 25, 24, 23, 22, 21, 20, 19, 16, 15, 14, 13, 12, 11, 10, 9, 8, 7, or 6 amino acids in length or a length defined by a range that is between any two of these numbers.

Alternative 131 includes the isolated polynucleotide of Alternative 127 or the vector of Alternative 128, wherein said peptide is between 6 amino acids and 20 amino acids in length, preferably between 8-16 amino acids in length, and most preferably between 9 and 15 amino acids in length.

Alternative 132 includes a protein complex comprising albumin or a fragment of albumin bound to the peptide of anyone of Alternatives 114 to 127.

Alternative 133 includes the protein complex of Alternative 132, wherein said protein complex is bound to a support.

Alternative 134 includes an isolated peptide comprising: $X_1 X_2 X_3 - X_8 X_9 X_{10} - X_{14} X_{15} X_{16}$, wherein $X_1$ and $X_{16}$ is any amino acid or absent; $X_2$ is selected from the group consisting of M, N, P, G, E, R, K $X_9$ is selected from the group consisting of T, R, K; $X_{15}$ is selected from the group consisting of P, D, E, Y, N, Q; and $X_3$-$X_8$ and $X_{10}$-$X_{14}$ is any amino acid.

Alternative 135 includes the isolated peptide according to Alternative 134, wherein $X_2$ is selected from the group consisting of K, N, P and $X_{15}$ is selected from the group consisting of P, D, E.

Alternative 136 includes the isolated peptide according to Alternative 135, wherein $X_2$ and $X_9$ are K and $X_{15}$ is E.

Alternative 137 includes the isolated peptide according to Alternative 136, wherein $X_5$-$X_8$ are F, F, V, K and $X_{10}$-$X_{11}$ are L, S.

Alternative 138 includes the isolated peptide according to Alternative 137, wherein said peptide is KLDTFFVKLSLFTE (SEQ ID NO: 58).

Alternative 139 includes a pharmaceutical composition comprising the isolated peptide according to any of Alternatives 134 to 138 and a pharmaceutically acceptable carrier, diluent or excipient.

Alternative 140 includes an antibody, monoclonal antibody or functional fragment thereof comprising the isolated peptide according to any of Alternatives 134 to 138.

Alternative 141 includes the antibody, monoclonal antibody or functional fragment thereof according to Alternative 140, is a single domain antibody (SdAb).

Alternative 142 includes a kit comprising the isolated peptide according to any of Alternatives 134 to 138 and/or the antibody, monoclonal antibody or a functional fragment thereof according to any of Alternatives 140 to 141 and instructions how to use said kit.

Alternative 143 includes an in vitro method comprising the steps of; (a) providing immune cells; (b) contacting said immune cells with the isolated peptide according to any of Alternatives 134 to 138 or the antibody, monoclonal antibody or functional fragment thereof according to any of Alternatives 140 to 141; and (c) determining a modulating effect of said immune cells such as by detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin. Optionally, the method includes detecting one or more of enhanced cytotoxicity, cytokine production, cell migration, and/or cell proliferation.

BRIEF DESCRIPTION OF THE DRAWINGS

FIG. 9A depicts effects for K5 and K6. FIG. 9B depicts effects for K12 and K13.

FIG. 18B is a contrast-enhanced image of FIG. 18A, so as to depict the binding data for non biotinylated IL-2 (triangles;

FIG. 19 illustrates the α-chain of the IL-2 receptor (CD25) binding P3028 (A) at the IL-2 binding site (B).

FIG. 23 illustrates identification of P3028 inhibitors in solution. Based on previous analyses potential binders of P3028 were synthesized on a chip. FIG. 23A illustrates results for assays 1-14. FIG. 23B illustrates results for assays 15-28. FIGS. 23A and 23B represent the left and right sides, respectively, of a single graph that was enlarged to show the text more clearly. The Y axis has been reproduced in FIG. 23B for reference.

FIG. 24 illustrates stimulatory activity of P28R on suppressed proliferative response to IL-2.

FIG. 28 illustrates single amino acid substitutions of peptide P28R having rampo scores greater than 500.

FIG. 30 illustrates rampo scores for binding of P3028 to internal deletion mutants, and single amino acid substitution mutants of peptide P28R.

FIG. 31 illustrates favorable electrostatic interactions and hydrophobic interactions between peptide 3028 and peptide KKL15.

FIG. 32 illustrates alignments of cyclic peptides identified as binding to P3028 in positional scan experiments (SEQ ID NOs: 265-267) and linear peptides identified as binding to P3028 (SEQ ID NOs: 2, and 268-293).

PBMC's from healthy control samples, and (FIG. 33B) PBMC's from cancer patients.

Figure 34:
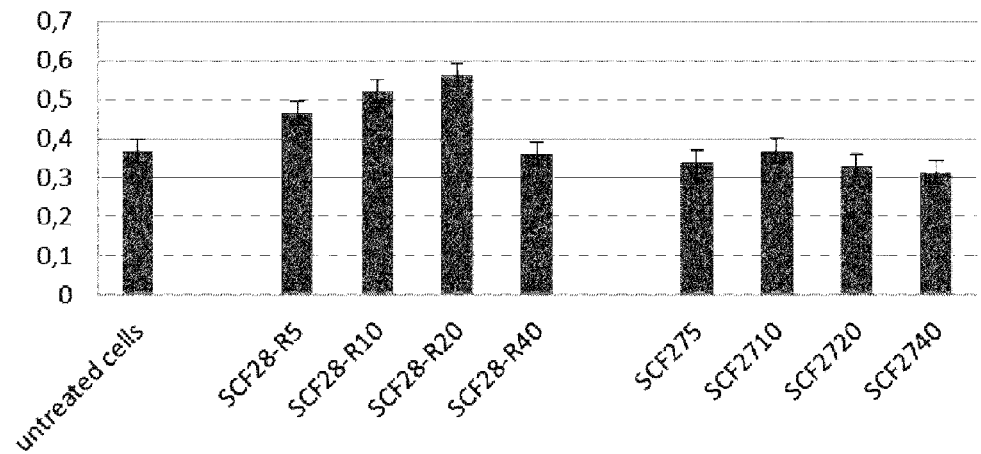

FIG. 34 illustrates effect of P28R (aka "SCF 28R") (N=9) and P27 (aka "SCF 27") (N=8) on PBMCs from cancer patients, MTS measurements, day 7.

Figure 35:
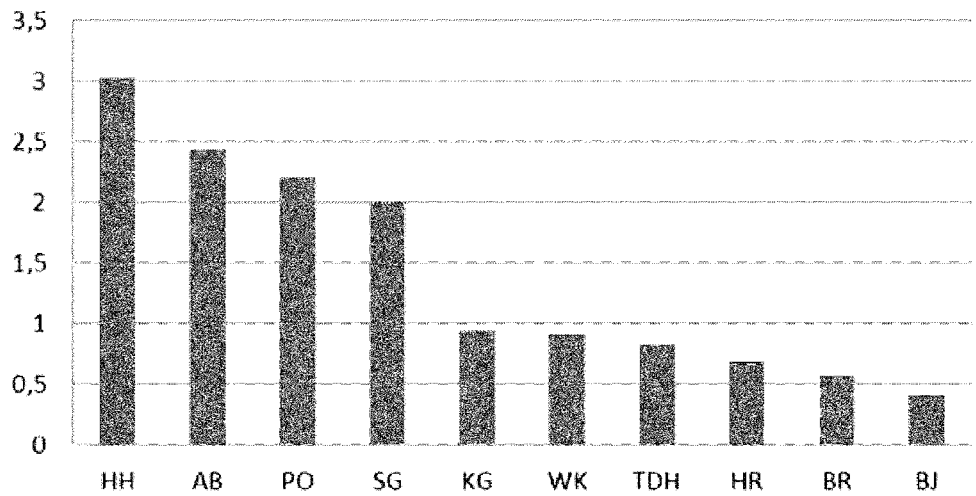

FIG. 35 illustrates response to IL-2 in cancer patients cells, measured by BrdU incorporation.

Figure 36A:
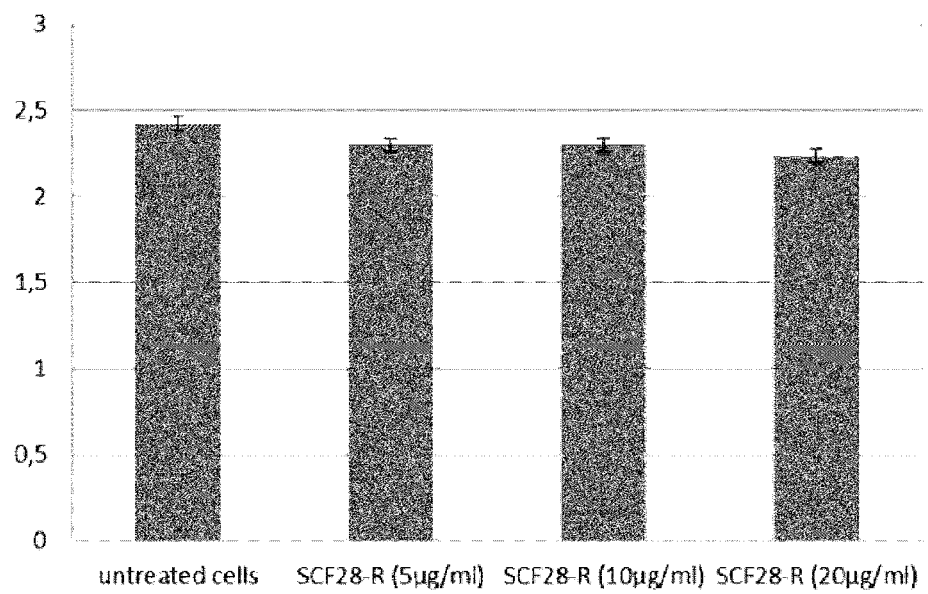
Figure 36B:
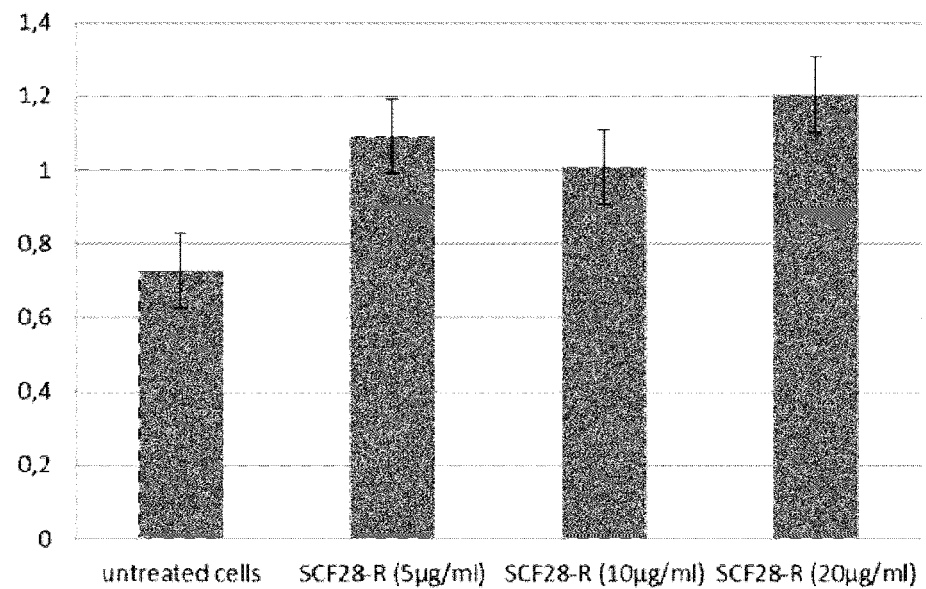

FIG. 36 illustrates effect of P28R (aka "P28") on IL-2 induced proliferation in cells of (FIG. 36A) high responders, and (FIG. 36B) low responders.

Figure 37:
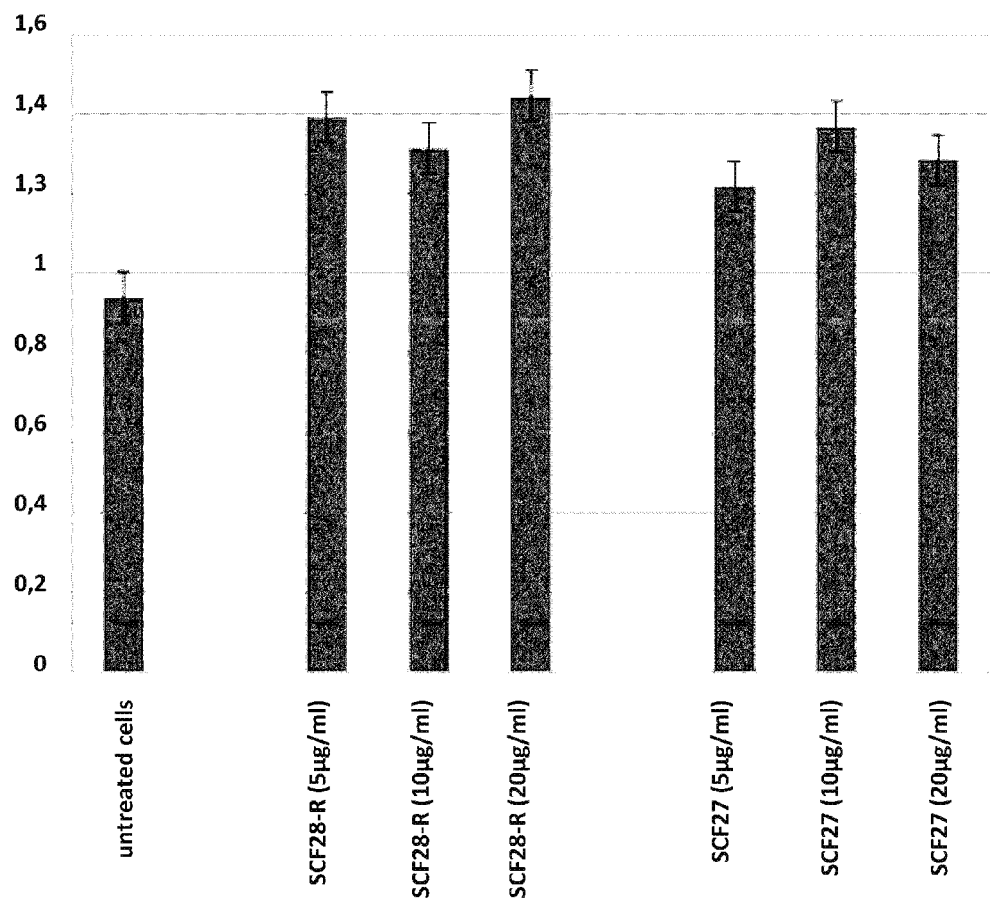

FIG. 37 illustrates effect of P28R (aka "SCF 28R") and P27 (aka "SCF 27") on IL-2 stimulation of PBMCs from cancer patients, based on BrdU incorporation.

Figure 38A:
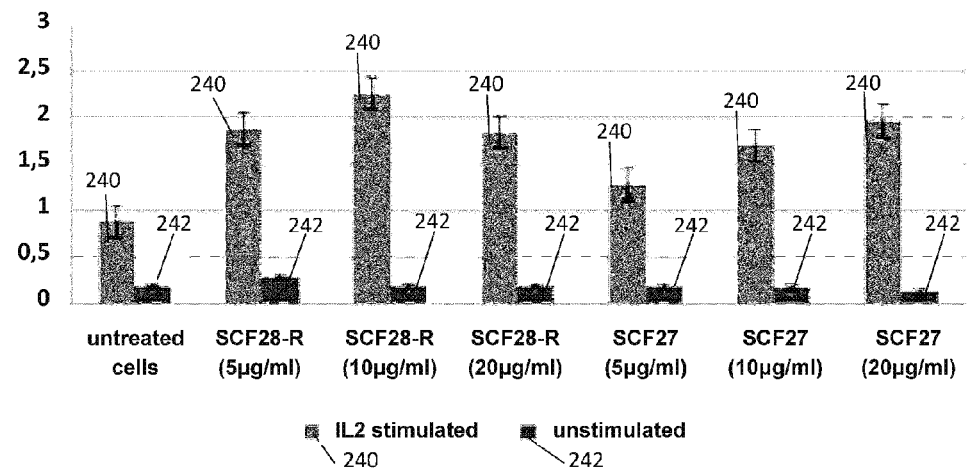
Figure 38B:
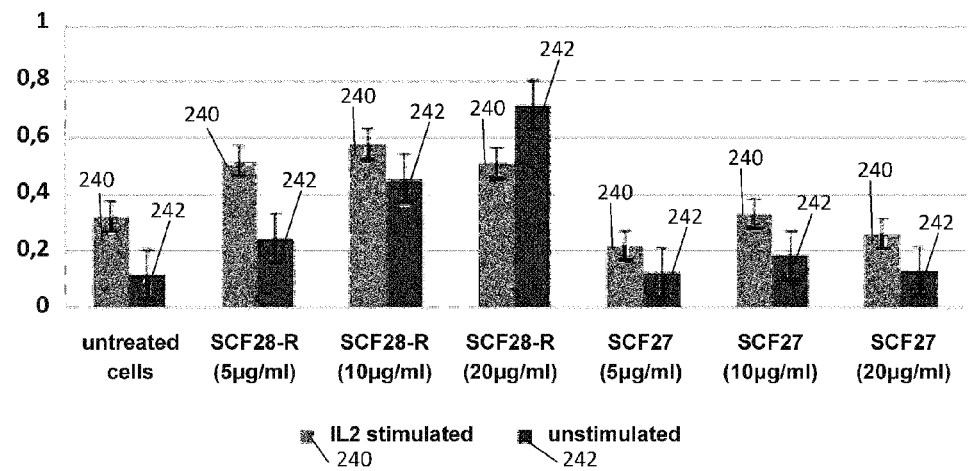
Figure 38C:
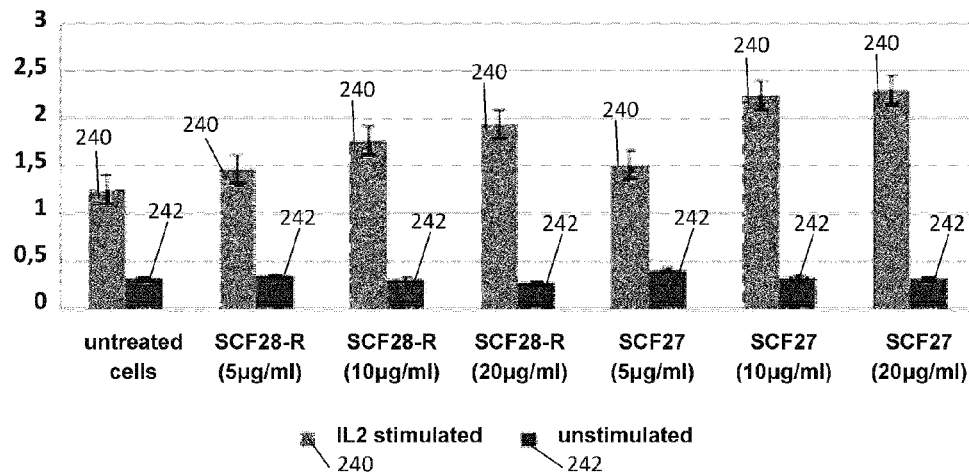
Figure 38D:
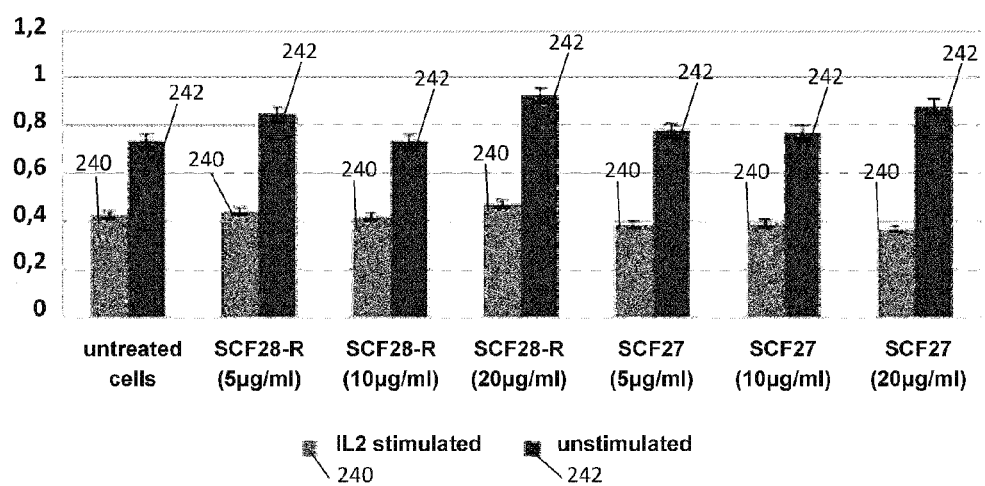

FIG. 38 illustrates effect of P28R (aka "SCF 28R") and P27 (aka "SCF 27") on IL-2-induced proliferation based on BrdU incorporation (FIGS. 38A, 38C) and MTS incorporation (FIGS. 38B, 38D). Shown are cells of two different patients, (FIGS. 38A, 38B) and (FIGS. 38C, 38D) respectively.

Figure 39:
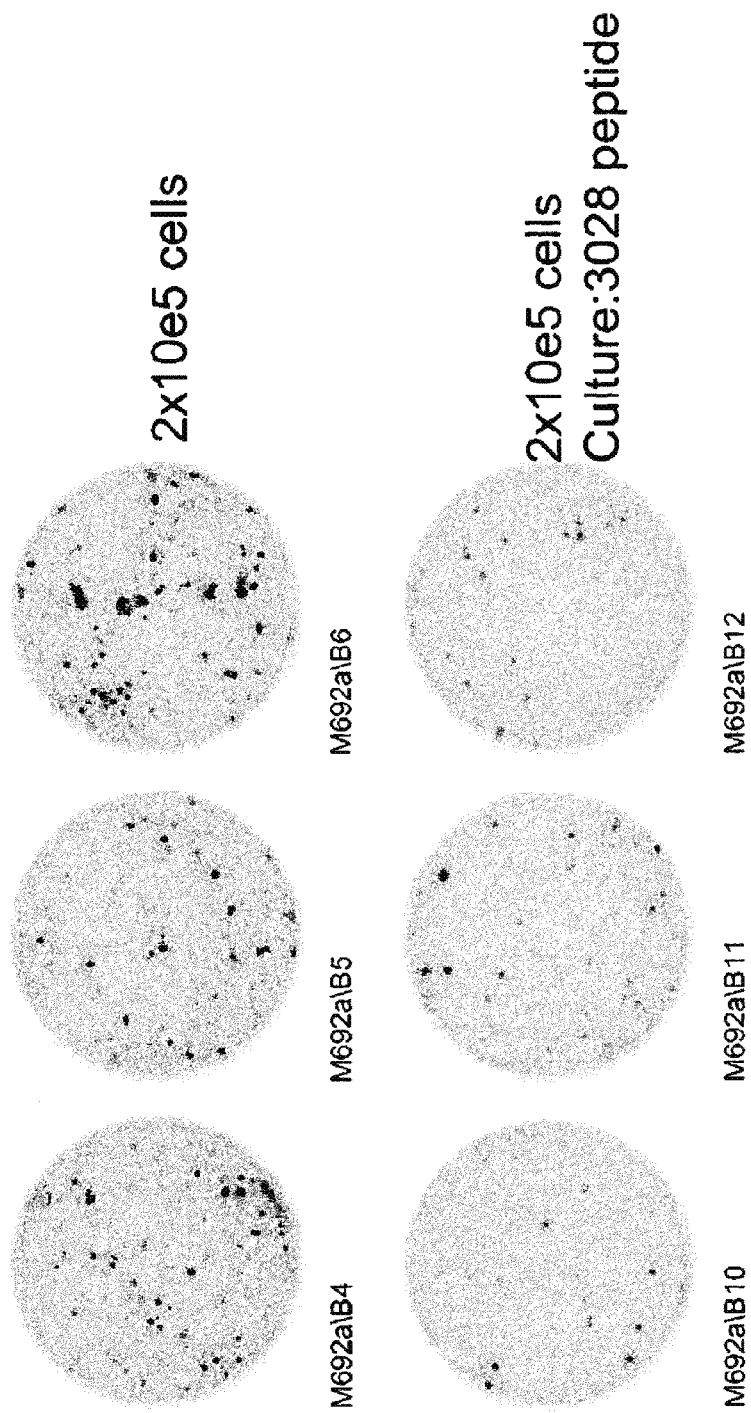

FIG. 39 illustrates enzyme linked immunosorbant spot assays of cells with (bottom row) and without (top row) P3028 peptide.

Figure 40:
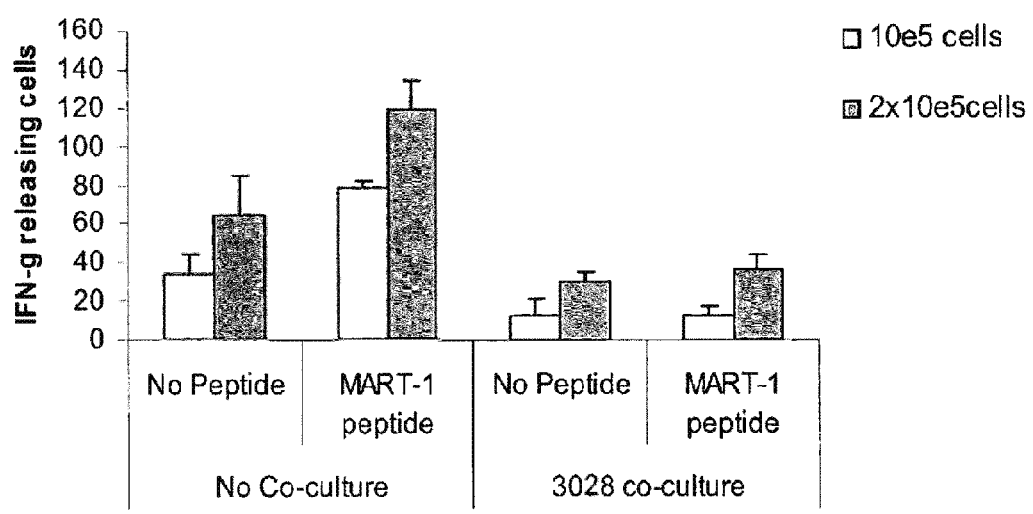

FIG. 40 illustrates data from enzyme linked immunosorbant spot assays of cells with and without P3028 peptide.

Figure 41A:
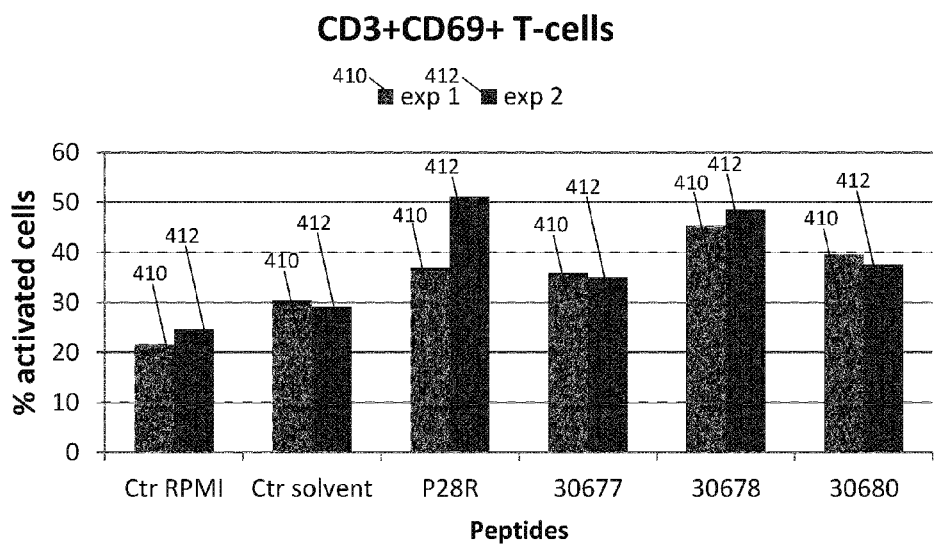
Figure 41B:
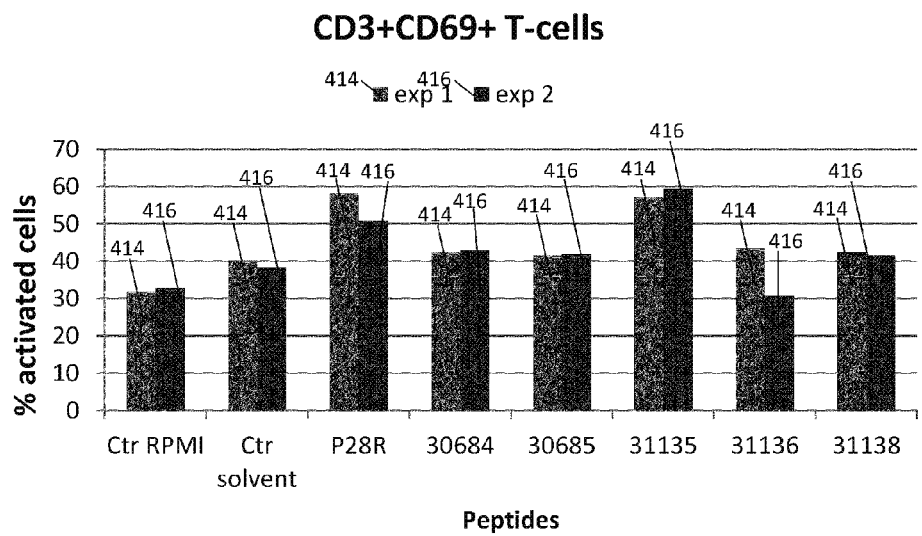

FIG. 41 is a series of graphs illustrating effects of modified peptides on activation of PBMCs from healthy control person. PBMCs were incubated with the peptides (40 μg/mL) for 24 hours in RPMI plus 10% human AB serum. Activation is determined as percentage of cells with enhanced marker CD69 using flow cytometry. FIG. 41A illustrates results of two experiments (410 and 412) performed for each peptide. FIG. 41B illustrates results of two experiments (414 and 416) performed for each peptide.

Figure 42A:
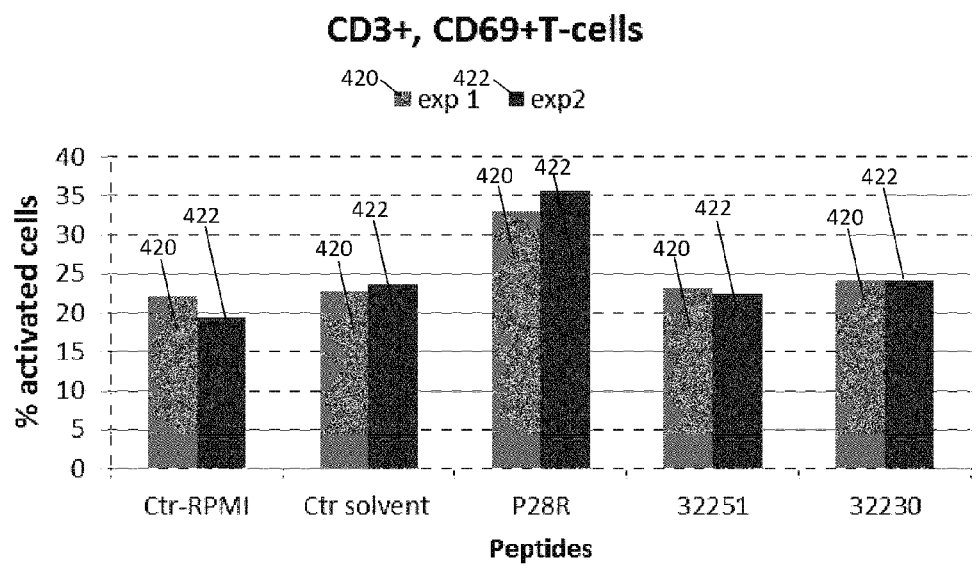
Figure 42B:
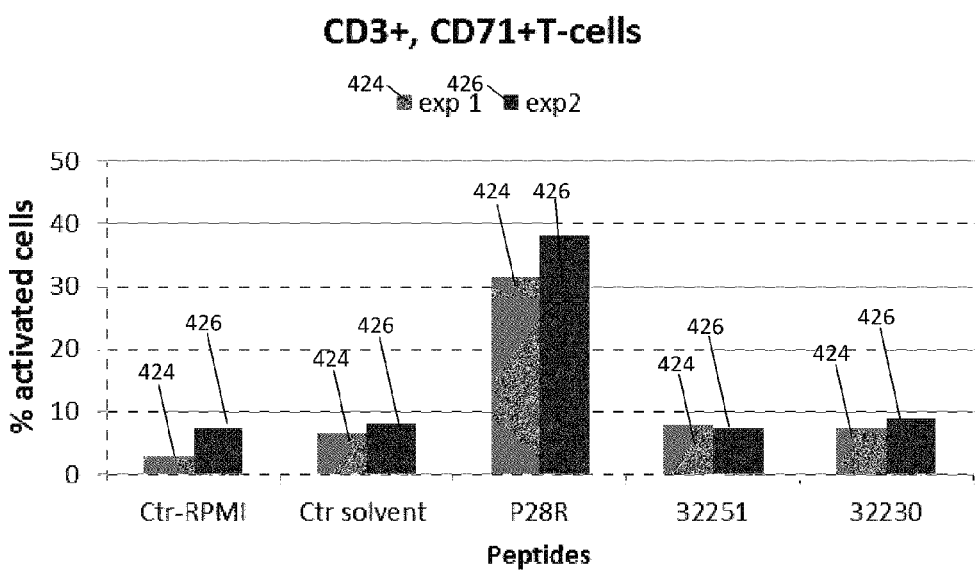

FIG. 42 is a series of graphs illustrating effects of the full length peptide P28R and the 6 amino acid central sequence (32230, FFVKLS, SEQ ID NO: 62) in culture medium containing normal human AB serum. Activation is determined as percentage of cells with enhanced marker CD69 or CD71 using flow cytometry. PBMCs were incubated with the peptides (40 μg/mL) for 24 hours in RPMI plus 10% human AB serum. FIG. 42A illustrates the results of two experiments (420 and 422) performed for each peptide. FIG. 42B illustrates the results of two experiments (424 and 426) performed for each peptide.

Figure 43:
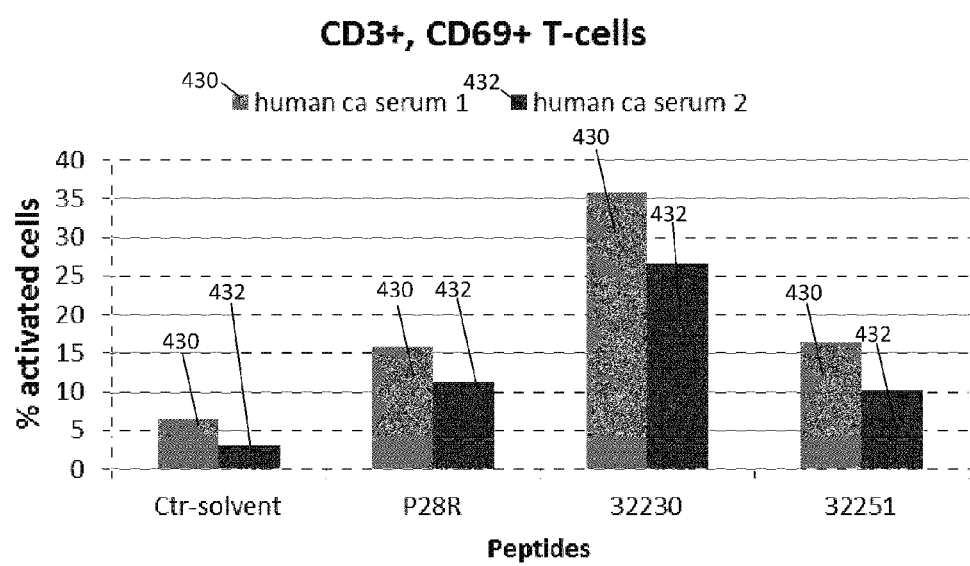

FIG. 43 is a graph illustrating a comparison of the full length peptide P28R and the 6 amino acid central sequence (32230, FFVKLS, SEQ ID NO: 62) in culture medium containing sera from two different cancer patients ("human ca serum 1" 430 and ("human ca serum 2" 432).

Figure 44A:
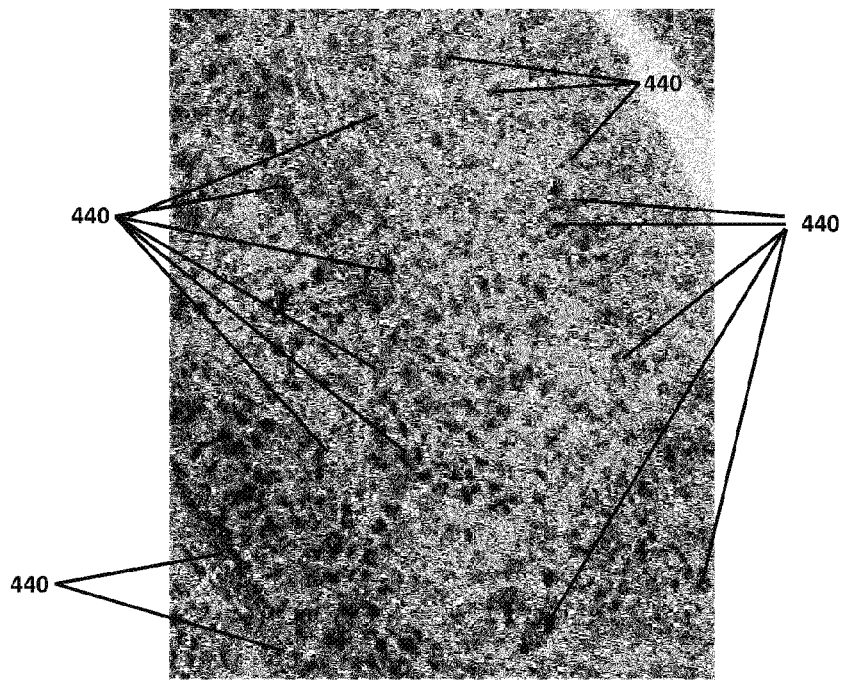
Figure 44B:
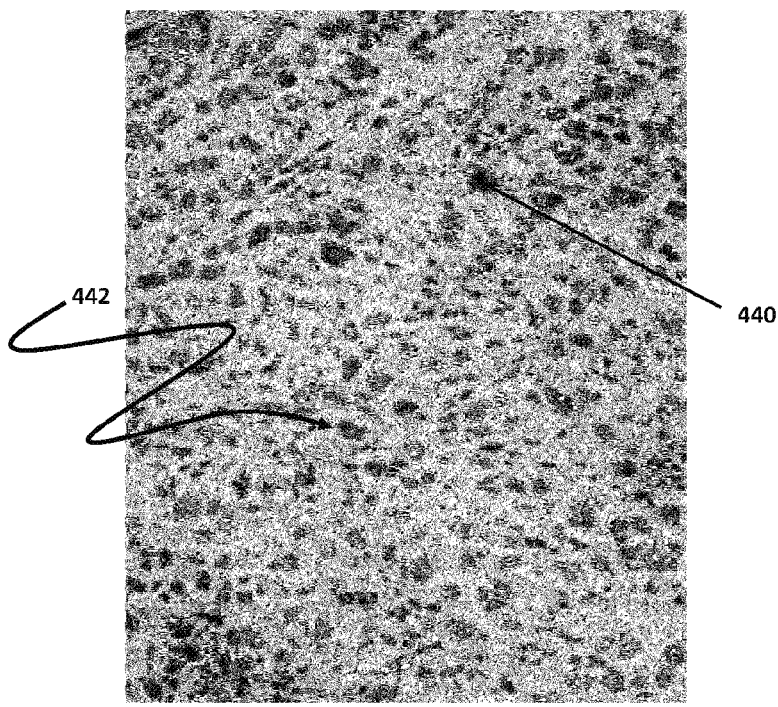

FIG. 44 is a series of microscope images illustrating P28R treatment of human prostate cancer, PC3, in a xenograft model in nude mice. Tumor was injected intra-tumorally with P28R (FIG. 44A) and only the drug solvent (FIG. 44B). Staining for Caspase 3 440 (demonstrating induction of apoptosis) and an absence of staining 442 are depicted.

Figure 45A:
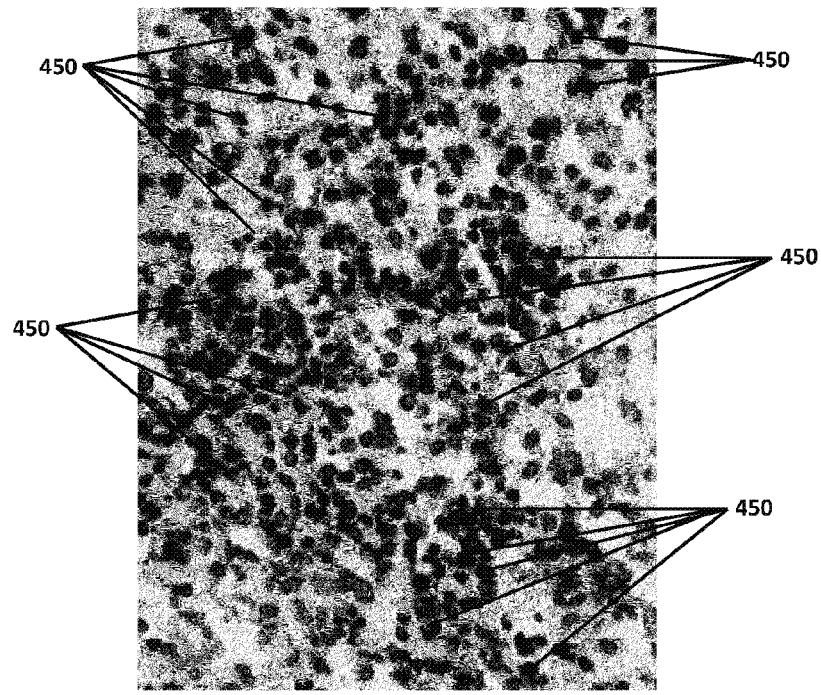
Figure 45B:
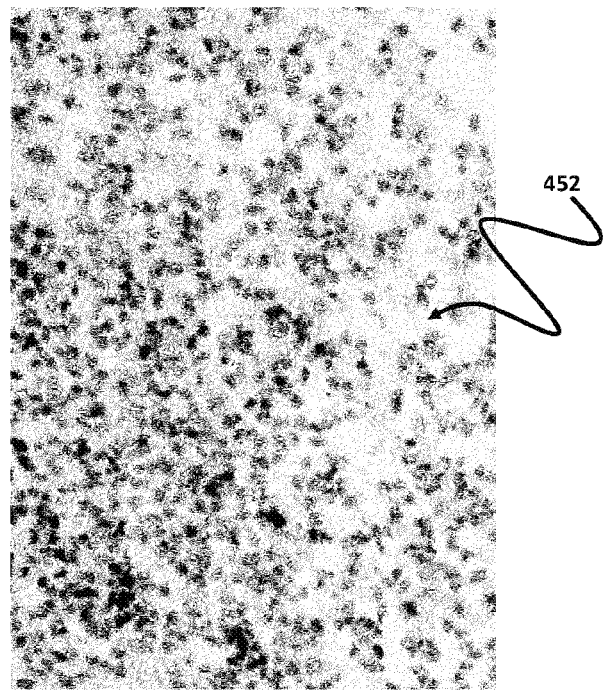

FIG. 45 is a series of microscope images illustrating intra-tumoral treatment of B16 melanoma with P28R. The inflammatory infiltrate was demonstrated after 3 days of treatment using a polyclonal rabbit antibody directed against CD45 (FIG. 45A), and control sections were incubated with rabbit IgG at the same concentration (FIG. 45B). Staining 450 and an absence of staining 452 are depicted.

Figure 46A:
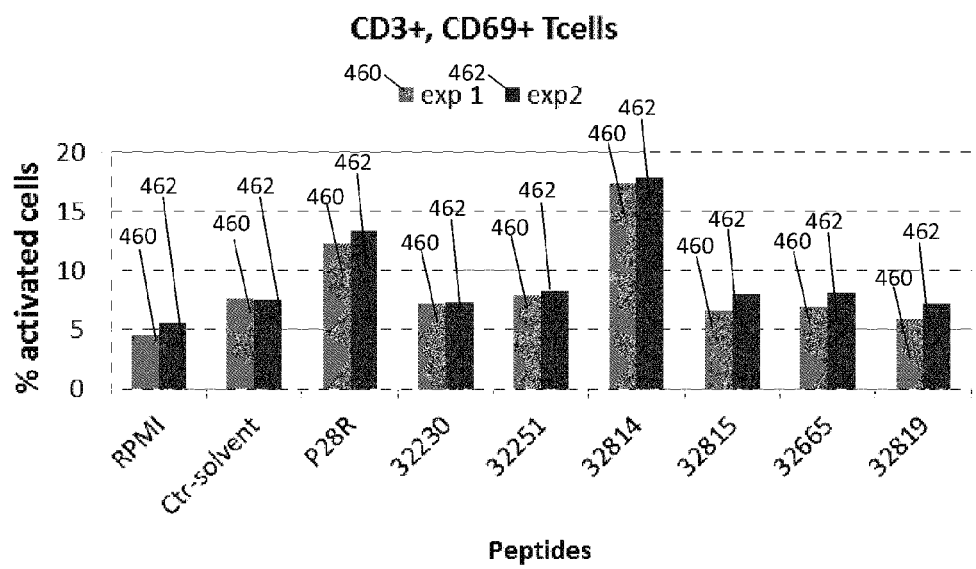
Figure 46B:
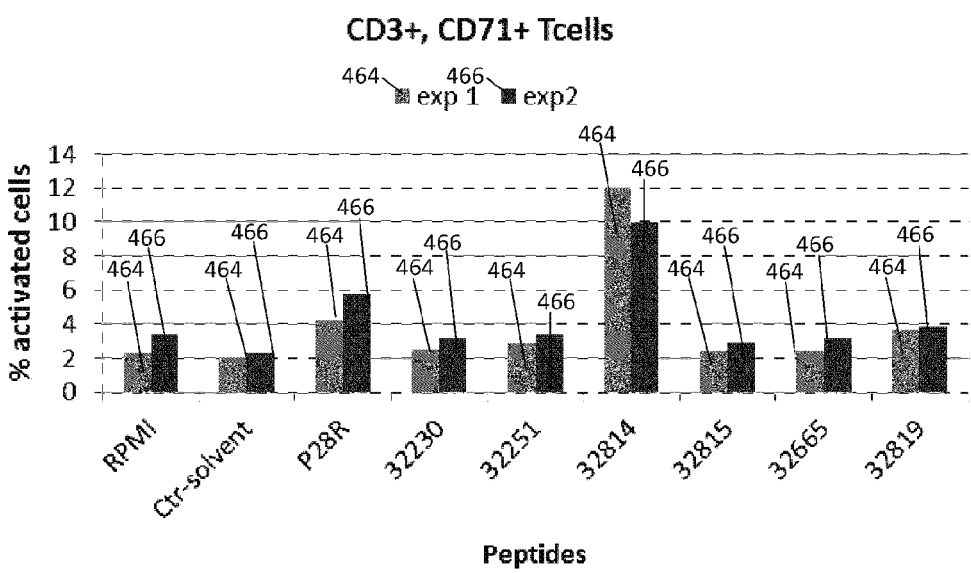

FIG. 46 is a series of graphs illustrating Effect of modified peptides on activation of PBMCs from healthy control person. Activation is determined as percentage of cells with enhanced marker CD69 (FIG. 46A, showing results of two experiments, exp 1 460 and exp 2 462) or CD71 (FIG. 46B, showing results of two experiments, exp 1 464 and exp 2 466) using flow cytometry. PBMCs were incubated with the peptides (40 μg/mL) for 48 hours in RPMI plus 10% human AB serum.

Figure 47A:
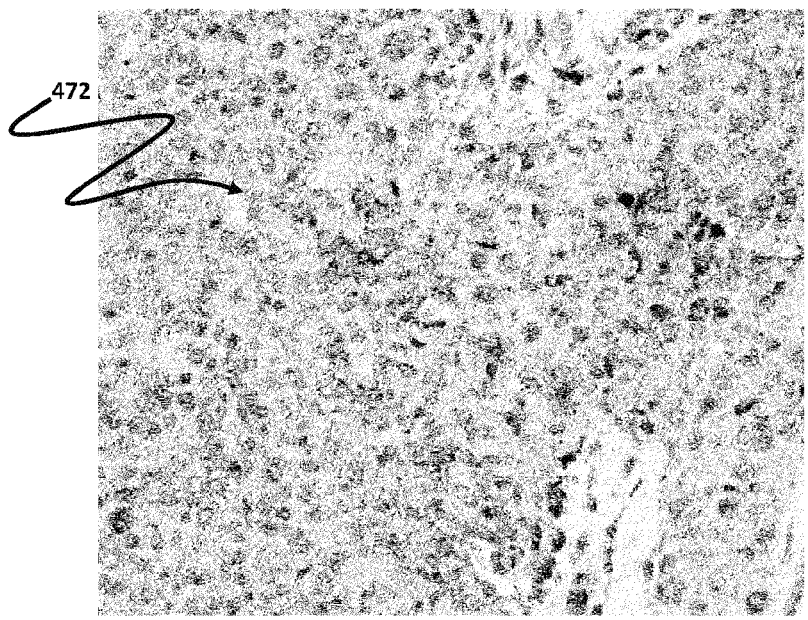
Figure 47B:
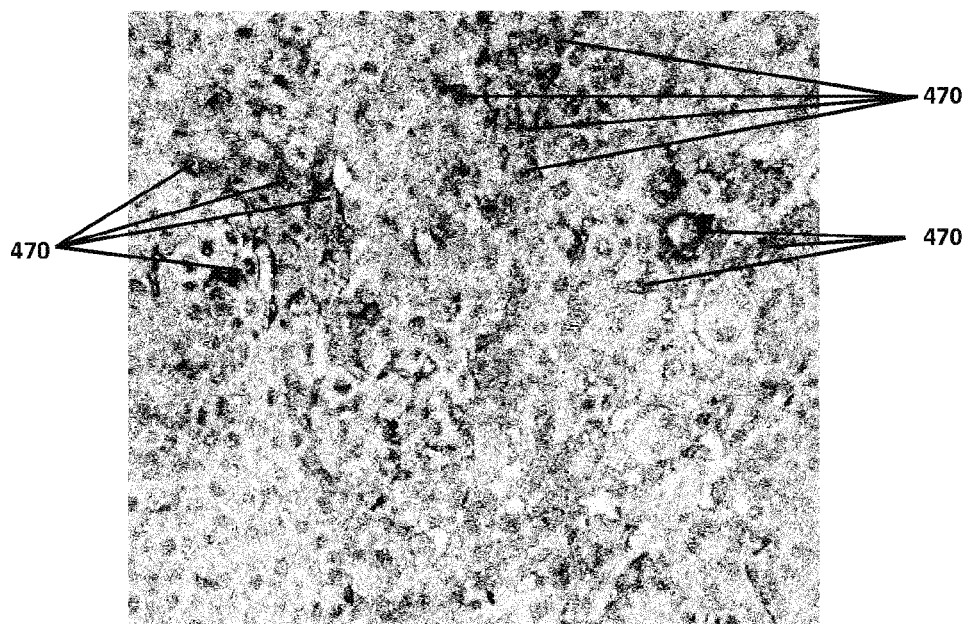

FIG. 47 is a series of microscope images illustrating occurrence of the immunoinhibitory 3028 structure in two areas (FIG. 47A and FIG. 47B, respectively) of a human breast cancer. Immunohistochemical staining (470) using biotinylated P28R is depicted. An absence of staining 472 is observed in FIG. 47A.

DETAILED DESCRIPTION OF THE INVENTION

Figure 2:
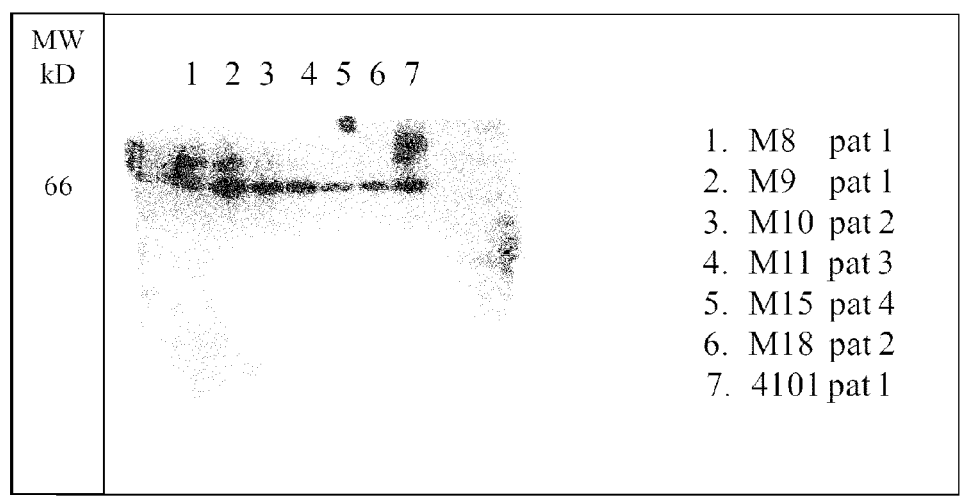
FIG. 2 illustrates Western blot performed on tumor extracts using antibodies directed against the 3028-structure.

Several immunoregulatory peptide inhibitors, which interact with immunoregulatory peptides that cause immunosuppression in a human (e.g., a human having cancer, enduring or chronic infectious or inflammatory disease), have been developed. Preferred immunoregulatory peptide inhibitors bind to proteins or peptides that comprise the P3028 structure and/or the P3028 sequence (SEQ ID NO: 185). With reference to some embodiments and description herein, the P3028 structure refers to polypeptides, such as peptides, proteins, and the like that include the P3028 sequence (SEQ ID NO: 185). The P3028 structure can include macromolecules such as peptides, proteins, and the like that are recognized by antibodies that bind specifically to P3028 structures (see Example 1 and FIG. 2). For example, aggregates of albumin, denatured albumin and other damaged albumins can include the P3028 structure. In some contexts in the present application, the P3028 structure, P3028 sequence, and P3028 are terms used interchangeably. Molecules having the P3028 structure interact with receptors on immune cells, such as the IL-2 receptor and the LFA-1 receptor, causing immunosuppression. As such, it is contemplated herein that peptides, proteins, albumin fragments, damaged albumin (e.g. denature albumin) and albumin aggregates can include the P3028 structure, and can interact with immune cell receptors such as the IL-2 receptor and LFA-1 receptor. Immunosuppression can be characterized by a reduced immune cell proliferation, spreading and migration, as well as, NK-cell cytotoxicity. In the presence of an immunoregulatory peptide inhibitor, as described herein; however, the immunosuppression mediated by the P3028 structure can be altered (e.g., reduced, ameliorated, eliminated, or removed altogether). In some experiments, for example, it was found that an immunoregulatory peptide inhibitor can remove a molecule including a P3028 structure from the LFA-1 receptor thereby altering the immunosuppression mediated by P3028 structure. Accordingly, the description that follows provides details on many different classes of immunoregulatory peptide inhibitors including, but not limited to, antibody or antibody fragment based immunoregulatory peptide inhibitors, peptide based immunoregulatory peptide inhibitors, peptidomimetic immunoregulatory peptide inhibitors, modified immunoregulatory peptide inhibitors (e.g., containing a D amino acid, N-terminal acetyl, or C terminal amide group), cyclic peptides inhibitors, and aptamer based immunoregulatory peptide inhibitors. Methods of using compositions (as described herein) to reduce immunosuppression or an aspect thereof (e.g., reducing a P3028-mediated inhibition of immune cell proliferation, spreading, migration, or NK-cell cytotoxicity), as well as, approaches to inhibit, reduce, or alter the progression of cancer or inflammatory disease are provided. The composition can comprise, consist of, or consist essentially of an immunoregulatory peptide inhibitor as described herein. Accordingly, immunoregulatory peptide inhibitors as described herein can be useful for ameliorating, reducing the symptoms of, reducing the severity of, and/or treating immunosuppression.

Immunoregulatory peptide inhibitors as described herein interact with or bind to proteins or peptides that comprise at least one of sequence SEQ ID NOs: 183-185 or 188-246. Such peptides can have immunoregulatory properties similar to P3028 sequences and structures (see Examples 17 to 26).

With reference to some embodiments in the following disclosure, amino acids, or amino acid residues can be referred to by either a three-letter or a one-letter code. Twenty amino acids are typically encoded by the genetic code, and can be referred to using the following codes or abbreviations herein: Arginine ("Arg" or "R"), Histidine ("His" or "H"), Lysine ("Lys" or "K"), Aspartic Acid ("Asp" or "D"), Glutamic Acid ("Glu" or "E"), Serine ("Ser" or "S"), Threonine ("Thr" or "T"), Asparagine ("Asp" or "N"), Glutamine ("Gln" or "Q"), Cysteine ("Cys" or "C"), Glycine ("Gly" or "G"), Proline ("Pro" or "P"), Alanine ("Ala" or "A"), Valine ("Val" or "V"), Isoleucine ("Be" or "I"), Leucine ("Leu" or "L"), Methionine ("Met" or "M"), Phenylalanine ("Phe" or "F"), Tyrosine ("Tyr" or "Y"), Tryptophan ("Trp" or "W").

With reference to some embodiments in the following disclosure by "peptide" is meant a protein and/or a fragment of a protein, which may have several different lengths (e.g., at least or equal to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 120, 140, 160, 180, 200, 240, 260, 300, 350, 400, 450, 500, 600, 700, 800, or 1000 amino acids or a range defined by any number in between these numbers).

With reference to some embodiments in the following disclosure, amino acids (and their residues) can be categorized according to various characteristics of the side chains of the alpha carbon of the amino acid. It is noted that the twenty naturally occurring amino acids encoded by the genetic code, and also synthetic amino acids are contemplated herein. As used herein "hydrophobic amino acid" (including pluralaizations and variations of this root term) refer to naturally occurring or synthetic amino acids having a hydrophobic side chain, for example A, V, I, L, M, F, Y, or W. As used herein, "positively charged amino acid" (including pluralaizations and variations of this root term) refer to naturally occurring or synthetic amino acids having a positively charged side chain, for example, R, H, or K. As used herein, "negatively charged amino acid" (including pluralaizations and variations of this root term) refer to naturally occurring or synthetic amino acids having a negatively charged side chain, for example, D or E. As used herein, "hydrophobic non-aromatic carbon chain amino acid" (including pluralaizations and variations of this root term) refer to naturally occurring or synthetic amino acids having a hydrophobic non-aromatic carbon side chain, for example, A, V, I, or L. As used herein, "polar uncharged amino acid" (including pluralaizations and variations of this root term) refer to naturally occurring or synthetic amino acids having a polar uncharged side chain, for example, S, T, N, or Q.

With reference to some embodiments and description herein, the bases of nucleic acids, such as DNA, RNA, and the like can be referred to by either the name of the base or a one letter code. One skilled in the art will appreciate that the genetic code is degenerate, in that for some amino acid residues, two or more three-base codons can encode the same amino acid. Thus, some one letter codes, and described herein, can represent one of two or more bases, for example to describe two or more possible nucleic acids that can encode a single amino acid. One-letter codes used herein include: "A" (adenine), "G" (guanine), "C" (cytosine), "T" (thymine), "R" (one of adenine or guanine), "Y" (one of cytosine or thymine), "M" (one of adenine or cytosine), "K" (one of guanine or thymine), "S" (one of cytosine or guanine), "W" (one of adenine or thymine), "H" (one of adenine, cytosine, or thymine), "B" (one of cytosine, guanine, or thymine), "V" (one of adenine, cytosine, or guanine), "D" (one of adenine, guanine, or thymine), and "N" (one of adenine, guanine, cytosine, or thymine).

The terms "de-blocking" and "unblocking" as used herein (including pluralization and variations of this root term) refers to displacing a bound immunoregulatory peptide or P3028 structure from a receptor. As such, de-blocking or unblocking a receptor shifts the equilibrium between receptor-bound and non-receptor-bound immunoregulatory peptide towards the "non-receptor-bound" category. For example, an LFA-1 receptor or IL-2 receptor can be de-blocked in accordance with embodiments herein by displacing a bound peptide P3028 from the LFA-1 receptor of IL-2 receptor. For example, an LFA-1 receptor or IL-2 receptor can be de-blocked in accordance with embodiments herein by displacing any immunoregulatory peptide comprising one or more sequences for Tables 1-4 from the LFA-1 receptor or IL-2 receptor.

The term "immune cell activation" as used herein, and pluralizations and variations of this root term (including such as "activating an immune cell"), refers to immune cell proliferation, activating or enhancing expression of CD69 and/or CD71, induction of secretion of a signal substance (e.g. IFNγ or IL-12), induction of secretion of a cytolytic molecule (e.g. perforin or granzyme B), enhanced cytotoxicity, cytokine production, cell migration, cell proliferation, or two or more of these listed items. By way of example, immune cell activation in accordance with some embodiments herein can occur if an immune cell proliferates, or if an immune cell begins to express detectable CD69, or if an immune cell increases its expression of CD71, or if an immune cell secretes IFNγ, IL-12, or IFNγ and IL-12.

Available data support a major role of the immune system in cancer control sample. Malignant tumors, however, can exploit a large number of immunoregulatory mechanisms to suppress immune mediated anti-tumor reactivity. Based on the observation that an increased serum concentration of interleukin-6 (IL-6) often is correlated to a poor prognosis in cancer patients of various diagnoses, the origin and induction of this cytokine was explored. It was found that proteolytic fragmentation or denaturation of normal serum albumin generated neo-structures, which exhibit immunoregulatory activity by binding to immune cells. Accordingly, a new class of immunoregulatory substances was discovered.

The existence of albumin sequences having neo-structures that bind to immune cells was identified using a human ex vivo model based on affinity chromatography over an "Artificial Cell Surface Column" (ACS). The effect of different albumin fragments on IL-2 induced proliferation of human immune cells (PBMCs) was analyzed in the ACS system (see Example 9). Briefly, PBMCs were cultured for seven days in the presence of IL-2 and the various synthetically prepared albumin fragments. Proliferation was measured as incorporation of $^3$H thymidine during the final 18 hours. One of the peptides, P3028 (also referred to as "peptide 3028" and having the amino acid sequence VFDEFKPLVEEPQNLIK—SEQ ID NO: 185) regularly inhibited IL-2 induced proliferation, but none of the other peptides identified by their binding to the artificial cell surface showed as much inhibitory activity as the P3028 sequence/structure (see FIG. 6). Accordingly, the immune cell proliferative response induced by LFA-1 or IL-2 could be inhibited by P3028, indicating that P3028 sequence/structure may be acting through at least the LFA-1 or IL-2 receptor.

The enhanced incorporation of $^3$HTdR can be the result of an enhanced specific activity of the intracellular thymidine pools and thereby an enhanced specific activity of DNA, thus, not necessarily mirroring an increase in the number of cells. It was therefore considered of be of importance to explore a different mode of stimulation of lymphocyte proliferation and to measure the response using a different method, the MTS technique (see Example 3). Accordingly, T-cells were stimulated in cultures on plates pre-coated with a monoclonal antibody directed against CD3 and the number of metabolically active cells was determined using MTS staining after 3 to 7 days of culture (see FIG. 8). As shown, P3028 sequence/structure had an inhibitory effect. It can be argued that the reduced MTS staining caused by P3028 sequence/structure might be due to a reduced cell metabolism; however, taken together the results from both models of lymphocyte proliferation, a reduced metabolism should reasonably reduce the endogenous thymidine pools and thereby result in an increased uptake of exogenous thymidine/specific activity of the thymidine pools, which then should be erroneously registered as an enhanced proliferation. The $^3$H-TdR was actually reduced in these experiments, indicating inhibition of proliferation. Accordingly, it was confirmed that peptides comprising the 3028 sequence effectively inhibited IL-2 mediated immune cell proliferation.

Peptide fragments encompassing the C- and N-terminal parts of P3028 were then synthesized and the ability of these peptides (separately and in combination) to inhibit IL-2 induced proliferation of immune cells was analyzed (see Example 6). An N-terminal fragment of P3028 (i.e., P3325 having the amino acid sequence VFDEFKPLVE (SEQ ID NO: 186)) and a C-terminal fragment of P3028 (i.e., P3218 having the amino acid sequence EPQNLIK) (SEQ ID NO: 187)) were synthesized. It was determined that the inhibitory activity of these two fragments of P3028 alone or in combination was weaker than P3028 (see FIG. 12) and the peptide fragments of 3028 do not inhibit the effect of P3028 on IL-2 induced proliferation (see FIG. 13).

It was then determined that peptides comprising the P3028 sequence/structure sequence not only interacted with the IL-2 receptor but also interacted with the LFA-1 receptor. In a first set of experiments, it was found that the P3028 peptide has the capacity to modulate the binding of an LFA-1 specific monoclonal antibody to the LFA-1 receptor on human immune cells (see Example 7). This LFA-1 specific monoclonal antibody is a potent inhibitor of IL-2 induced immune cell proliferation (see Vyth-Dreese et al., Eur. J. Immunol. 12:3292-3299 (1993)). A standard immunohistochemical staining procedure was employed in the presence and absence of the P3028 peptide. Briefly, immune cells (PBMCs) from healthy individuals and cancer patients were compared. The cells were fixed utilizing acetone, blocked with 10% human AB-serum with or without P3028, and incubated with a monoclonal anti-LFA-1 antibody and a secondary antibody followed by color development using Fast Red. As shown in FIG. 16A, a clear membrane staining 3 was found on PBMCs from healthy control samples in contrast to PBMCs from a patient with advanced cancer, which exhibited weak staining 5. However, when the PBMCs from this cancer patient were incubated with an antibody specific for the 3028 structure for 24 hours the membrane staining 3 appeared, indicating that the antibody bound the 3028-structure and thereby unblocked LFA-1 (see FIG. 16C) and the discussion infra.

Figure 18A:
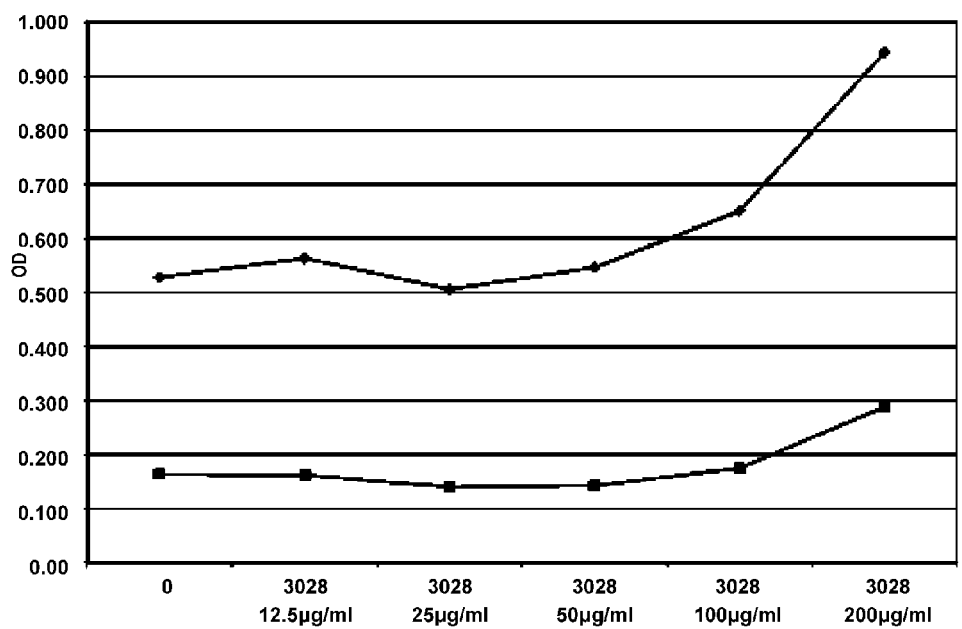
FIGS. 18A and 18B illustrates ELISA analysis showing that the binding of biotinylated IL-2 to rhuIL-2R.

Since P3028 sequence/structure significantly inhibited the proliferative response of immune cells to IL-2, the effect of P3028 sequence/structure on the binding of IL-2 to CD25 was studied. The fusion protein of CD25 and the Fc-part of IgG was bound to protein G coated micro-plates/ELISA plates and the plates were incubated with biotinylated IL-2 with or without the presence of P3028. Surprisingly, the binding of IL-2 to CD25 was enhanced by the presence of P3028, providing evidence of a three-part interaction between IL-2, CD25 and P3028 (see FIG. 18A-B). Even if the binding of IL-2 to CD25 is enhanced, the proper assembly of the high affinity receptor and/or signal transduction is blocked as the P3028 sequence/structure is a potent inhibitor of IL-2 induced proliferation. Using computer-assisted molecular modeling, it was determined that the P3028 sequence/structure binds to CD25 at the IL-2 binding site (see FIG. 19). These results provide greater evidence that the P3028 sequence/structure has at least a dual immunoregulatory capacity since it binds to both the LFA-1 receptor and the IL-2 receptor.

The ability of specific albumin fragments to impact NK-cell cytotoxicity was also evaluated. In these experiments, synthetic peptides corresponding to albumin fragments (P3028, P3026, and P3027) (SEQ ID NOs: 185, 183, and 184, respectively) were prepared and the amount of lysis of K562 target cells was assessed (see Example 4). Inhibition was not seen in the presence of the control sample peptide P3027 but P3028 and to a lesser degree P3026 caused a reduction in NK-cell cytotoxicity (see FIGS. 9A-B). Accordingly, peptides having the sequence of P3028 effectively inhibit NK-cell cytotoxicity.

Figure 11:
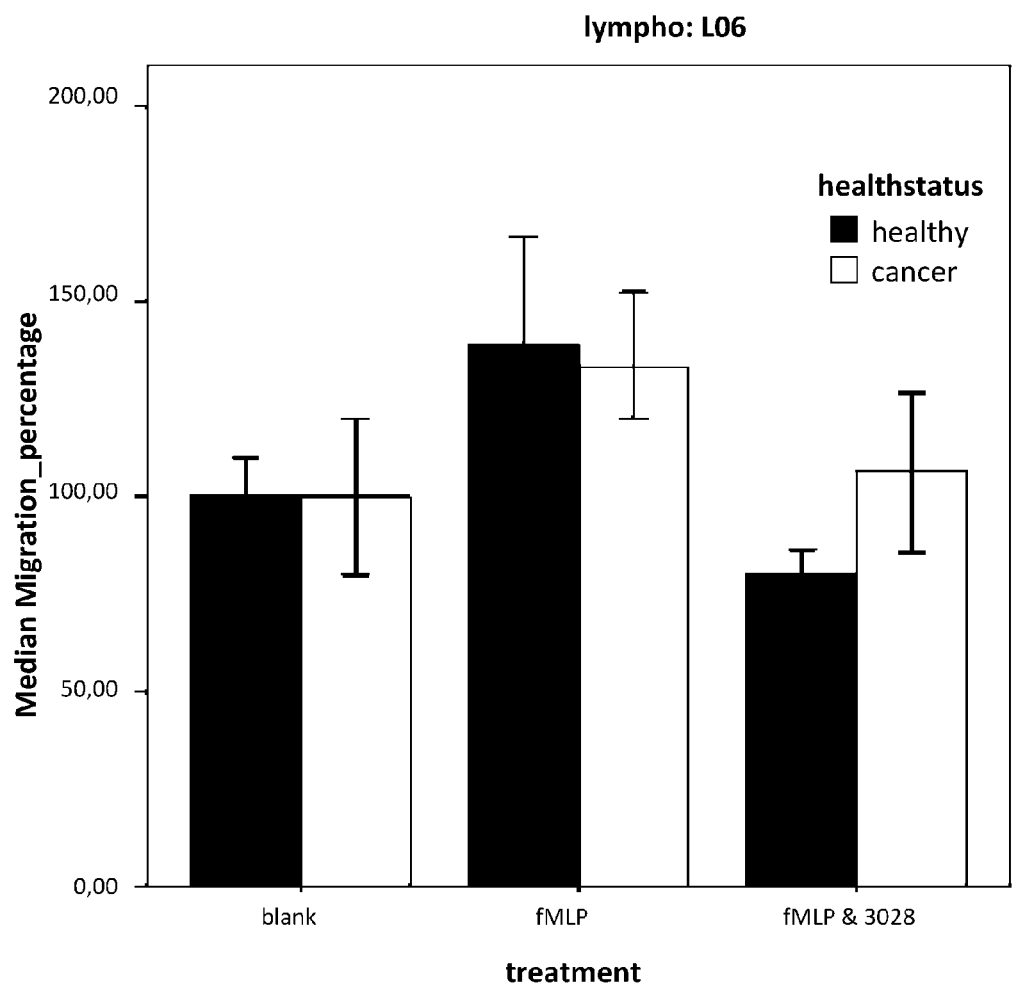
FIG. 11 illustrates effect of P3028 on migration of PBMCs studied using the Boyden chamber technique.

The ability of specific albumin fragments to inhibit leukocyte spreading and immune cell migration was also analyzed. Briefly, buffy coat cells were prepared from heparinized blood by Dextran assisted sedimentation. These cells were then washed twice in PBS and transferred to clean slides. The cells strongly adhered to the glass surface and spread out; however, pre-treatment of these cells with P3028 at a concentration of 10 µg/ml for 15 minutes efficiently inhibited the immune cell spreading (see Example 5). Similarly, the impact of P3028 on PBMC migration was studied using the Boyden chamber technique (see Example 5). As shown in FIG. 11, P3028 is a potent inhibitor of immune cell migration (p<0.002).

Antibodies specific for proteins having the P3028 sequence/structure were prepared, purified, and characterized (see Example 9). Polyclonal antibodies specific for P3028 were generated in rabbits or goats. Briefly, rabbits were immunized with P3028 and specific antibodies were affinity purified using P3028. These antibodies were found to bind to P3325 (the N-terminal fragment SEQ ID NO: 186) but not P3218 (the C-terminal fragment (SEQ ID NO: 187) of P3028.

In a next series of experiments, the expression of P3028 in malignant tumors (e.g., malignant melanoma, renal cell carcinoma, and colorectal cancer) was identified by immunohistochemical staining using affinity purified rabbit anti-3028 antibodies (see Example 9). The immunohistochemical staining of malignant melanoma, renal cell carcinoma, and colorectal cancer tissue slices showed that the P3028 sequence containing molecules are widely expressed and/or localized on cancer cells. These results were further supported by the demonstration of 3028-structures in tumor extracts prepared from malignant melanoma metastases using a Western technique (see Example 1). Appreciable 3028 structures (approximately, slightly larger than 66 kD) were identified by the Western blot but the 3028 sequence was also detected in full size albumin and larger molecules (see FIG. 2). These results provide evidence that molecules comprising the 3028 structure are generated not only by proteolytic fragmentation but also by denaturation. Accordingly, it was determined that P3028 sequence and/or molecules that comprise this sequence are present in and/or localized to tumor tissue.

An ELISA technique was then used to confirm that proteins and peptides comprising the 3028 sequence were present in human serum. Briefly, a sandwich assay was employed, wherein affinity purified anti-3028 antibodies were coated onto high protein binding ELISA microwells (capture antibody), and a 1% solution of heat-inactivated serum, spiked with increasing concentrations of P3028, was then added to the wells. After washing, a biotinylated mouse anti-human albumin monoclonal antibody was added and the amount of bound antibody was detected with HRP-conjugated streptavidin and TMB chromogen substrate (see Example 1). The serum concentration was found to be in the range of 1.2-1.6 µg/ml P3028 equivalents in one serum pool from 5 healthy control samples, 1 healthy control sample serum and 2 sera obtained from cancer patients. The amount of 3028 containing molecules was determined as the amount of P3028, which inhibits 50% of the binding of 3028 structures in the serum to the capture antibody (directed against the 3028 epitope) in the sandwich ELISA (see FIG. 3). The amount of these 3028-substances in serum may be considerably more as the molecular weight of albumin is about 35 times more than that of P3028, but their epitope specific reactivity is accurately determined using the method described above.

Experiments were then performed using a first class of inhibitors that are specific for the P3028 sequence/structure. The proliferative response of human immune cells from healthy individuals and cancer patients after IL-2 induction were analyzed in the presence and absence of antibodies specific for the P3028 sequence/structure (see Example 9). That is, the proliferative response of PBMCs from a patient having renal cell carcinoma and a patient having malignant melanoma were compared to the proliferative response of PBMCs obtained from a healthy individual in the presence and absence of antibodies specific for the P3028 sequence/structure. It was determined that in the presence of the antibodies that are specific for the P3028 sequence/structure, enhanced proliferation of the PBMCs after IL-2 induction was seen. That is, the antibody inhibitor for the P3028 sequence/structure was able to remove the blockade on IL-2-induce proliferation of the immune cells mediated by the P3028 sequence/structure. These results demonstrate that a binding partner for the P3028 sequence/structure (e.g., an antibody or binding fragment thereof specific for P3028), can reduce the immune suppression mediated by the P3028 sequence/structure.

The P3028 sequence/structure is a potent physiological inhibitor of the immune system, and is a possible target for therapeutic compositions that can modulate immune activity. Antibodies directed against the P3028 sequence/structure reversed cancer-related immunosuppression, which was modeled as reduced proliferative response of PBMCs to IL-2 in a human ex vivo model (see Example 9). Moreover, the outcome in this model correlated to over-all survival of the cancer patients (see Example 2). Therefore, it was contemplated that additional binding partners for the P3028 sequence/structure (e.g., peptides, cyclic peptides, peptidomimetics, antibodies and portions thereof) may be useful for inhibiting the P3028 sequence/structure-mediated immune suppression.

Three peptide-based binding partners for the P3028 sequence/structure were initially developed and the binding capacity of these inhibitors with P3028 in solution was tested, as shown in FIG. 23 (see Example 10). Only one molecule, SCF28, had a solubility sufficient to allow testing in biological human ex vivo models. Based on this structure, a first drug candidate, P28R (SEQ ID NO: 2), was developed.

Figures 26A, 26B:
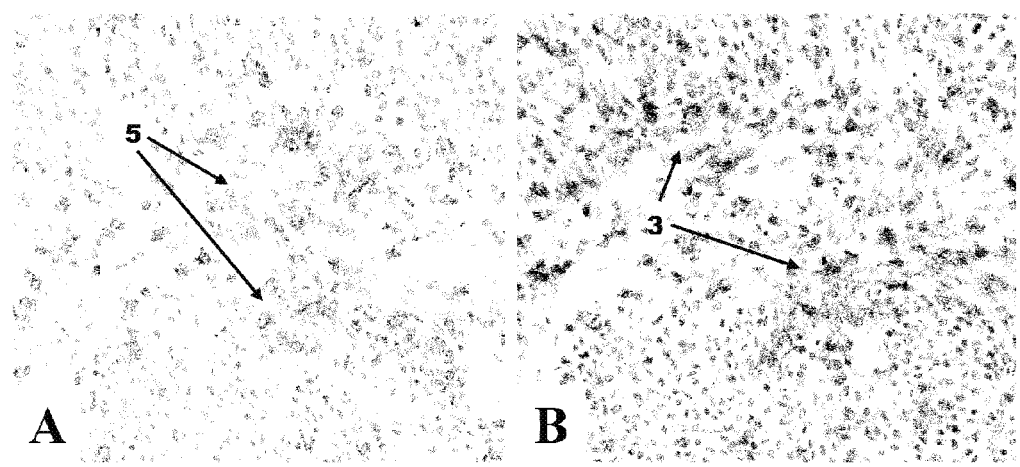
FIG. 26 illustrates breast cancer tissue incubated with buffer (FIG. 26A) or P28R (FIG. 26B) stained by an antibody directed against LFA-1.

Since P28R strongly bound to P3028, the ability of P28R to inhibit the function of the P3028 sequence/structure was tested. As described above, the β2-integrins plays a major role in the normal function of the immune system. However, the binding of the P3028 sequence/structure, to the β2-integrin LFA-1 has a substantial immunosuppressive effect. As demonstrated above (see Example 7), in assays staining for LFA-1, the membrane staining of PBMCs from cancer patients is markedly decreased compared to normal control samples. The exposure of LFA-1 could, however, be enhanced by incubating PBMCs from cancer patients with an antibody directed against the inhibitory P3028 sequence/structure (see Example 7 and FIG. 16C). Similarly incubation of fresh frozen tumour sections with peptide P28R (SEQ ID NO: 2) de-blocks LFA-1 of tumour infiltrating lymphocytes (i.e. displaces a bound immunoregulatory peptides or P3028 structures from the LFA-1 receptors), resulting in an enhanced binding of the anti-CD11a antibody (FIG. 26). These results showed that the LFA-1 receptor was unblocked by removal of the P3028 structure by the antibody. To test the ability of P28R to inhibit the P3028 structure, fresh frozen tumor sections without fixation were incubated for 4-20 hours in the presence of the drug candidate, P28R before staining for LFA-1 (see Example 15). For comparison, tumor sections were incubated with phosphate buffered saline only. As shown in FIG. 26, P28R effectively unblocked the LFA-1 receptor (e.g. displaced bound immunoregulatory peptides or 3028 structures from the LFA-1 receptor) and thereby markedly enhanced the functional expression of LFA-1 enabling migration and cytotoxic activity of these cells. Accordingly, P28R decreases the binding of P3028 to LFA-1 and effectively inhibits the immune suppression mediated by P3028. It is contemplated that incubation with P28 core (SEQ ID NO: 62) in accordance with some embodiments herein also de-blocks LFA-1 (e.g. displaces bound immunoregulatory peptides or 3028 structures from the LFA-1 receptor).

As such, the receptors of P3028 include LFA-1 and the alpha chain of the IL-2 receptor (CD25). Binding of a monoclonal antibody to CD11a (the alpha chain of LFA-1) was used to study the possible occurrence of a physiological blocker of LFA-1 and the de-blocking activity of P28R and antibodies directed to P3028. Accordingly, it is further contemplated that, similar to the LFA-1 receptor, the IL-2 receptor can be de-blocked by immunoregulatory peptide inhibitors as described herein (e.g. bound immunoregulatory peptides or 3028 structures can be displaced from the IL-2 receptor). As such, in some embodiments, an immunoregulatory peptide inhibitor as described herein deblocks an IL-2 receptor, for example an IL-2 receptor that has been blocked by any one or more of the peptides listed in Tables 1-4 (e.g. a peptide comprising SEQ ID NO: 185).

Figure 15:
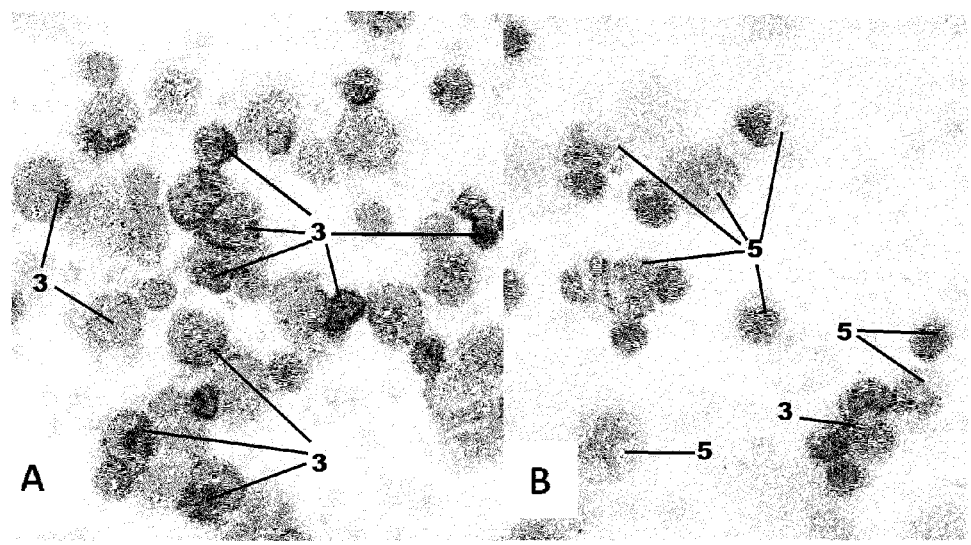
FIG. 15 illustrates inhibition of the binding of an anti-LFA-1, mAb, to mononuclear blood cells by P3028.
Figure 16:
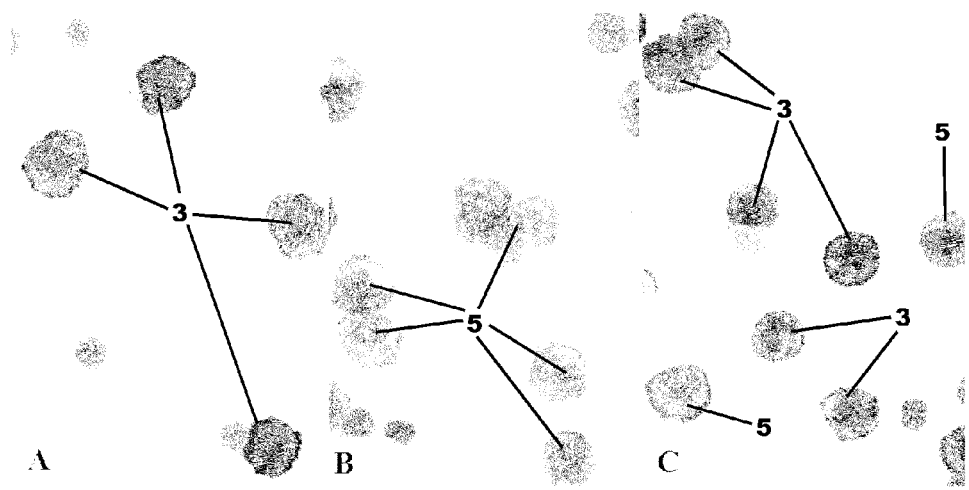
FIG. 16 illustrates staining of LFA-1 on PBMCs from a healthy control sample (A), and a cancer patient before (B) and after (C) treatment with an antibody directed against the inhibitory P3028.

Incubation of PBMCs from healthy controls with P3028 (FIGS. 15 and 17) or cancer patient sera (FIG. 17) blocks the binding of the anti-CD11a antibody to LFA-1. Furthermore, incubation of PBMCs from advanced cancer patients with an antibody directed against P3028 restitutes the binding of the anti-CD11a antibody to LFA-1 (FIG. 16). P3028 can bind to PBMCs (see FIG. 15A depicting no peptide added, and FIG. 15B, depicting preincubation with peptide 3028; anti-LFA-1 mAb HIM was inhibited by preincubation with peptide 3028, indicating binding to mononuclear blood cells by peptide 3028).

Figure 24A:
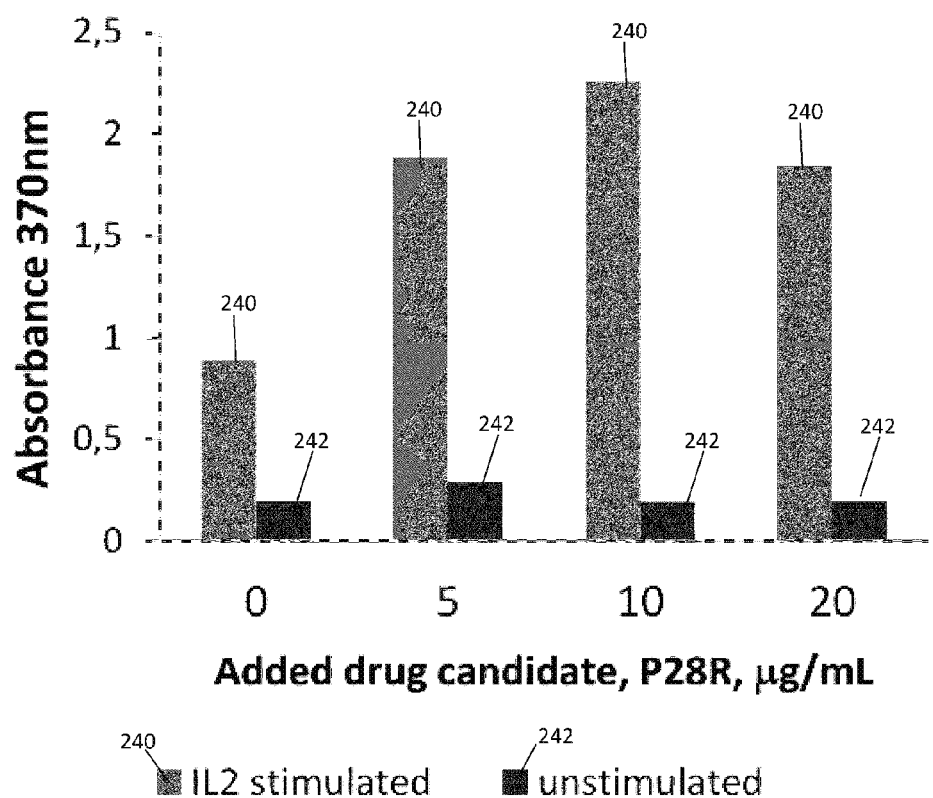
FIGS. 24A, 24B, 24C, and 24D respectively illustrate stimulatory activity for four different cancer patients.
Figure 24B:
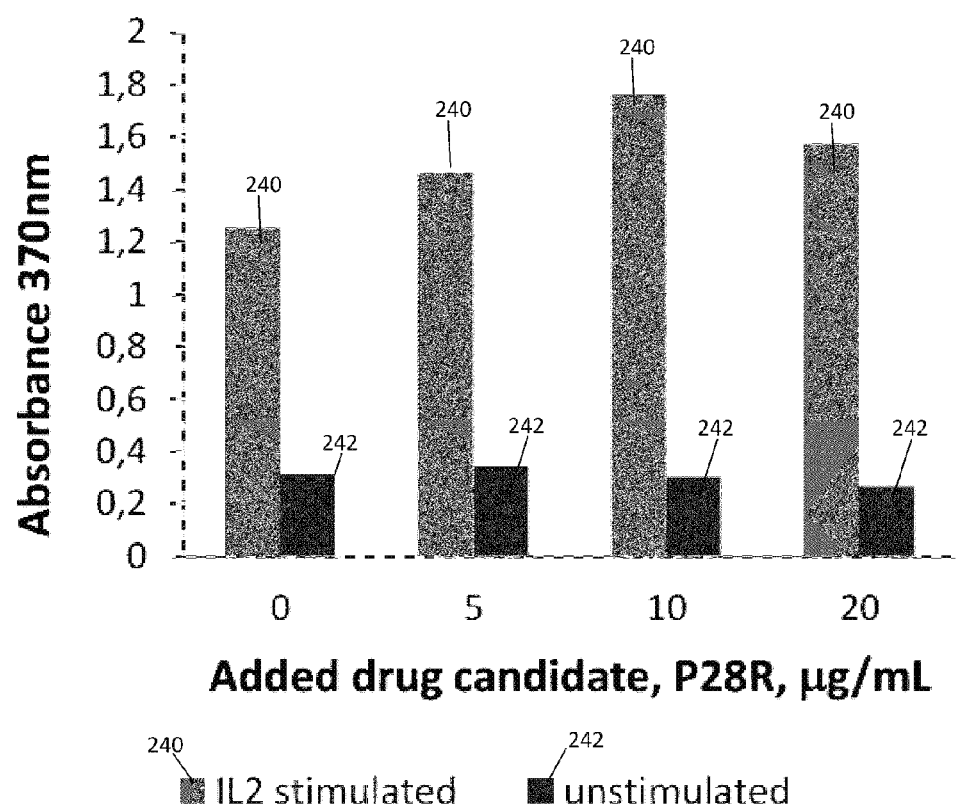
Figure 24C:
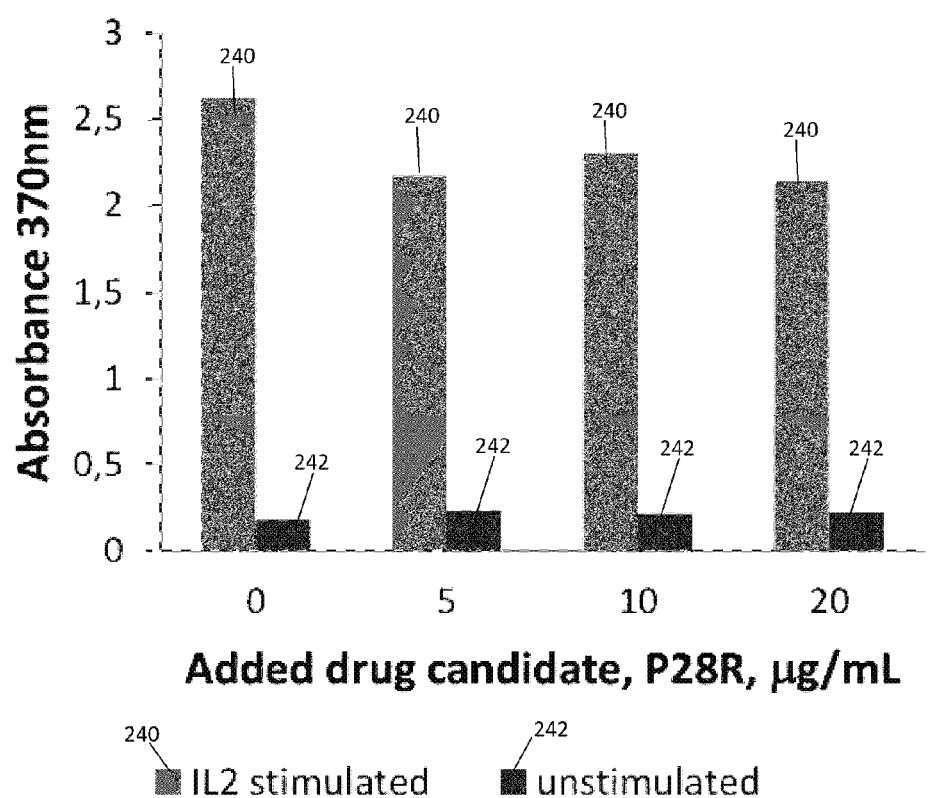
Figure 24D:
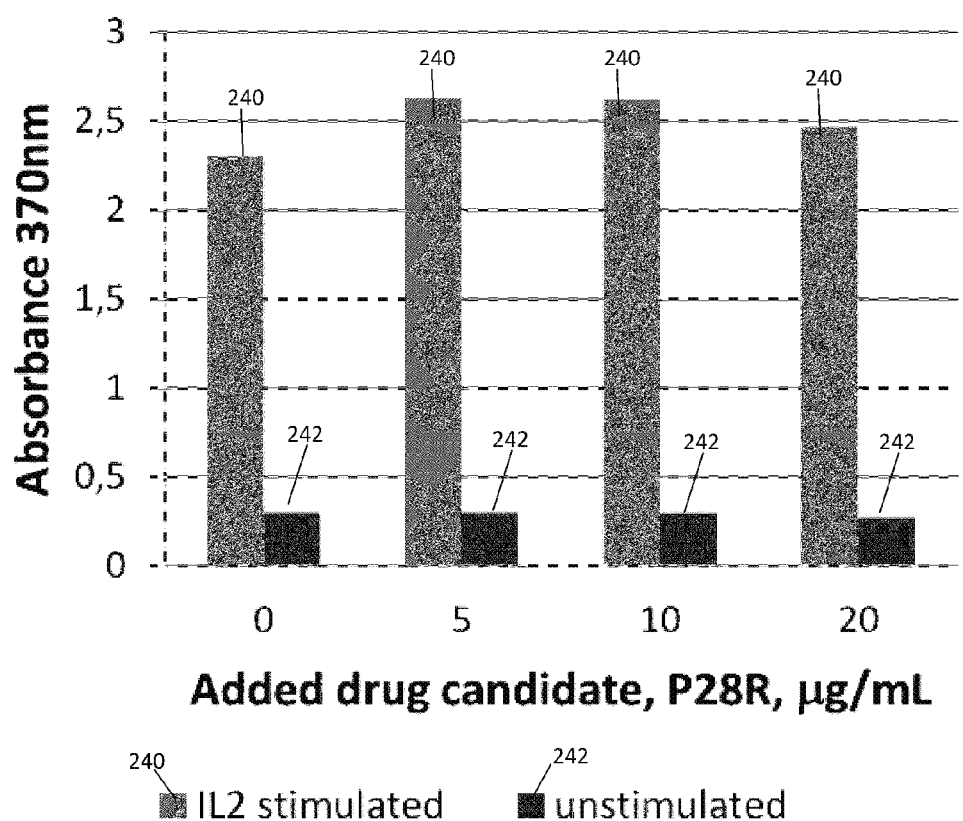

Since P28R unblocks LFA-1 receptors that are suppressed by the P3028 sequence/structure (e.g. displaces bound immunoregulatory peptides or 3028 structures from the LFA-1 receptor), the ability of P28R to enhance immune stimulation was tested in human ex vivo models. The stimulatory activity of P28R on PBMCs was measured using the MTS or CFSE techniques in 7 healthy control samples and 7 cancer patients of various diagnoses (see Example 13). Even in the absence of other types of stimulation, P28R has a significant stimulatory activity in 6 out of 7 cancer patients; whereas PBMCs from control samples showed only weak or no stimulation (see Example 13). Similar to the studies on the efficacy of antibodies directed against P3028 to reverse cancer related immunosuppression above (see Example 9; see FIG. 22), the ability of the P28R inhibitor to unblock the IL-2 receptor and thereby induce immune cell proliferation was investigated. Cultures of PBMCs from four different treatment naïve patients were each treated with P28R, and proliferation of PBMCs was measured. While PBMC's that had high proliferative activity before P28R treatment were largely unaffected by the drug (see FIG. 24C and FIG. 24D), PBMCs with a low initial proliferation were markedly stimulated (see FIG. 24A and FIG. 23B; see Example 13). Thus, the P28R inhibitor effectively induces immune cell proliferation when the immune cells are bound and suppressed by the P3028 sequence/structure, even in the absence of additional stimulation.

Since cancer cells have been shown to be enriched for P3028 structures (see Example 1 and FIGS. 1-2), the ability of P28R to specifically bind cancer cells was investigated. The binding of biotinylated P28R to tumors was studied. Three breast cancers, two renal cell carcinomas and four malignant melanomas were analyzed. Notably, all of the different types of tumors analyzed in the experiments bound P28R. The stained breast cancer section, shown in FIG. 25, for example, exhibits a strong positive signal, indicating the presence of the inhibitory P3028-structure in this tumor, and ability of P28R to bind to this tumor (see Example 14).

Since the P3028-structure inhibits lymphocyte migration, as well as, cytotoxic activity (see Examples 4 and 5), an immune system mediated attack against positively-staining tumor areas is expected to be efficiently suppressed so long as the a P3028-containing structure is present and not sequestered by a binding partner for the P3028 sequence/structure (e.g., an antibody, binding fragment thereof, and/or an inhibitory peptide, such as P28R, or a peptidomimetic corresponding to the P28R structure). Consistent with the observation that P3028 strongly binds the LFA-1 receptor, lymphocytes were not stained by this procedure since the P3028 structure was blocked by binding to LFA-1 on these cells.

Figure 27:
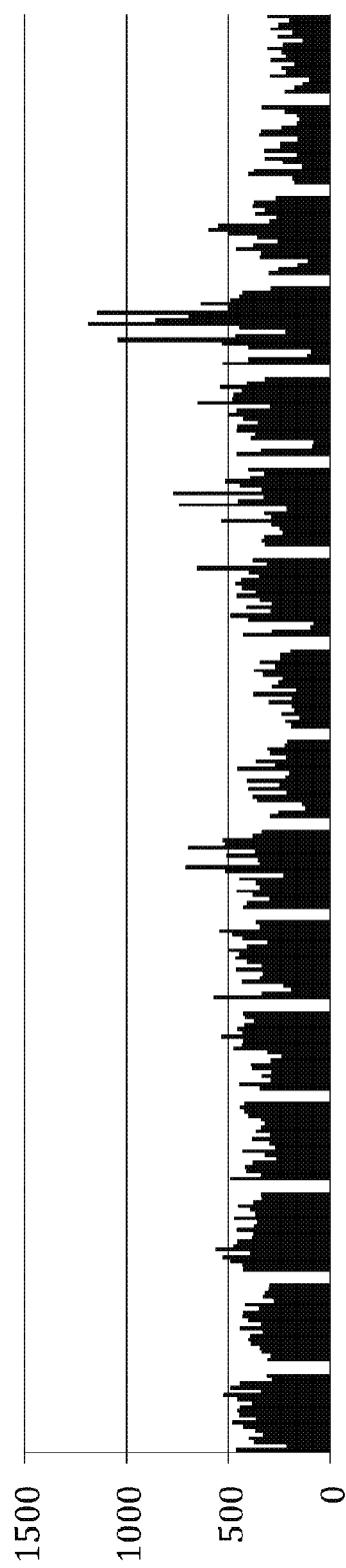
FIG. 27 illustrates rampo scores for binding of P3028 to peptides having single amino acid substitutions of each position of P28R.

Based on the ability of P28R to bind the P3028 sequence/structure, unblock the LFA-1 receptor, and ameliorate the P3028 sequence/structure-dependent immunosuppression, P28R was used as a template compound to identify additional compounds that bind to and sequester P3028. Variants of the P28R structure were synthesized, and tested for the ability to bind P3028 using PEPSCAN technology (see Example 12). A library of peptides that include each genetically-coded amino acid substitution at each amino acid position of P28R (i.e., 19 substitutions for each position) was synthesized. Each peptide was affixed to a support pin, and the peptide library was incubated with P3028. The binding of the candidate inhibitors to P3028 was detected by a sandwich ELISA, where a rabbit anti-mouse peroxidase (rampo) secondary antibody was employed (see Example 12). The binding of each peptide was then assigned a rampo score (see FIG. 27). Peptide P28R had rampo values ranging between about 262 and 460 with a mean value of 370. In some embodiments, the immunoregulatory peptide inhibitor as disclosed herein, is selected for a desired P3028 binding rampo score. In some embodiments, the desired P3028 binding rampo score is greater than or equal to the rampo score of P28R. It is also contemplated that some peptides that bind to P3028 with less affinity than P28R have therapeutic application. Some peptides with binding affinities that are less than P28R, for example, may modulate signal transduction events differently than P28R by virtue of the fact that the affinity to P3028 is less. Accordingly, embodiments also include any peptide that binds to P3028, wherein said peptides have a rampo score that is less than that exhibited by P28R. Accordingly, contemplated embodiments include peptides that bind with any affinity to P3028 (e.g., any one or more of the peptides provided in Table 5.1, preferably peptides that modulate the immune system (e.g., modulate, upregulate or down regulate a marker of the immune system or immunosuppression, such as reducing a P3028-mediated inhibition of immune cell proliferation, spreading, migration, or NK-cell cytotoxicity).

A total of 31 substitutions of peptide P28R (SEQ ID NOs: 3-33) had rampo values greater than 500 (see FIG. 28), indicating that these 31 peptides (strong binding partners for P3028) can be used to efficiently bind and sequester P3028 and thereby reduce P3028-mediated immunosuppression. Table 6.1 lists these 31 peptides that were evaluated in assays and shown to have appreciable binding to P3028. Additionally, the binding strength of substituted peptides at each position (based on rampo score) was compared to the binding strength of a P28R (SEQ ID NO: 2) control sample for the same position (see Example 12). Peptides that bound with a rampo score substantially equal to or greater than that of the P28R control sample (i.e., at peptides that bound to P3028 with at least 98% of the rampo score of the P28R control sample) were identified (SEQ ID NOs: 268-393). Table 6.2 lists these 126 peptides that were shown to have appreciable binding to P3028. It is noted that these 126 peptides include the 31 peptides of Table 6.1. Accordingly, 126 different binding partners for P3028 were identified by this initial screen and these molecules or variants thereof (e.g., variants having D amino acids, N-terminal amides, and/or C terminal acetyl groups or peptidomimetics or aptamers corresponding to these binding partners) can be used to inhibit the binding of the P3028 sequence/structure to an immune cell and thereby alleviate, or reduce P3028-dependent immunosuppression. One variant of P28R, Peptide KKL15 (SEQ ID NO: 1), which lacks only a C-terminal arginine, is thought to bind to the P3028 sequence/structure through both charged and hydrophobic interactions. As shown in FIG. 31, positively charged amino acids of KKL15 interact with negatively charged amino acids on P3028 and hydrophobic amino acids generate hydrophobic contacts enhancing the interaction.

Figure 30A:
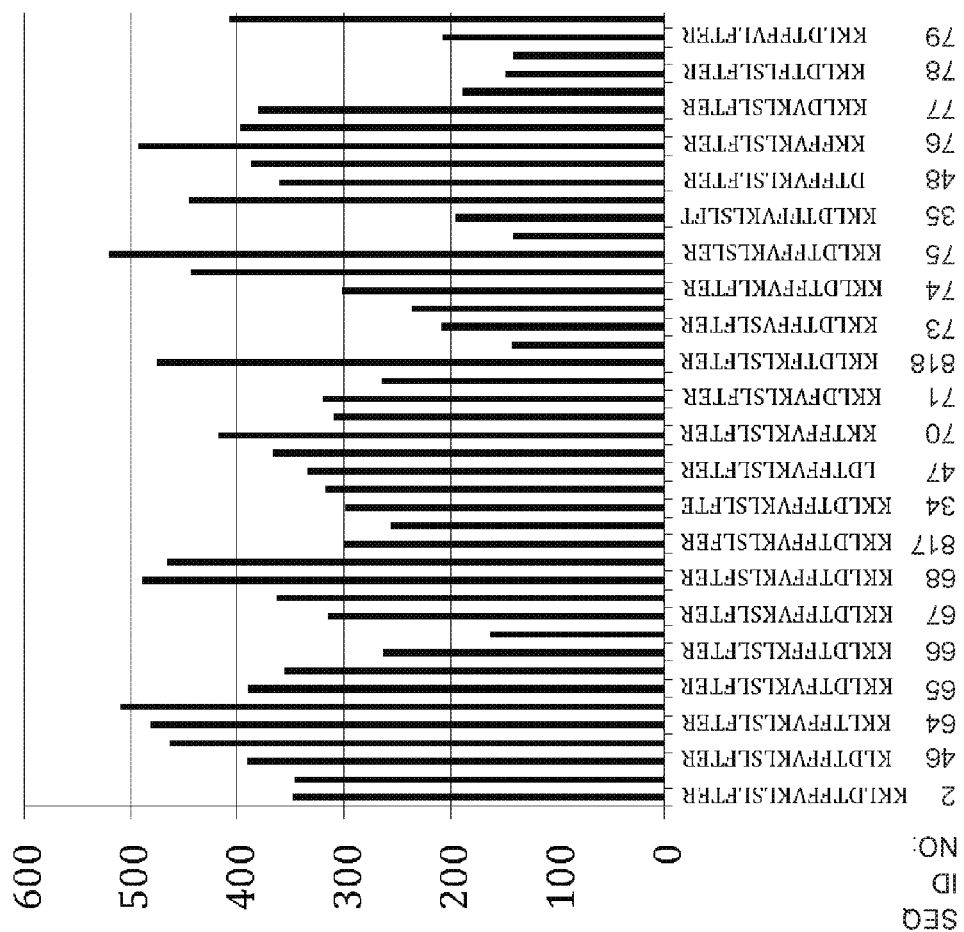
FIGS. 30A and 30B represent the left and right sides, respectively, of a single graph that was enlarged to show the text more clearly. For reference, the Y axis has been reproduced in FIG. 30B.
Figure 30B:
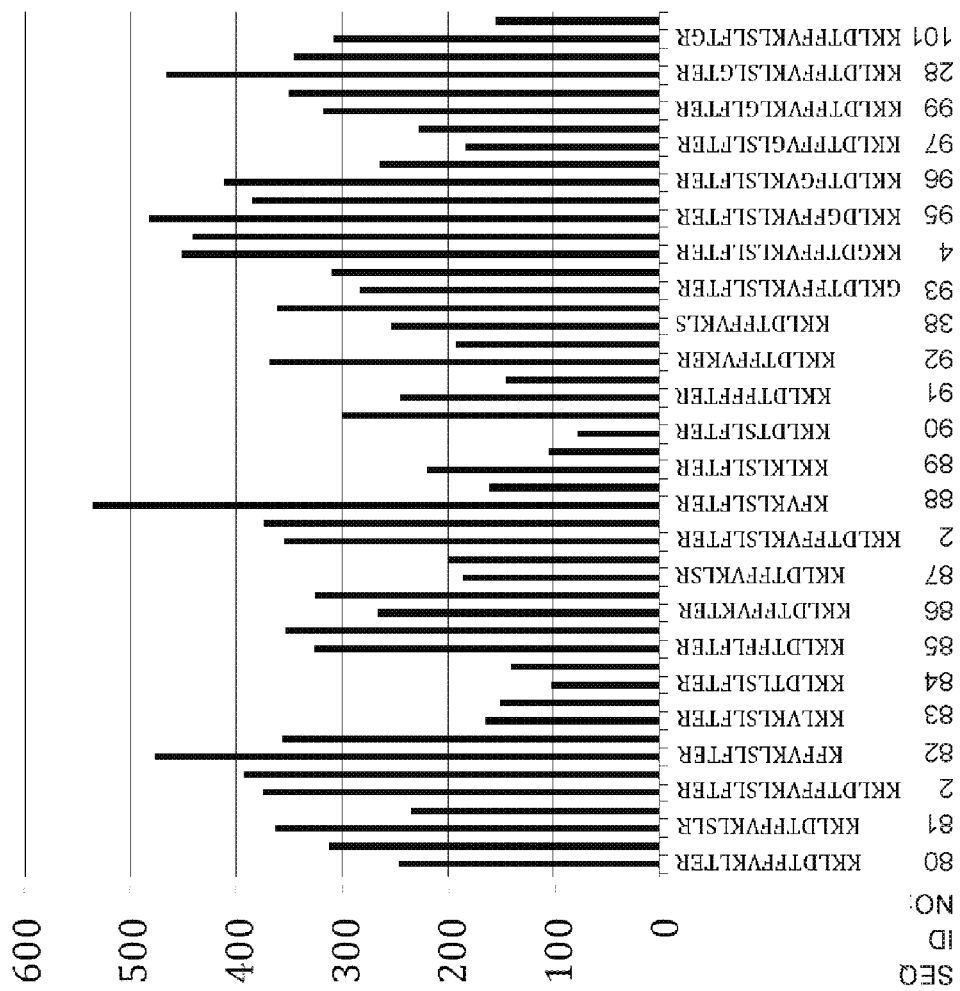

To further map the P3028 binding domain of P28R, deletions, and truncations of P28R were synthesized, and tested for binding to P3028 using the PEPSCAN assay. This approach led to the development of many more binding partners for P3028. While deletion of residues 6-9 ("FFVK"—SEQ ID NO: 182) and the C-terminal amino acids tended to reduce the binding of peptides to P3028 based on rampo score (see Example 12 and FIG. 30), several deletions and truncations of peptide P28R have a rampo score comparable to, or higher than peptide P28R (see, e.g., SEQ ID NOs: 34, 64-66, 68, and 76). Additionally, peptides deleted up to at least 8 amino acids from the N-terminus of P28R (see, e.g., SEQ ID NOs: 46-53) retained a high affinity to P3028, as measured by rampo score, providing evidence that inhibitors that are smaller than P28R can be useful for binding to and sequestering P3028, preventing the interaction of P3028 with immune cell receptors, such as the IL-2 or LFA-1 receptors, thereby reducing P3028-induced immunosuppression.

Because P28R was shown to have a modulatory effect on IL-2 stimulation of immune cell proliferation (see Example 2), it was further investigated whether P28R would have a modulatory effect on other aspects of IL-2 stimulation of immune cells. PBMC's from eight healthy control samples and nine cancer patients with various diagnoses were cultured in a modified version of the ex vivo model of Example 2 for seven days in the presence of various doses of P28R (either "no P28R" control samples, or 5 μg/mL, 10 μg/ml, or 20 μg/ml of P28R). A dose dependent stimulation of the mitochondrial metabolism measured as conversion of MTS was observed in 5/8 (see FIG. 33A) control samples and 9/9 cancer patients (see FIG. 33B). Similar results were obtained when the PBMCs were cultured for only three days (see Example 28).

To identify the effectiveness of other inhibitors of immunomodulatory peptides, the effect of P28R (SEQ ID NO: 2) on mitochondrial metabolism based on MTS conversion was compared to the effect of a closely related peptide P27. P27 has the sequence KKLDTFFKKLSLFTER (SEQ ID NO: 264), and is a variant of P28R that differs in that V8 of P28R is substituted to K8 in P27. P28R binds to P3028 more efficiently than P27 (P27 binds P3028 with a rampo score of 253, while a P28R control sample binds P3028 with a rampo score of 308; see Example 12). The concentrations were either untreated control samples, 5 μg/mL ("SCF28-R5" and "SCF275"), 10 μg/ml ("SCF28-R10" and "SCF2710"), 20 μg/ml ("SCF28-R20" and "SCF2720"), or 40 μg/ml ("SCF28-R40" and "SCF2740"). The results are shown in FIG. 34. While P28R stimulated the cells of cancer patients in a dose-dependent manner, P27 had no effect (see Example 29).

The effect of P28R (SEQ ID NO: 2) on IL-2 induced proliferation was also measured in a BrdU incorporation assay. PBMCs from six healthy control samples and ten cancer were harvested in a modified version of the ex vivo model. Four out of six control samples had a high proliferative response to IL-2 compared to four out of ten cancer patient samples (see FIG. 35). These differences in proliferative response to IL-2 in PBMCs demonstrated the difference existence of high and low responders to IL-2 stimulation (see Example 30).

The response of high responders and low responders to various doses of P28R was compared. Cells from either high responders or low responders were cultured with various doses of P28R (see FIGS. 36A and 36B). IL-2-induced proliferation was measured as BrdU incorporation. While P28R had no stimulatory effect in cells from patients with a high response to IL-2 (N=4) (see FIG. 36A), P28R had a stimulatory effect on cells from patients with a low response to IL-2 (N=6) (see FIG. 36B). Accordingly effects of P28R on binding to and blocking immunoinhibitory activity of P3028 were demonstrated in the ex vivo model, as addition of P28R to the cultures had no effect on proliferation when added to PBMCs from healthy controls and cancer patients with a normal proliferative rate, but the proliferation of PBMCs from immunosuppressed cancer patients were significantly stimulated by P28R. Without being limited by any theory, in some embodiments P28R (SEQ ID NO: 2) or P28 core (SEQ ID NO: 62) binds to a blocker of immune cell proliferation, and induces immune cell proliferation.

The effect of P27 (SEQ ID NO: 264) was then compared to the effect of P28R (SEQ ID NO: 2) on IL-2 induced proliferation as measured by BrdU Incorporation. PBMCs from low responder cancer patients were with various concentrations of either P28R of P27, ranging from no peptide ("untreated cells"), to 5 μg/mL, 10 μg/ml, or 20 μg/ml. As shown in FIG. 37, both P28R and P27 enhanced the proliferative rate of PBMC's induced by IL-2 as measured by BrdU incorporation. When comparing the results shown in FIG. 37 to those of FIG. 34, P27 was observed to enhance IL-2 stimulation of cell proliferation as measured by BrdU incorporation, but not mitochondrial metabolism as measured by MTS conversion. On the other hand, P28R was observed to enhance both MTS conversion and BrdU incorporation in response to IL-2 stimulation (see Example 31).

The different effects of different inhibitors of immunoregulatory peptides on BrdU incorporation and MTS conversion were further investigated. The effects of P28R on IL-2 stimulation of immune cell proliferation differed significantly, depending on which assay was used (see FIG. 38). Peptide P28R had a stimulatory activity of MTS conversion in seven day cultures of PBMCs in 100% of cancer patients examined (N=9) and in 63% of healthy control samples examined (N=8). In contrast, P28R stimulated incorporation of BrdU in seven day cultures of PBMCs from only 17% (N=6) and 20% of (N=10) patients. P28R stimulated IL-2 induced proliferation, measured as incorporation of BrdU, in PBMC cultures from cancer patients with a low proliferative response to IL-2. On the other hand, PBMCs from 67% of healthy control samples examined (N=3) and 50% of cancer patients (N=4) were not stimulated by IL-2 when the effect was measured as MTS conversion (see Example 32 and FIG. 38). However, PBMCs from all these persons ("non-responders") who did not respond when measured with MTS were significantly stimulated by IL-2 when the effect was measured as incorporation of BrdU (see FIG. 38). In two patients, the response to IL-2, measured as BrdU incorporation, was enhanced by P28R (see FIGS. 38A and 38C), but this effect of P28R was only observed in one of these patients when MTS conversion was used (see FIG. 38B). Thus, while in one patient (see FIGS. 38A and 38B) the stimulatory activity of IL-2 was registered using both BrdU and MTS, in the other patient, the stimulatory activity of IL-2 was registered using BrDU only (see FIG. 38C) (see Example 32). Based on these observations, it was contemplated that effects on the metabolic activity measured as MTS conversion does not always correlate with DNA synthesis measured as incorporation of BrdU, and different populations of patients can respond differently to inhibitors of immunoregulatory peptides.

It was contemplated that other molecules that bind to P3028 could be identified. These additional binding molecules could also potentially block P3028. Looped 6-mere peptides were synthesized, and 6-meres that demonstrated appreciable binding to P3028 were identified (see Table 12, SEQ ID NOs: 265-267) (see Example 19). It was observed that two of the 6-meres with the strongest binding to P3028 based on rampo score possessed homology to linear peptides that bind 3028 (see FIG. 32).

In addition to P3028, several other albumin fragments and synthetic peptides were found to bind to the immune cells. Some of these fragments can have immunomodulatory activity similar to P3028, can bind to immune cells similar to P3028, and/or can bind to immunomodulatory antibodies that recognized P3028. In a first set of experiments, albumin fragments were generated by trypsin digestion and the tryptic fragments were found to bind to immune cells in the ACS system described herein (see Example 17). Table 1 provides a listing of trypsin-generated fragments of albumin, which bind to immune cells in the ACS system, as detected by MALDI-TOF analysis.

TABLE 1

Trypsin-generated albumin fragments that bind to ACS

| SEQ ID NO: | Percent Absorbed | Sequence | Albumin Positions |
| --- | --- | --- | --- |
| 194 | 71% | KYLYEIAR | 161-168 |
| 195 | 64% | KVPQVSTPTLVEVSR | 438-452 |
| 196 | 60% | VFDEFKPLVEEPQNLIK | 397-413 |
| 197 | 59% | VPQVSTPTLVEVSR | 439-452 |
| 198 | 42% | RPCFSALEVDETYVPK | 509-524 |
| 199 | 41% | FQNALLVR | 427-434 |
| 200 | 36% | SLHTLFGDK | 89-97 |
| 201 | 36% | LKECCEKPLLEK | 299-310 |
| 202 | 35% | LCTVATLR | 98-105 |
| 203 | 34% | YLYEIAR | 162-168 |
| 204 | 32% | CCAAADPHECYAK | 384-396 |
| 205 | 29% | AAFTECCQAADK | 187-198 |
| 206 | 26% | CCTESLVNR | 500-508 |
| 207 | 25% | QEPERNECFLQHK | 118-130 |
| 208 | 23% | AVMDDFAAFVEK | 570-581 |
| 209 | 22% | NECFLQHK | 123-130 |
| 210 | 20% | ONCELFEQLGEYK | 414-426 |
| 211 | 18% | QEPERNECFLQHK | 118-130 |
| 212 | 13% | VHTECCHGDLLECADDR | 265-281 |
| 213 | 8% | FKDLGEENFK | 35-44 |
| 214 | 3% | YICENQDSISSK | 287-298 |
| 215 | 2% | LDELRDEGK | 206-214 |
| 216 | 1% | DDNPNLPR | 131-138 |

In a second set of experiments, denatured human serum albumin was degraded by asparaginase (ASN-N), and the ability of these proteolytic fragments to bind with immune cells was evaluated in the ACS system. Again, the immune cell binding peptides were identified by comparing adsorbed and unadsorbed peptide solutions using the MALDI TOF technique. These peptides are shown in Table 2.

TABLE 2

Asp-N-generated albumin fragments that bind to ACS

| SEQ ID NO: | Percent Absorbed | Sequence | Albumin Positions |
| --- | --- | --- | --- |
| 217 | 100% | DHVKLVNEVTEFAKTCVA | 62-79 |
| 218 | 100% | DDKETCFAEEGKKLVAASQAALGL | 586-609 |
| 219 | 87% | DRVTKCCTESLVNRRPCFSALEV | 495-517 |
| 220 | 86% | DETYVPKEFNAETFTHA | 518-535 |
| 221 | 65% | DSISSKLKECCEKPLLEKSHCIAEVEN | 293-319 |
| 222 | 65% | DKLCTVATLRETYGEM | 96-112 |
| 223 | 100% | YSVVLLLRLAKTYETTLEKCCAAADPHEC YAKVF | 364-398 |
| 224 | 100% | KLCTVATLRETYGEMADCCAKQEPERNEC FLQHK | 96-130 |
| 225 | 100% | ICTLSEKERQIKKQTALVELVKHKPKATK EQLKAVM | 536-572 |
| 226 | 100% | LAKYICENQDSISSKLKECCEKPLLEKHC IAEVEN | 283-319 |
| 227 | 100% | VFLGMFLYEYARRHPDYSVVLLLRLAKTY ETT LEKCCAAA | 348-388 |
| 228 | 100% | LGEENFKALVLIAFAQYLQQCPFEDHVKL VNEVTEFAKTCVA | 37-79 |
| 229 | 100% | RVTKCCTESLVNRRPCFSALEVDETYVPK EFNAETFTFHA | 495-535 |
| 230 | 37% | YLSVVLNQLCVLHEKTPVSDRVTKCCCTE SLVNRRPFSALEV | 475-517 |

Additionally, several synthetic peptides were synthesized, as shown in Table 3, and the binding of these molecules to immune cells using the ACS system was evaluated.

TABLE 3

Synthetic albumin peptides

| SEQ ID NO: | Peptide Name | Sequence | Albumin Positions |
| --- | --- | --- | --- |
| 183 | 3026 | NEETFLKKYLYEIARRHPYFYAP | 153-176 |
| 184 | 3027 | ELFEQLGEYKFQNALLVR | 417-434 |
| 188 | 3029 | KVPQVSTPTLVEVSR | 438-452 |
| 189 | 2604 | KLVNEVTEFAKT | 65-76 |
| 190 | 2605 | NEETFLKKYLYE | 153-168 |
| 191 | 2606 | LDELRDEGKAS | 205-217 |
| 192 | 2607 | EMADCCAKQEPE | 110-122 |
| 193 | 2608 | ELFEQLGEYKF | 417-427 |

Additionally, several albumin fragment peptides bind specifically to an dHSA-specific antibody with immunomodulatory effects (mAb A) (see Example 18). These peptides are shown in Table 4.

TABLE 4

Albumin peptides that bind to monoclonal antibody mAb A

| SEQ ID NO: | Sequence | Albumin Positions |
|---|---|---|
| 231 | LYNEVTEFAK | 066-075 |
| 232 | SLHTLFGDK | 089-097 |
| 233 | LCTVATLR | 098-105 |
| 234 | ETYGEMADCCAK | 106-117 |
| 235 | YLYEIAR | 162-168 |
| 236 | LDELRDEGK | 206-214 |
| 237 | YICENQDSISSK | 287-298 |
| 238 | LKECCEKPLLEK | 299-310 |
| 239 | HPDYSVVLLLR | 362-372 |
| 240 | CCAAADPHECYAK | 384-396 |
| 241 | QNCELFEQLGEYK | 414-426 |
| 242 | FQNALLVR | 427-434 |
| 243 | CCTESLVNR | 500-508 |
| 244 | AVMDDFAAFVEK | 570-581 |
| 245 | LSQRFPK | 243-249 |
| 246 | DDNPNLPR | 131-138 |

It is contemplated that inhibitors to any one or more of the peptides listed in Tables 1-4 can be generated in much the same way that inhibitors to P3028 were generated. In brief, polyclonal and monoclonal antibodies that are specific for any one or more of the peptides in Tables 1-4 can be easily generated using conventional techniques in immunology. Antibody binding fragments can also be prepared and isolated using conventional techniques in immunology. These antibodies or antibody fragments can be human, or humanized, as described herein. Using an approach similar to that described supra and in Examples 9 and 10, these peptide inhibitors can be evaluated on a chip based assay and biochemical assays, such as immune cell proliferation in the presence and absence of the peptide inhibitors, can be evaluated. The section below provides more information on the development of immunoregulatory peptide inhibitors, preferably inhibitors of P3028.

It is contemplated that inhibitors of any one or more of the peptides listed in Tables 1-4 can comprise modifications of the P28R (SEQ ID NO: 2) or P28 core (SEQ ID NO: 62) sequence, and further can be useful for reducing inhibition of the LFA-1 receptor, or for stimulating immune cells. To identify modification to inhibitor peptides in accordance with some embodiments herein, positional scan data was used to study the influence of substitution of different types of amino acids in each position of P28R (SEQ ID NO: 2) on the binding of P3028 (SEQ ID NO: 185). Each amino acid in the peptide sequence of P28R (SEQ ID NO: 2) was exchanged with all of the naturally occurring amino acids, and binding of P3028 (SEQ ID NO: 185) to each peptide on a solid phase chip was assessed (see, e.g. Example 36). A number of optional modifications to P28R in accordance with embodiments herein are summarized in Tables 5.3, 5.4, 5.5, 5.6, and 13. Optionally, an inhibitor peptide in accordance with some embodiments herein can comprise one or more of the modifications of Table 5.3 or Table 13. Optionally, an inhibitor peptide comprises a central core of positions 2, 5-11, and 15 as provided in Table 5.3, and the remaining position are omitted or substituted with substantially any amino acid. Optionally, an inhibitor peptide comprises a central core of positions K2, T5-S11, and E15 of SEQ ID NO: 2, and the remaining position are omitted or substituted with substantially any amino acid.

From the positional scan data it is also noted that a "core peptide" can be identified, FFVKLS (SEQ ID NO: 62) (referred to herein as "P28 core"). In some embodiments, a peptide comprising, consisting of, or consisting essentially of P28 core (SEQ ID NO: 62) is provided. The peptide can comprise no more than about 30 amino acid residues, for example no more than about 30, 29, 28, 27, 26, 25, 24, 23, 22, 21, 20, 19, 18, 17, 16, 15, 14, 13, 12, 11, 10, 9, 8, 7, or 6 amino acid residues. In some embodiments, the core peptide de-blocks an LFA-1 receptor (e.g. displaces bound immunoregulatory peptides or 3028 structures from the LFA-1 receptor) that has been bound by one or more immunoregulatory peptides of Tables 1-4.

Based on the positional scan data, it is contemplated that substitutions of SEQ ID NO: 2 can be useful in accordance with some embodiments herein for binding P3028, de-blocking the LFA-1 receptor from P3028-mediated inhibition (e.g. displacing bound P3028 peptide and P3028-structure containing molecules from the LFA-1 receptor), and/or stimulating immune cells. The activity of peptide P28R (SEQ ID NO: 2) and modifications of P28R was studied in a human ex vivo model using PBMCs from a healthy control human in short term cultures, and with PBMC activation measured as a percentage of cells with enhanced CD69 (see Example 37). It was observed that P28R (SEQ ID NO: 2) and peptide 31135 (KKLDTFFVYLSLFTER) (SEQ ID NO: 589) directly stimulate healthy PBMC's in this ex vivo model, but peptides 30677 (KKLDTFFVKLSLMTER) (SEQ ID NO: 583), 30678 (KKLDTFFVKLQLFTER) (SEQ ID NO: 584), 30680 (KKLDTVMVKLQLMTER) (SEQ ID NO: 585), 30864 (KSLDTFFVKLSLFTER) (SEQ ID NO: 587); 30685 (KKLDTFFVKLSLFTFR) (SEQ ID NO: 588); and 31136 (KKLDTFFVNLSLFTER) (SEQ ID NO: 590), and 31138 (KKLDTFFVDLSLFTER) (SEQ ID NO: 591) did not stimulate the healthy PBMC's in this ex vivo model (see FIGS. 41A and 41B). As such, in some embodiments, a composition comprising, consisting essentially of, or consisting of P28R (SEQ ID NO: 2), peptide 31135 (SEQ ID NO: 589), or a combination of P28R and peptide 31135 is provided to directly stimulate immune cells. As such, in some embodiments, a composition comprising, consisting essentially of a peptide of SEQ ID NO: 2, SEQ ID NO: 62, or any of SEQ ID NOs: 583-586 or 587-595, or a combination of these peptides is provided.

It is noted that peptide 31135 comprises a Y at the position corresponding to position 9 of SEQ ID NO: 2 and position 4 of SEQ ID NO: 62. (see Tables 5.3 and 5.5). In some embodiments, a composition comprising, consisting essentially of, or consisting of a modified peptide comprising a modification of P28R comprising a Y at position 9 of SEQ ID NO: 2 is provided. Optionally, the immune cells can comprise healthy immune cells. Optionally, the immune cells can comprise immune cells in cancer patient serum, for example cancer patient immune cells. In some embodiments, a composition comprising, consisting essentially of, or consisting of a modified peptide comprising a modification of P28 core comprising a Y at position 4 of SEQ ID NO: 62 is provided. Optionally, the immune cells can comprise healthy immune cells. Optionally, the immune cells can comprise immune cells in cancer patient serum, for example cancer patient immune cells.

As P28R (SEQ ID NO: 2) can bind to P3028 and stimulate PBMC's from healthy controls in short term cultures, for example when in a culture medium comprising RPMI plus 10% normal human AB serum (see Example 37), it is contemplated that truncations of P28R in accordance with some embodiments herein can be useful for binding to inhibitors of any one or more of the peptides listed in Tables 1-4. Truncations of P28R were assessed for their ability to activate PBMC's (see Example 38). PBMCs were incubated with the peptides (40 μg/mL) for 24 hours in RPMI plus 10% human AB serum. PBMC activation was measured as percent cells with enhanced expression of either CD69 (FIG. 42A) or CD71 (FIG. 42B) using flow cytometry. As shown in FIGS. 42A and 42B, peptide P28R (SEQ ID NO: 2) effectively activated healthy PBMC's in this ex vivo model, but peptide 32251 (SEQ ID NO: 592) and peptide 32230 ("P28 core") (FFVKLS) (SEQ ID NO: 62) did not. However, PBMCs were also incubated with the peptides in cancer sera from dogs, or in caner sera from human cancer patients (see FIG. 43). It was observed that full length peptide P28R (SEQ ID NO: 2) and the P28 core peptide (peptide 32230) (SEQ ID NO: 62) activated PBMCs in the presence of cancer serum. As such, it is contemplated that in accordance with some embodiments herein, P28R, P28 core, or combinations of these peptides are useful for stimulating immune cells in the serum of a subject that has cancer.

In some embodiments, a peptide comprising, consisting of, or consisting essentially of P28 core (SEQ ID NO: 62) is provided. Optionally, the peptide comprising, consisting of, or consisting essentially of P28 core (SEQ ID NO: 62) can bind to P3028 peptide. It was observed that P28 core peptide (SEQ ID NO: 62) can bind the 3028 peptide as efficiently as the full length peptide P28R, and can induce activation (e.g. proliferation, enhanced expression of CD69 and/or CD71, secretion of IL-12 of IFNγ, or secretion of perforin or granzyme B, enhanced cytotoxicity, cell migration, or cytokine production) of PBMC's in cancer serum (see Example 38 and FIG. 43), but that in an ex vivo model comprising short term cultures of PBMC's, the P28 core peptide (SEQ ID NO: 62) not stimulate PBMC activation (CD69 and CD71) as the P28R peptide does (see FIGS. 42A and 42B). Accordingly, in some embodiments, a peptide comprising, consisting of, or consisting essentially of P28 core (SEQ ID NO: 62) binds to P3028 peptide as efficiently or substantially as efficiently as P28R (SEQ ID NO: 2). In some embodiments, P28R (SEQ ID NO: 2 is provided to bind to P3028 and de-block cellular receptors (e.g. displaces bound immunoregulatory peptides or 3028 structures from the cellular receptors). Optionally P28R can further have a direct stimulatory activity on immune cells. In some embodiments, P28 core (SEQ ID NO: 62) is provided to bind to P3028 and de-block cellular receptors (e.g. displaces bound P3028 peptides or 3028 structures from the cellular receptors).

It has also been observed that, biotinylated P28R has been shown to bind directly to PBMCs as demonstrated by immunocytochemistry or rosetting of P28R coated beads (binding of beads to the cells). Accordingly, in some embodiments, P28R is provided to bind directly to PBMCs. In some embodiments, P28R comprising a detectable moiety is provided to bind to PBMCs. In some embodiments, P28R comprising a toxin is provided to bind to PBMCs. In some embodiments, peptide 31135 comprising a toxin or a detectable moiety is provided.

The effect of P28R (SEQ ID NO:2) on cancer cells was further studied in in vivo models in nude and immunocompetent mice. P28R was injected intra-tumorally into human pancreas cancer in a xenograft model in nude mice, and induced tumor cell apoptosis after one day (see Example 39). P28R induced Caspase 3, a marker of ongoing apoptosis, while treatment of tumors with the drug solvent only did not induce Caspase 3 (see FIGS. 44A and 44B). In some embodiments, P28R (SEQ ID NO: 2) has a direct cytotoxic action on tumor cells, for example, prostate cancer cells. In some embodiments, a peptide of Table 5.3, or a modified P28R peptide comprising at least one modification of Table 5.2 has a direct cytotoxic action on tumor cells, for example prostate cancer cells.

As it was observed that P28R has an immunostimulatory effect (see, e.g. Example 37), the capacity of P28R (SEQ ID NO: 2) to activate the immune system was also evaluated. P28R, 40 microgram in 100 microliter was injected intratumorally into B16 melanoma in B16 melanoma-inoculated immunocompetent mice, C57Bl (see Example 40). Tumors were taken out after 3 days, and sections were immunohistochemically stained using a polyclonal rabbit anti-CD45 antibody. The dominating cells in the tumors after P28R treatment were inflammatory cells, as indicated by CD45 immunostaining 450 (see FIG. 45A). The staining was not observed 452 in a control tumor section incubated with rabbit IgG at the same concentration (FIG. 45B). It is contemplated that in some embodiments P28R (SEQ ID NO: 2), P28 core (SEQ ID NO: 62), a peptide of SEQ ID NO: 586 or 589, or a modified P28R peptide comprising at least one modification of Table 5.2 can activate the immune system, for example to direct an immune response against tumor cells. In some embodiments, one or more of the listed peptides is administered at or near a tumor. In some embodiments, one or more of the listed peptides is administered peri-tumorally. In some embodiments, one or more of the listed peptides is administered systemically.

As it is contemplated that modifications of P28R can be useful for immune cell stimulation, the influence of various amino acid substitutions and additions to P28R on the immunostimulatory effect was further studied. Effects of modified peptides on the activation of PBMCs from a healthy control person were assessed (see Example 41). PBMCs were incubated with the peptides (40 μg/mL) for 48 hours in RPMI plus 10% human AB serum, and PBMC activation was determined by flow cytometry based on the percentage of cells with enhanced marker CD69 or CD71. Peptides P28R (SEQ ID NO: 2), P28 core (peptide 32230) (SEQ ID NO: 62), 32251 (KKLDTFFPKLSLFTER) (SEQ ID NO: 592), 32814 (RKLDTFFVKLSLFTERRR) (SEQ ID NO: 586), 32815 (KKLDQFFVKLSQHNER) (SEQ ID NO: 595), 32665 (KKLDTFMVKLSQHTER) (SEQ ID NO: 593), and 32819 (KKLDTFFVKLSLFTER(C(PEG24))) (SEQ ID NO: 594) were tested. As shown in FIG. 46, peptide 32814 (SEQ ID NO: 586), had a stimulatory effect in short term cultures similar to that of P28R (SEQ ID NO: 2) (batch CS8040) for both CD69 enhancement (see FIG. 46A) and CD71 enhancement (see FIG. 46B). Accordingly, it is contemplated herein that In addition to therapeutic applications, diagnostic applications of P28R and truncations and modifications thereof were also contemplated. For example, information about patients systemic and local (intra-tumoural) immune status can be obtained using reagents comprising P28R, or a truncation or modification thereof.

It is contemplated that the occurrence of immunoinhibitory 3028-structures in tumors can be identified by immunohistochemical staining using either an antibody directed against P3028 or using labeled P28R (SEQ ID NO: 2) or P28 core (SEQ ID NO: 62), for example biotinylated P28R or P28 core. FIG. 47 shows two areas of a human breast cancer stained using biotinylated P28R. Staining 470 is observed in FIG. 47B. Staining is not observed in FIG. 47A. An absence of staining is indicated 472.

As such, areas of tumors comprising P3028 structures (as well as areas not comprising these structures) can be identified using labeled peptides in accordance with embodiments herein. In some embodiments, a peptide of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 is provided, and further comprises a detectable moiety. The peptide comprising the detectable moiety can bind to one or more immunoregulatory peptides of Tables 1-4, for example P3028 (SEQ ID NO: 185).

Ameliorating Immunosuppression

As the inhibitors of immunoregulatory peptides described herein can be useful for removing immunosuppression, some embodiments herein comprise methods of ameliorating, reducing the symptoms of, reducing, or treating immunosuppression. In some embodiments a subject suffering from immunosuppression is identified. The subject can comprise a human, or a non-human mammal. A composition comprising at least one of the inhibitors of immunoregulatory peptides described herein can be administered to the patient. The composition can comprise at least one peptide comprising, consisting of, or consisting essentially of any one of SEQ ID NOs: 1-33, 34, 46-53, 62, 64-66, 68, 76, 94-96, 98, 265-393, 583-586, 587-595, or a modified P28R or P28 core peptide comprising one or more of the modifications of Table 5.3 or Table 13. The peptide can have length is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids or a length defined by a range between any two of these numbers. Optionally, the composition can further comprise a buffer as described herein, for example, Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO or TES. Optionally, the composition can further comprise a degradable particle as described herein. The composition can be administered to the subject via a variety of routes, for example, systemically, at the site of immunosuppression (e.g. if there is local immunosuppression by a tumor), or near the site of immunosuppression, for example within 10 cm 9 cm, 8 cm, 7 cm, 6 cm, 5 cm, 4 cm, 3 cm, 2 cm, 1 cm, or 0.5 cm of the site of immunosuppression. Optionally a second therapeutic agent can be administered in addition to the composition, for example prior to, concurrently with, or subsequent to the administration of the composition. For example, the second therapeutic agent can comprise an immunostimulatory agent. Optionally, activation of immune cells (e.g. enhanced expression of CD69 and/or CD71, secretion of IL-12 of IFNγ, or secretion of perforin or granzyme B, enhanced cytotoxicity, cytokine production, cell migration, and/or cell proliferation) of the subject can be detected. For example, activation of immune cells can be detected as enhanced expression of one or more markers of immune cells, for example CD69, CD71, and the like. Activation of immune cells (e.g. enhanced expression of CD69 and/or CD71, secretion of IL-12 of IFNγ, or secretion of perforin or granzyme B, enhanced cytotoxicity, cytokine production, cell migration, and/or cell proliferation) can be detected by a number of techniques known to the skilled artisan, for example flow cytometry, immunohistochemistry, ELISA, western blotting, immunoblotting, quantitative PCR, detection of BUdR incorporation to measure proliferation, and the like. Without being limited by any theory, different types of immunosuppressor cells, regulatory T-cells, immature dendritic cells (iDC), tumor associated macrophages (TAM) and myeloid derived suppressor cells (MDSC), can function immunosuppression, and further, other immunosuppressor mechanisms, such as serum blocking factors, circulating immune complexes, enhanced IL-1Ra production and enhanced intra-tumoral proteolytic activity can function in cancer related immunosuppression. As such, in some embodiments, treatment, amelioration, reduction, or reduction of the symptoms of immunosuppression can be determined by a change in activity, phenotype, or proliferation of an immunosuppressive cell, or a change in expression level or localization of an immunosuppressive factor.

Inhibitors of Immunoregulatory Peptides

Some embodiments include inhibitors of immunoregulatory peptides such as P3028 and/or one or more of the immunoregulatory peptides listed in Tables 1-4 (SEQ ID NOs: 183-184, and 188-246), also referred to as blockers of albumin derived immunoregulatory peptides, binding partners for immunoregulatory peptides, or immunoregulatory peptide inhibitors. The immunoregulatory peptide inhibitors can include, but are not limited to: peptides, cyclic peptides, peptidomimetics, proteins, nucleic acids, antibodies; antibody fragments, nucleic acid aptamers; peptide aptamers; and small molecules. The following section provides more details on antibody or antibody fragment-based immunoregulatory peptide inhibitors.

Antibody or Antibody Fragment-Based Immunoregulatory Peptide Inhibitors

Some embodiments include antibody or antibody fragment based immunoregulatory peptide inhibitors. Methods that use these immunoregulatory peptide inhibitors to inhibit immunosuppression in a subject (e.g., a subject having cancer or a pathogenic infection such as a bacterial or viral infection) are also contemplated. The core antibody structural unit is known to comprise a tetramer. Each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Heavy chains are classified as mu, delta, gamma, alpha, or epsilon, and define the antibody's isotype as IgM, IgD, IgG, IgA, and IgE, respectively. An additional isotype, IgY is found in avian hosts. The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), or Chothia & Lesk J. Mol. Biol. 196:901-917 (1987); Chothia et al., Nature 342:878-883 (1989).

Accordingly, some embodiments include a composition that comprises, consists of, or consists essentially of an immunoregulatory peptide inhibitor that comprises an antibody or antibody fragment comprising a domain, which binds to one or more regions of an immunoregulatory peptide, such as P3028 or one or more of the immunoregulatory peptides provided in Tables 1-4 (SEQ ID NOs: 183-184 and 188-246). In some embodiments, the antibody or antibody fragment is from a mouse, rabbit, rat, hamster, guinea pig, goat, donkey, bovine, horse, camel, cow, chicken, or human host. In some embodiments, the antibody or fragment is of isotype IgG, IgM, IgA, IgD, IgE, or IgY. In some embodiments, the antibody or fragment is part of a collection of polyclonal antibodies. In some embodiments, the antibody is monoclonal. In some embodiments, the antibody or fragment is chimeric. In some embodiments, the antibody or fragment includes at least one region form a human host, which can be at least one of the following Fc; Fab; light chain variable region; light chain CDR1, CDR2, or CDR3; heavy chain variable region; heavy chain CDR1, CDR2, or CDR3; light chain framework region; light chain FR1, FR2, FR3, or FR4; heavy chain framework region; heavy chain FR1, FR2, FR3, or FR4. In some embodiments, the antibody includes at least one CDR or FR of a non-human host. In some embodiments, the antibody regions are in accordance with the definition of Kabat. In some embodiments, the antibody regions are in accordance with the definition of Chothia. In some embodiments, the antibody regions are in accordance with a combination of the definition of Kabat and Chothia. In some embodiments, the antibody or antibody fragment mimics one or more of the peptides described in Table 5.1, Table 5.4, Table 5.5, or Table 5.6.

Antibodies can be readily produced using conventional techniques in immunology, for example techniques described in (U.S. Pat. Nos. 8,142,784 and 7,628,986). Antibodies generated in non-human hosts can be humanized, for example by substituting at least one variable region of the antibody of the non-human host into a human antibody. Moreover, human antibodies can be generated, for example in a transgenic host animal. Transgenic animals (e.g., mouse, such as XENOMOUSE) can be engineered, upon immunization, to produce a full repertoire of human antibodies in the absence of endogenous immunoglobulin production (Jakobovits et al. (1993) Proc. Natl. Acad. Sci. USA, 90:2551; Jakobovits et al. (1993) Nature 362:255-258; Bruggermann et al. (1993) Year in Immuno. 7:33; and U.S. Pat. No. 5,591,669; U.S. Pat. No. 5,589,369; U.S. Pat. No. 5,545,807). Moreover, phage display technology (McCafferty et al. (1990) Nature 348:552-553) can be used to produce human antibodies and antibody fragments in vitro, from immunoglobulin variable (V) domain gene repertoires from unimmunized donors (Johnson, Kevin S. and Chiswell, David J. (1993) Current Opinion in Structural Biology 3:564-571). A repertoire of V genes from unimmunized human donors can be constructed and antibodies to a diverse array of antigens (including self-antigens) can be isolated essentially (Marks et al. (1991) J. Mol. Biol. 222:581-597; Griffith et al. (1993) EMBO J. 12:725-734; U.S. Pat. No. 5,565,332; U.S. Pat. No. 5,573,905). Many phage display libraries are known, or can be generated, for example those of (U.S. Pat. No. 7,985,840). Human antibodies may also be generated by in vitro activated B cells (U.S. Pat. No. 5,567,610; U.S. Pat. No. 5,229,275). Thus, some embodiments include generating antibodies that bind to P3028 (SEQ ID NO: 185) and/or the peptides of Tables 1-4 (SEQ ID NOs: 183-184 and 188-246). In some embodiments, the antibodies are humanized antibodies that include at least one variable region of a non-human host antibody. In some embodiments, the antibodies are human antibodies generated in a non-human host, for example a transgenic animal. In some embodiments, the transgenic animal is a transgenic mouse. In some embodiments, the antibodies are generated in vitro. In some embodiments, the antibodies are generated using phage display technology. In some embodiments, the antibodies are generated in activated B cells in vitro.

Antibodies and antibody fragments can be configured to deliver cytotoxic compounds to a target site. Thus, some embodiments include antibodies and/or antibody fragments bound to cytotoxic compounds as described herein. In some embodiments, the antibodies or antibody fragments are bound to the cytotoxic compounds via a cleavable linker as described herein.

Some embodiments include a composition that comprises, consists of, or consists essentially of an immunoregulatory peptide inhibitor that comprises antibodies or a binding fragment thereof, which specifically binds to P3028 (SEQ ID NO: 185). Some embodiments include antibodies or fragments thereof, which specifically bind to a fragment of P3028 (SEQ ID NOs: 186 and 187). Exemplary antibodies that bind to P3028 are described in Example 9.

In some embodiments, the antibody or fragment thereof described above can be used to inhibit or sequester P3028. In some embodiments, the antibody or fragment thereof specific for P3028 can be administered to a patient having at least one immune cell bound to P3028 so as to unblock at least one of the patient's LFA-1 or IL-2 receptors. In some embodiments, the antibody or fragment thereof can be administered to a patient in need of treatment immunosuppression, as described herein, thereby stimulating or enhancing an immune response of said patient. For example, the antibody or fragment thereof can be provided to a patient in need of an inhibition of immunosuppression (e.g., a subject that has cancer or a pathogenic infection such as a bacterial or viral infection). After providing the antibody or fragment thereof the patient can be evaluated for an inhibition of immunosupression, which can be accomplished by determining immune cell infiltration of a tumor or a reduction in a bacterial or viral infection, for example, or an improved immune response by the PBMCs of said subject.

In other embodiments, the antibody or fragment thereof can be used to detect the presence of P3028, for example, in a biological sample. The antibody or fragment thereof can be used to detect the formation of a complex, for example when an immunoregulatory peptide inhibitor (e.g., a peptide SEQ ID NOs: 1-33, 34, 46-53, 64-66, 68, 76, 94-96, 98 or 264-393) is attached to a support, and the antibody is used as a primary antibody or fragment thereof is used to detect the presence of P3028 bound to the inhibitor.

Some embodiments include an antibody or fragment thereof that specifically binds to an immunoregulatory peptide inhibitor of P3028 (e.g., an antibody or fragment thereof that mimics or has at least 70%, 75%, 80%, 85%, 90%, 95%, or 98% identity to one or more of the peptides of Table 5.1). The antibody or fragment thereof can specifically bind to a peptide that includes at least one of SEQ ID NOs: 1-33, 34, 46-53, 64-66, 68, 76, 94-96, 98 or 264-393. In some embodiments, the antibody or fragment thereof specific for an immunoregulatory peptide inhibitor of P3028 can be used to detect the presence of an immunoregulatory peptide inhibitor of P3028 in a biological sample. The antibody or fragment thereof specific for an immunoregulatory peptide inhibitor of P3028 can also be used to detect the formation of a complex, for example, if P3028 is attached to a support, and the antibody or fragment thereof is used as a primary antibody to detect the presence of an immunoregulatory peptide inhibitor bound to P3028.

In some embodiments, the antibody or fragment thereof specific for an immunoregulatory peptide inhibitor of P3028 can be used to isolate or identify the presence of an inhibitor of P3028. For example, the antibody or fragment thereof can be used to purify an inhibitor to be used for stimulating an immune cell of a human, and/or for binding to the cancer cell of a human.

In some embodiments, the antibody or fragment thereof specific for an immunoregulatory peptide inhibitor of P3028 can be used to detect the presence of P3028. For example, the antibody or fragment thereof specific for an immunoregulatory peptide inhibitor of P3028 can be used for immunohistochemical staining of a biological sample to detect the presence of a cancer cell that has been contacted with an immunoregulatory peptide inhibitor. For example, the antibody specific for an immunoregulatory peptide inhibitor of P3028 can be used in flow cytometry to detect and/or isolate immune or cancer cells that are bound to an immunoregulatory peptide inhibitor. The following section provides more details on peptide-based immunoregulatory peptide inhibitors.

Peptide-Based Immunoregulatory Peptide Inhibitors

In some embodiments, an isolated peptide that comprises a domain, which binds to one or more regions of an immunoregulatory peptide, such as P3028, is provided. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated. An isolated peptide can exist, for example, in a substantially salt form, crystal form, lyophilized form, in solution (for example aqueous solution which can include buffer), and/or in a pharmaceutically carrier or diluent. An isolated peptide can exist in a substantially pure form, for example a composition that includes at least or equal to about 1% of the peptide by weight, for example at least or equal to about 1%, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.5, 99, 99.5, 99.9, 99.99, or 99.999% peptide by weight.

In some embodiments, the isolated immunoregulatory peptide inhibitors described herein (e.g., a peptide comprising, consisting of, or consisting essentially of any one of SEQ ID NOs: 1-33, 34, 46-53, 62, 64-66, 68, 76, 94-96, 98, 265-393, 583-586, 587-595, or a modified P28R or P28 core peptide comprising one or more of the modifications of Table 5.3 or Table 13 have lengths that are less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. For example, an immunoregulatory peptide inhibitor consisting of the sequence (FVKL) (SEQ ID NO: 63) can bind to P3028 with a comparable rampo score to immunoregulatory peptide inhibitors, which comprise FVKL (SEQ ID NO: 63), that are 6 to 16 amino acids in length (see FIG. 29 and Example 12). Additionally, amino acids sequences near an N terminal, C terminal, or exposed loop of a peptide are more likely to be accessible to potential binding targets rather than incorporated into a higher-order peptide structure, thus permitting a peptide of 1100 amino acids or less to bind P3028. Therefore, some embodiments of the invention concern compositions and methods of use thereof (e.g., a method of binding P3028 or a method of reducing P3028-mediated immunosuppression), which comprise, consist of, or consist essentially of any one or more of immunoregulatory peptide inhibitors described herein (e.g., any one or more of the peptides provided in Table 5.1, 5.4, 5.5, or 5.6). Desirably these peptides (e.g., any one or more of the peptides of Table 5.1, 5.4, 5.5, or 5.6) have lengths that are less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

TABLE 5.1

Sequences and Corresponding Rampo Scores

| SEQ ID | Sequence | RAMPO Score |
|---|---|---|
| 367 | KKLDTFFVKLSLMTER | 1190 |
| 22 | KKLDTFFVKLSLMTER | 1190 |
| 370 | KKLDTFFVKLSLQTER | 1144 |
| 23 | KKLDTFFVKLSLQTER | 1144 |
| 364 | KKLDTFFVKLSLHTER | 1046 |
| 24 | KKLDTFFVKLSLHTER | 1046 |
| 368 | KKLDTFFVKLSLNTER | 862 |
| 25 | KKLDTFFVKLSLNTER | 862 |
| 348 | KKLDTFFVKLQLFTER | 768 |
| 15 | KKLDTFFVKLQLFTER | 768 |
| 346 | KKLDTFFVKLMLFTER | 744 |
| 16 | KKLDTFFVKLMLFTER | 744 |
| 321 | KKLDTFMVKLSLFTER | 712 |
| 9 | KKLDTFMVKLSLFTER | 712 |
| 323 | KKLDTFSVKLSLFTER | 700 |
| 10 | KKLDTFSVKLSLFTER | 700 |
| 369 | KKLDTFFVKLSLPTER | 696 |
| 26 | KKLDTFFVKLSLPTER | 696 |
| 343 | KKLDTFFVKVSLFTER | 658 |
| 14 | KKLDTFFVKVSLFTER | 658 |
| 355 | KKLDTFFVKLSQFTER | 651 |
| 19 | KKLDTFFVKLSQFTER | 651 |
| 372 | KKLDTFFVKLSLSTER | 635 |
| 27 | KKLDTFFVKLSLSTER | 635 |
| 382 | KKLDTFFVKLSLENER | 599 |
| 31 | KKLDIFFVKLSLFNER | 599 |
| 313 | KKLDTAFVKLSLFTER | 575 |
| 7 | KKLDTAFVKLSLFTER | 575 |
| 287 | KKGDTFFVKLSLFTER | 563 |
| 94 | KKGDTFFVKLSLFTER | 563 |
| 4 | KKGDTFFVKLSLFTER | 563 |
| 383 | KKLDTFFVKLSLPER | 551 |
| 32 | KKLDTFFVKLSLPER | 551 |
| 319 | KKLDTVFVKLSLFTER | 547 |
| 8 | KKLDTVFVKLSLFTER | 547 |
| 359 | KKLDTFFVKLSVFTER | 545 |
| 20 | KKLDTFFVKLSVFTER | 545 |
| 345 | KKLDTFFVKLHLFTER | 535 |
| 308 | KKLDQFFVKLSLFTER | 535 |
| 18 | KKLDTFFVKLHLFTER | 535 |
| 6 | KKLDQFFVKLSLFTER | 535 |
| 363 | KKLDTFFVKLSLGTER | 531 |
| 100 | KKLDTFFVKLSLGTER | 531 |
| 28 | KKLDTFFVKLSLGTER | 531 |
| 285 | KKEDTFFVKLSLFTER | 528 |
| 5 | KKEDTFFVKLSLFTER | 528 |
| 325 | KKLDTFVVKLSLFTER | 527 |
| 11 | KKLDTFVVKLSLFTER | 527 |
| 361 | KKLDTFFVKLSLATER | 525 |
| 29 | KKLDTFFVKLSLATER | 525 |
| 279 | RKLDTFFVKLSLFTER | 523 |
| 3 | RKLDTFFVKLSLFTER | 523 |
| 349 | KKLDTFFVKLTLFTER | 520 |
| 17 | KKLDTFFVKLTLFTER | 520 |
| 324 | KKLDTFTVKLSLFTER | 517 |
| 320 | KKLDTFLVKLSLFTER | 517 |
| 13 | KKLDTFLVKLSLFTER | 517 |
| 12 | KKLDTFTVKLSLFTER | 517 |
| 322 | KKLDTFQVKLSLFTER | 511 |
| 371 | KKLDTFFVKLSLRTER | 502 |
| 30 | KKLDTFFVKLSLRTER | 502 |
| 381 | KKLDTFFVKLSLMER | 501 |
| 353 | KKLDTFFVKLSMFTER | 499 |
| 21 | KKLDTFFVKLSMFTER | 499 |
| 317 | KKLDTPFVKLSLFTER | 497 |
| 334 | KKLDTFFVKGSLFTER | 495 |
| 373 | KKLDTFFVKLSLTTER | 494 |
| 298 | KKLATFFVKLSLFTER | 494 |
| 280 | TKLDTFFVKLSLFTER | 493 |
| 284 | KKDDTFFVKLSLFTER | 492 |
| 356 | KKLDTFFVKLSRFTER | 483 |
| 273 | IKLDTFFVKLSLFTER | 483 |
| 318 | KKLDTTFVKLSLFTER | 481 |
| 357 | KKLDTFFVKLSSFTER | 478 |
| 288 | KKHDTFFVKLSLFTER | 477 |

TABLE 5.1-continued

Sequences and Corresponding Rampo Scores

| SEQ ID | Sequence | RAMPO Score |
|---|---|---|
| 305 | KKLDMFFVKLSLFTER | 475 |
| 293 | KKQDTFFVKLSLFTER | 473 |
| 339 | KKLDTFFVKQSLFTER | 470 |
| 365 | KKLDTFFVKLSLFTER | 468 |
| 315 | KKLDTMFVKLSLFTER | 467 |
| 314 | KKLDTIFVKLSLFTER | 466 |
| 268 | AKLDTFFVKLSLFTER | 466 |
| 378 | KKLDTFFVKLSLFHER | 463 |
| 354 | KKLDTFFVKLSNFTER | 462 |
| 350 | KKLDTFFVKLSAFTER | 462 |
| 396 | KKLDTFFVKLSLFTER | 460 |
| 351 | KKLDTFFVKLSHFTER | 460 |
| 336 | KKLDTFFVKMSLFTER | 460 |
| 291 | KKMDTFFVKLSLFTER | 460 |
| 310 | KKLDSFFVKLSLFTER | 458 |
| 275 | MKLDTFFVKLSLFTER | 457 |
| 852 | KKLDIFFVKLSIFTER | 456 |
| 329 | KKLDTFFPKLSLFTER | 456 |
| 278 | QKLDTFFVKLSLFTER | 455 |
| 289 | KKIDTFFVKLSLFTER | 454 |
| 347 | KKLDTFFVKLNLFTER | 451 |
| 296 | KKTDTFFVKLSLFTER | 451 |
| 304 | KKLDCFFVKLSLFTER | 449 |
| 274 | LKLDTFFVKLSLFTER | 449 |
| 366 | KKLDTFFVKLSLLTER | 448 |
| 397 | KKLDTFIVKLSLFTER | 446 |
| 374 | KKLDTFFVKLSLVTER | 446 |
| 316 | KKLDINFVKLSLFTER | 446 |
| 398 | KKLDTFFVKLSLFTER | 445 |
| 276 | NKLDTFFVKLSLFTER | 445 |
| 302 | KKLWTFFVKLSLFTER | 443 |
| 399 | KKLDTFFVKLSLFTER | 442 |
| 281 | VKLDTFFVKLSLFTER | 442 |
| 340 | KKLDTFFVKRSLFTER | 439 |
| 400 | KKLDTFFVKLSLFTER | 437 |
| 358 | KKLDTFFVKLSTFTER | 437 |
| 338 | KKLDTFFVKPSLFTER | 436 |
| 306 | KKLDNFFVKLSLFTER | 436 |
| 401 | KKLDTSFVKLSLFTER | 432 |
| 402 | KNLDTFFVKLSLFTER | 432 |
| 283 | KKCDTFFVKLSLFTER | 432 |
| 375 | KKLDTFFVKLSLWTER | 430 |
| 309 | KKLDRFFVKLSLFTER | 430 |
| 300 | KKLITFFVKLSLFTER | 430 |
| 403 | KKLDTFFVKLSLFTER | 428 |
| 272 | HKLDTFFVKLSLFTER | 428 |
| 307 | KKLDPFFVKLSLFTER | 427 |
| 282 | KKADTFFVKLSLFTER | 427 |
| 404 | KKLDTFAVKLSLFTER | 426 |
| 332 | KKLDTFFVKASLFTER | 426 |
| 405 | KPLDTFFVKLSLFTER | 425 |
| 312 | KKLDYFFVKLSLFTER | 425 |
| 406 | KKLDTFFVKLSLFTER | 424 |
| 303 | KKLYTFFVKLSLFTER | 422 |
| 311 | KKLDWFFVKLSLFTER | 418 |
| 407 | KRLDTFFVKLSLFTER | 417 |
| 299 | KKLETFFVKLSLFTER | 417 |
| 335 | KKLDTFFVKISLFTER | 415 |
| 408 | KKLDTFFVKLSLFTER | 414 |
| 409 | KKLDTFCVKLSLFTER | 411 |
| 328 | KKLDTFFLKLSLFTER | 411 |
| 410 | KKLDTQFVKLSLFTER | 410 |
| 360 | KKLDTFFVKLSWFTER | 409 |
| 411 | KKLDTLFVKLSLFTER | 408 |
| 412 | KGLDTFFVKLSLFTER | 405 |
| 413 | KKLTTFFVKLSLFTER | 405 |
| 387 | KKLDTFFVKLSLFTDR | 404 |
| 333 | KKLDTFFVKFSLFTER | 403 |
| 414 | KKLDTFFVKLSLFTER | 402 |
| 415 | KKLDTFFVKLYLFTER | 402 |
| 416 | KKLDTFFIKLSLFTER | 401 |
| 417 | KMLDTFFVKLSLFTER | 400 |
| 362 | KKLDTFFVKLSLCTER | 400 |
| 342 | KKLDTFFVKTSLFTER | 399 |
| 270 | EKLDTFFVKLSLFTER | 396 |

TABLE 5.1-continued

Sequences and Corresponding Rampo Scores

| SEQ ID | Sequence | RAMPO Score |
|---|---|---|
| 418 | KHLDTFFVKLSLFTER | 394 |
| 295 | KKSDTFFVKLSLFTER | 393 |
| 286 | KKFDTFFVKLSLFTER | 393 |
| 419 | KKLDTFFVKLVLFTER | 392 |
| 420 | KKLDHFFVKLSLFTER | 391 |
| 421 | KFLDTFFVKLSLFTER | 390 |
| 422 | KKLDTFFVKLSFFTER | 389 |
| 277 | PKLDTFFVKLSLFTER | 387 |
| 290 | KKKDTFFVKLSLFTER | 386 |
| 95 | KKLDGFFVKLSLFTER | 386 |
| 423 | KKLMTFFVKLSLFTER | 384 |
| 344 | KKLDTFFVKYSLFTER | 382 |
| 424 | KKLDTFEVKLSLFTER | 381 |
| 425 | KKLDTFWVKLSLFTER | 380 |
| 426 | KKLFTFFVKLSLFTER | 380 |
| 385 | KKLDTFFVKLSLFVER | 380 |
| 327 | KKLDTFFGKLSLFTER | 379 |
| 427 | KKLDTFFVKLSLFTER | 377 |
| 297 | KKVDTFFVKLSLFTER | 377 |
| 428 | KKLDTFFVKLSLFTER | 375 |
| 379 | KKLDTFFVKLSLFTER | 375 |
| 429 | KKLDVFFVKLSLFTER | 374 |
| 386 | KKLDTFFVKLSLFWER | 374 |
| 331 | KKLDTFFVRLSLFTER | 374 |
| 292 | KKNDTFFVKLSLFTER | 374 |
| 269 | DKLDTFFVKLSLFTER | 373 |
| 430 | KKLDTFFVKLSLFTER | 371 |
| 431 | KKLDTFFVKLSGFTER | 370 |
| 294 | KKRDTFFVKLSLFTER | 370 |
| 432 | KKLDTFRVKLSLFTER | 369 |
| 384 | KKLDTFFVKLSLFSER | 369 |
| 271 | GKLDTFFVKLSLFTER | 367 |
| 93 | GKLDTFFVKLSLFTER | 367 |
| 391 | KKLDTFFVKLSLFTER | 366 |
| 337 | KKLDTFFVKNSLFTER | 365 |
| 330 | KKLDTFFRKLSLFTER | 365 |
| 433 | KKLDTFHVKLSLFTER | 364 |
| 434 | KKLDTYFVKLSLFTER | 364 |
| 435 | KKLPTFFVKLSLFTER | 364 |
| 436 | KKPDTFFVKLSLFTER | 361 |
| 380 | KKLDTFFVKLSLFLER | 360 |
| 326 | KKLDTFFFKLSLFTER | 358 |
| 437 | KKLDTFPVKLSLFTER | 356 |
| 438 | KKLDTFFVKLSKFTER | 355 |
| 439 | KKLDTFFVKLSLFTPR | 351 |
| 341 | KKLDTFFVKSSLFTER | 351 |
| 440 | KQLDTFFVKLSLFTER | 350 |
| 441 | KELDTFFVKLSLFTER | 349 |
| 442 | KKLDTFFVKLSLFTER | 348 |
| 443 | KKLDTFNVKLSLFTER | 348 |
| 444 | KKLDTWFVKLSLFTER | 348 |
| 376 | KKLDTFFVKLSLFFER | 348 |
| 445 | KKLDTFFVTLSLFTER | 347 |
| 446 | KKLDTGFVKLSLFTER | 347 |
| 96 | KKLDTFGVKLSLFTER | 347 |
| 447 | KKLDAFFVKLSLFTER | 346 |
| 448 | KKLQTFFVKLSLFTER | 345 |
| 449 | KKLCTFFVKLSLFTER | 344 |
| 450 | KKLDTFFVKLSLFTQR | 344 |
| 451 | KKLSTFFVKLSLFTER | 344 |
| 452 | KKYDTFFVKLSLFTER | 344 |
| 453 | SKLDTFFVKLSLFTER | 344 |
| 454 | KLLDTFFVKLSLFTER | 343 |
| 377 | KKLDTFFVKLSLFGER | 343 |
| 455 | KKLDTFFVKLSCFTER | 342 |
| 456 | KKLDEFFVKLSLFTER | 341 |
| 457 | KKLDTFFVKLCLFTER | 341 |
| 458 | KKWDTFFVKLSLFTER | 341 |
| 459 | KKLDTFFVKLSLFTYR | 340 |
| 460 | KKLDTKFVKLSLFTER | 337 |
| 461 | KDLDTFFVKLSLFTER | 335 |
| 462 | KKLDTCFVKLSLFTER | 335 |
| 463 | KKLDTFYVKLSLFTER | 334 |
| 464 | KKLDTFFVKLRLFTER | 333 |
| 465 | FKLDTFFVKLSLFTER | 332 |

TABLE 5.1-continued

Sequences and Corresponding Rampo Scores

| SEQ ID | Sequence | RAMPO Score |
|---|---|---|
| 466 | KKLDTHFVKLSLFTER | 332 |
| 467 | KILDTFFVKLSLFTER | 331 |
| 468 | KTLDTFFVKLSLFTER | 331 |
| 469 | KKLDTFFVQLSLFTER | 330 |
| 470 | KKLDTFFVKLPLFTER | 328 |
| 471 | KKLDTFFVKLSLFTKR | 324 |
| 472 | KKLDTFFVKLWLFTER | 324 |
| 473 | KKLDTFFVKLKLFTER | 323 |
| 474 | KKLDTFFVKLDLFTER | 322 |
| 475 | KKLDTFFVKLSYFTER | 320 |
| 476 | KKLDTFFVKLSLFTER | 319 |
| 477 | KKLDTFFVKLALFTER | 318 |
| 478 | KKLDTFFVKLSLFTHR | 318 |
| 479 | KKLHTFFVKLSLFTER | 317 |
| 480 | KKLRTFFVKLSLFTER | 317 |
| 481 | KVLDTFFVKLSLFTER | 317 |
| 482 | KKLDTFFVKWSLFTER | 316 |
| 483 | YKLDTFFVKLSLFTER | 315 |
| 484 | KKLDLFFVKLSLFTER | 311 |
| 393 | KKLDTFFVKLSLFTEY | 311 |
| 390 | KKLDTFFVKLSLFTEN | 311 |
| 485 | KALDTFFVKLSLFTER | 309 |
| 486 | KKLDTRFVKLSLFTER | 309 |
| 487 | KKLDTFFVKLSLFTER | 308 |
| 488 | KKLDTFFVHLSLFTER | 306 |
| 489 | KKLDTFFVKLSLFAER | 305 |
| 490 | KWLDTFFVKLSLFTER | 304 |
| 491 | KKLLTFFVKLSLFTER | 303 |
| 492 | KKLDTFDVKLSLFTER | 301 |
| 493 | KKLDTFFVKLSLFQER | 301 |
| 494 | KYLDTFFVKLSLFTER | 301 |
| 495 | KKLDTFFAKLSLFTER | 299 |
| 496 | KKLDTFFTKLSLFTER | 298 |
| 497 | KKLDTFFVKLSPFTER | 297 |
| 388 | KKLDTFFVKLSLFTEF | 297 |
| 498 | KKLNTFFVKLSLFTER | 296 |
| 499 | KCLDTFFVKLSLFTER | 295 |
| 500 | KKLDDFFVKLSLFTER | 295 |
| 501 | KKLDIFFVKLSLFTER | 293 |
| 502 | KKLDTFFVKHSLFTER | 293 |
| 392 | KKLDTFFVKLSLFTET | 292 |
| 503 | KKLDTFFVKLSLYTER | 291 |
| 389 | KKLDTFFVKLSLFTEK | 291 |
| 504 | KKLDFFFVKLSLFTER | 290 |
| 505 | KKLDTFFVKLILFTER | 289 |
| 99 | KKLDTFFVKLGLFTER | 288 |
| 506 | KKLDTFFVKKSLFTER | 285 |
| 507 | WKLDTFFVKLSLFTER | 284 |
| 508 | KKLDTFFVKCSLFTER | 283 |
| 509 | KKLDTFFVMLSLFTER | 283 |
| 510 | KSLDTFFVKLSLFTER | 281 |
| 511 | KKLDTFFVSLSLFTER | 274 |
| 512 | KKLKTFFVKLSLFTER | 274 |
| 513 | KKLDTFFQKLSLFTER | 271 |
| 514 | KKLDTFFVKLSLFYER | 270 |
| 515 | KKLGTFFVKLSLFTER | 264 |
| 33 | KKLDTFFVKLSLFRER | 264 |
| 516 | KKLDTFFVKLSLFTER | 260 |
| 517 | KKLDTFFVKLSLFKER | 259 |
| 518 | KKLDTFFVNLSLFTER | 256 |
| 519 | KKLDTFFCKLSLFTER | 254 |
| 520 | KKLDTFFVKLSLFCER | 254 |
| 521 | KKLDTFFVKLSLFTEV | 254 |
| 264 | KKLDTFFKKLSLFTER | 253 |
| 522 | KKLDTFFVKLFLFTER | 250 |
| 523 | KKLDTFFVVLSLFTER | 248 |
| 524 | KKLDTFFVKLSLFTMR | 247 |
| 525 | KKLDTFFVKLSLFTLR | 246 |
| 526 | KKLDTFFVWLSLFTER | 245 |
| 527 | KKLDTFFVELSLFTER | 240 |
| 528 | KKLDTFFVKLSLFTEH | 239 |
| 529 | KKLDTFFVKLSLFTEM | 238 |
| 530 | KKLDKFFVKLSLFTER | 237 |
| 531 | KKLDTFFVKLSLFTRR | 237 |
| 532 | KKLDTFFVKLELFTER | 234 |

TABLE 5.1-continued

Sequences and Corresponding Rampo Scores

| SEQ ID | Sequence | RAMPO Score |
| --- | --- | --- |
| 533 | KKLDTFFVKLSLFTEP | 234 |
| 534 | KKLDTFFVPLSLFTER | 233 |
| 101 | KKLDIFFVKLSLFTGR | 233 |
| 535 | KKLDTFKVKLSLFTER | 232 |
| 536 | KKLDTEFVKLSLFTER | 229 |
| 537 | KKLDTFFWKLSLFTER | 228 |
| 538 | KKLDTFFVKLSLFTEA | 226 |
| 539 | KKLDTFFVKLSLFTWR | 226 |
| 540 | KKLDTFFMKLSLFTER | 221 |
| 541 | KKLDTFFVCLSLFTER | 220 |
| 542 | KKLDTFFVKLSLKTER | 220 |
| 543 | KKLDTFFVKLSLFTEG | 218 |
| 544 | KKLDTFFVKLSLFTEL | 217 |
| 545 | KKLDTFFSKLSLFTER | 216 |
| 546 | CKLDTFFVKLSLFTER | 215 |
| 547 | KKLDTFFHKLSLFTER | 213 |
| 548 | KKLDTFFVKLLLFTER | 213 |
| 549 | KKLDTFFYKLSLFTER | 211 |
| 550 | KKLDTFFNKLSLFTER | 203 |
| 551 | KKLDTFFVKLSLFTEW | 202 |
| 552 | KKLDTFFVYLSLFTER | 198 |
| 553 | KKLDTDFVKLSLFTER | 193 |
| 554 | KKLDTFFVALSLFTER | 191 |
| 555 | KKLDTFFVILSLFTER | 190 |
| 98 | KKLDTFFVGLSLFTER | 188 |
| 97 | KKLDTFFVGLSLFTER | 188 |
| 556 | KKLDTFFVKLSLFTCR | 185 |
| 557 | KKLDTFFVKLSLFTES | 184 |
| 558 | KKLDTFFVKLSLFTEI | 176 |
| 559 | KKLDTFFVKLSLFTEC | 175 |
| 560 | KKLDTFFVFLSLFTER | 174 |
| 561 | KKLDTFFVKLSLFTAR | 174 |
| 562 | KKLDTFFVLLSLFTER | 166 |
| 563 | KKLDTFFVKLSLFTSR | 165 |
| 564 | KKLDTFFVKLSLFTIR | 163 |
| 565 | KKLDTFFVKLSLFTVR | 163 |
| 566 | KKLDTFFVKLSLFTNR | 161 |
| 567 | KKLDTFFVKLSLFDER | 159 |
| 568 | KKLDTFFVKLSLFTTR | 152 |
| 569 | KKLDTFFVDLSLFTER | 149 |
| 570 | KKLDTFFEKLSLFTER | 139 |
| 571 | KKLDTFFVKLSLFTFR | 137 |
| 572 | KKLDTFFVKLSLFTED | 133 |
| 573 | KKLDTFFVKLSLFTEQ | 133 |
| 574 | KKLDTFFDKLSLFTER | 122 |
| 575 | KKLDTFFVKLSLDTER | 112 |
| 576 | KKLDTFFVKLSLFEER | 110 |
| 577 | KKLDTFFVKLSLFTEE | 107 |
| 578 | KKLDTFFVKDSLFTER | 102 |
| 579 | KKLDTFFVKLSLETER | 98 |
| 580 | KKLDTFFVKLSDFTER | 89 |
| 581 | KKLDTFFVKLSEFTER | 82 |
| 582 | KKLDTFFVKESLFTER | 81 |

As shown in Example 12, at least 31 single amino acid substitutions of P28R shown in Table 6.1 (SEQ ID NOs: 3-34) bind to P3028 with a higher rampo score than P28R. Additionally at least 4 single substitutions of glycine residues for residues of P28R (SEQ ID NOs: 94-96 and 98) bind to P3028 with a rampo scores at least comparable to P28R, for example a rampo score greater than about 500. Additionally at least 129 single amino acid substitutions bind to P3028 with a rampo score at least substantially equal to (i.e., at least 98% of) P28R, as shown in Table 6.2 (SEQ ID NOs: 268-393). Additionally, truncations of at least the N terminal arginine of P28R (SEQ ID NO: 34), and up to the first 8 C terminal amino acids of P28R (SEQ ID NOs: 46-53) provide peptides with rampo scores at least comparable to P28R. Additionally, at least some internal amino acid residue deletions of P28 (SEQ ID NOs: 64-66, 68, 76) provide peptides with ramp scores at least comparable to P28R. Thus, contemplated herein are peptides that include substitutions of P28R that include combinations of two or more of the substitutions of SEQ ID NOs: 3-34. Moreover, contemplated herein are peptides that include at least one deletion of P28R as in SEQ ID NOs: 34, 46-53, 64-66, 68, and/or 74, and at least one substitution (of a non-deleted residue) of P28R as in SEQ ID NOs: 3-34, 94-96, 98 and/or 268-393.

Accordingly, some embodiments concern compositions that comprise, consist of, or consist essentially of an immunoregulatory peptide inhibitor that comprises, consists of, or consists essentially of Formula (I):

Formula (I): (SEQ ID NO: 166)

$XX_1VKX_2X_3X_4$.

wherein X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent.

$X_1$ can be one of FF, FM, FS, FV, FT, FL, AF, AM, AS, AV, AT, AL, VF, VM, VS, VV, VT, or VL.

$X_2$ can be one of LS, LQ, LM, LT, LH, VS, VQ, VM, VT, or VH.

$X_3$ can be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR.

$X_4$ is an optional sequence, and can be ER, or E, or absent.

In some embodiments, if X is absent, $X_1$ is FF, and $X_2$ is LS.

In some embodiments, the isolated peptide comprising Formula (I) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (II):

Formula (II):
(SEQ ID NO: 173)
$X_{20}TFFVKLSX_{21}X_{22}$ wherein $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent.

$X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent.

$X_{22}$ is an optional sequence, and can be ER, or E, or absent.

In some embodiments, the isolated peptide comprising Formula (II) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (III):

Formula (III):

Formula (III):
(SEQ ID NO: 178)
$X_{30}X_{31}VKLX_{32}LX_{33}TEX_{34}$ wherein $X_{30}$ is an optional sequence, and can be KKLDTF (SEQ ID NO: 179), KLDTF (SEQ ID NO: 180), LDTF (SEQ ID NO: 181), DTF, TF, or F, or absent.

$X_{31}$ is an optional sequence, and can be F, S, M, V, T, or L, or absent. In some embodiments, $X_{31}$ is F.

$X_{32}$ can be S, Q, M, T, or H. In some embodiments, $X_{32}$ is S.

$X_{33}$ can be F, M, Q, H, N, P, S, G, A, or R. In some embodiments, $X_{34}$ is F.

$X_{34}$ is an optional sequence, and can be R, or absent.

In some embodiments, the isolated peptide comprising Formula (III) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (VII):

Formula (VII):
(SEQ ID NO: 394)
$X_{700}K\ X_{701}X_{702}X_{703}\ X_{704}X_{705}X_{706}K\ X_{707}\ X_{708}\ X_{709}$
$X_{710}\ X_{711}E\ X_{712}$, wherein $X_{700}$ is an optional sequence, and can be K, A, D, E, G, H, I, L, M, N, P, Q, R, T, or V, or absent.

$X_{701}$ is an optional sequence, and can be L, A, C, D, E, F, G, H, I, K, M, N, Q, R, S, T, or V, or absent.

$X_{702}$ is an optional sequence, and can be D, A, E, I, V, W, or Y, or absent.

$X_{703}$ is an optional sequence, and can be T, C, M, N, P, Q, R, S, W, or Y, or absent.

$X_{704}$ is an optional sequence, and can be F, A, I, M, N, P, T, or V, or absent.

$X_{705}$ is an optional sequence, and can be F, L, M, Q, S, T or V, or absent.

$X_{706}$ is an optional sequence, and can be V, F, G, L, P, or R, or absent.

$X_{707}$ is an optional sequence, and can be L, A, F, G, I, M, N, P, Q, R, S, T, V, or Y, or absent.

$X_{708}$ is an optional sequence, and can be S, H, M, N, Q, or T, or absent.

$X_{709}$ is an optional sequence, and can be L, A, H, I, M, N, Q, R, S, T, V, or W, or absent.

$X_{710}$ is an optional sequence, and can be F, A, C, G, H, I, L, M, N, P, Q, R, S, T, V, or W, or absent.

$X_{711}$ is an optional sequence, and can be T, F, G, H, I, L, M, N, P, S, V, or W, or absent.

$X_{712}$ is an optional sequence, and can be R, F, K, N, R, T, or Y, or absent.

In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (VIII):

Formula (VIII):
(SEQ ID NO: 395)
$X_{800}K\ X_{801}K\ X_{802}E\ X_{803}$ wherein $X_{800}$ is K, A, D, E, G, H, I, L, M, N, P, Q, R, T, V, or K, or absent.

$X_{801}$ is LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID

NO: 711), LDTFF (SEQ ID NO: 712), TFFV (SEQ ID NO: 713), LDF, LDTE (SEQ ID NO: 714), FFV, LDV, LV, or L, or absent;

wherein $X_{802}$ is LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent; and wherein $X_{803}$ is R, F, K, N, R, T, or Y, or absent.

In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of any one or more of the peptides set forth in Table 5.1. In some embodiments, the isolated peptide from Table 5.1 used in these compositions has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the peptide comprises one of SEQ ID NOs: 1-33, 34, 46-53, 64-66, 68, 76, 94-96 or 98. Again, this isolated peptide can have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Figure 29:
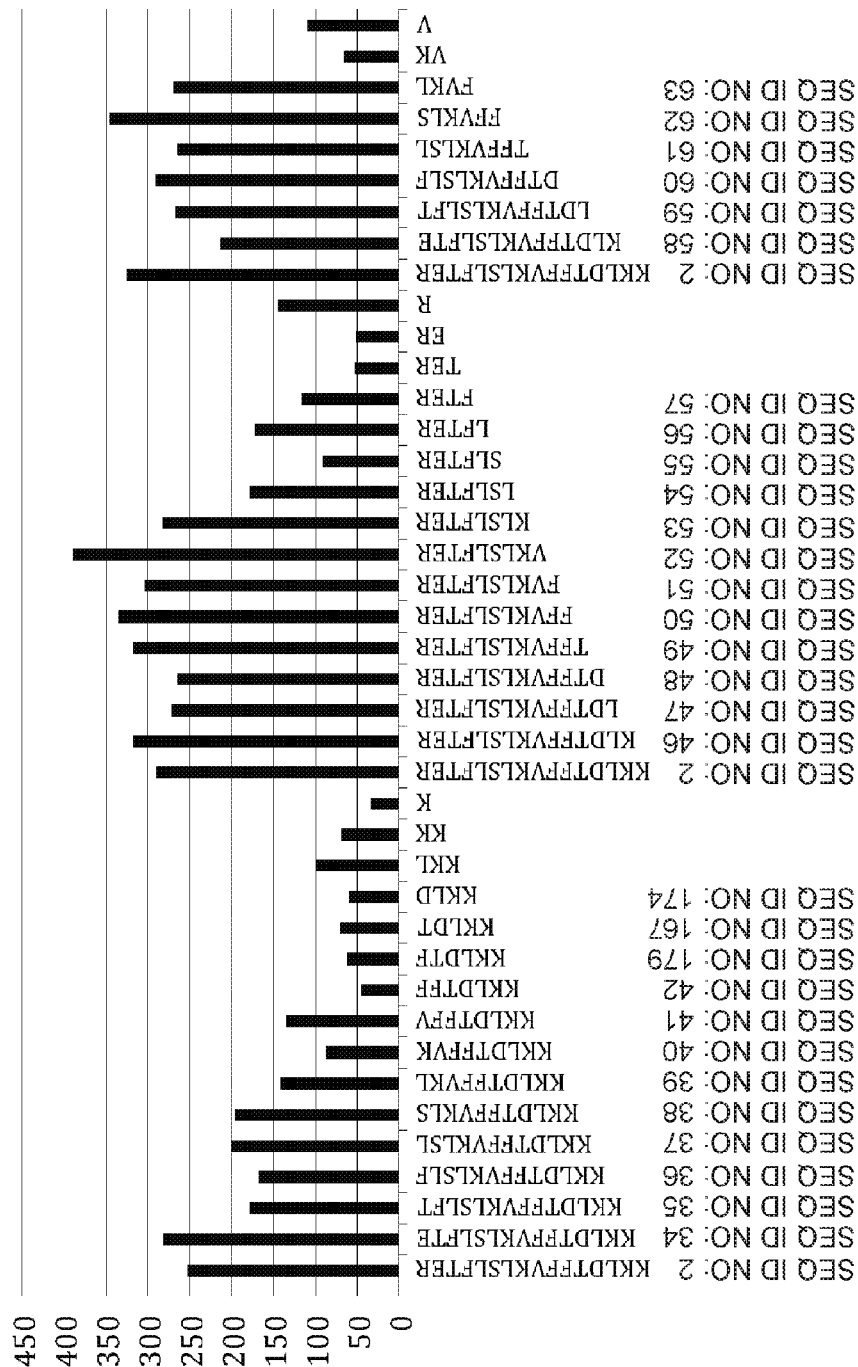
FIG. 29 illustrates rampo scores for binding of P3028 to P28R and N-terminal and/or C-terminal truncations of peptide P28R.

Embodiments of the invention also include immunoregulatory peptide inhibitors that have a specific affinity to P3028 sequences or structures. In some embodiments, the immunoregulatory peptide inhibitors have specific affinity to P3028 sequences or structures as measured by a rampo assay in which the immunoregulatory peptide inhibitors are affixed to a solid phase, P3028 is added, and the enzymatic activity of a rampo secondary antibody is measured so as to detect binding (see Example 12). In some embodiments, the immunoregulatory peptide inhibitors bind to P3028 structures or sequences with a rampo score that is at least substantially equal to the rampo score of P28R (see Example 12, Table 6.2). Preferably, the immunoregulatory peptide inhibitors have a specific affinity to P3028 by this rampo assay of at least or equal to about 300 rampo units, for example, at least or equal to about 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 820, 840, 860, 880, 900, 920, 940, 960, 980, 1000, 1020, or 1040 rampo units, including ranges between any two of the listed values. In some embodiments, the immunoregulatory peptide inhibitors bind to P3028 structures or sequences with a rampo score of at 500 (see Example 12, Table 6.1). Exemplary peptides with affinity to P3028 are provided in Example 12 (see Tables 6.1, 6.2, and FIGS. 29-30).

Similarly, embodiments include isolated immunoregulatory peptide inhibitors that have an affinity to any one or more of the immunoregulatory peptides listed in Tables 1-4 (SEQ ID NOs: 183-184 and 188-246). In some embodiments, the immunoregulatory peptide inhibitors have specific affinity to any one or more of the immunoregulatory peptides listed in Tables 1-4 (SEQ ID NOs: 183-184 and 188-246), as measured by a rampo assay in which the immunoregulatory peptide inhibitors are affixed to a solid phase, any one or more of the immunoregulatory peptides listed in Tables 1-4 (SEQ ID NOs: 183-184 and 188-246) is added, and the enzymatic activity of a rampo secondary antibody is measured so as to detect binding. For example, aspects of the invention include any peptide provided in Table 5.1 and any of the methods described herein can be practiced using one or more of the peptides described in Table 5.1. Preferably, the immunoregulatory peptide inhibitors have a specific affinity to any one or more of the immunoregulatory peptides listed in Tables 1-4 (SEQ ID NOs: 183-184 and 188-246) by this rampo assay of at least or equal to about 300 rampo units, for example, at least or equal to about 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 820, 840, 860, 880, 900, 920, 940, 960, 980, 1000, 1020, or 1040 rampo units, including ranges between any two of the listed values.

Peptide Sequence Variations

A number of sequence variations to the immunoregulatory peptide inhibitor P28R (KKLDTFFVKLSLFTER; SEQ ID NO: 2) have been shown to have immunostimulatory activity and/or cytotoxicity to tumor cells (see Examples 37-40). Without being limited by any theory, SEQ ID NO: 2 and variations of SEQ ID NO: 2 as described in Table 5.3 for example, one or more of the peptides of Table 5.4 can be useful for binding peptide 3028 (SEQ ID NO: 185), binding a peptide or albumin fragment that comprises SEQ ID NO: 185, binding any one or more of the peptides listed in Tables 1-4, directly stimulating immune cells, and/or killing tumor cells in accordance with some embodiments herein (see Examples 36-40). As such, in some embodiments, a immunoregulatory peptide inhibitor peptide comprises, consists of, or consists essentially of an amino acid sequence with one or more of the modifications to SEQ ID NO: 2 as shown in Table 5.3, for example, 1, 2, 3, 4, 5, 6, 7, 8, 9, or 10 modifications, for example, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10 variations. The inhibitor peptide can further comprise a further variation at one or more of positions 1, 3-4, 12-14, or 16 in SEQ ID NO: 2, wherein the further variation comprises any amino acid or the absence of an amino acid, for example, 1, 2, 3, 4, 5, 6, or 7 further variations:

TABLE 5.3

| Position in KKLDTFFVKLSLFTER (SEQ ID NO: 2) | Type of Variation | Exemplary Amino Acids for Variations |
|---|---|---|
| K1 | Any type of amino acid | Any amino acid or absent |
| K2 | Positive charged amino acid | R, H, K |
| L3 | Any type of amino acid | Any amino acid or absent |
| D4 | Any type of amino acid | Any amino acid or absent |
| T5 | Polar uncharged amino acid | S, T, N, Q |
| F6 | Hydrophobic or uncharged polar amino acid | A, V, I, L, F, Y, W, S, T, N, Q |
| F7 | Hydrophobic or uncharged polar amino acid | A, V, I, L, F, Y, W, S, T, N, Q |
| V8 | Hydrophobic, non-aromatic carbon chain amino acids that are not M | A, V, I, L |
| K9 | Positively charged amino acids, T, Q, or Y | R, H, K, T, Q, Y |
| L10 | Any type of amino acid except negatively charged | R, H, K, S, T, N, Q, C, U, G, P, A, V, I, L, M, F, Y, W |
| S11 | Polar uncharged amino acids | S, T, N, Q |
| L12 | Any type of amino acid except negatively charged | R, H, K, S, T, N, Q, C, U, G, P, A, V, I, L, M, F, Y, W |

TABLE 5.3-continued

| Position in KKLDTFFVKLSLFTER (SEQ ID NO: 2) | Type of Variation | Exemplary Amino Acids for Variations |
|---|---|---|
| F13 | Any type of amino acid except negatively charged | R, H, K, S, T, N, Q, C, U, G, P, A, V, I, L, M, F, Y, W |
| T14 | Any type of amino acid except negatively charged | R, H, K, S, T, N, Q, C, U, G, P, A, V, I, L, M, F, Y, W |
| E15 | Negatively charged amino acids | D, E |

In some embodiments, the varied peptide does not comprise a M at position 8. In some embodiments, the varied peptide does not comprise a M at position 9. In some embodiments, the varied peptide does not comprise a M at position 15. In some embodiments, the modified peptide does not comprise a M at any of positions 8, 9, or 15.

Accordingly, in some embodiments, the peptide inhibitor comprising a variation of P28R comprises, consists essentially of, or consists of a peptide of Formula (IX): Formula (IX)

$X_{901}X_{902}X_{903}X_{904}X_{905}X_{906}X_{907}X_{908}X_{909}X_{910}X_{911}$-$X_{912}X_{913}X_{914}X_{915}X_{916}X_{917}$, wherein $X_{901}$ is any amino acid or absent, $X_{902}$ is a positively charged amino acid, F, or N, $X_{903}$ is any amino acid, $X_{904}$ is any amino acid, $X_{905}$ is a polar uncharged amino acid, R, Y, or W, $X_{906}$ is a hydrophobic or uncharged polar amino acid, $X_{907}$ is a hydrophobic or uncharged polar amino acid, $X_{908}$ is a hydrophobic, non-aromatic carbon chain amino acid that is not M or F, $X_{909}$ is a positively charged amino acid, T, Q, or Y, $X_{910}$ is any amino acid that is not negatively charged, $X_{911}$ is a polar uncharged amino acid or H, $X_{912}$ is any amino acid that is not negatively charged, $X_{913}$ is any amino acid that is not negatively charged, $X_{914}$ is any amino acid that is not negatively charged, $X_{915}$ is a negatively charged amino acid, Y, or Q, $X_{916}$ is any amino acid that is not negatively charged, and $X_{917}$ is one or more positively charged amino acids or is absent.

Optionally, $X_{901}$ comprises a positively charged amino acid. Optionally, $X_{901}$ is an R or K. Optional, $X_{917}$ comprises or consists of RR.

A number of peptide inhibitors based on variation of peptides described herein have been shown to stimulate immune cells (see Example 36). Exemplary varied peptides are shown in Table 5.4. Accordingly, in some embodiments, the peptide inhibitor comprises, consists of, or consists essentially of a peptide of Table 5.4. Additional exemplary varied peptides shown to have low binding to P3028 (see Example 36) or low stimulation of healthy PBMC's in healthy serum (see Example 37) are shown in Tables 5.5 and 5.6. In some embodiments, a peptide comprising, consisting of, or consisting essentially of a peptide of Table 5.4, 5.5, or 5.6 is provided.

TABLE 5.4

Peptides with "high" binding to P3028 based on postional scans

| SEQ ID NO: | Amino Acid Sequence (variation(s) to SEQ ID NO: 2 are underlined) | May also be referred to as: |
|---|---|---|
| 583 | KKLDTFFVKLSLMTER | 30677 |
| 584 | KKLDTFFVKLQLFTER | 30678 |
| 585 | KKLDTVMVKLQLMTER | 30680 |
| 586 | RKLDTFFVKLSLFTERRR | 32814 |

TABLE 5.5

Peptides with "low" binding to P3028 based on positional scans

| SEQ ID NO: | Amino Acid Sequence (variation(s) to SEQ ID NO: 2 are underlined) | May also be referred to as: |
|---|---|---|
| 587 | KSLDTFFVKLSLFTER | 30684 |
| 588 | KKLDTFFVKLSLFTFR | 30685 |
| 589 | KKLDTFFVYLSLFTER | 31135 |
| 590 | KKLDTFFVNLSLFTER | 31136 |
| 591 | KKLDTFFVDLSLFTER | 31138 |

TABLE 5.6

Additional modification of P28R

| SEQ ID NO: | Amino Acid Sequence (variation(s) to SEQ ID NO: 2 are underlined) | May also be referred to as: |
|---|---|---|
| 592 | KKLDTFFPKLSLFTER | 32251 |
| 593 | KKLDTFMVKLSQHTER | 32665 |
| 594 | KKLDTFFVKLSLFTER(C(PEG24)) | 32819 |
| 595 | KKLDQFFVKLSQHNER | 32815 |

Embodiments of the invention also include peptides and proteins with identity to an isolated immunoregulatory peptide inhibitor described herein. The term "identity" is meant to include nucleic acid or protein sequence homology or three-dimensional homology. Several techniques exist to determine nucleic acid or peptide sequence homology and/or three-dimensional homology to peptides. These methods are routinely employed to discover the extent of identity that one sequence, domain, or model has to a target sequence, domain, or model. A vast range of functional immunoregulatory peptide inhibitors (e.g., an immunoregulatory peptide inhibitor for P3028 sequence or structures) can incorporate features of peptide inhibitors disclosed herein, thus providing for a vast degree of identity to the immunoregulatory peptide inhibitors of SEQ ID NOs: 1-33, 34, 46-53, 64-66, 68, 76, 94-96, 98, 264-393, 583-586, or 589. For example, a fusion protein having a small region of an inhibitor can exhibit a low degree of overall identity to an immunoregulatory peptide inhibitor of SEQ ID NOs: 1-33, 34, 46-53, 64-66, 68, 76, 94-96, 98, 264-393, 583-586, or 589, yet retain the ability to function as inhibitor (e.g., an inhibitor of P3028, such as a molecule that binds to P3028), or to enhance immune cell stimulation via the LFA-1 and/or IL-2 receptor (e.g., modulate, upregulate or down regulate a marker of the immune system or immunosuppression, such as reducing a P3028-mediated inhibition of immune cell proliferation, spreading, migration, or NK-cell cytotoxicity), or to enhance immune cell stimulation. Thus, embodiments of the invention can have from 1% identity to 100% identity to the sequences of SEQ ID NOs: 1-33, 34, 46-53, 62, 64-66, 68, 76, 94-96, 98, 264-393, 583-586, or 589. That is, embodiments can have at least or equal to about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of SEQ ID NOs: 1-33, 34, 46-53, 64-66, 68, 76, 94-96, 98, 264-393, 583-586, or 589. Preferably, these peptides or modified peptides also retain the ability to modulate the immune system (e.g., modulate, upregulate or down regulate a marker of the immune system or immunosuppression, such as reducing a P3028-mediated inhibition of immune cell proliferation, spreading, migration, or NK-cell cytotoxicity).

Embodiments also include compositions that comprise multimers of isolated immunoregulatory peptide inhibitors and/or isolated immunoregulatory peptide inhibitors bound to a support. Some embodiments include compositions that comprise multimers of immunoregulatory peptide inhibitors that include multiple copies of a single immunoregulatory peptide inhibitor. Some embodiments include compositions that comprise multimers that include two or more different immunoregulatory peptide inhibitors. Some multimers include at least or equal to two immunoregulatory peptide inhibitors, for example 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 99, 100, or 101 immunoregulatory peptide inhibitors. In some embodiments, the multimers are of the same immunoregulatory peptide inhibitor and in other embodiments, the multimers are of different immunoregulatory peptide inhibitors. Accordingly, some embodiments concern compositions that comprise one or more immunoregulatory peptide inhibitors and in some embodiments, the one or more immunoregulatory peptide inhibitor are multimers of the same molecule.

Methods of Making Peptide-Based Immunoregulatory Peptide Inhibitors

Many methods of making peptides are known in the art. Examples of methods of making peptides can be found in U.S. Pat. No. 6,495,674, hereby expressly incorporated by reference in its entirety. In some embodiments, peptide inhibitors are chemically synthesized. Chemical synthesis of peptides is also well-known. For example, solid phase chemical synthesis can be used to produce peptides of up to at least about 100 amino acids in length. Accordingly, in some embodiments, the immunoregulatory peptide inhibitor is a synthetic peptide.

In other embodiments, immunoregulatory peptide inhibitors are prepared by recombinant DNA technology using techniques well known in the art. Such methods can be used to construct expression vectors containing nucleotide sequences encoding an immunoregulatory peptide inhibitor, for example, and appropriate transcriptional and translational control signals. These methods can include, for example, in vitro recombinant DNA techniques, synthetic techniques, and in vivo genetic recombination. Alternatively, RNA capable of encoding a peptide inhibitor can be chemically synthesized using, for example, synthesizers. See, for example, the techniques described in Oligonucleotide Synthesis, 1984, Gait, M. J. ed., IRL Press, Oxford, which is incorporated by reference herein in its entirety. Alternatively, a DNA or RNA encoding a peptide or protein substantially longer that the peptide inhibitor can be provided, in which the peptide inhibitor is flanked by protease target sites, thus producing the peptide inhibitor from a larger peptide or protein. Exemplary proteases include thrombin, trypsin, chymotrypsin, LysC, GluC, and AspN. Alternatively, a DNA or RNA encoding two or more copies of the peptide inhibitor can be provided, in which the peptide inhibitors are flanked by protease target sites, thus producing the peptide inhibitor from a larger peptide or protein. Thus, in some embodiments, the peptide inhibitor of P3028 is produced by a ribosome.

In several embodiments, the immunoregulatory peptide inhibitors are expressed in a cell line. For example, some cells are provided a nucleic acid encoding one or more immunoregulatory peptide inhibitors, said cells are made to express the peptides of SEQ ID NOs: 1-33, 34, 46-53, 64-66, 68, 76, 94-96, 98, 264-393, 583-586, or 589 or any one or more of the peptides provided in Table 5.1 and the immunoregulatory peptide inhibitors are isolated and/or purified. Exemplary nucleic acids are listed in Table 5.2, SEQ ID NOs: 102-165.

A variety of host-expression vector systems can be utilized to express inhibitor peptides of some embodiments of the invention. Where the immunoregulatory peptide inhibitor is a soluble peptide, it can be recovered from the culture, i.e., from the host cell in cases where the peptide or polypeptide is not secreted, and from the culture media in cases where the peptide or polypeptide is secreted by the cells. However, the expression systems also encompass engineered host cells that express the peptide or functional equivalents in situ, i.e., anchored in the cell membrane. Purification or enrichment of the peptide from such expression systems can be accomplished using appropriate detergents and lipid micelles and methods well known to those skilled in the art. However, such engineered host cells themselves can be used in situations where it is important not only to retain the structural and functional characteristics of the peptide, but to assess biological activity, e.g., in drug screening assays.

The expression systems that can be used for purposes of the invention include, but are not limited to, microorganisms such as bacteria (e.g., *E. coli* or *B. subtilis*) transformed with recombinant bacteriophage DNA, plasmid DNA or cosmid DNA expression vectors containing nucleotide sequences encoding inhibitor peptides; yeast (e.g., *Saccharomyces, Pichia*) transformed with recombinant yeast expression vectors containing the nucleotide sequences encoding inhibitor peptides; insect cell systems infected with recombinant virus expression vectors (e.g., baculovirus) containing sequences encoding inhibitor peptides; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequences encoding inhibitor peptides; mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter); or cell-free expression systems, which can include cell lysates or fractions thereof, and nucleic acids encoding the inhibitor peptides.

In bacterial systems, a number of expression vectors can be advantageously selected depending upon the use intended for the peptide being produced. For example, when a large quantity of such a peptide is to be produced, for the generation of pharmaceutical compositions or for raising antibodies to the peptide, for example, vectors which direct the expression of high levels of fusion protein products that are readily purified can be desirable. Such vectors include, but are not limited, to the *E. coli* expression vector pUR278 (Ruther et al., EMBO J., 2:1791 (1983), in which the inhibitor peptide coding sequence can be ligated individually into the vector in frame with the lacZ coding region so that a fusion protein is produced; ON vectors (Inouye & Inouye, Nucleic Acids Res., 13:3101-3109 (1985); Van Heeke & Schuster, J. Biol. Chem., 264:5503-5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The peptide coding sequence can be cloned individually into non-essential regions (for example the polyhedrin gene) of the virus and placed under control of an AcNPV promoter (for example the polyhedrin promoter). Successful insertion of peptide coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., J. Virol. 46: 584 (1983); and Smith, U.S. Pat. No. 4,215,051).

In mammalian host cells, a number of viral-based expression systems can be utilized. In cases where an adenovirus is used as an expression vector, the nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the peptide in infected hosts. (E.g., see Logan & Shenk, Proc. Natl. Acad. Sci. USA 81:3655-3659 (1984)). Specific initiation signals can also be required for efficient translation of inserted nucleotide sequences encoding peptides. These signals include the ATG initiation codon and adjacent sequences.

In cell free systems, cellular extracts, or fractions thereof are provided for the translation of nucleic acids into polypeptides in vitro. Cell free systems can include, for example *E. coli* extracts, yeast extracts. The extracts can be lysates. The extracts can be purified, for example, to enrich for ribosomes and/or to remove undesired materials such as debris or host genomic DNA. Nucleic acids encoding immunoregulatory peptide inhibitors in cell-free systems can include plasmid DNA, linear DNA, or RNA.

In some embodiments, immunoregulatory peptide inhibitors are isolated or purified after expression. Isolation or purification can include affinity purification. In some embodiments, the peptide product of the expression system includes an affinity tag, for example GST separated by a cleavable linker, for example a thrombin or factor Xa protease cleavage site. After affinity purification, the affinity tag can be cleaved, producing a substantially pure peptide that does not have an affinity tag or cleavage site. In some embodiments, purification results in a composition that is at least or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.5, 99, 99.5, 99.9, 99.99, or 99.999% peptide by weight. The section below provides more information on pharmaceutically acceptable carriers and diluents that can be used with the embodiments described herein.

D Amino Acids and Non-Natural Amino Acids

Some embodiments include compositions that comprise, consist, or consist essentially of one or more immunoregulatory peptide inhibitors that include at least one D amino acid. With the exception of glycine, the chiral carbon of an amino acid can exist as the D or the L isomer. Typically, amino acids synthesized by ribosomes are in the L configuration. However, peptides that include D amino acids, or a combination of D and L amino acids can have activity, for example as ligands or inhibitors. For example, a peptide including at least one D amino acid can bind to the P3028 sequence/structure and inhibit the ability of the P3028 sequence/structure to bind to the LFA-1 receptor and/or the IL-2 receptor.

Accordingly, some embodiments include immunoregulatory peptide inhibitors that comprise at least one non-natural amino acid. Non-natural amino acids include amino acids having R groups other than the R group of the 20 amino acids encoded by the standard genetic code. Non-natural amino acids can exist in the L or D configuration. Thus, some embodiments include peptides having non-natural amino acids in the D configuration and/or the L configuration. Exemplary non-natural amino acids are described in U.S. Pat. Nos. 8,153,758, 7,888,533, 6,344,483, each of which is expressly incorporated by reference in its entirety herein. Some embodiments concern a composition that comprises, consists of, or consists essentially of one or more of the immunoregulatory peptide inhibitors described herein (e.g., an immunoregulatory peptide inhibitor of the P3028 sequence/structure, such as one or more of the immunoregulatory peptide inhibitors provided by of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein said immunoregulatory peptide inhibitor comprises at least one D amino acid. Similarly, some embodiments concern a composition comprising immunoregulatory peptide inhibitor of the P3028 sequence/structure, wherein said immunoregulatory peptide inhibitors (e.g., any one or more of the immunoregulatory peptide inhibitors provided by of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 comprises at least one non-natural amino acid. Further embodiments include a composition comprising an immunoregulatory peptide inhibitor (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein each non-glycine amino acid of the immunoregulatory peptide inhibitor is a D amino acid.

The crystal structure of the IL-2 receptor (CD25) has been solved, and computer modeling of P3028 binding to the IL-2 binding site of the IL-2 receptor has been performed (see FIG. 19). Moreover, the crystal structure of the ligand binding domain of IL-2 is known (see Qu, A and Leahy, D J, Proc. Natl. Acad. Sci. USA 1995, 92: 10277-10281, which is expressly incorporated by reference in its entirety). Moreover, favorable interactions between P3028 and at least one immunoregulatory peptide inhibitor can facilitate the selection of additional amino acid residues, D amino acid residues, and/or non-natural amino acid residues to maintain favorable interactions.

In some embodiments, at least some of these immunoregulatory peptide inhibitors include D amino acids positions that are selected using rational design or P3028 sequence/structure inhibitors. As noted in U.S. Pat. No. 7,957,912, rational design of peptides can start with a protein backbone structure and designs the amino acid sequence to modify the protein's properties, while maintaining its three dimensional folding properties. In some embodiments, large numbers of sequences can be manipulated using computer modeling, allowing for the design of protein structures (sequences, subsequences, etc.). Aspects of rational design are described in a number of publications, including, e.g., Malakauskas and Mayo (1998) "Design, Structure and Stability of a Hyperthermophilic Protein Variant" Nature Struc. Biol. 5:470; Dahiyat and Mayo (1997) "De Novo Protein Design: Fully Automated Sequence Selection" Science, 278, 82-87. DeGrado, (1997) "Proteins from Scratch" Science, 278:80-81; Dahiyat, Sarisky and Mayo (1997) "De Novo Protein Design: Towards Fully Automated Sequence Selection" J. Mol. Biol. 273:789-796; Dahiyat and Mayo (1997) "Probing the Role of Pachng Specificity in Protein Design" Proc. Natl. Acad. Sci. USA, 94:10172-10177; Hellinga (1997) "Rational Protein Design—Combining Theory and Experiment" Proc. Natl. Acad. Sci. USA, 94: 10015-10017; Su and Mayo (1997 j "Coupling Backbone Flexibility and Amino Acid Sequence Selection in Protein Design" Prot. Sci. 6:1701-1707; Dahiyat, Gordon and Mayo (1997) "Automated Design of the Surface Positions of Protein Helices" Prot. Sci., 6:1333-1337; Dahiyat and Mayo (1996) "Protein Design Automation" Prot. Sci., 5:895-903.

In some embodiments, a library of variant of immunoregulatory peptide inhibitors of the P3028 sequence/structure containing one or more D amino acids and/or non-natural amino acids is screened for binding to the P3028 sequence/structure. In some embodiments, the library is screened for binding to P3028 (see Examples 10 and 12). In some embodiments, the library is screened for inhibiting binding of the P3028 sequence/structure to the LFA-1 receptor (see Example 15).

In some embodiments, a lead molecule is used as a template for directed drug design. A lead peptide, for example, can include, but is not limited to one or more of the exemplary immunoregulatory peptide inhibitors that bind to the P3028 sequence/structure provided herein, such as in Example 12, (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13). The lead peptide can be synthesized to include at least one D amino acid and/or at least one non-natural amino acid. In some embodiments, the binding activity of the first generation artificial immunoregulatory peptide inhibitor is then detected, for example by evaluating the binding affinity for the P3028 sequence/structure, as described herein. Additionally, the immunostimulatory activity of the first generation artificial immunoregulatory peptide inhibitor can be detected, for example by evaluating the stimulation of an LFA-1 and/or IL-2 dependent response in a cell having a LFA-1 receptor or IL-2 receptor, which can be inhibited by the P3028 sequence/structure. Once the binding and/or immunostimulatory activity of the first generation artificial immunoregulatory peptide inhibitor is obtained, at least one additional modification is made to the lead peptide and this second generation immunoregulatory peptide inhibitor is evaluated for binding to the P3028 sequence/structure and immunostimulatory activity. The additional modification can include, but is not limited to the addition or substitution, of at least one additional D amino acid and/or a non-natural amino acid. By iteratively conducting this screening and modification procedure, more immunoregulatory peptide inhibitors can be made.

Additionally, any one or more of the immunoregulatory peptide inhibitors described herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 can comprise an N-terminal acetyl group and/or a C-terminal amide group. Furthermore, any one or more of the immunoregulatory peptide inhibitors described herein that comprise at least one D amino acid and/or at least one non-natural amino acid (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 can be prepared to comprise an N-terminal acetyl group and/or a C-terminal amide group).

Peptidomimetics

Some embodiments include compositions that comprise, consist of, or consist essentially of peptidomimetic-based immunoregulatory peptide inhibitors. Peptidomimetics can include, but are not limited to small-molecule compounds having at least one biochemical interaction that a peptide also has. Some peptidomimetics can include a small molecule backbone. Some peptidomimetics can include at least one R group of a naturally-occurring amino acid covalently bonded to a small molecule backbone. Some peptidomimetics are substituted into at least one position of a known peptide sequence. Accordingly, some embodiments include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory peptide inhibitor comprises at least one peptidomimetic substitution (e.g., a non-peptide bond, a small molecule backbone, or an artificial peptide linkage).

Some embodiments include a composition that comprises, consists of, or consists essentially of one or more of the exemplary isolated immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein said immunoregulatory inhibitors comprise a peptidomimetic substitution, which includes two or more monomers, wherein each monomer comprises a small molecule backbone covalently bound to at least one R group. More embodiments, include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein said immunoregulatory inhibitors comprise at least one peptidomimetic small molecule backbone, wherein each backbone molecule includes one of an aryl group, for example a benzene, pyrrole, furan, thiophene, imidazole, oxazole, thiazole, triazole, pyrazole, pyridine, pyrazine, pyridazine and pyrimidine, and the like; a cycloalkane or heterocycloalkane; a cycloalkene or heterocycloalkene; or a combination of two or more of the listed molecules. Each R group can be the R group of a naturally occurring amino acid, or optionally can be a synthetic molecule. Each R group can be different, but two or more R groups can be the same. Some peptidomimetics include a first monomer that binds to a first position of P3028, for example, and a second monomer that binds to a second position of P3028, in which the first and second monomers are covalently bonded (see, for example, the approach of Chen et al., ACS Chemical Biology 2009; 4(9): 769-81, hereby expressly incorporated by reference in its entirety). The peptidomimetic backbone that is incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, can include a derivative of a (3-turn peptidomimetic cyclic compound of formula (IV), as taught by U.S. Pat. No. 6,881,719, hereby expressly incorporated by reference in its entirety:

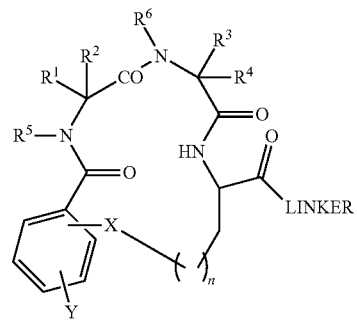

Formula (IV)

In some embodiments, R1 and R3 of the above Formula (IV) include R groups of natural and/or synthetic amino acids. Some embodiments include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise a peptidomimetic substitution that includes a polymer of two or more derivatives of Formula (IV). In some embodiments, individual peptidomimetic monomers or dimers derived from Formula (IV) are selected for their ability to bind the P3028 sequence/structure, and are then assembled into polymers, thus producing a peptidomimetic polymer that specifically binds the P3028 sequence/structure.

As described in U.S. Pat. No. 7,816,324, peptidomimetics of either Formula (V) or Formula (VI) can be modified to mimic alpha-helix motifs that bind to peptides.

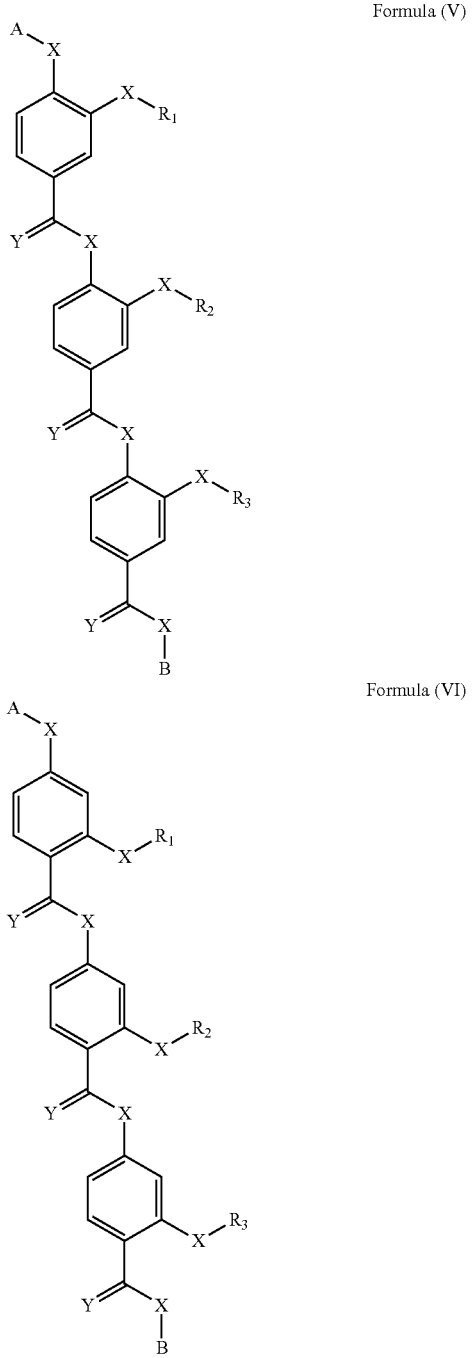

Formula (V)

Formula (VI)

Accordingly, aspects of the invention include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise a peptidomimetic substitution that incorporates the scaffold of formula V or formula VI, which provide a rigid structure and places and orients substituents as an alpha-helix does. Substitution on the rigid tris-benzamide, for instance, can allow placement of three functional groups ($R_1$-$R_3$) corresponding to the side chains of amino acids found at the i, i+4, and i+7 positions of an ideal alpha-helix, bound by the peptide. As shown in FIG. 19, P3028 is modeled to bind to alpha helix-containing regions of the IL-2 receptor. Thus, some embodiments include a composition that comprises, consists of, or consists essentially of one or more of the exemplary immunoregulatory peptide inhibitors that bind to P3028 provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise a peptidomimetic substitution that incorporates a peptidomimetic of formula V or formula VI, wherein $R_1$-$R_3$ are selected from positions on a known binding partner of P3028, for example the alpha subunit of the IL-2 receptor (CD25) (SEQ ID NO: 247), the LFA-1 receptor (CD11a—SEQ ID NO: 248 and CD18—SEQ ID NO: 249), or a peptide of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13.

Embodiments also include a library of peptidomimetics. In some embodiments, the library of peptidomimetics is selected and/or synthesized using a rational design approach. As disclosed in U.S. Pat. No. 7,816,324, hereby expressly incorporated by reference in its entirety, a peptidomimetic library can be developed based on based on a structural knowledge of the interface of protein complexes. Thus, in some embodiments, peptidomimetic compounds are based on the structure of P3028, and its interactions with known binding partners, for example the IL-2 receptor for which the crystal structure is known (see FIG. 19), the LFA-1 receptor, for which the crystal structure is known, the KKL15 peptide (see Example 11), and known inhibitors of the P3028 sequence/structure (e.g., SEQ ID NOs: 1-33, 34, 46-53, 64-66, 68, 76, 94-96, 98, or 264-393 or any one or more of the peptides provided in Table 5.1). In some embodiments, alpha.-helix mimetics may be used to modulate protein-protein or protein-peptide interaction. Thus, synthetic scaffolds that mimic key elements found in the interface between the P3028 sequence/structure and its binding partners is contemplated for the development of small molecule immunoregulatory protein inhibitors. In some embodiments, the molecules of the peptidomimetic library are attached to a support, chip, surface, or substrate, for example a microarray, as in U.S. Pat. No. 7,153,68, hereby expressly incorporated by reference in its entirety. The section below provides more details on aptamer-based immunoregulatory peptide inhibitors.

Cyclic Peptides

Some embodiments include at least one cyclic peptide immunoregulatory peptide inhibitor. Cyclic peptides, sometimes referred to as "looped peptides" are known in the art, and can be chemically synthesized (see, e.g., U.S. Pat. No. 7,589,170, hereby expressly incorporated by reference in its entirety herein), or synthesized in vivo (see, e.g., U.S. Pat. No. 7,252,952, hereby expressly incorporated by reference in its entirety herein). As taught in U.S. Pat. No. 7,589,170, cyclisation can be accomplished, for example by disulfide bond formation between two side chain functional groups, amide or ester bond formation between one side chain functional group and the backbone alpha-amino or carboxyl function, amide or ester bond formation between two side chain functional groups, amide bond formation between the backbone alpha-amino and carboxyl functions, or via a linker connecting two or more positions of the peptide.

A portion of a peptide can be cyclized, or optionally, the entire peptide can be cyclized, thereby forming a cyclic peptide. Thus, in some embodiments, the N terminus of the peptide is bonded to the C terminus of the peptide, thereby cyclizing the entire peptide. In some embodiments, the N terminus is bonded to the C terminus via an alpha-amide linkage. In some embodiments, the N terminus is bonded to the C terminus via a non-alpha-amide linkage, for example a bond between the side chain of a Ser (S) or Thr(T) and the C-terminal carboxyl group, a disulfide bond between two Cys (C) residues, or a thioether between a Trp (W) and Cys (C) residue, or a synthetic linker molecule. In some embodiments, the C terminus is bonded to an internal amino acid via a non-alpha-amide linkage, for example, a bond between the side chain of a Ser (S) or Thr(T) and the C-terminal carboxyl group, or a synthetic linker molecule. In some embodiments, the N terminus or the C terminus is bonded to an internal amino acid, or two internal amino acids are bonded to each other via a non-alpha-amide linkage, for example a disulfide bond between two Cys (C) residues, or a thioether between a Trp (W) and Cys (C) residue.

In some embodiments, a cyclic peptide immunoregulatory peptide inhibitor includes a single cyclic polypeptide structure. In some embodiments, a cyclic peptide immunoregulatory peptide inhibitor includes two or more cyclic polypeptide structures, for example 2, 3, 4, 5, 6, 7, 8, 9, 10, 11, or 12 cyclic polypeptide structures. Each cyclic polypeptide structure can include at least two amino acid residues, for example, about 2, 3, 4, 5, 6, 7, 8, 9, 10, 11, 12, 13, 14, 15, 16, 17, 18, 19, 20, 25, 26, 27, 28, 29, 30, 35, or 40 amino acid residues or a range that is defined by any two of these numbers.

In some embodiments, a library of cyclic peptides is screened for cyclic peptides that bind to albumin-derived immunoregulatory peptides, for example, the peptides of Tables 1-4 or 5.4 (SEQ ID NOs: 183-184, 188-246). Screening of cyclic peptides libraries is described in PCT Publication WO 95/09344, hereby incorporated by reference in its entirety. In some embodiments, a library of cyclic peptides is synthesized. In some embodiments, each looped peptide in the library has the same length, for example 5-meres, 6-meres, 7-meres, 8-meres, 9-meres, 10-meres, 11-meres, or 12-meres. In some embodiments, the library includes cyclic peptides of two or more lengths. As shown in Example 12, a library of 6-meres was synthesized and was screened for peptides that bind to P3038. Positional scans (i.e., single amino acid substitutions at each position) of a lead cyclic peptide (SEQ ID NO: 265) identified as exhibiting appreciable binding to P3028 were performed to identify additional cyclic 6-meres that bind to P3028. It was observed that the two 6-meres that bound to P3028 with the highest affinity (SEQ ID NOs: 266-267) had homology to linear peptides that bind to P3028 (see FIG. 32). Thus, it is contemplated herein that aspects of linear peptides that bind to albumin-derived immunoregulatory peptides can be incorporated into cyclic peptides, thus producing cyclic peptides that bind albumin-derived immunoregulatory peptides.

In some embodiments, inhibitors of albumin-derived immunoregulatory peptides or structures, or a portion thereof is cyclized. In some embodiments, a peptide of any of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a portion thereof is modified to facilitate cyclization. In some embodiments, amino residues containing side chains that can for cyclic structures, for example Cysteine, are added to the N terminus, C terminus, and/or internal positions of any of the peptide of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13.

Aptamers

Aptamers are small molecules that specifically bind to a target molecule. Aptamers can include oligonucleotide aptamers, for example DNA, RNA, or synthetic oligonucleotides. In some embodiments, oligonucleotide aptamers include oligonucleotides with a synthetic backbone, for example morpholinos. Aptamers can also include peptide aptamers. Aspects of the invention include a composition that comprises, consists of, or consists essentially of an aptamer (e.g., nucleic acid based or peptide based), wherein said aptamer corresponds or mimics one or more of the exemplary immunoregulatory peptide inhibitors that bind to the P3028 sequence/structure provided herein (e.g., any one or more of the immunoregulatory peptide inhibitors provided by of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13). Some embodiments of the invention include aptamers that bind specifically to the P3028 sequence/structure.

Some embodiments include a library of oligonucleotide aptamers. Oligonucleotide aptamers that bind to the P3028 sequence/structure can be readily developed given the teachings described herein. As described in U.S. Pat. No. 7,745, 607, which is hereby expressly incorporated by reference in its entirety herein, an aptamer that binds specifically to a target, for example the P3028 sequence/structure can be identified by interacting an antisense oligonucleotide with a library oligonucleotide having a complementary antisense binding domain to form a double stranded duplex, said library oligonucleotide further having a random nucleotide domain; ii) immobilizing the duplex structure on a solid support; iii) incubating the duplex structure in the presence of the P3028 sequence/structure; and iv) collecting library oligonucleotides that dissociate from the duplex structure and bind to the P3028 sequence/structure. Alternatively, a library of oligonucleotides can be provided in which the library oligonucleotide is hybridized to a biotinylated antisense oligonucleotide to form a duplex molecule. The duplex molecules are immobilized on a surface, for example avidin-coated beads. A target, such as P3028 is provided and contacted with the oligonucleotides. Oligonucleotides which have bound to the target, are collected and amplified. Similar screening approaches can be used to identify peptide-based aptamers that bind to the P3028 sequence/structure. Peptide based aptamers that bind to the P3028 sequence/structure, can mimic the immunoregulatory peptide inhibitors described herein (e.g., any one or more of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), and variants thereof. The section below discusses many of the modifications that can be incorporated in an immunoregulatory peptide inhibitor described herein.

Modifications

Embodiments described herein also include a composition that comprises, consists of, or consists essentially of one or more of the exemplary isolated immunoregulatory peptide inhibitors that bind to the P3028 sequence/structure provided herein (e.g., any one or more of the immunoregulatory peptide inhibitors provided by (SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise at least one modification (e.g., glycosylation, nitrosylation, a cytotoxin, a detectable moiety, or a radionuclide). Glycosylation can include the addition of polyethylene glycol (PEG). The addition of PEG can increase the solubility of one or more of the immunoregulatory peptide inhibitors described herein in aqueous solution, protect the molecule from attack by a host's immune system, and/or increase the half-life of the molecule in the host.

In some embodiments, the immunoregulatory peptide inhibitors are directly bound to a cytotoxin. In some embodiments, a peptide consisting of, consisting essentially of, or comprising one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 is covalently bound to a cytotoxin. In some embodiments, the immunoregulatory peptide inhibitor is attached to the toxin via a linker. In some embodiments, a peptide consisting of, consisting essentially of, or comprising one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 is attached to a cytotoxin via a linker. A wide array of linker technologies can be employed. Linkers can be cleavable or non-cleavable. It is known that in many cases, the full cytotoxic potential of a drug can be observed when the cytotoxic molecules are released from a conjugates, for example an inhibitor of an immunoregulatory peptide, in unmodified form at the target site. One of the cleavable linkers that has been employed for the preparation of cytotoxin conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (Biochem. Biophys. Res. Commun. 102:1048-1054 (1981)). Yang and Reisfeld used the same technique to conjugate daunorubicin to an anti-melanoma antibody (J. Natl. Canc. Inst. 80:1154-1159 (1988)). Recently, Dillman et al. also used an acid-labile linker in a similar fashion to prepare conjugates of daunorubicin with an anti-T cell antibody (Cancer Res. 48:6097-6102 (1988)). An alternative approach, explored by Trouet et al. involved linking daunorubicin to a targeting molecule via a peptide spacer arm (Proc. Natl. Acad. Sci. 79:626-629 (1982)). This was done under the premise that free drug could be released from such a conjugate by the action of lysosomal peptidases. One skilled in the art will appreciate that cleavable linker approaches employed for conjugating cytotoxins to antibodies can also be employed to conjugate a peptide, for example one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a cytotoxin.

Exemplary cytotoxins that can be incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) include: radiotoxins, monomethylauristatin-E, monomethylauristatin-F, aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, saporin, semustine streptozocin, tamoxifen, taxanes, testosterone propionate, thalidomide, thioguanine, thiotepa, teniposide, topotecan, uracil mustard, velcade, vinblastine, vinorelbine, vincristine, ricin, for example ricin A chain, abrin, ribonuclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin.

Exemplary detectable moieties (which may also be referred to herein as "detectable labels" that can be incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) or to an antibody that binds specifically to P3028 include: a radiolabel, a fluorophore, biotin, a fluorescent protein, colloidal gold, and/or a coenzyme. Radiolabels can include $^{3}H$ and $^{14}C$. Fluorophores can include Alexa-Fluor dyes, Pacific Blue, Pacific Orange, Cascade Blue, Cascade Yellow and R-phycoerythrin, fluorescein (FITC), rhodamine, Texas red, BODIPY family dyes, Cy2, Cy3, C5, and Cy7. Fluorescent proteins can include Blue, Cyan, Green, Yellow, and Red fluorescent proteins. In some embodiments, fluorescent labels include a FRET pair. For example, a single peptide can be attached to a FRET donor and FRET acceptor, which are configured so that the FRET acceptor is substantially within a FRET radius of the FRET donor when the peptide is in a first configuration (for example, bound to target), but not when the peptide is in a second configuration (for example, unbound to target). For example, a first peptide can be attached to a FRET acceptor, and a second peptide can be attached to a FRET donor, so that the FRET acceptor is substantially within a FRET radius of the FRET donor when the first peptide and second peptide are each bound to a target, for example a target cell, but not when at least one peptide is unbound to the target. In some embodiments, fluorescent label includes a fluorophore and a quencher. The fluorophore and quencher can each be attached to the peptide so that the quench absorbs electromagnetic radiation emitted by the fluorophore when the peptide is in a first configuration (for example, bound to target), but not when the peptide is in a second configuration (for example, unbound to target). Coenzymes can include vitamins such as biotin.

Exemplary radionuclides that can be incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) or an antibody that binds specifically to P3028 include: $^{111}I$, $^{131}I$, $^{90}Y$, $^{67}Cu$, $^{186}Re$, $^{188}Re$, $^{212}Bi$ or $^{211}At$. Preferable radiolabeled immunoregulatory peptide inhibitors are able to deliver more than 6000 rads to a tumor, for example, and have sufficient affinity so that the patient's bone marrow is not exposed to more than 300 rads. The section that follows describes in greater detail some of the embodiments, which encompass protein complexes comprising an immunoregulatory peptide inhibitor described herein.

In some embodiments, a diagnostic kit is provided. The kit can include any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 or an antibody that binds specifically to any of the peptides of SEQ ID NOs: 183-185 or 188-246, for example P3028 (SEQ ID NO: 185). The kit can also include a detectable moiety as described herein. In some embodiments, the peptide inhibitor or antibody of the kit is biotinylated.

Carrier Molecules

Some embodiments include a carrier molecule. Carrier molecules, can for example, increase the stability or half-life, increase the solubility, increase the absorption, target the peptide to an appropriate cell, organ or tissue, and/or minimize an immune response against a therapeutic molecule.

Exemplary carrier molecules include human serum albumin; a polymer having a plurality of acid moieties (see PCT Pub. No. WO 01/93911); anionic group-containing amphiphilic block copolymers that, when used as a drug carrier for a cationic therapeutic molecule can improve stability of that molecule (see PCT Pub. No. WO 03/00778); cyclodextrin and acids for improving the properties of basic therapeutic molecules (European Pat. No. 0 681 481); lipids as carriers for hydrophobic therapeutic molecules (see PCT Pub. No. WO 04/064731); immunoglobulins; and Fc fragments as carriers for improving half-life and minimizing immune response (see U.S. Pat. No. 7,736,653). In some embodiments, an immunoregulatory peptide inhibitor (e.g., a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) includes or is joined to a carrier. In some embodiments, an immunoregulatory peptide inhibitor (e.g. a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) includes two or more carriers.

In some embodiments, an immunoregulatory peptide inhibitor is provided with a degradable particle. Without being limited by any theory, it is contemplated that a degradable particle can permit an immunoregulatory particle to be soluble and exert its activity for a controlled period of time in the systemic circulation. Accordingly, in some embodiments, a degradable particle comprising an immunoregulatory peptide inhibitor (for example, a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) is provided. In some embodiments the degradable particle comprising the immunoregulatory peptide inhibitor is administered to a subject in need. Optionally, the degradable particle can be administered systemically. Optionally, the degradable particle can be administered locally, for example at or near a site of immunosuppression (e.g. within 10 cm, 9 cm, 8 cm 7 cm, 6 c, 5 cm, 4 cm, 3 cm, 2 cm, 1 cm, or 0.5 cm of the site of immunosuppression or a range defined by any two of these numbers). In some embodiments, the subject suffers from LFA-1 receptor blockage by an immunoregulatory peptide sequence of any of Tables 1-4. Optionally, the degradable particle can be coadministered with one or more additional therapeutic agents. For example, if a the immunoregulatory peptide inhibitor is useful for de-blocking an LFA-1 receptor (e.g. displaces bound immunoregulatory peptides or 3028 structures from the LFA-1 receptor), a therapeutic agent that stimulates an immune response, for example via an LFA-1 receptor can be useful for co-administering with the immunoregulatory peptide inhibitor and degradable particle. In some embodiments, the additional therapeutic agent is administered at the same time as the immunoregulatory peptide inhibitor, for example as part of the degradable particle. In some embodiments, the additional therapeutic agent is administered after the immunoregulatory peptide inhibitor, for example at least about 1, 2, 3, 4, 5, 6, 7, 8, 9, 10, 11, 12, 13, 14, 15, 16, 17, 18, 19, 20, 21, 22, 23, 24 hours afterwards, or about 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days afterwards or a range defined by any two of aforementioned times. A variety of suitable degradable particles can be used in accordance with embodiments herein. In some embodiments, the degradable particle comprises a sphere, for example a microsphere. In some embodiments, the degradable particle comprises a nanoparticle. In some embodiments, the degradable particle comprises a starch or sugar. In some embodiments, the degradable particle comprises an organic polymer or a combination of organic polymers, for example, polyesters, polyphosphate esters, polyphosphazenes, polyorthoesters, polyanhydrides, polycarbonates, polyamides, poly-lactic acid, a poly-glycoloyic acid, or a combination of two or more polymers, for example two or more of the listed polymers.

Protein Complexes Some embodiments include a composition comprising an isolated protein complex that comprises an immunoregulatory peptide inhibitor. The isolated protein complex can include an immunoregulatory peptide, for example P3028 (SEQ ID NO: 185) or any one or more of the immunoregulatory peptides described in Tables 1-4 (SEQ ID NOs: 183-184 and 188-246) and at least one immunoregulatory peptide inhibitor (e.g., any one or more of the peptides provided in Table 5.1). In some embodiments, the isolated protein complex includes peptide 3028 (SEQ ID NO: 185) and an inhibitor peptide that includes the sequence of SEQ ID NOs: 1-33, 34, 46-53, 64-66, 68, 76, 94-96 or 98 or any one or more of the peptides provided in Table 5.1. Exemplary protein complexes that include each of the peptides SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 bound to the P3028 sequence/structure are provided in Examples 10, 11 and 12 and Table 5.1. The protein complex can include at least one favorable electrostatic interaction between an amino acid residue of P3028 or a variant thereof, and an amino acid of an inhibitor peptide or peptide mimetic. The protein complex can include at least one favorable hydrophobic interaction between an amino acid residue of P3028 or a variant thereof, and an amino acid of an inhibitor peptide or peptide mimetic (see Example 11). In some embodiments, the protein complex includes a variant of P3028 having at least about 80% identity to P3028, for example greater than or equal to about 80%, 81%, 82%, 83%, 84%, 85%, 86%, 87%, 88%, 89%, 90%, 91%, 92%, 93%, 94%, 95%, 96%, 97%, 98%, or 99% identity to P3028. The protein complex can further include at least one protein bound to a cancer cell, for example a surface protein. Thus, in some embodiments, the isolated protein complex can localize to the surface of a cancer cell.

Accordingly, some embodiments include a method of making a protein complex that comprises one or more of the immunoregulatory peptide inhibitors described herein. The methods can be practiced, for example, by binding an immunoregulatory peptide inhibitor, as described herein to P3028, or a variant or fragment thereof. The method can optionally include detecting the presence of the complex, which can be accomplished by rampo studies, as described herein.

Some embodiments include methods of binding a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a molecule that comprises the P3028 sequence/structure (SEQ ID NO: 185). Some embodiments include methods of binding a peptide comprising, consisting of, or consisting essentially of at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a molecule comprising a variant of the P3028 sequence/structure (SEQ ID NO: 185). Some embodiments include methods of binding a peptide including at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a protein that comprises the P3028 sequence/structure or a fragment of P3028 (SEQ ID NO: 185), wherein the fragment of P3028 has a length of at least about 10 amino acids, more preferably 11 amino acids, more preferable 12 amino acids, more preferably 13 amino acids, more preferably 14 amino acids, more preferably 15 amino acids, more preferably 16 amino acids, or more preferably 17 amino acids. In some embodiments, the binding includes favorable hydrophilic and/or electrostatic interactions between members of the protein complex. In some embodiments, the binding includes covalent bonds between members of the protein complex, for example through crosslinking. Crosslinking can be induced chemically, and/or via electromagnetic radiation, for example electromagnetic radiation in the ultraviolet spectrum.

In some embodiments, the peptide comprises at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13. Exemplary supports include a pin, bead, surface, matrix, artificial cell surface, or cell surface. For example, the peptide can be affixed via an affinity tag to a support. In some embodiments, P3028, or a variant or fragment thereof is affixed to a support. In some embodiments, the peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 is affixed to a support, and P3028 or a variant or fragment thereof is dissolved in a solvent. In some embodiments, the peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 is dissolved in a solvent, and P3028, or a variant or fragment thereof is affixed to a support. In some embodiments, the peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 and P3028 are each dissolved in a solvent, for example serum.

In some embodiments, the binding occurs in an organism, for example in extracellular matrix, and/or serum or in a biological sample obtained from an organism, such as a human. Biological samples can include at least one cell, tissue, or extracellular composition of an organism, include extracts, purified extracts, and/or fractions thereof. Exemplary biological samples include whole blood, serum, bone marrow, isolated immune cells, and tumor biopsies. Isolated immune cells can include leukocytes, and peripheral blood mononuclear cells (PBMC's), for example lymphocytes, monocytes, or macrophages. The method can include delivering at least one member of the complex, for example a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13, to the organism. In some embodiments, the binding occurs in vitro, for example in a buffer solution or in a biological sample. The method can include adding at least one member of the complex, for example a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13, to a solution that contains the remaining members of the complex. Alternatively, the method can include adding two or more members of the complex to a solution for example a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 and P3028 or a fragment or variant thereof. In some embodiments, a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 is added to a biological sample.

Some embodiments include detecting the presence of the complex. Some embodiments include detecting the presence of the P3028 sequence/structure bound to a peptide that is affixed to a support (see Example 12), for example by ELISA. Some embodiments include detecting the presence of a complex by FRET. For example a FRET donor fluorophore can be attached to a first member of the complex, and a FRET acceptor fluorophore can be attached to a second member of the complex, so that FRET transfer occurs only when the complex is formed. Some embodiments include detecting the presence of a complex by cessation of quenching. For example a member of the complex can be attached to a fluorophore and a quencher for electromagnetic radiation emitted by the fluorophore, so that when the complex member is unbound, the fluorophore is substantially within the quencher radius, and the quencher absorbs electromagnetic radiation emitted by the fluorophore (e.g., a quencher can be attached to the N terminal and a fluorophore attached to the C terminal, or a quencher can be attached to the C terminal, and a fluorophore attached to the N terminal). Upon complex formation, the fluorophore can be outside of the quencher radius, thus permitting detection of electromagnetic radiation emitted by the fluorophore.

Some embodiments include detecting the presence of the complex by detecting of complex function. For example, an immune cell in which peptide 3028 is bound to the LFA-1 and/or IL-2 receptor can exhibit reduced IL-2-induced proliferation, T cell receptor stimulation, leukocyte spreading, immune cell migration, and/or NK cell cytotoxicity (see Examples 2-6). Direct or indirect detection of increased IL-2-induced proliferation, T cell receptor stimulation, leukocyte spreading, immune cell migration, and/or NK cell cytotoxicity, for example increase in comparison to an untreated control sample in which at least one member of the complex was not added, can detect complex formation. For example, as shown in Example 13, the formation of a complex between the P3028 sequence/structure and an immunoregulatory peptide inhibitor can increase lymphocyte stimulation. For example, as shown in Example 1, the formation of a complex can unblock the LFA-1 receptor. Thus, some embodiments include detecting complex formation indirectly by, for example, detecting increased lymphocyte stimulation, detecting unblocked LFA-1 receptor, and/or detecting immune cell stimulation via an unblock LFA-1 receptor, as compared to a control sample that is known to lack complex formation.

Some embodiments include detecting the presence of the complex by detecting localization of complex members. In some embodiments, detecting the presence of the complex includes detecting the presence of an immunoregulatory peptide inhibitor including at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a peptidomimetic that binds specifically to the P3028 sequence/structure on tumor cells. As shown in Example 1, the P3028 sequence/structure can bind to tumor cells. As shown in Example 14, an inhibitor of the P3028 sequence/structure can bind to tumor cells, for example by binding to the P3028 sequence/structure. Thus, in some embodiments, the presence of an inhibitor of the P3028 sequence/structure, for example, at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 on a tumor cell can indicate complex formation. Thus, complex formation can be detected by colocalization of an inhibitor with at least one marker of a tumor cell. Colocalization can be detected, for example by immunohistochemistry or flow cytometry. In some embodiments, the inhibitor is labeled, for example with a fluorophore or radiolabel. In some embodiments, the inhibitor is detected, for example with a primary antibody that specifically binds to the inhibitor. The section that follows describes in greater detail some of the nucleic acid embodiments, which encode an immunoregulatory peptide inhibitor.

Nucleic Acids Encoding Inhibitor Peptides

Some embodiments include isolated nucleic acids encoding an immunoregulatory peptide inhibitor. One skilled in the art will appreciate that for a given peptide sequence, a nucleic acid sequence encoding that peptide sequence can readily be determined, and due to the degeneracy of the genetic code, more than one nucleic acid sequence can encode any one peptide. A nucleic acid sequence encoding a peptide can be incorporated into an expression vector using known techniques, as well. Expression vectors can be used to produce the peptide in an expression system, for example a host cell, a host organism, a cell-free expression system, and the like. Expression vectors can also be used to produce a peptide in an organism, for example a patient in need of blocking of immunosuppression, as described herein. Exemplary expression vectors include plasmid DNA, such as a pVAX construct, bacteriophage DNA, cosmid DNA, artificial chromosomes such as BACs and YACs, retrovirus systems, for example lentivirus, DNA virus systems, for example adenovirus or vaccinia virus (e.g., MVA). For peptides that do not have an N-terminal amino acid that corresponds to a translation start codon (typically Met corresponding to ATG), expression vectors can include an in-frame translation start codon. Such an amino acid can be separated from the N-terminal of the peptide by a cleavable linker, for example a peptide sequence that is cleaved by a protease. Expression vectors can include transcriptional regulatory sequences, for example core promoters, transcriptional enhancers, and/or insulator sequences. Such sequences can facilitate the assembly of transcriptional machinery (for example RNA Polymerase III), and the subsequent production of a transcript encoding the peptide (for example, by facilitating a heterochromatic environment that is favorable to transcription).

In some embodiments, an expression vector encodes two or more copies of a peptide, and/or two or more unique peptides. In some embodiments, an expression vector encodes two or more peptides, and each peptide is under the control of a unique transcription unit (e.g., promoter, transcriptional enhancers, and/or transcription terminator). In some embodiments, a nucleic acid encoding two or more peptides is under the control of a single transcription unit. In such embodiments, a sequence encoding an individual peptide can be under the control of an individual translation start site, for example an Internal Ribosome Entry Site (IRES). In such embodiments, a single nucleic acid can encode a protein or polypeptide encoding two or more peptides, which are separated by at least one protease target site.

One skilled in the art will appreciate that polynucleotides encoding peptides, such as peptide inhibitors, can be readily constructed based upon the sequence of the peptide. Exemplary polynucleotides encoding the sequences of immunoregulatory peptide inhibitor peptides of (SEQ ID NOs: 2-33) are provided in Table 5.2. One skilled in the art will appreciate that due to the degeneracy of the genetic code, a given polypeptide can be encoded by more than one polynucleotide may encode. Thus, provided herein, for example in Table 5.2, are consensus polynucleotides that account for typical degeneracy of the genetic code, as well as exemplary polynucleotides. The polynucleotides of Table 5.2 are provided by way of example, and include SEQ ID NOs: 102-165. On skilled in the art will further appreciate that additional polynucleotides can encode peptide inhibitors such as the peptide inhibitors disclosed herein (e.g., polynucleotides encoding any one or more of the peptides provided in Table 5.1 are embodiments). For example, polynucleotides can be modified post-transcriptionally, for example by alternative splicing, and/or by enzymes such as RNA-specific adenosine deaminase (ADAR) that can modify the bases of polynucleotides.

TABLE 5.2

Polynucleotides encoding peptide inhibitors of the P3028 sequence/structure

| Seq ID NO | Description |
| --- | --- |
| 102 | Consensus polynucleotide encoding P28R (SEQ ID NO: 2) |
| 103 | Exemplary NT encoding P28R (SEQ ID NO: 2) |
| 104 | Consensus polynucleotide encoding SEQ ID NO: 3 |
| 105 | Exemplary NT encoding SEQ ID NO: 3 |
| 106 | Consensus polynucleotide encoding SEQ ID NO: 4 |
| 107 | Exemplary NT encoding SEQ ID NO: 4 |
| 108 | Consensus polynucleotide encoding SEQ ID NO: 5 |
| 109 | Exemplary NT encoding SEQ ID NO: 5 |
| 110 | Consensus polynucleotide encoding SEQ ID NO: 6 |
| 111 | Exemplary NT encoding SEQ ID NO: 6 |
| 112 | Consensus polynucleotide encoding SEQ ID NO: 7 |
| 113 | Exemplary NT encoding SEQ ID NO: 7 |
| 114 | Consensus polynucleotide encoding SEQ ID NO: 8 |
| 115 | Exemplary NT encoding SEQ ID NO: 8 |
| 116 | Consensus polynucleotide encoding SEQ ID NO: 9 |
| 117 | Exemplary NT encoding SEQ ID NO: 9 |
| 118 | Consensus polynucleotide encoding SEQ ID NO: 10 |
| 119 | Exemplary NT encoding SEQ ID NO: 10 |
| 120 | Consensus polynucleotide encoding SEQ ID NO: 11 |
| 121 | Exemplary NT encoding SEQ ID NO: 11 |
| 122 | Consensus polynucleotide encoding SEQ ID NO: 12 |
| 123 | Exemplary NT encoding SEQ ID NO: 12 |
| 124 | Consensus polynucleotide encoding SEQ ID NO: 13 |
| 125 | Exemplary NT encoding SEQ ID NO: 13 |
| 126 | Consensus polynucleotide encoding SEQ ID NO: 14 |
| 127 | Exemplary NT encoding SEQ ID NO: 14 |
| 128 | Consensus polynucleotide encoding SEQ ID NO: 15 |
| 129 | Exemplary NT encoding SEQ ID NO: 15 |
| 130 | Consensus polynucleotide encoding SEQ ID NO: 16 |
| 131 | Exemplary NT encoding SEQ ID NO: 16 |
| 132 | Consensus polynucleotide encoding SEQ ID NO: 17 |
| 133 | Exemplary NT encoding SEQ ID NO: 17 |

TABLE 5.2-continued

Polynucleotides encoding peptide inhibitors of the P3028 sequence/structure

| Seq ID NO | Description |
| --- | --- |
| 134 | Consensus polynucleotide encoding SEQ ID NO: 18 |
| 135 | Exemplary NT encoding SEQ ID NO: 18 |
| 136 | Consensus polynucleotide encoding SEQ ID NO: 19 |
| 137 | Exemplary NT encoding SEQ ID NO: 19 |
| 138 | Consensus polynucleotide encoding SEQ ID NO: 20 |
| 139 | Exemplary NT encoding SEQ ID NO: 20 |
| 140 | Consensus polynucleotide encoding SEQ ID NO: 21 |
| 141 | Exemplary NT encoding SEQ ID NO: 21 |
| 142 | Consensus polynucleotide encoding SEQ ID NO: 22 |
| 143 | Exemplary NT encoding SEQ ID NO: 22 |
| 144 | Consensus polynucleotide encoding SEQ ID NO: 23 |
| 145 | Exemplary NT encoding SEQ ID NO: 23 |
| 146 | Consensus polynucleotide encoding SEQ ID NO: 24 |
| 147 | Exemplary NT encoding SEQ ID NO: 24 |
| 148 | Consensus polynucleotide encoding SEQ ID NO: 25 |
| 149 | Exemplary NT encoding SEQ ID NO: 25 |
| 150 | Consensus polynucleotide encoding SEQ ID NO: 26 |
| 151 | Exemplary NT encoding SEQ ID NO: 26 |
| 152 | Consensus polynucleotide encoding SEQ ID NO: 27 |
| 153 | Exemplary NT encoding SEQ ID NO: 27 |
| 154 | Consensus polynucleotide encoding SEQ ID NO: 28 |
| 155 | Exemplary NT encoding SEQ ID NO: 28 |
| 156 | Consensus polynucleotide encoding SEQ ID NO: 29 |
| 157 | Exemplary NT encoding SEQ ID NO: 29 |
| 158 | Consensus polynucleotide encoding SEQ ID NO: 30 |
| 159 | Exemplary NT encoding SEQ ID NO: 30 |
| 160 | Consensus polynucleotide encoding SEQ ID NO: 31 |
| 161 | Exemplary NT encoding SEQ ID NO: 31 |
| 162 | Consensus polynucleotide encoding SEQ ID NO: 32 |
| 163 | Exemplary NT encoding SEQ ID NO: 32 |
| 164 | Consensus polynucleotide encoding SEQ ID NO: 33 |
| 165 | Exemplary NT encoding SEQ ID NO: 33 |

Accordingly, embodiments described herein also include a composition that comprises, consists of, or consists essentially of an isolated nucleic acid or polynucleotide that encodes one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96 or 98 or any one or more of the peptides provided in Table 5.1). Vectors, constructs, and plasmids comprising the aforementioned nucleic acids or polynucleotides are also embodiments. The following section discusses additional components that may be included in one or more of the compositions described herein.

Pharmaceutical Compositions

In some embodiments, a pharmaceutical composition comprising, consisting essentially of or consisting of a peptide inhibitor (e.g., any one or more of the peptides provided in Table 5.1) is provided. The pharmaceutical composition can include a peptide inhibitor as described herein and a pharmaceutically acceptable ingredient as described herein. Exemplary pharmaceutically acceptable ingredients include diluents, carriers, excipients and/or buffers. In some embodiments, the peptide inhibitor comprises, consists of, or consists essentially of a peptide inhibitor as described herein. For example, a composition can comprise, consist of, or consist essentially of a peptide inhibitor that comprises, consists of, or consists essentially of the peptide of Formula (I), $XX_1VKX_2X_3X_4$ (SEQ ID NO: 166). In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides comprising Formula (I). have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (II) $X_{20}TFFVKLSX_{21}X_{22}$, (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides comprising Formula (II) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (III) $X_{30}X_{31}VKLX_{32}LX_{33}TEX_{34}$ (SEQ ID NO: 178), or of SEQ ID NOs: 1-33, 34, 46-53, 64-66, 68, 76, 94-96 or 98. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R, or absent. In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, the isolated peptides comprising Formula (III) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (VIII), $X_{800}$K $X_{801}$K $X_{802}$E $X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. Additionally, a composition can comprise, consist of, or consist essentially of a peptide inhibitor that comprises, consists of, or consists essentially of any one or more of the peptides set forth in Table 5.1. In some embodiments, the isolated peptide from Table 5.1 used in these compositions has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

The pharmaceutical composition can comprise one or more other pharmaceutical acceptable pharmaceutical ingredients, such as a pharmaceutically acceptable diluent, carrier, excipient and/or buffer. "Pharmaceutically acceptable" means a non-toxic compound that does not decrease the effectiveness of the biological activity of the active ingredients. Such pharmaceutically acceptable additives, diluents buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The pharmaceutical composition can include a buffer. The term "buffer" is intended to refer to an aqueous solution containing an acid-base mixture with the purpose of stabilizing pH. Examples of buffering agents are magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Other examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The pharmaceutical composition can include a diluent. The term "diluent" is intended to refer to an aqueous or non-aqueous solution with the purpose of diluting the compounds in the pharmaceutical preparation. The diluent may be one or more of saline, water, polyethylene glycol, propylene glycol or ethanol.

The pharmaceutical composition can include an excipient. The excipient can be one or more of carbohydrates, surfactants, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The pharmaceutical composition can include a carrier. In some embodiments, the carrier is a non-aqueous carrier. Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The pharmaceutical composition can be formulated for a extended release. In some embodiments, the pharmaceutical composition is formulated as a gel or gel-like substance for extended release. The gel or gel-like substance can remain stable under physiological conditions for about 3 days, 4, 5, 6, 7, 8, 9, 10, 11, 12, 13, or 14 days, 3-4 days, 3-5, 3-6, 3-7, 3-8, 3-9, 3-10, 3-11, 3-12, 3-13, 3-14, 4-5, 4-6, 4-7, 4-8, 4-9, 4-10, 4-11, 4-12, 4-13, 4-14, 5-6, 5-7, 5-8, 5-9, 5-10, 5-11, 5-12, 5-13, 5-14, 6-7, 6-8, 6-9, 6-10, 6-11, 6-12, 6-13, 6-14, 7-8, 7-9, 7-10, 7-11, 7-12, 7-13, 7-14, 8-14, 9-14, or 10-14 days. In some embodiments, the gel comprises an inhibitor peptide comprising, consisting of, or consisting essentially of any of SEQ ID NOs: 1-33, 34, 46-53, 64-66, 68, 76, 94-96, 98, 264-393, or 583-586, in which the inhibitor peptide is not water soluble and a buffer or adjuvant selected to formulate a gel when combined with the inhibitor peptide. Without being limited by any theory, in accordance with some embodiments herein, gels can be suitable for slow release of the inhibitor peptide.

The pharmaceutical composition can be formulated for solubility in aqueous solution. By way of example, an inhibitor peptide consisting of or consisting essentially of SEQ ID NO: 589 has been shown to be soluble in aqueous solution. As such, in some embodiments, a pharmaceutical composition comprises an inhibitor peptide consisting of or consisting essentially of SEQ ID NO: 589 solubleized or partially solubleized in an aqueous solution. Optionally, the aqueous solution can be provided as an adjuvant.

Administration Form

The pharmaceutical formulations described herein may be administered locally or systemically. Routes of administration include topical, ocular, nasal, pulmonar, buccal, parenteral (intravenous, subcutaneous, and intramuscular), oral, vaginal and rectal. Most commonly used being oral administration.

In some embodiments, for example if immune cell invasion of a tumor, cytotoxicity of a tumor, or deblocking of a an immune cell receptor of a tumor is desired, the pharmaceutical formulation is administered at or near a tumor. For example, the pharmaceutical formulation can be administered peri-tumorally, or within 10 cm of the tumor, for example within 10 cm, 9, 8, 7, 6, 5, 4, 3, 2, 1, or 0.5 cm of the tumor or a range defined by any two of these distances.

The pharmaceutical compositions will be administered to a patient in a therapeutically effective amount or dose. A therapeutically effective amount includes a dose of pharmaceutical composition sufficient to at least partially arrest a symptom of a disorder from which a patient is suffering. The exact dose is dependent on the manner of administration, the nature and severity of the disorder. Depending on the general health, sex, age and body weight of the patient different doses may be needed. The administration of the dose can be carried out both by single administration in the form of an individual dose unit or else several smaller dose units and also by multiple administration of subdivided doses at specific intervals, for example daily intervals (e.g., 1, 2, 3, 4, 5, 6, 7, 8, 9, 10, 11, 12, 13, 14, 15, 16, 17, 19, 20, 21, 22, 23, 24, 25, 26, 27, 28, 29, or 30 days between doses, including ranges between any two of the listed values). Exemplary dosing can comprise doses in the milligram, microgram, or nanogram-range, for example milligrams, micrograms, or nanograms per kg of body weight of the subject. The active compounds or substances may also be administered together or separately depending on the administration form. Exemplary dosing regiments in accordance with some embodiments herein include "prime boost" approaches in which a first dose of compound or substance is administered in a first administration, and second dose of compound or substance is administered in second administration. Optionally, additional subsequent administrations (e.g. third, fourth, fifth, sixth, seventh, eighth, ninth, or tenth) are performed. Optionally, the first dose is greater than a subsequent dose (e.g. the second dose, or if performed, third, fourth, fifth, sixth, seventh, eighth, ninth, or tenth), for example at least 1.1×, 1.2×, 1.5×, 2×, 3×, 4×, 5×, 10×, 20×, 30×, 40×, 50×, 100×, 200×, 500×, 1000×, 2000×, 5000×, or 10000× of the subsequent dose. Optionally, the subsequent dose (e.g. second, third, fourth, fifth, sixth, seventh, eighth, ninth, or tenth) is greater than the first dose, for example at least 1.1×, 1.2×, 1.5×, 2×, 3×, 4×, 5×, 10×, 20×, 30×, 40×, 50×, 100×, 200×, 500×, 1000×, 2000×, 5000×, or 10000× of the first dose. In some embodiments a subsequent dose (e.g. second dose after first dose, third dose after second dose, if performed, fourth dose after fifth dose, if performed) is administered at least one day after the preceding dose, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 90, or 100 days after, including ranges between any two of the listed values.

Suitable preparation forms are, for example granules, powders, tablets, coated tablets, (micro) capsules, microgranulates effervescent powders or granules, suppositories, injectable solution in ampule form and also preparations with protracted release of active compounds, in whose preparation excipients, diluents or carriers are customarily used as described above. Other preparations may be those which give rise to different release profiles of the active ingredients which are well-known for a person skilled in the art. Examples include sustained-release, sustained-action, extended-release, time-release or timed-release, controlled-release, modified release, or continuous-release. The advantages of sustained-release tablets or capsules are that they can often be taken less frequently than immediate-release formulations of the same drug, and that they keep steadier levels of the drug in the bloodstream. Today, many time-release drugs are formulated so that the active ingredient is embedded in a matrix of insoluble substance(s) (for example some acrylics, or chitin) such that the dissolving drug must find its way out through the holes in the matrix. Some drugs are enclosed in polymer-based tablets with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some formulations, the drug dissolves into the matrix, and the matrix physically swells to form a gel, allowing the drug to exit through the gel's outer surface. Micro-encapsulation is also regarded as a more complete technology to produce complex dissolution profiles. Through coating an active pharmaceutical ingredient around an inert core, and layering it with insoluble substances to form a microsphere it is possible to obtain more consistent and replicable dissolution rates. In some embodiments, the composition comprises at least about at least 0.1% of the immunoregulatory peptide inhibitor by weight, for example, at least 0.1%, 0.2%, 0.5%, 1%, 2%, 3%, 4%, 5%, 6%, 7%, 8%, 9%, 10%, 20%, or 30% of the immunoregulatory peptide inhibitor by weight, including ranges between any two of the listed values. All of those being well-known for a person skilled in the art.

Methods of Detecting the Presence of an Albumin or Albumin Fragment

Some embodiments include methods of detecting the presence of an albumin or albumin fragment in a biological sample by contacting an immunoregulatory peptide inhibitor with the biological sample thereby allowing the binding of the immunoregulatory peptide inhibitor to the albumin or albumin fragment and detecting the presence of the bound immunoregulatory peptide inhibitor. In some embodiments, a method of detecting the presence of the P3028 sequence/structure or a fragment thereof can include contacting a biological sample comprising the P3028 sequence/structure with an immunoregulatory peptide inhibitor or antibody that binds to the P3028 sequence/structure and detecting the presence of the bound immunoregulatory peptide inhibitor. Optionally, the immunoregulatory peptide inhibitor or antibody comprises a detectable moiety as described herein.

The immunoregulatory peptide inhibitor used in these methods can comprise, consist of, or consist essentially of a peptide as described herein. For example, the peptide inhibitor can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. Additionally, the peptide inhibitor can comprise, consist of, or consist essentially of and/or SEQ ID NOs: 1-33, 34, 46-53, 64-66, 68, 76, 94-96 or 98, as described herein. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO:

725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}$ $X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally, $X_{901}$ is an R or K. Optionally, $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in or any one or more of the peptides provided in Table 5.1, 5.4, 5.5, 5.6, or any variation or combination of variations of P28R or P28 core as provided in Tables 5.3 and 13. In some embodiments, the isolated peptide from in or any one or more of the peptides provided in Table 5.1, 5.4, 5.5, 5.6, or any variation or combination of variations of P28R or P28 core as provided in Tables 5.3 and 13 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Accordingly, once the immunoregulatory peptide inhibitor is bound to an albumin fragment or albumin comprising the P3028 sequence/structure, the presence of the inhibitor is detected, thus detecting the presence of the P3028 sequence/structure.

In some methods for detecting the presence of albumin or an albumin fragment comprising the P3028 sequence/structure, the immunoregulatory peptide inhibitor comprises a peptide that comprises, consists of, or consists essentially of a peptide as described herein. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. Additionally, the peptide inhibitor can comprise, consist of, or consist essentially of and/or SEQ ID NOs: 1-33, 34, 46-53, 64-66, 68, 76, 94-96 or 98 as described herein. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO:

723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immunoregulatory peptide inhibitor is attached to a support (see Example 12). Exemplary supports include surfaces, a test strip, petri dish, matrices, resin, or beads. In some embodiments, the immunoregulatory peptide inhibitor is dissolved in solution (see Example 10). In some embodiments, a biological sample possibly containing the P3028 sequence/structure is contacted with the inhibitor in solution (see Examples 10 and 12). The biological sample can include blood, serum, immune cells, immune cell lysates, tumor cells, or tumor cell lysates. After contact with the immunoregulatory peptide inhibitor, the support having the protein complex disposed thereon is optionally washed so as to remove any unbound or loosely affixed immunoregulatory peptide inhibitor. If the P3028 sequence/structure was present in the sample, the presence of the P3028 sequence/structure bound to the inhibitor attached to the support is detected, for example using a rampo assay. If the P3028 sequence/structure was not present in the sample, no bound protein is detected.

In some embodiments, the immunoregulatory peptide inhibitor is attached to a detectable label, as described herein. Exemplary detectable labels include biotin, fluorophores, radiolabels, and enzymes. In some embodiments, a biological sample that possibly contains the P3028 sequence/structure is provided. The sample can include, blood, plasma, serum, isolated immune cells, isolated cancer cell, a tissue biopsy, and/or a tumor biopsy. The inhibitor of peptide 3028 (the immunoregulatory peptide inhibitor) is contacted with the biological sample. The sample then can be optionally washed. If the P3028 sequence/structure is present, the detectable label will be present in the biological sample (see Example 14). If the P3028 sequence/structure was not present, no label is detected. Exemplary methods of detecting the detectable label include microscopy, histological sectioning, immunoassays, immunohistochemistry, flow cytometry, immunoblotting, ELISA, and ELISpot (see FIG. 39). For example, a histological section can be examined to determine cells and/or tissues that contain the P3028 sequence/structure. For example, a sample of dissociated immune and/or tumor cells can be screened for cells bound to the P3028 sequence/structure using frozen or plastic section techniques. The section below provides more detail on approaches to treat, prevent, or inhibit immunosuppression in a subject in need thereof (e.g., a subject that has cancer or a pathogenic infection, such as a viral infection or a bacterial infection).

Method of Treating, Preventing, or Inhibiting Immunosuppression

Many conditions and diseases are associated with immunosuppression, for example, many types of cancer, infection, and inflammatory disease are associated with immunosuppression. Thus, exemplary conditions associated with immunosuppression that can be treated, prevented, or inhibited using one or more of the immunoregulatory peptide inhibitors described herein include many types of cancer, such as colorectal cancer, renal cancer, breast cancer, skin cancer, ovarian cancer, prostate cancer, pancreatic cancer, lung cancer, or hematopoietic cell cancer. These conditions can also be treated, prevented, ameliorated, or inhibited using one or more of the immunoregulatory peptide inhibitors described herein. Exemplary conditions associated with immunosuppression that can be treated, prevented, or inhibited by using one or more of the immunoregulatory peptide inhibitors described herein further include hormonal imbalances, such as increased and/or ectopic cortisol activity.

Accordingly, some embodiments include methods of treating, preventing, or reducing immunosuppression or one or more of the aforementioned infections or diseases in a human. In some embodiments, the method includes identifying a patient having a condition associated with immunosuppression (e.g., cancer). Such an identification step can be accomplished by clinical evaluation (e.g., CT, MRI, or PET scan) or diagnostic assay. The method further includes administering to the identified or selected patient a composition comprising, consisting of, or consisting essentially of an immunoregulatory peptide inhibitor sequence, or a nucleic acid encoding such a molecule as described herein. For example, the composition comprising, consisting of, or consisting essentially of an immunoregulatory peptide inhibitor can include any one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the composition is administered peri-tumorally, or near a tumor, for example within 10, 9, 8, 7, 6, 5, 4, 3, 2, 1, or 0.5 cm of a tumor. In some embodiments, the composition is administered systemically. In some embodiments, the composition is administered in conjunction with a second therapeutic agent, for example a therapeutic agent selected to stimulate an immune cell after an LFA-1 receptor of the immune cell has been de-blocked (e.g. bound immunoregulatory peptides or 3028 structures have been displaced from the LFA-1 receptor). In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the composition comprising, consisting of, or consisting essentially of the immunoregulatory peptide inhibitor used in these methods can comprise, consist of, or consist essentially of a peptide as described herein, or a nucleic acid encoding such a molecule. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173), as described herein. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the isolated peptide used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, a nucleic acid encoding such a peptide inhibitor can be provided, for example a nucleic acid of SEQ ID NOs: 102-165. Preferably, the immunoregulatory peptide inhibitor used in the aforementioned methods is P28R, a derivative thereof, or a nucleic acid encoding such a molecule (e.g., any one or more of the immunoregulatory peptide inhibitors comprise, consist of, or consist essentially of a peptide as described herein. For example, the peptide inhibitor can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (VII), $X_{700}K X_{701}X_{702}X_{703} X_{704}X_{705}X_{706}K X_{707} X_{708} X_{709} X_{710} X_{711}E X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, TV, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent.

In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, + or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, the isolated peptides have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of a peptide inhibitor that comprises, consists of, or consists essentially of any one or more of the peptides set forth in Table 5.1, 5.4, 5.5, or 5.6 or any variation or combination of variations of P28R or P28 core as provided in Tables 5.3 and 13 In some embodiments, the isolated peptide from Table 5.1, 5.4, 5.5, or 5.6 or any variation or combination of variations of P28R or P28 core as provided in Tables 5.3 and 13 has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. For example, a nucleic acid encoding such a peptide inhibitor can be provided, by SEQ ID NOs: 102-165.

The immunoregulatory peptide inhibitors used in the aforementioned methods can comprise at least one D amino acid, at least one non-natural amino acid, an N-terminal acetyl group, or a C terminal amide group and said immunoregulatory peptide inhibitors can be glycosylated or joined to PEG, a cytotoxin, or radionuclide. The peptide can be administered to at least one cell of the patient. The administration can be performed in vivo, for example therapeutically. The administration can be performed ex vivo, for example as a diagnostic tool, or as an ex vivo therapy to stimulate immune cells of the patient before the immune cells are administered to the patient. Administration of an immunoregulatory peptide inhibitor comprising, consisting, or consisting essentially of a peptide inhibitor as described herein, or a nucleic acid encoding such a molecule to human immune cells, and detection of immune cell stimulation is described in Example 13). For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is be one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, Y, or absent. In some embodiments, $X_{703}$ is an optional sequence, and can be T, C, M, N, P, Q, R, S, W, Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

A nucleic acid encoding such a peptide inhibitor can be provided, for example a nucleic acid of SEQ ID NOs: 102-165. Following administration of the immunoregulatory peptide inhibitor, stimulation of human immune cells of the human can be detected (e.g., an increase in immune cell proliferation, migration of NK cell cytotoxicity). Once the immunoregulatory peptide inhibitor has been administered, these methods can, optionally, include measuring or observing a reduction in immunosuppression in the patient (e.g., an increase in immune cell proliferation, migration, or spreading or NK-cell cytotoxicity can be evaluated or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation).

As mentioned above, some embodiments include a step of identifying a patient suffering from immunosuppression. This analysis can include generally determining the immune cell activity of the patient, for example determining the quantity of at least one immune cell type, for example leukocytes, PBMC's, lymphocytes, monocytes, macrophages in a biological sample of the patient. The presence of the P3028 sequence/structure in the serum of a patient, and/or on a cancer cell of a patient (an evaluation that can be accomplished using a labeled immunoregulatory peptide inhibitor) is also indicative of suppression of the immune system of the patient. Accordingly, some embodiments of the invention include detecting the presence of the P3028 sequence/structure in a biological sample of a patient, for example a sample that includes blood, plasma, serum, or a cancer cell biopsy. Examples, methods, and compositions for detecting the presence of Peptide 3028 in a biological sample of a patient can be found in U.S. Pat. Nos. 7,960,126, 8,133,688, 8,110,347, and US Publication Nos. 2010/0323370 and 2011/0262470, each of which is hereby expressly incorporated by reference in its entirety. The P3028 sequence/structure can be detected, for example, by immunoassays, a blotting technique, ELISA, ELISpot, flow cytometry, cytometric bead assay, proteomics, and/or immunohistochemistry of a biological sample, using at least one antibody that binds to the P3028 sequence/structure. The P3028 sequence/structure can also be detected, for example, by mass spectrometry of a biological sample of a patient or a fraction thereof. The P3028 sequence/structure can further be detected by direct detection of a labeled peptide inhibitor of the P3028 sequence/structure as described herein, for example by histological staining, fluorescent microscopy, immunohistochemistry, or colorimetric enzymatic assays (see Example 14). The P3028 sequence/structure can also be detected, for example, functionally, by comparing an immune cell contacted by a patient's serum to an immune cell contacted by control sample serum known not to contain the P3028 sequence/structure. In some embodiments, the serum is denatured. Exemplary immune cells include PBMCs. In some embodiments, the serum is not denatured. The immune cells can be optionally stimulated, for example, by IL-2 or lipopolysaccharide (LPS). In some embodiments, the immune cells are analyzed for IL-6 production.

In some embodiments, a patient suffering from immunosuppression can be identified by diagnosing the patient with cancer. In some embodiments, cancer cells can be identified, and the patient can thus be identified, by detecting the binding of cells of the patient to the P3028 sequence/structure (see Example 7) or an inhibitor of the P3028 sequence/structure (see Example 14). Exemplary cancers that can be identified, and that are associated with immunosuppression include breast cancer, renal cell carcinoma, and malignant melanoma.

The administration of the immunoregulatory peptide inhibitor to the patient can be accomplished by a variety of approaches. In some embodiments, the immunoregulatory peptide inhibitor is administered directly to the patient. The immunoregulatory peptide inhibitor can be administered intravenously, intraperitoneally, subcutaneousously, intramuscularly, topically, transdermally, orally, and/or peri-tumorally. In some embodiments, the immunoregulatory peptide inhibitor is administered at the site of a tumor, for example via direct injection. In some embodiments, the immunoregulatory peptide inhibitor is administered near a tumor, for example within 10 cm, 9 cm, 8 cm, 7 cm, 6 cm, 5 cm, 4 cm, 3 cm, 2 cm, 1 cm, or 0.5 cm of the tumor or a range defined by any tow of the aforementioned distances. In some embodiments, the immunoregulatory peptide inhibitor is administered with a pharmaceutically acceptable diluent or carrier, as described herein. In some embodiments, the immunoregulatory peptide inhibitor is administered ex vivo. Immune cells of the patient can be isolated from the patient, contacted with the inhibitor, and returned to the patient, for example. Examples 13 and 14 describe contacting immune cells of a patient with an inhibitor of the P3028 sequence/structure.

Any one or more of the immunoregulatory peptide inhibitors described herein can be employed with one or more of the aforementioned methods. In some embodiments, the immunoregulatory peptide inhibitor comprises at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the immunoregulatory peptide inhibitor includes at least one peptidomimetic inhibitor of the P3028 sequence/structure corresponding to any one or more of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the immunoregulatory peptide inhibitor is a small molecule inhibitor of Peptide 3028 corresponding to any one or more of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the immunoregulatory peptide inhibitor includes an antibody or fragment thereof that specifically binds to the P3028 sequence/structure. Antibodies that inhibit the P3028 sequence/structure are described in Example 9.

In some of the aforementioned methods, the immunoregulatory peptide inhibitor of the P3028 sequence/structure comprises a nucleic acid encoding an immunoregulatory peptide inhibitor, such as a peptide described herein. For example, the peptide inhibitor encoded by the nucleic acid can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, E, or absent. In some embodiments, the isolated peptides that comprise Formula (II) encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO:

626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acid used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acid used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, these isolated peptides encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acid used in these methods can comprise, consist of, or consist essentially of a peptide inhibitor that comprises, consists of, or consists essentially of any one or more of the peptides set forth in Table 5.1, 5.4, 5.5, 5.6, or any variation or combination of variations of P28R or P28 core as provided in Tables 5.3 and 13. In some embodiments, the isolated peptide from Table 5.1 5.4, 5.5, 5.6, or any variation or combination of variations of P28R or P28 core as provided in Tables 5.3 and 13, which is encoded by the nucleic acid used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

For example, a nucleic acid encoding such a peptide inhibitor can be provided, for example a nucleic acid of SEQ ID NOs: 102-165. The nucleic acid can be provided in an expression vector as described herein. The nucleic acid can be provided to the human by directly administering an expression vector comprising the nucleic acid that encodes the immunoregulatory peptide inhibitor to the human, for example via a retroviral or adenoviral vector or expression plasmid used in genetic immunization (e.g., pVAX). The expression vector can be provided to cells of the human ex vivo, and the cells can be returned to the human or in vivo using electroporation technology. Methods of delivering nucleic acids to a host cell via viral vectors are described in U.S. Pat. No. 7,572,906, which is expressly incorporated by reference in its entirety herein. Methods of transducing immune cells with an adenovirus ex vivo and returning them to a patient are described in U.S. Pat. No. 8,012,468, which is expressly incorporated by reference in its entirety herein. In some embodiments, a host cell, is contacted with a vector encoding the immunoregulatory peptide inhibitor of P3028. The vector can replicates in the host cell. In some embodiments, the host cell is also contacted with a "helper-expression vector," i.e., a viral genome that promotes the replication of the vector in an uninfected host. In some embodiments, the inhibitor is administered as in Example 16. In some embodiments, the cell is contacted ex vivo. In some embodiments, the cell is an immune cell. In some embodiments, the cell is one of a lymphocyte, a PBMC, or a leukocyte. In some embodiments, the inhibitor is administered as in Example 13.

Preferably, a therapeutically effective amount of the immunoregulatory peptide inhibitor is provided. For a patient already suffering from P3028-dependent immunosuppression, a therapeutically effective amount of inhibitor may include a dose of immunoregulatory peptide inhibitor sufficient to at least partially arrest a symptom of immunosuppression (e.g., an amount sufficient to improve proliferation or migration of immune cells). In some embodiments, a therapeutically effective amount includes at least about 1 nanogram of substantially pure immunoregulatory peptide inhibitor, for example, at least or equal to about 1 nanogram, 2, 3, 4, 5, 6, 7, 8, 9, 10, 15, 20, 25, 30, 40, 50, 60, 70, 80, 90, 100, 120, 140, 160, 180, 200, 250, 300, 350, 400, 450, 500, 550, 600, 650, 700, 750, 800, 850, 900, 950, 1000 nanograms, 1 microgram, 2, 3, 4, 5, 6, 7, 8, 9, 10, 15, 20, 25, 30, 40, 50, 60, 70, 80, 90, 100, 120, 140, 160, 180, 200, 250, 300, 350, 400, 450, 500, 550, 600, 650, 700, 750, 800, 850, 900, 950, 1000 micrograms, about 1 milligram, 2, 3, 4, 5, 6, 7, 8, 9, 10, 15, 20, 25, 30, 40, 50, 60, 70, 80, 90, 100, 120, 140, 160, 180, 200, 250, 300, 350, 400, 450, 500, 550, 600, 650, 700, 750, 800, 850, 900, 950, 1000 milligrams, or 1.1 gram, 1.2, 1.3, 1.4, 1.5, 1.6, 1.7, 1.8, 1.9, 2, 2, 3, 3.5, 4, 4.5, 5, 5.5, 6, 6.5, 7, 7.5, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 99, 100, 105, 110, 120, 130, 140, 150, 160, 170, 180, 190, 200, 250, 300, 350, 400, 450, or 500 grams, including ranges between any two of the listed values can be provided to a patient in need.

In some embodiments, a therapeutically effective amount can be provided according to a schedule that includes one, or more than one administration of a therapeutically effective amount of inhibitor, for example at least or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 99, 100, 105, 110, 120, 130, 140, 150, 160, 170, 180, 190, 200, 250, 300, 350, 400, 450, or 500 administrations. An administration can be provided hourly or less, for example no more than once every 1, 2, 3, 4, 5, 6, 7, 8, 9, 10, 11, 12, 13, 14, 15, 16, 17, 18, 19, 20, 21, 22, 23, 24 hours, or no more than once every 1 day, 1.5, 2, 2.5, 3, 3.5, 4, 4.5, 5, 5.5, 6, 6.5, 7, 7.5, 8, 9, 10, 11, 12, 13, 15, 16, 17, 18, 19, 20, 21, 22, 23, 24, 25, 26, 27, 28, 29, 30, or 31 days.

By some methods, after administration of the immunoregulatory peptide inhibitor, a reduction in immunosuppression is measured, detected, or observed. In some embodiments, a reduction in immunosuppression is detected, measured, or observed by obtaining a biological sample from the patient that received the immunoregulatory peptide inhibitor and detecting a reduction in immune cell receptor binding to P3028 and/or a detecting immune cell proliferation after IL-2 induction of the immune cells present in the biological sample. In some embodiments, the analysis of the biological sample obtained from the patient above is compared to the same analysis (e.g., determining the amount of immune cell receptor binding to the P3028 sequence/structure or IL-2 induced immune cell proliferation) conducted on a control biological sample, for example, a biological sample from the same patient taken prior to administration of the immunoregulatory peptide inhibitor or a biological sample taken from a healthy human. Examples 9 and 13 describe detection of a reduction of immunosuppression in cells contacted by serum as compared to a control sample.

As mentioned above, a reduction in immunosuppression can be detected as an increase in immune cell stimulation, for example immune cell proliferation or immune cell cytotoxicity. A reduction in P3028-induced immunosuppression, which can be measured in the methods described supra, can include: increased T-Cell receptor stimulation (see Example 3); increased NK-Cell cytotoxicity (see Example 4); increased leukocyte spreading (see Example 5); increased immune cell migration (see Example 5); and/or IL-2 Induced Proliferation (see Example 6). Decreased IL-6 production can also an improvised prognosis for cancer patients, for example cancer patients suffering from immunosuppression (see U.S. Pat. No. 8,110,347, herein expressly incorporated by reference in its entirety). Desirably, a reduction in immunosuppression is detected by an increased proliferative response of PBMC's to IL-2, as shown in Example 9, or by detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation.

In some embodiments, the reduction in immunosuppression is detected by detecting the presence or quantity of markers from immune cells and/or serum and/or albumin collected from a patient. In some embodiments, the detection includes collecting patient serum, blood, and/or patient albumin, and contacting the patient serum, plasma, blood, or albumin with an immune cell ex vivo. In some embodiments, the immune cell is also contacted with IL-2. The proliferative response of the immune cell to IL-2 can be used to detect a decrease in immunosuppression. The immune cell can be a patient cell, or a cell from another human, or a cell from cell culture. In some embodiments, the reduction in immunosuppression can be detected by detecting effects of increased immune system activity, for example reduction in cancer cell number, a reduction in tumor size, or a reduction or inhibition of cancer cell proliferation. In some embodiments, cancer cells can be identified, and cancer cells can thus be quantified, by detecting cells that bind to the P3028 sequence/structure (see Example 7) or an inhibitor of the P3028 sequence/structure (see Example 14).

Methods of Inhibiting Binding of an Albumin Fragment to a Receptor

Additional methods include approaches for inhibiting the binding of an albumin fragment to an immune cell receptor (e.g., an LFA-1 and/or an IL-2 receptor). The method can include identifying a human suffering from immunosuppression, as described herein. The immunosuppression can be caused by one or more immunoregulatory peptide or structure. Exemplary immunoregulatory peptides or structures include P3028 sequence/structures, and/or proteins or peptides that comprise, consist of, or consist essentially of the sequences of SEQ ID NOs: 183-185 or 188-246. The method can also include contacting an immune cell with a peptide that comprises, consists of, or consists essentially of a peptide inhibitor as described herein. For example, the peptide used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide used in these methods can comprise, consist of, or consist essentially of Formula (II), $X_{20}TFFVKLSX_{21}X_{22}$ (SEQ ID NO: 173), In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent;

$X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. The immune cell can be in the presence of human serum, for example albumin or an albumin fragment as described herein.

Some embodiments of the invention include methods of inhibiting the binding of a human albumin fragment (e.g., an albumin fragment having the P3028 sequence/structure) to an LFA-1 receptor or IL-2 receptor. P3028, an albumin fragment, can bind to the LFA-1 receptor and the IL-2 receptor (see Examples 7 and 8) and this binding can be inhibited by providing a composition that comprises, consists essentially of, or consists of an immunoregulatory peptide inhibitor. In some embodiments, methods of inhibiting binding of P3028 to the LFA-1 or IL-2 receptor include contacting or binding an immunoregulatory peptide inhibitor to P3028 in vivo or in vitro, and, optionally, detecting an inhibition of binding of P3028 to an LFA-1 receptor or an IL-2 receptor. Binding of P3028 to the LFA-1 receptor and IL-2 receptor can be inhibited by binding P3028 to an antibody that binds specifically to P3028, for example (see Example 9). These methods can also be practiced by binding a peptide-based immunoregulatory peptide inhibitor that has the capacity to remove or inhibit P3028's blockage of the LFA-1 receptor, for example the P28R immunoregulatory peptide inhibitor (SEQ ID NO: 2) (see Example 16) or the P28 core peptide (SEQ ID NO: 62) (see Example 38).

Preferably, the composition that comprises, consists of, or consists essentially of an immunoregulatory peptide inhibitor used in these methods includes an immunoregulatory peptide inhibitor that comprises, consists of, or consists essentially of the Formula (I), $XX_1VKX_2X_3X_4$ (SEQ ID NO: 166), as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. $X_3$ can be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173), as described herein. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178), as described herein. In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R, or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LILFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. Additionally, a nucleic acid encoding such a peptide inhibitor can be provided, for example, a nucleic acid of SEQ ID NOs: 102-165.

Preferably, the immunoregulatory peptide inhibitor used in the aforementioned methods is P28R, a derivative thereof, or a nucleic acid encoding such a molecule (e.g., any one or more of the immunoregulatory peptide inhibitors provided SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a nucleic acid encoding such a molecule. The immunoregulatory peptide inhibitors used in the aforementioned methods can comprise at least one D amino acid, at least one non-natural amino acid, an N-terminal acetyl group, or a C terminal amide group and said immunoregulatory peptide inhibitors can be glycosylated, nitrosylated, carbonylated, oxidized, or joined to a linked pharmacokinetic modifier, PEG, a cytotoxin, or radionuclide.

Some embodiments include removing a bound ligand of the LFA-1 receptor or the IL-2 receptor from the receptor (e.g., a molecule comprising P3028). As shown in Example 15, binding of an inhibitor of P3028 sequence/structure to P3028 can increase the availability of the LFA-1 receptor to an antibody that specifically binds the LFA-1 receptor, when compared to a control sample in which the inhibitor was not bound to P3028. In some embodiments, P3028 is bound to the inhibitor, thus removing the binding of P3028 from the IL-2 receptor (see Examples 9 and 13).

Methods of Binding Cancer Cells with an Immunoregulatory Peptide Inhibitor

Embodiments also include methods of binding cancer cells with an immunoregulatory peptide inhibitor (e.g., an immunoregulatory peptide inhibitor having a cytotoxin, radionuclide, or detectable label). These methods are practiced by contacting cancer cells (e.g., in vitro or in vivo) with a composition that comprises, consists of, or consists essentially of any one or more of the immunoregulatory peptide inhibitors described herein. For example, the peptide inhibitor used in these methods can comprise, consist of, or consist essentially of Formula (I), $XX_1\ VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, X$_{705}$ is an optional sequence, and can be F, L, M, Q, S, T, or V, or absent. In some embodiments, X$_{706}$ is an optional sequence, and can be V, F, G, L, P, or R, or absent. In some embodiments, X$_{707}$ is an optional sequence, and can be L, A, F, G, I, M, N, P, Q, R, S, T, V, or Y, or absent. In some embodiments, X$_{708}$ is an optional sequence, and can be S, H, M, N, Q, or T, or absent. In some embodiments, X$_{709}$ is an optional sequence, and can be L, A, H, I, M, N, Q, R, S, T, V, or W, or absent. In some embodiments, X$_{710}$ is an optional sequence, and can be F, A, C, G, H, I, L, M, N, P, Q, R, S, T, V, or W, or absent. In some embodiments, X$_{711}$ is an optional sequence, and can be T, F, G, H, I, L, M, N, P, S, V, or W, or absent. In some embodiments, X$_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), X$_{800}$K X$_{801}$K X$_{802}$E X$_{803}$ (SEQ ID NO: 395), as described herein. In some embodiments, X$_{800}$ is an optional sequence, and can be K, A, D, E, G, H, I, L, M, N, P, Q, R, T, V, or K, or absent. In some embodiments, X$_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, X$_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. Additionally, a nucleic acid encoding such a peptide inhibitor can be provided, for example a nucleic acid of SEQ ID NOs: 102-165.

Preferably, the immunoregulatory peptide inhibitor used in the aforementioned methods is P28R, P28 core, a derivative thereof, or a nucleic acid encoding such a molecule (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a nucleic acid encoding such a molecule (e.g., SEQ ID NOs: 102-165)). The immunoregulatory peptide inhibitors used in the aforementioned methods can comprise at least one D amino acid, at least one non-natural amino acid, an N-terminal acetyl group, or a C terminal amide group and said immunoregulatory peptide inhibitors can be glycosylated or joined to PEG, a cytotoxin, or radionuclide.

Once the immunoregulatory peptide inhibitor or antibody that binds specifically to any immunoregulatory peptide of Tables 1-4 is bound to the cancer cell, it can be detected. That is, optionally, the method above includes a detecting step whereby the binding of the immunoregulatory peptide inhibitor is determined directly or indirectly. In some embodiments, the binding of the immunoregulatory peptide inhibitor is directly detected as in Example 14. In some embodiments, the binding of the immunoregulatory peptide inhibitor is indirectly detected. As described herein, the presence of P3028 on cancer cells can locally suppress an immune response. Thus, in some embodiments, detecting the binding of an immunoregulatory peptide inhibitor to a cancer cell can also include a step of detecting a reversal of immunosuppression, as described in Example 13. Reversal of immunosuppression can be determined, for example as a reversal of impaired PBMC proliferation (see Examples 2 and 13), reversal of T cell receptor stimulation (see Example 3), reversal of decreased NK cell cytotoxicity (see Example 4), reversal of decreased leukocyte spreading (see Example 5) or decreased immune cell migration (see Example 6), or increased IL-2 induced proliferation (see Examples 6 and 9). In some embodiments, cancer cells are bound to an immunoregulatory peptide inhibitor in vivo. Example 16 describes delivery of an inhibitor of P3028 to cancer cells in vivo. Example 42 describes detection of an inhibitor of P3028 on cancer cells.

In some embodiments, the detection of an immunoregulatory peptide inhibitor can occur on tissue biopsies obtained from a human. In some embodiments, the tissue biopsies can include putative cancer cells, or the biopsies can be screened for cancer cells. By these methods, the tissue biopsies are contacted with an immunoregulatory peptide inhibitor, as described herein. Preferably, the immunoregulatory peptide inhibitor comprises a detectable label, as described herein. In some embodiments, live cells are contacted with the immunoregulatory peptide inhibitor (see Example 14). In some embodiments, histological sections are bound with the immunoregulatory peptide inhibitor. The detectable label is then detected, thus permitting identification of cancer cells which cannot be attacked by the immune system. The detectable label can be detected through methods known in the art, for example by immunoassays, a blotting technique, ELISA, ELISpot, flow cytometry, cytometric bead assay, proteomics, and/or immunohistochemistry.

Methods of Delivering a Cytotoxin or Radionuclide to a Cancer Cell

Additional embodiments include methods of delivering a cytotoxin or radionuclide to a cancer cell. Some embodiments include targeting a radioactive substance (e.g., $^{111}$I, $^{131}$I, $^{90}$Y, $^{67}$Cu, $^{186}$Re, $^{188}$Re, $^{212}$Bi or $^{211}$At) or a therapeutic compound (e.g., a toxin) to a cancer cell. As described herein, immunoregulatory peptide inhibitors, for example peptide P28R, bind to cancer cells, but not to healthy immune cells, for example lymphocytes (see Example 14). Thus in some embodiments, binding of a therapeutic compound to a cancer cell can be mediated by the immunoregulatory peptide inhibitor. In some embodiments, a therapeutic compound, for example a cytoxin, a radiotoxin, or the like as described herein is attached to the immunoregulatory peptide inhibitor that binds to P3028.

These methods are practiced by contacting cancer cells (e.g., in vitro or in vivo) with a composition that comprises, consists of, or consists essentially of any one or more of the immunoregulatory peptide inhibitors described herein, which comprises a radioactive substance (e.g., $^{111}$I, $^{131}$I, $^{90}$Y, $^{67}$Cu, $^{186}$Re, $^{188}$Re, $^{212}$Bi or $^{211}$At) or a therapeutic compound (e.g., a toxin). In some embodiments, the immunoregulatory peptide inhibitor used in these methods comprises, consists of or consists essentially of a peptide as described herein. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173), as described herein. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO:

712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in or any one or more of the peptides provided in Table 5.1, 5.4, 5.5, 5.6, or any variation or combination of variations of P28R or P28 core as provided in Tables 5.3 and 13. In some embodiments, the isolated peptide from or any one or more of the peptides provided in Table 5.1, 5.4, 5.5, 5.6, or any variation or combination of variations of P28R or P28 core as provided in Tables 5.3 and 13 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Preferably, the immunoregulatory peptide inhibitor used in the aforementioned methods is P28R, a derivative thereof, or a nucleic acid encoding such a molecule (e.g., any one or more of the immunoregulatory peptide inhibitors provided by SEQ ID NOs: 1-33, 34, 46-53, 64-66, 68, 76, 94-96 or 98 or any one or more of the peptides provided in Table 5.1). The immunoregulatory peptide inhibitors used in the aforementioned methods can comprise at least one D amino acid, at least one non-natural amino acid, an N-terminal acetyl group, or a C terminal amide group and said immunoregulatory peptide inhibitors can be glycosylated or joined to PEG.

Once the immunoregulatory peptide inhibitor comprising the cytotoxin or radionuclide has contacted the cancer cell, (e.g., in a human patient) the toxin and/or radionuclide can induce cancer cell death. In some embodiments, the cancer cell death comprises apoptosis. Optionally, cell death can comprise Caspase 3 activation (see Example 39). In some embodiments, peptide P28R (SEQ ID NO: 2) or a pharmaceutical composition comprising or consisting essentially of P28R is administered peri-tumorally or near a tumor (for example within 10 cm, 9 cm, 8 cm, 7 cm, 6 cm, 5 cm, 4 cm, 3 cm, 2 cm, 1 cm, or 0.5 cm of the tumor), and induces cell death of tumor cells. In some embodiments, the tumor comprises prostate cancer cells. In some embodiments, the tumor comprises a melanoma, for example a B16 melanoma. In some embodiments, at least about 10 ng/100 ml of peptide inhibitor are administered peri-tumorally, for example about 10 ng/100 ml, 20 ng/100 ml, 30 ng/100 ml, 40 ng/100 ml, 50 ng/100 ml, 60 ng/100 ml, 70 ng/100 ml, 80 ng/100 ml, 90 ng/100 ml, 100 ng/100 ml, 200 ng/100 ml, 300 ng/100 ml, 400 ng/100 ml, 500 ng/100 ml, 600 ng/100 ml, 700 ng/100 ml, 800 ng/100 ml, 900 ng/100 ml, 1 µg/100 ml, 2 µg/100 ml, 3 µg/100 ml, 4 µg/100 ml, 5 µg/100 ml, 6 µg/100 ml, 7 µg/100 ml, 8 µg/100 ml, 9 µg/100 ml, 10 µg/100 ml 20 µg/100 ml, 30 µg/100 ml, 40 µg/100 ml, 50 µg/100 ml, 100 µg/100 ml, 200 µg/100 ml, 500 µg/100 ml, 1000 µg/100 ml, including ranges between any two of the listed values, for example about 10 ng-100 ng/100 ml, 10 ng-200 ng/100 ml, 10 ng-500 ng/100 ml, 10 ng-1 µg/100 ml, 20 ng-10 µg/100 ml, 100 ng-200 ng/100 ml, 100 ng-500 ng/100 ml, 100 ng-1 µg/100 ml, 200 ng-10 µg/100 ml, 200 ng-500 ng/100 ml, 200 ng-1 µg/100 ml, 200 ng-10 µg/100 ml, 1 µg-100 µg/100 ml, 1 µg-500 µg/100 ml, about 1 µg-1000 µg/100 ml, 5 µg-100 µg/100 ml, 5 µg-500 µg/100 ml, 5 µg-1000 µg/100 ml, 10 µg-100 µg/100 ml, 10 µg-500 µg/100 ml, 10 µg-1000 µg/100 ml, 50 µg-100 µg/100 ml, 50 µg-500 µg/100 ml, 50 µg-1000 µg/100 ml, 100 µg-500 µg/100 ml, or about 100 µg-1000 µg/100 ml. In some embodiments, the pharmaceutical composition is administered systemically. In some embodiments, the pharmaceutical composition is administered in conjunction with a second therapeutic agent, for example a therapeutic agent selected to stimulate an immune cell after an LFA-1 receptor of the immune cell has been de-blocked (e.g. bound immunoregulatory peptides or 3028 structures have been displaced from the LFA-1 receptor).

Optionally, these methods include the steps of observing or monitoring the cancer or progression of the cancer of the patient. In some embodiments, the immunoregulatory peptide inhibitor comprising the cytotoxin or radionuclide is administered to a cancer patient having colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer. In some embodiments, a biological sample of a human is screened for binding of immunoregulatory peptide inhibitor prior to administering the immunoregulatory peptide inhibitor comprising the cytotoxin or radionuclide. For, example, an immunoregulatory peptide inhibitor or antibody that binds specifically to an immunoregulatory peptide of any one of Tables 1-4 bound to a detectable label can be administered to a biological sample as in Example 14 or Example 41. From detection of the detectable label, it can be confirmed that cancer cells are bound by immunoregulatory peptide inhibitor, and then the same immunoregulatory peptide inhibitor comprising the cytotoxin or radionuclide can be provided to the patient.

Methods of Inhibiting the Proliferation of Cancer Cells

Some embodiments of the invention include methods of inhibiting the proliferation of cancer cells. The method can include identifying a human cancer patient. The patient can be suffering from one or more cancers, for example colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer. The method can include contacting immune cells of the human by an immunoregulatory peptide inhibitor. In some embodiments, contacting the immune cells comprises intra-tumoral administration, or administration near a tumor, for example within 10, 9, 8, 7, 6, 5, 4, 3, 2, 1, or 0.5 cm of the tumor. In some embodiments, the immunoregulatory peptide inhibitor comprises, consists of or consists essentially of a peptide as described herein. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}$TFFVKLS$X_{21}X_{22}$ (SEQ ID NO: 173), as described herein. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}$VKL$X_{32}$L$X_{33}$TE$X_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}$K $X_{701}X_{702}X_{703}$ $X_{704}X_{705}X_{706}$K $X_{707}$ $X_{708}$ $X_{709}$ $X_{710}$ $X_{711}$E $X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1, 5.4, 5.5, 5.6, or any variation or combination of variations of P28R or P28 core as provided in Tables 5.3 and 13. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the method includes providing to the human a polynucleotide encoding such a peptide inhibitor (e.g., any one or more of the peptides provided in Table 5.1, 5.4, 5.5, 5.6, or any variation or combination of variations of P28R or P28 core as provided in Tables 5.3 and 13). For example, a polynucleotide encoding such a peptide inhibitor can be provided, for example a nucleic acid of SEQ ID NOs: 102-165.

Reduction of cancer-associated immunosuppression can induce and/or enhance an immune response against cancer cells. An immune response against cancer cells can reduce cancer cell proliferation, and/or cause cancer cells to undergo cell death or apoptosis. Thus, the method can include detecting an inhibition in the proliferation of cancer cells of the patient. The method can include detecting an induction of cell death or apoptosis of cancer cells of the patient. The method can include detecting an inhibition in the proliferation of cancer cells of the patient, and an induction of cell death or apoptosis of cancer cells of the patient. Apoptosis can be identified as known in the art, for example by neutral red assay, by trypan blue exclusion of dead cells, by acridine orange staining, by TUNEL staining, and/or by detection of cleaved PARP, and/or cleaved caspases.

Methods of Removing Ligands Bound to the LFA-1 Receptor

Some embodiments of the invention include methods of removing a ligand bound to the LFA-1 receptor of human lymphocytes. The methods can include contacting human lymphocytes with an immunoregulatory peptide inhibitor, or a polynucleotide encoding such an inhibitor. In some embodiments, the immunoregulatory peptide inhibitor comprises, consists of or consists essentially of a peptide as described herein. For example, the peptide inhibitor used in these methods can comprise, consist of, or consist essentially of Formula (I), XX$_1$VKX$_2$X$_3$X$_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, X$_1$ is one of FF, FM, FS, FV, FT, FL, AF, AM, AS, AV, AT, AL, VF, VM, VS, VV, VT, or VL. In some embodiments, X$_2$ is one of LS, LQ, LM, LT, LH, VS, VQ, VM, VT, or VH. In some embodiments, X$_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, X$_4$ is an optional sequence, and can be ER, or E, or absent. In some embodiments, if X is absent, X$_1$ is FF, and X$_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), X$_{20}$TFFVKLSX$_{21}$X$_{22}$ (SEQ ID NO: 173), as described herein. In some embodiments, X$_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. X$_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, X$_{22}$ is an optional sequence, and can be ER, E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), X$_{30}$X$_{31}$VKLX$_{32}$LX$_{33}$TEX$_{34}$ (SEQ ID NO: 178). In some embodiments, X$_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, X$_{31}$ is an optional sequence, and can be F, S, M, V, T, or L, or absent. In some embodiments, X$_{31}$ is F. In some embodiments, X$_{32}$ can be S, Q, M, T, or H. In some embodiments, X$_{32}$ is S. X$_{33}$ can be F, M, Q, H, N, P, S, G, A, or R. In some embodiments, X$_{34}$ is F. X$_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), X$_{700}$K X$_{701}$X$_{702}$X$_{703}$ X$_{704}$X$_{705}$X$_{706}$K X$_{707}$ X$_{708}$ X$_{709}$ $X_{710}$ $X_{711}$E $X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}$K $X_{801}$K $X_{802}$E $X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1, 5.4, 5.5, 5.6, or any variation or combination of variations of P28R or P28 core as provided in Tables 5.3 and 13. In some embodiments, the isolated peptide from Table 5.1, 5.4, 5.5, 5.6, or any variation or combination of variations of P28R or P28 core as provided in Tables 5.3 and 13 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, the method includes providing to the human a polynucleotide encoding such a peptide inhibitor. For example, a polynucleotide encoding such a peptide inhibitor can be provided, for example a nucleic acid of SEQ ID NOs: 102-165.

As shown herein (see Examples 15 and 24; see FIGS. 15, 16, 17 and 26), immunoregulatory peptide inhibitors can bind to immunoregulatory peptide sequences/structures, thus preventing immunoregulatory peptide sequences/structures from binding to the LFA-1 receptor. Exemplary immunoregulatory peptides can include P3028 structures/sequences. Exemplary immunoregulatory peptides can include peptides of SEQ ID NOS: 183-185 or 188-246. Thus, the methods can include detecting a reduced binding of a ligand for the LFA-1 receptor as described herein. Reduced binding of a ligand can be detected using an antibody that recognizes at least one epitope of the LFA-1 receptor that is blocked when a ligand in bound to it, for example the antibody of Example 15 and 23. Reduced binding of a ligand can be detected using an antibody that binds specifically to a ligand of the LFA-1 receptor, for example an antibody that binds specifically to an immunoregulatory peptide such as P3028 sequence/structure and the like (see Example 9).

Methods of Identifying a Patient in Need

It is contemplated herein that different populations of patients can have different albumin-derived immunoregulatory peptides, and that a given albumin-derived immunoregulatory peptide can have different effects in different individual patients. As shown in Example 30, some cancer patients have immune cells with a high proliferative response to IL-2, while other cancer patients have immune cells with a low proliferative response to IL-2. As shown in Examples 31 and 32, different populations of patients can respond differently to the same inhibitor of immunoregulatory peptides. Additionally, a given inhibitor can modulate the immune system in some patients, but not in other patients. Thus, some embodiments of the invention include methods of identifying a patient in need. A patient in need can include a patient having albumin-derived immunoregulatory peptides bound to at least some of his or her immune cells. A patient in need can include a patient that is likely to respond to an inhibitor of an immunoregulatory peptide. In some embodiments, immune cells of a patient can be isolated. The presence of immunoregulatory structures on the immune cells can be detected. The effect of an inhibitor of an immunoregulatory peptide on the immune cells can be detected. If an immunoregulatory structure is present and/or if immune cell function is modulated by the inhibitor, the patient can be classified as a patient in need. Optionally, an effective dose of the inhibitor can be determined. A therapeutically effective dose of the inhibitor can be administered to the patient in need.

Some embodiments include methods of detecting the presence of immunoregulatory peptides in an in vitro assay. In vitro methods of detecting the presence of albumin-derived immunoregulatory peptides bound to immune cells, immunoregulatory sequences and structures, and in vitro methods of detecting the effects of albumin-derived immunoregulatory peptides on immune cell activity are provided in U.S. Pat. No. 8,182,983, hereby expressly incorporated by reference in its entirety herein; U.S. Pat. No. 7,960,126, hereby expressly incorporated by reference in its entirety herein; U.S. Pat. No. 8,133,688 hereby expressly incorporated by reference in its entirety herein; U.S. Pat. No. 8,110,347, hereby expressly incorporated by reference in its entirety herein; and U.S. Pub. No. 2011/0262470, hereby expressly incorporated by reference in its entirety herein.

Some embodiments include detecting the response of inhibited immune cells to an inhibitor of immunoregulatory peptides. In some embodiments, immune cells are isolated from a patient. In some embodiments, the immune cells include PBMCs. In some embodiments, the immune cells are contacted with an inhibitor of immunoregulatory peptides.

In some embodiments, the immune cells are contacted with an inhibitor that comprises a peptide comprising, consisting of or consisting essentially of at least one peptide of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, 6.1, 6.2, or 12 or any variation or combination of variations of P28R or P28 core as provided in Tables 5.3 and 13.

In some embodiments, the immune cells are contacted with an inhibitor that comprises a peptide comprising, consisting of or consisting essentially of Formula (I), XX1VKX2X3X4 (SEQ ID NO: 166). In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, X1 is one of FF, FM, FS, FV, FT, FL, AF, AM, AS, AV, AT, AL, VF, VM, VS, VV, VT, or VL. In some embodiments, X2 can be one of LS, LQ, LM, LT, LH, VS, VQ, VM, VT, or VH. In some embodiments, X3 can be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the peptide comprises one of SEQ ID NOs: 2-33. In some embodiments, the isolated peptides that comprise Formula (I) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR (SEQ ID NO: 815), LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R, or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K, A, D, E, G, H, I, L, M, N, P, Q, R, T, or V, or absent. In some embodiments, $X_{701}$ is an optional sequence, and can be L, A, C, D, E, F, G, H, I, K, M, N, Q, R, S, T, or V, or absent. In some embodiments, $X_{702}$ is an optional sequence, and can be D, A, E, I, V, W, or Y, or absent. In some embodiments, $X_{703}$ is an optional sequence, and can be T, C, M, N, P, Q, R, S, W, or Y, or absent. In some embodiments, $X_{704}$ is an optional sequence, and can be F, A, I, M, N, P, T, or V, or absent. In some embodiments, $X_{705}$ is an optional sequence, and can be F, L, M, Q, S, T, or V, or absent. In some embodiments, $X_{706}$ is an optional sequence, and can be V, F, G, L, P, or R, or absent. In some embodiments, $X_{707}$ is an optional sequence, and can be L, A, F, G, I, M, N, P, Q, R, S, T, V, or Y, or absent. In some embodiments, $X_{708}$ is an optional sequence, and can be S, H, M, N, Q, or T, or absent. In some embodiments, $X_{709}$ is an optional sequence, and can be L, A, H, I, M, N, Q, R, S, T, V, or W, or absent. In some embodiments, $X_{710}$ is an optional sequence, and can be F, A, C, G, H, I, L, M, N, P, Q, R, S, T, V, or W, or absent. In some embodiments, $X_{711}$ is an optional sequence, and can be T, F, G, H, I, L, M, N, P, S, V, or W, or absent. In some embodiments, $X_{712}$ is an optional sequence, and can be R, F, K, N, R, T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV (SEQ ID NO: 596), GDTFFV (SEQ ID NO: 597), EDTFFV (SEQ ID NO: 598), LDQFFV (SEQ ID NO: 599), LDTAFV (SEQ ID NO: 600), LDTVFV (SEQ ID NO: 601), LDTFMV (SEQ ID NO: 602), LDTFSV (SEQ ID NO: 603), LDTFVV (SEQ ID NO: 604), LDTFTV (SEQ ID NO: 605), LDTFLV (SEQ ID NO: 606), LDGFFV (SEQ ID NO: 607), LDTFGV (SEQ ID NO: 608), LDTFFK (SEQ ID NO: 609), ADTFFV (SEQ ID NO: 610), CDTFFV (SEQ ID NO: 611), DDTFFV (SEQ ID NO: 612), FDTFFV (SEQ ID NO: 613), HDTFFV (SEQ ID NO: 614), IDTFFV (SEQ ID NO: 615), KDTFFV (SEQ ID NO: 616), MDTFFV (SEQ ID NO: 617), NDTFFV (SEQ ID NO: 618), QDTFFV (SEQ ID NO: 619), RDTFFV (SEQ ID NO: 620), SDTFFV (SEQ ID NO: 621), TDTFFV (SEQ ID NO: 622), VDTFFV (SEQ ID NO: 623), LATFFV (SEQ ID NO: 624), LETFFV (SEQ ID NO: 625), LITFFV (SEQ ID NO: 626), LVTFFV (SEQ ID NO: 627), LWTFFV (SEQ ID NO: 628), LYTFFV (SEQ ID NO: 629), LDCFFV (SEQ ID NO: 630), LDMFFV (SEQ ID NO: 631), LDNFFV (SEQ ID NO: 632), LDPFFV (SEQ ID NO: 633), LDRFFV (SEQ ID NO: 634), LDSFFV (SEQ ID NO: 635), LDWFFV (SEQ ID NO: 636), LDYFFV (SEQ ID NO: 637), LDTIFV (SEQ ID NO: 638), LDTMFV (SEQ ID NO: 639), LDTNFV (SEQ ID NO: 640), LDTPFV (SEQ ID NO: 641), LDTTFV (SEQ ID NO: 642), LDTFQV (SEQ ID NO: 643), LDTFFF (SEQ ID NO: 644), LDTFFG (SEQ ID NO: 645), LDTFFL (SEQ ID NO: 646), LDTFFP (SEQ ID NO: 647), LDTFFR (SEQ ID NO: 648), LDTFIV (SEQ ID NO: 649), LDTSFV (SEQ ID NO: 650), LDTFAV (SEQ ID NO: 651), LDTFCV (SEQ ID NO: 652), LDTQFV (SEQ ID NO: 653), LDTLFV (SEQ ID NO: 654), LTTFFV (SEQ ID NO: 655), LDTFFI (SEQ ID NO: 656), LDHFFV (SEQ ID NO: 657), LMTFFV (SEQ ID NO: 658), LDTFEV (SEQ ID NO: 659), LDTFWV (SEQ ID NO: 660), LFTFFV (SEQ ID NO: 661), LDVFFV (SEQ ID NO: 662), LDTFRV (SEQ ID NO: 663), LDTFHV (SEQ ID NO: 664), LDTYFV (SEQ ID NO: 665), LPTFFV (SEQ ID NO: 666), PDTFFV (SEQ ID NO: 667), LDTFPV (SEQ ID NO: 668), LDTFNV (SEQ ID NO: 669), LDTWFV (SEQ ID NO: 670), LDTGFV (SEQ ID NO: 671), LDAFFV (SEQ ID NO: 672), LQTFFV (SEQ ID NO: 673), LCTFFV (SEQ ID NO: 674), LSTFFV (SEQ ID NO: 675), YDTFFV (SEQ ID NO: 676), LDEFFV (SEQ ID NO: 677), WDTFFV (SEQ ID NO: 678), LDTKFV (SEQ ID NO: 679), LDTCFV (SEQ ID NO: 680), LDTFYV (SEQ ID NO: 681), LDTHFV (SEQ ID NO: 682), LHTFFV (SEQ ID NO: 683), LRTFFV (SEQ ID NO: 684), LDLFFV (SEQ ID NO: 685), LDTRFV (SEQ ID NO: 686), LLTFFV (SEQ ID NO: 687), LDTFDV (SEQ ID NO: 688), LDTFFA (SEQ ID NO: 689), LDTFFT (SEQ ID NO: 690), LNTFFV (SEQ ID NO: 691), LDDFFV (SEQ ID NO: 692), LDIFFV (SEQ ID NO: 693), LDFFFV (SEQ ID NO: 694), LKTFFV (SEQ ID NO: 695), LDTFFQ (SEQ ID NO: 696), LGTFFV (SEQ ID NO: 697), LDTFFC (SEQ ID NO: 698), LDKFFV (SEQ ID NO: 699), LDTFKV (SEQ ID NO: 700), LDTEFV (SEQ ID NO: 701), LDTFFW (SEQ ID NO: 702), LDTFFM (SEQ ID NO: 703), LDTFFS (SEQ ID NO: 704), LDTFFH (SEQ ID NO: 705), LDTFFY (SEQ ID NO: 706), LDTFFN (SEQ ID NO: 707), LDTDFV (SEQ ID NO: 708), LDTFFE (SEQ ID NO: 709), LDTFFD (SEQ ID NO: 710), LTFFV (SEQ ID NO: 711), LDTFF (SEQ ID NO: 712), TFFV (SEQ ID NO: 713), LDF, LDTE (SEQ ID NO: 714), FFV, LDV, LV, or L, or absent. In some embodiments, $X_{802}$ is an optional sequence, and can be LSLFT (SEQ ID NO: 715), VSLFT (SEQ ID NO: 716), LQLFT (SEQ ID NO: 717), LMLFT (SEQ ID NO: 718), LTLFT (SEQ ID NO: 719), LHLFT (SEQ ID NO: 720), LSQFT (SEQ ID NO: 721), LSVFT (SEQ ID NO: 722), LSMFT (SEQ ID NO: 723), LSLMT (SEQ ID NO: 724), LSLQT (SEQ ID NO: 725), LSLHT (SEQ ID NO: 726), LSLNT (SEQ ID NO: 727), LSLPT (SEQ ID NO: 728), LSLST (SEQ ID NO: 729), LSLGT (SEQ ID NO: 730), LSLAT (SEQ ID NO: 731), LSLRT (SEQ ID NO: 732), LSLFN (SEQ ID NO: 733), LSLFP (SEQ ID NO: 734), LSLFR (SEQ ID NO: 735), LGLFT (SEQ ID NO: 736), ASLFT (SEQ ID NO: 737), FSLFT (SEQ ID NO: 738), GSLFT (SEQ ID NO: 739), ISLFT (SEQ ID NO: 740), MSLFT (SEQ ID NO: 741), NSLFT (SEQ ID NO: 742), PSLFT (SEQ ID NO: 743), QSLFT (SEQ ID NO: 744), RSLFT (SEQ ID NO: 745), SSLFT (SEQ ID NO: 746), TSLFT (SEQ ID NO: 747), YSLFT (SEQ ID NO: 748), LNLFT (SEQ ID NO: 749), LSAFT (SEQ ID NO: 750), LSHFT (SEQ ID NO: 751), LSIFT (SEQ ID NO: 752), LSNFT (SEQ ID NO: 753), LSRFT (SEQ ID NO: 754), LSSFT (SEQ ID NO: 755), LSTFT (SEQ ID NO: 756), LSWFT (SEQ ID NO: 757), LSLCT (SEQ ID NO: 758), LSLIT (SEQ ID NO: 759), LSLLT (SEQ ID NO: 760), LSLTT (SEQ ID NO: 761), LSLVT (SEQ ID NO: 762), LSLWT (SEQ ID NO: 763), LSLFF (SEQ ID NO: 764), LSLFG (SEQ ID NO: 765), LSLFH (SEQ ID NO: 766), LSLFI (SEQ ID NO: 767), LSLFL (SEQ ID NO: 768), LSLFM (SEQ ID NO: 769), LSLFS (SEQ ID NO: 770), LSLFV (SEQ ID NO: 771), LSLFW (SEQ ID NO: 772), LYLFT (SEQ ID NO: 773), LVLFT (SEQ ID NO: 774), LSFFT (SEQ ID NO: 775), LSGFT (SEQ ID NO: 776), LSKFT (SEQ ID NO: 777), LSCFT (SEQ ID NO: 778), LCLFT (SEQ ID NO: 779), LRLFT (SEQ ID NO: 780), LPLFT (SEQ ID NO: 781), LWLFT (SEQ ID NO: 782), LKLFT (SEQ ID NO: 783), LDLFT (SEQ ID NO: 784), LSYFT (SEQ ID NO: 785), LALFT (SEQ ID NO: 786), WSLFT (SEQ ID NO: 787), LSLFA (SEQ ID NO: 788), LSLFQ (SEQ ID NO: 789), LSPFT (SEQ ID NO: 790), HSLFT (SEQ ID NO: 791), LSLYT (SEQ ID NO: 792), LILFT (SEQ ID NO: 793), KSLFT (SEQ ID NO: 794), CSLFT (SEQ ID NO: 795), LSLFY (SEQ ID NO: 796), LSLFK (SEQ ID NO: 797), LSLFC (SEQ ID NO: 798), LFLFT (SEQ ID NO: 799), LELFT (SEQ ID NO: 800), LSLKT (SEQ ID NO: 801), LLLFT (SEQ ID NO: 802), LSLFD (SEQ ID NO: 803), LSLDT (SEQ ID NO: 804), LSLFE (SEQ ID NO: 805), DSLFT (SEQ ID NO: 806), LSLET (SEQ ID NO: 807), LSDFT (SEQ ID NO: 808), LSEFT (SEQ ID NO: 809), ESLFT (SEQ ID NO: 810), SLFT (SEQ ID NO: 811), LSFT (SEQ ID NO: 812), LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Figure 33A:
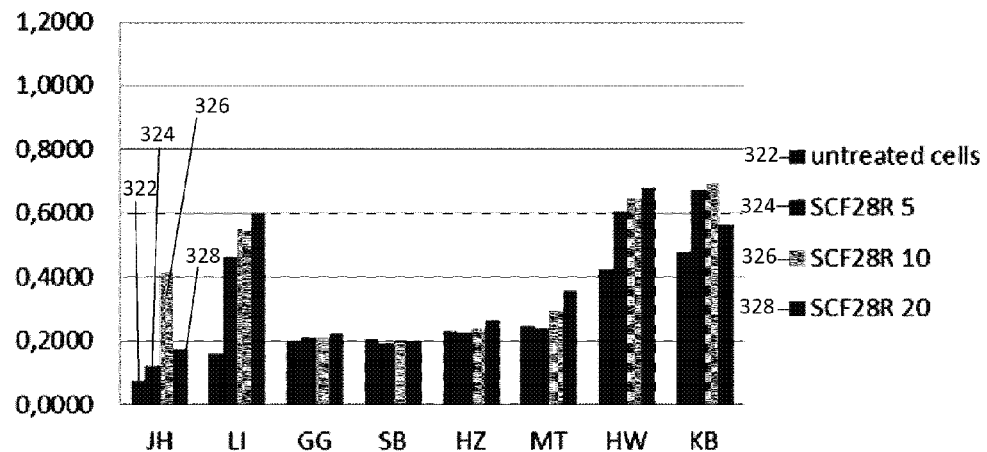
FIGS. 33A and 33B illustrate effects of various concentrations of peptide P28R on MTS bioreduction in (FIG. 33A)
Figure 33B:
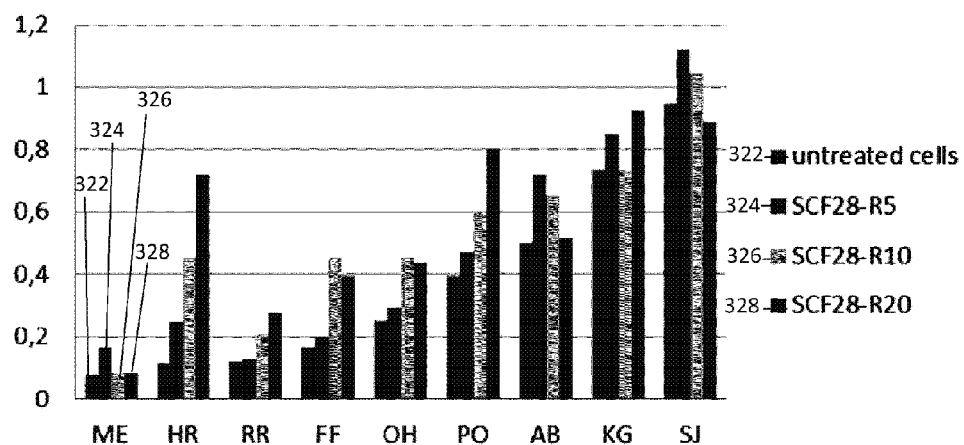

In some embodiments, the immune cells are contacted with an inhibitor that comprises, consists of, or consists essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, the response of the immune cells is detected. In some embodiments, the response to IL-2 stimulation is detected (see Example 2). In some embodiments, T cell stimulation is detected (see Example 3). In some embodiments, NK-Cell cytotoxicity is assayed (see Example 4). In some embodiments, leukocyte spreading is detected (see Example 5). In some embodiments, unblocking of the LFA-1 receptor is detected (see Example 6). In some embodiments, binding of P28R to the tumor can be demonstrated. In some embodiments, binding of P3028 (SEQ ID NO: 185) to the IL-2 receptor is detected (see Example 8). In some embodiments, MTS conversion by the immune cells is detected, for example in response to immune cell stimulation (see Examples 31-32). In some embodiments, BrdU incorporation by the immune cells is detected, for example in response to immune cell stimulation (see Examples 31-32). It is contemplated herein that some patients will exhibit some immune cell responses in response to the inhibitor, but will not exhibit other immune cells responses in response to that same inhibitor (see Example 31-32, and FIGS. 34, 37, and 38, showing, among other results, that P28R enhanced the IL-2 induced stimulation of BrdU uptake and MTS conversion in one patient, but enhanced BrdU updated and not MTS conversion in another patient). Thus, some embodiments include detecting two or more immune cell responses described herein. Detection of two or more immune cell responses can allow the identification of a patient that is likely to elicit a first response, but not a second response, and can be useful in guiding clinical decisions such as which inhibitors or combinations of inhibitors to apply, and whether to apply additional therapies to the patient in need. In some embodiments, detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin is performed. In some embodiments, detecting activation or stimulation of an immune cell includes detecting one or more of enhanced cytotoxicity, cytokine production, cell migration, and/or cell proliferation In some embodiments, optionally, an effective dose of the inhibitor for the patient in need is determined. In some embodiments, cells of the patient are contacted in vitro with two or more doses of the inhibitor, and an immune response. As shown in FIGS. 33A, 33B, and 34, P28R can have dose-dependent immunomodulatory effects, for example on mitochondrial metabolism (see Example 28 and 29).

As shown in FIG. 34, increasing doses of P28R (SEQ ID NO: 2) were provided to the immune cells of cancer patients in vitro. A dose of 20 μg/ml of P28R resulted in significantly higher MTS conversion than a dose of 40 μg/ml of P28R. Thus, one skilled in the art will appreciate that some embodiments include determining an effective dose of an inhibitor for the cells of a patient in vitro, and then providing an appropriate dose of the inhibitor to the patient.

Materials and Methods

Except when stated otherwise, the following materials and or methods were used as appropriate in the Examples provided below.

Human Serum

Human serum was collected in serum collection tubes without additives (Vacutainer, Becton Dickinson, Franklin Lakes, N.J.) at the same time as blood samples for isolation of PBMC. The sera were heat-inactivated at 56EC for 30 minutes.

Isolation of PBMC's

To isolate PBMC's, venous blood was drawn from healthy volunteers or from cancer patients in glass vacuum tubes with acid dextrose citrate solution A as anti-coagulant (Vacutainer, Becton Dickinson, Franklin Lakes, N.J.). Erythrocytes were removed by sedimentation on 2% dextran T500 solution (Amersham Pharmacia Biotech AB, Uppsala, Sweden) in 0.9% NaCl (this step was omitted for cultures with PHA-stimulation—see below). PBMC were then isolated by Ficoll-Paque Plus (GE Healthcare Bio-Sciences AB, Uppsala, Sweden) density gradient centrifugation after which the cells were washed twice in RPMI 1640 Dutch's modification (Gibco, InVitrogen AB, Stockholm, Sweden) with 2% human serum albumin (HSA) (Pharmacia & Upjohn, Stockholm, Sweden) (RPMI/2% HSA). For cell cultures with PHA-stimulation, PBMC were washed in Hank's Balanced Salt Solution (HBSS) with 10% autologous plasma instead of RPMI/2% HSA. Cell viability was assessed by exclusion of 0.05% Trypan Blue and was always above 95%. The cell suspension was stained with Turk's solution and the number of lymphocytes and monocytes in the PBMC preparation were counted in a hemocytometer.

PBMCs were suspended in RPMI/2% HSA and the cell concentration adjusted to 5×105 lymphocytes/ml.

IL-2 Induced Proliferation of PBMC in Uncoated and Coated Culture Plates

Pre-coating of culture plates with HSA and HSA/IgG. Round-bottomed, 96-well tissue culture plates (Costar, Corning Inc. NY, US) were pre-coated with HSA only or HSA and pooled human IgG for intravenous injection (Gammagard, Baxter AS, DK). HSA was diluted in RPMI1640 without supplements to a concentration of 10 mg/ml. In some experiments, 1 mg/ml IgG was mixed into a solution of 9 mg/ml HSA in RPMI (HSA/IgG). 200 μl of HSA or HSA/IgG were then added to each well of the plate. The plates were incubated at 4° C. for 30 minutes after which the wells were washed twice with 200 μl of RPMI1640. The coated plates were used immediately.

100 μl of RPMI1640 supplemented with 200 IU/ml penicillin, 200 μl/ml streptomycin, 4 mM L-glutamine (all from Sigma Chemical Co. MO, US) and 20% heat-inactivated human serum (autologous or from cancer patients) were added to uncoated, HSA or HSA/IgG coated tissue culture microtiter plates. PBMC, isolated from healthy individuals or patients with metastatic renal cell carcinoma, were diluted in RPMI/2% HSA at a concentration of $5\times10^5$/ml and 100 μl were added to the microtiter wells. Interleukin-2 (IL-2, Proleukin, Chiron, NL), at a final concentration of 120 IU/well, was added to some wells. Cells were cultured for 7 days in a humidified, 5% $CO_2$-atmosphere at 37° C. Proliferation was assayed by incorporation of 1.6 μCi/well of [$^3$H]-thymidine (Amersham Int., UK) during the last 18 hrs. Mean values of dpm (disintegrations per minute) of triplicates were used for the calculations.

Interleukin-2 (IL-2) Induced Proliferation of PBMC in the Presence of Albumin Peptides Cultures for IL-2 induced proliferation was set up with PBMC from healthy donors and autologous serum as described above with the exception that PBMC were first pre-incubated for 30 min at room temperature with the indicated albumin peptides at a concentration of 10 μg/ml.

Interleukin-2 (IL-2) Induced Proliferation of PBMC in the Presence of Albumin Peptides in Coated and Uncoated Tissue Culture Plates Round-bottomed, 96-well tissue culture plates (Costar, Corning Inc. NY, US) were pre-coated with HSA only or HSA and pooled human IgG for intravenous injection (Gammagard, Baxter AS, DK) as follows; HSA was diluted in RPMI1640 without supplements to a concentration of 10 mg/ml. A mixture of 1 mg/ml IgG in a solution of 9 mg/ml HSA in RPMI (HSA/IgG) was also prepared. 200 μl of HSA or HSA/IgG were then added to each well of the plate. The plates were incubated at 4° C. for 30 minutes after which the wells were washed twice with 200 μl of RPMI1640. The coated plates were used immediately. 100 μl of RPMI1640 supplemented with 200 IU/ml penicillin, 200 μl/ml streptomycin, 4 mM L-glutamine (all from Sigma Chemical Co. MO, US) and 20% heat-inactivated human serum (autologous) were added to the HSA or HSA/IgG coated tissue culture microtiter wells. PBMC, isolated from healthy individuals, were diluted in RPMI/2% HSA and peptides were added directly to the cell suspension at a concentration of 10 μg/ml. One hundred μl of this cell suspension ($5\times10^4$ lymphocytes) was then added per well providing a final concentration of 5 μg/ml peptide per well. IL-2 (Proleukin, Chiron, NL), at a final concentration of 120 IU/well, was added to the wells. Cells were cultured for 7 days in a humidified, 5% $CO_2$-atmosphere at 37° C. Proliferation was assayed by incorporation of 1.6 μCi/well of [$^3$H]-thymidine (Amersham Int., UK) during the last 18 hrs. Mean values of dpm (disintegrations per minute) of triplicates were used for the calculations.

Albumin Peptides

Synthetic albumin peptides were custom prepared by CSBio Co, Menlo Park, Calif. Peptides were >95% pure as confirmed by HPLC. Peptides were kept freeze dried at minus 20° C. Peptides were reconstituted in sterile H2O (Sigma) for use in ELISA or in RPMI1640 (GIBCO) for use in cell culture experiments. Peptides were sterile filtered through a 0.22 μm syringe filter (Millipore Co) before use in cell culture experiments.

ELISA for the Detection of Murine Antibodies Binding to Human Albumin

Duplicate wells in Hibinding microtitre plates (Costar 2592, Corning Inc, NY, USA) were coated with 100 μl of dHSA diluted in PBS at various concentrations or, alternatively, control albumin sample at the same concentrations. The plates were incubated at room temperature overnight. The wells where then washed with wash buffer consisting of 0.05% TWEEN-20 reagent in PBS (Sigma) followed by blocking for 1 h at 25° C. with 200 μl 0.1% gelatin prepared from bovine skin (Sigma) in PBS followed by washing in wash buffer. Either of two murine monoclonal antibodies (IgG1) with specificity for denatured, human albumin (anti-dAbclh040801 or anti-dAlbclh040809) was added at 1 μg/ml in ELISA reagent diluent (0.01% gelatin (Sigma) and 0.05% TWEEN-20 reagent (Sigma) in 20 mM Tris-buffered saline (TBS, Sigma)). The antibodies were incubated for 1.5 h at 25° C. followed by washing. Envision-HRP (DakoCytomation Norden A/S, Glostrup, Denmark) was added diluted 1/5 to 1/10 in ELISA reagent diluent and incubated for 30 min at 25° C. followed by washing. Finally, a substrate solution consisting of H2O2 and tetramethylbenzidine (R&D Systems Europe, Ltd, Abingdon, UK) was added. The reaction was stopped with 1M H2SO4 and the optical density measured as absorbance (Abs) at dual wavelengths, 450 nm and 570 nm, with a Multiscan EX microplate reader (Labsystems).

ELISA with Rabbit-Anti 3028 Antiserum

Duplicate wells in Hi-binding microtitre plates (Costar 2592, Corning Inc, NY, USA) were coated with 100 μl of P3028 (10 ug/ml), denatured HSA (denHSA, 4.5 ug/ml) or control HSA sample (4.5 ug/ml). All coating reagent were diluted in PBS and incubated at room temperature overnight. The wells where then washed with wash buffer consisting of 0.05% TWEEN-20 reagent in PBS (Sigma) followed by blocking for 1 hr at 25° C. with 200 μl 0.5% gelatin prepared from bovine skin (Sigma) in PBS followed by washing in wash buffer. Rabbit preimmune sera or anti-3028 sera, diluted 1/1000 000 in ELISA reagent diluent (0.01% gelatin and 0.05% TWEEN-20 reagent in PBS), were added and incubated for 1 h at 25° C. followed by washing. Biotinylated horse anti-rabbit/mouse IgG (VECTASTAIN ELITE reagent, Vetor Laboratories Inc, CA, USA) diluted 1/5 in ELISA reagent diluent was then added and the plates incubated for 1 h at 25° C. followed by washing. Next, HRP-conjugated strreptavidine (R&D systems Europe, Ltd, UK) was added. Finally, after washing in wash buffer, substrate solution consisting of $H_2O_2$ and tetramethylbenzidine (R&D Systems) was added. The reaction was stopped with 1M $H_2SO_4$ and the optical density measured as absorbance (A) at dual wavelengths, 450 nm and 570 nm, with a Multiscan EX microplate reader (Labsystems).

Statistical Considerations

Comparisons of the means of different patient groups or different test occasions were performed using an unpaired t-test. Time to progression and survival was analyzed using the Kaplan-Meier method and Logrank test.

Comparisons between the proliferative response to PHA in different groups or at different test occasions were done on logarithmated mean values of dpm of triplicates using unpaired t-test. For the determination of the effect of addition of CHL on the proliferative response of PHA-stimulated PBMCs, a modulation index (MI) was calculated according to the following formula: MI=log (dpm PHA+drug/dpm PHA).

Example 1

Serum Peptides with Immune Inhibitory Activities

Identification of Immunoregulatory Peptides

An artificial cell surface (ACS) was prepared by selectively biotinylating cell surface structures of PBMCs and after lysing the cells binding the biotinylated proteins to streptavidin columns (see Example 17 for further description of the ACS). The mixture of peptides obtained after trypsination was adsorbed by ACS and the binding peptides were identified by comparing adsorbed and unabsorbed peptide solutions using the MALDI TOF ms technique. Based on their degree of binding and their spatial relation to previously identified immunoregulatory structures, four new peptides were selected to be synthesized and investigated for their immunoregulatory activity, primarily the effect on the proliferative response to IL-2. One of these peptides, P3028 (SEQ ID NO: 185) was found to have multiple immunoinhibitory activities.

Expression of the P3028 Epitope in Malignant Tumors

Figure 1:
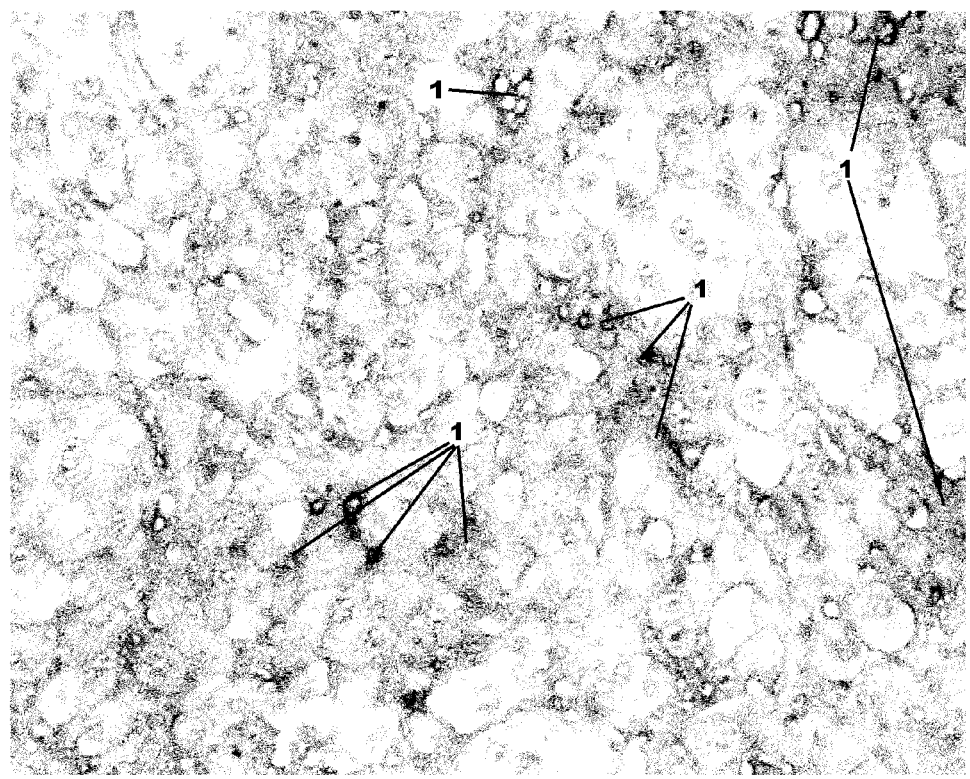
FIG. 1 illustrates immunohistochemical staining of a malignant melanoma metastases using affinity purified rabbit antibodies directed to the P3028 epitope.

Rabbit polyclonal antibodies against P3028 were generated and affinity purified (see Example 9). To determine the localization of P3028 in tumor cells, sections of malignant metastases were immunostained using the anti-P3028 rabbit polyclonal antibodies. Tissue sections were prepared from formalin fixed biopsies from cancer patients. Sections were de-paraffinased and blocked with 10% normal, human AB-serum in Hank's balanced salt solution supplemented with 0.01 M Hepes (BSS, GIBCO BRL) for one hour prior to staining. Sections were then stained with 10 ug/ml affinity purified rabbit anti-P3028 diluted in BSS with 2% AB-serum and 0.1 g/ml saponin for 30 min. After washing in BSS with 0.1 g/ml saponin, Ultravison One alkaline phosphatase polymer specific for mouse and rabbit Ig (Lab Vision Co., CA, USA) was added. Excess polymer was then washed from the sections with BSS with 0.1 g/ml saponin. Bound polymer complex was the detected by naphthol phosphate substrate and liquid Fast Red chromogen (Lab Vision Corp.) The sections were counter stained in Mayer's haematoxylin and mounted in Glycergel. As shown in FIG. 1, structures 1 to which anti-P3028 antibodies bind are widely expressed in human malignant tumors, e.g., malignant melanoma, renal cell carcinoma and colorectal cancer.

Western blotting was performed on extracts of malignant melanoma metastases to detect the presence of P3028 structures. Western blotting was performed using standard techniques, and P3028 structures were detected using affinity purified Rabbit polyclonal antibodies against P3028 (see Example 9). P3028 structures in tumor extracts from malignant melanoma metastases were identified in the extracts of 7 out of 7 mestases from 4 patients that were screened (see FIG. 2). The P3028 peptide was present in all patients. Additionally, the P3028 structure was present in full-length albumin. In addition this structure was found in larger molecules. These results are compatible with the P3028 structure being generated not only by proteolytic fragmentation but also by denaturation.

Occurrence of P3028 Structures in Serum

Substances exposing the structure of P3028 were determined in human serum by using affinity purified antibodies in a sandwich ELISA. That is, the ability to detect P3028 structures in human serum was confirmed.

A sandwich ELISA was performed to detect albumin exposing the P3028 epitope in serum as follows: An affinity polyclonal purified rabbit antisera, specific for human albumin P3028, was coated onto high protein binding ELISA microwells (capture antibody; see Example 9). A 1% solution of heat-inactivated serum (from a serum pool of 5 healthy control samples, 1 healthy control serum sample and 2 sera obtained from cancer patients), spiked with increasing concentrations of P3028, was then added to the wells. After washing, a biotinylated mouse anti-human albumin monoclonal antibody was added and the amount of bound antibody was detected with HRP-conjugated streptaviddin and TMB chromogen substrate. (One representative experiment out of two is shown FIG. 3).

Figure 3:
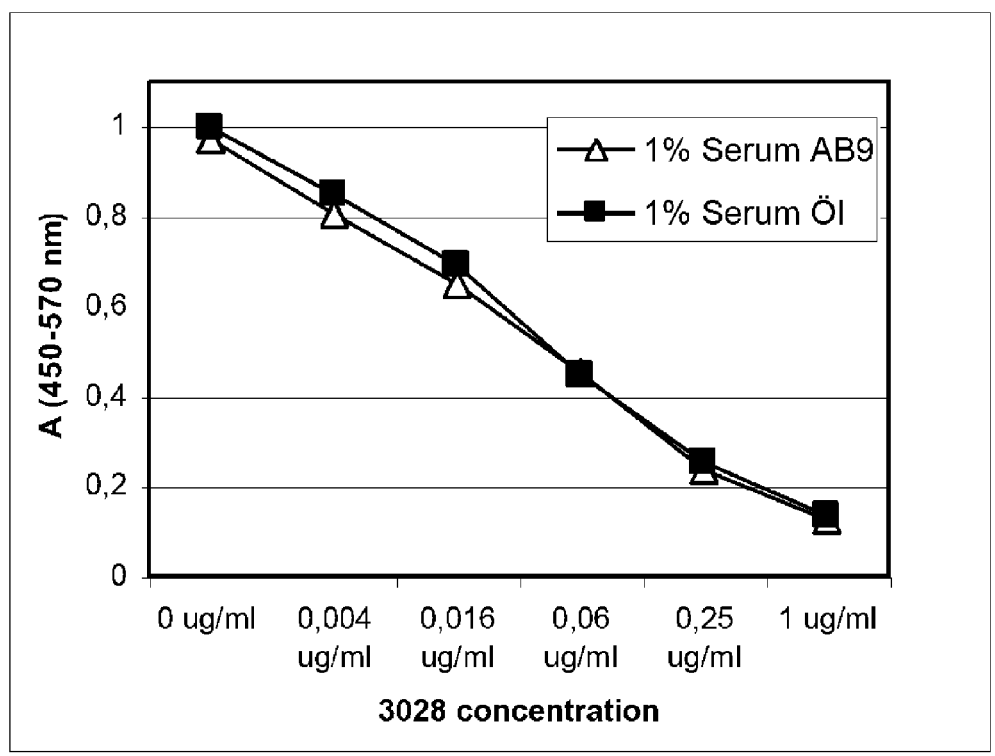
FIG. 3 illustrates Sandwich ELISA detecting albumin exposing the P3028 epitope in serum; competition with the P3028 peptide.

The amount of P3028 structures were determined as the amount of P3028, which inhibits 50% of the binding of P3028 structures in the serum to the capture antibody (see FIG. 3). The serum concentration was determined to be in the range of 1.2-1.6 μg/ml P3028 equivalents in one serum pool from 5 healthy control samples, 1 healthy control serum sample and 2 sera obtained from cancer patients. The amount of these P3028-substances in serum can be considerably more as the molecular weight of albumin is about 35 times more than that of P3028. The epitope specific reactivity of P3028-substances was accurately determined using the methods of this Example.

Example 2

Effect of ACS-Identified Peptides on IL-2 Induced Proliferation

Human Ex Vivo Model for Immunosuppression in Cancer Patients

Interleukin-2 (IL-2) plays a major role in initiation and activation of an immune response and its capacity to induce lymphokine activated killer cells (LAK-cells), T-cell proliferation and cytotoxicity. Accordingly, a human ex vivo model of IL-2 stimulation of immune cells was developed. This model was useful for studying the effects of immune system modulators, such as P3028, and inhibitors thereof.

The model included PBMCs isolated from venous blood samples from healthy blood donors (control samples) or cancer patients. One hundred pl of culture medium (RPMI 1640 Dutch's modification (Gibco, InVitrogenAB, Stockholm, Sweden) supplemented with 200 IV/ml penicillin, 200 ug/ml streptomycin, 4 mM L-glutamine (all from Sigma Chemical Co. MO, US) and 20% heat-inactivated human serum) were added to roundbottomed, 96-well tissue culture plates (Costar, Corning Inc. NY, US). One hundred ul of PBMCs in RPMI/2% HSA ($5 \times 10^4$ lymphocytes) was then added per well followed by IL-2 (Proleukin, Chiron, NL) at a final concentration of 120 IU/well. Control sample wells without IL-2 was set up in parallel. Cells were cultured for 7 days in a humidified, 5% CO2-atmosphere at 37° C. Cell proliferation was assayed by incorporation of 1.6 pCi/well of [$^3$H]-thymidine (Amersham Int., UK) during the last 18-24 h hrs. Mean values of dpm (disintegrations per minute) of triplicate wells were used for the calculations.

Figure 4:
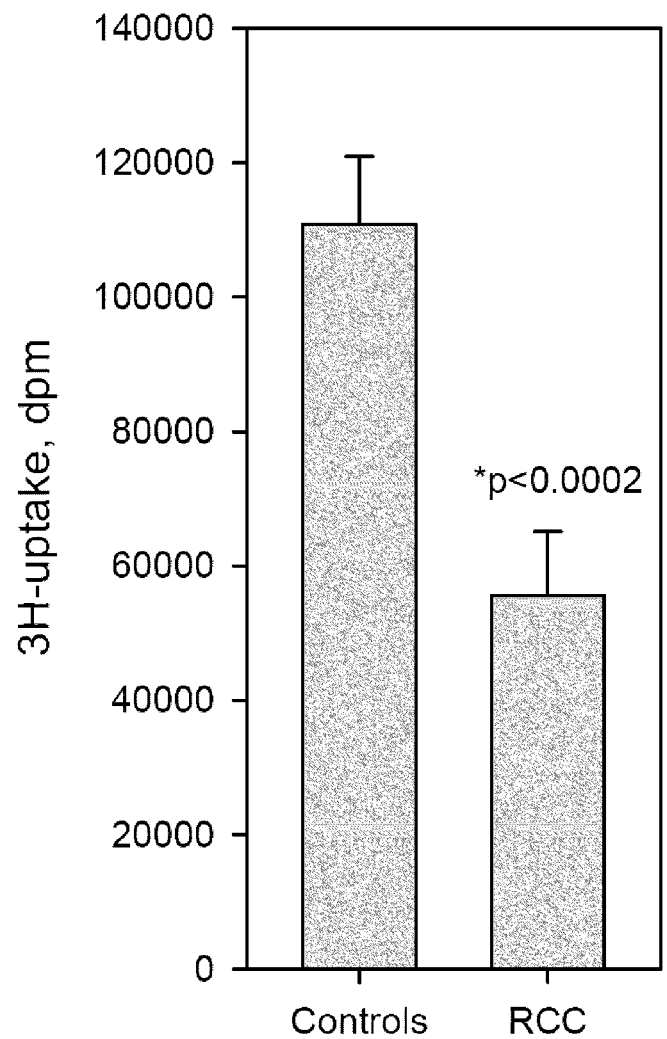
FIG. 4 illustrates IL-2 induced proliferation by PBMCs from healthy control samples and human immune cells (PBMC) from renal cell carcinoma patients (RCC) cultured in 10% autologous sera.

IL-2 induced proliferation by PBMC from healthy control samples and PBMC from renal cell carcinoma patients (RCC) cultured in 10% autologous sera was studied using this model. Results of the study are shown in FIG. 4. IL-2 induced proliferation was significantly reduced (p<0.0002) for PBMC's cultured in serum of a renal carcinoma patient as compared to a healthy control sample.

Correlation Between IL-2 Response in Ex Vivo Model and Overall Survival of Renal Cell Carcinoma Patients The response to IL-2 in this model was demonstrated to correlate to overall survival of renal cell carcinoma patients. Patients, included in the analyses of over-all survival according to proliferative response of PBMCs to interleukin-2, were diagnosed with systemic metastatic renal cell carcinoma. They were previously untreated and scheduled for Interleukin-2 treatment (Proleukin, Chiron, NL). Blood samples were taken prior to initiation of treatment. Survival curves were plotted using the method of Kaplan and Meier and time to progression and survival comparisons between subgroups were performed using the log rank test. In addition, the prognostic significance of the level of LPS-stimulated IL-6 production was also calculated using Cox regression.

Figure 5:
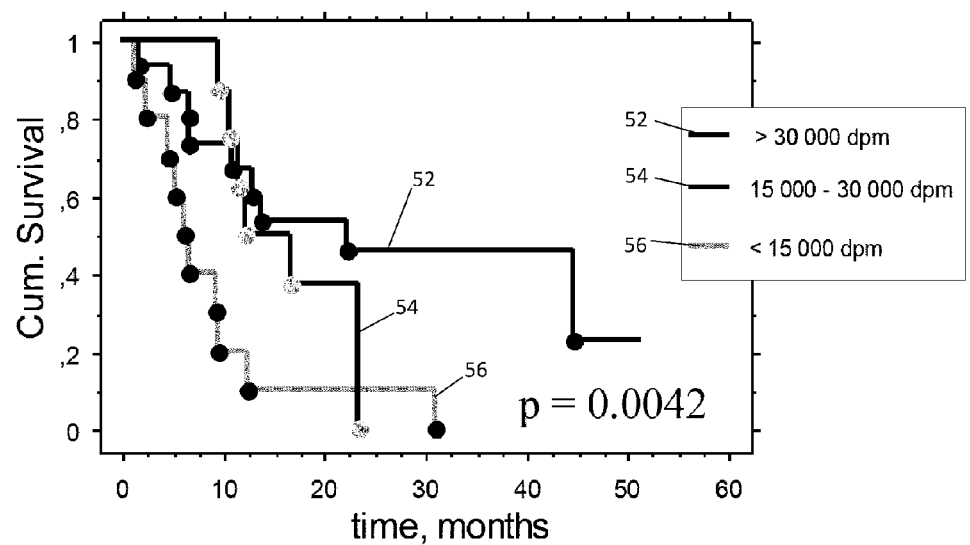
FIG. 5 illustrates a Kaplan Meyer analysis of renal cell carcinoma patients according to proliferative response to IL-2.

FIG. 5 illustrates a Kaplan Meyer analysis of renal cell carcinoma patients according to proliferative response to IL-2. Patients were classified as having a proliferative response of >30,000 dpm 52, 15,000-30,000 dpm 54, or <15,000 dpm 56. A log rank analysis we performed, and overall patient survival correlated with proliferative response (p=0.0042). As illustrated in FIG. 5, patients with the lowest IL-2 induced proliferation of PBMCs in autologous serum in the ex vivo model 56 also had the lowest overall survival time. Thus, a low proliferative rate indicates a poor survival.

Effect of Different Peptides on IL-2 Induced Proliferation

Figure 6:
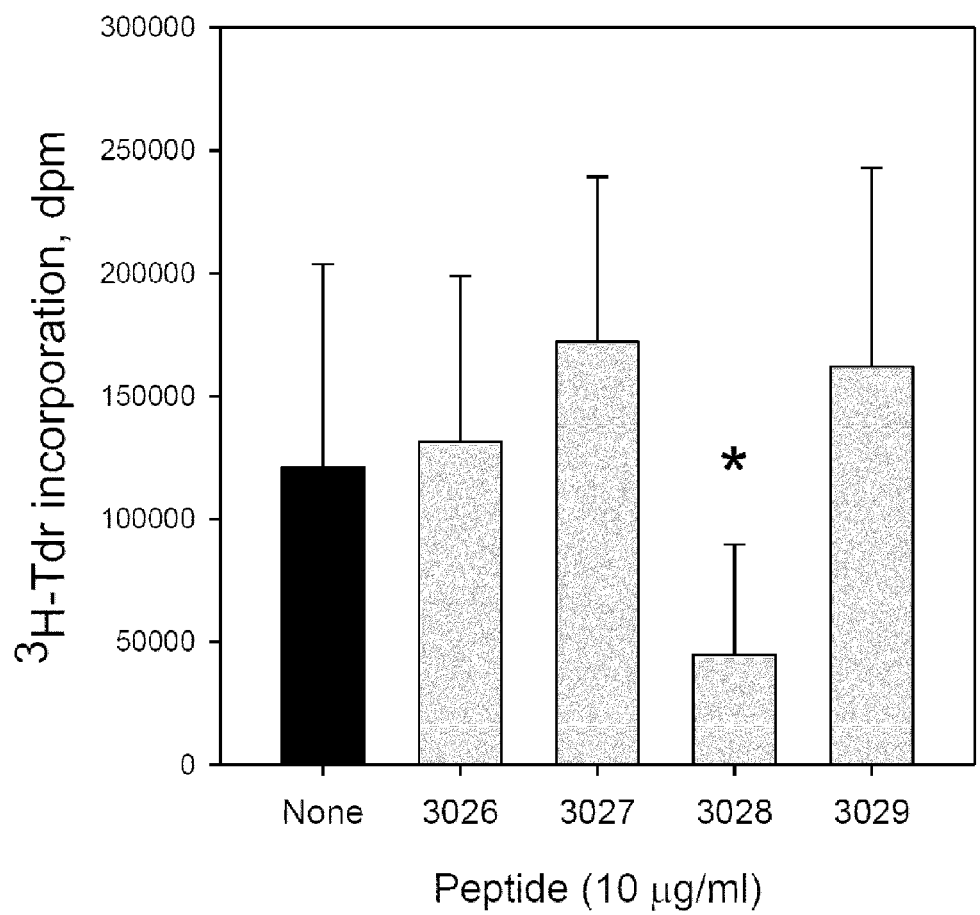
FIG. 6 illustrates analysis of the effect of four different peptides on IL-2 induced proliferation of PBMCs from healthy control samples.

The effect of different peptides on IL-2 induced proliferation was analyzed in the human ex vivo model, using PBMCs from healthy control samples. PBMCs were cultured for 7 days in the presence of IL-2 (20 U/ml) and the peptides. A control sample was also performed in which no peptide was added ("None"). Proliferation was measured as incorporation of $^3$H-thymidine during the final 18 hours. The peptides included P3026 (SEQ ID NO: 183), P3027 (SEQ ID NO: 184), P3028 (SEQ ID NO: 185), and P3029 (SEQ ID NO: 186). One of the peptides, P3028, regularly inhibited IL-2 induced proliferation (p<0.0006, as compared to control sample; n=17), but none of the other peptides identified by their binding to the artificial cell surface had any inhibitory activity (For P3026, P3027, P3029 n=4 or 5). FIG. 6 illustrates the analysis of the effect of the four different peptides.

Figure 7:
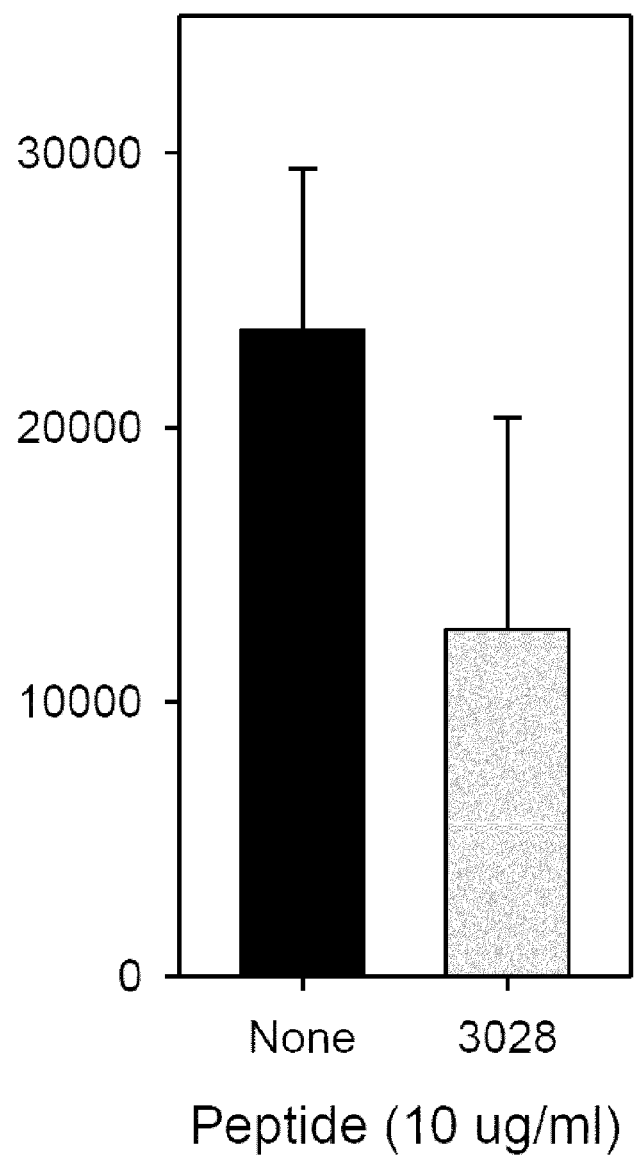
FIG. 7 illustrates inhibition of the proliferative response to IL-2 by P3028 in the human ex vivo model using cancer patient PBMCs.

The inhibition of the proliferative response to IL-2 by P3028 was also observed for cancer patient PBMCs studied in the human ex vivo model. The ex vivo model of IL-2 stimulation was constituted using the PBMCs of a cancer patient, and IL-2 stimulation was compared in the presence and absence of P3028. As illustrated in FIG. 7, the inhibitory activity of P3028 on IL-2 induced proliferation can be demonstrated also in cultures with cancer patient PBMCs, even if the response to IL-2 was already suppressed (see FIG. 7).

Example 3

Effect of P3028 on T-Cell Receptor Stimulation

To examine the effects of P3028 on T cell receptor stimulation, Blood for PBMC isolation was provided from healthy control samples in 50 ml transfusion bags with acid dextrose citrate solution A. Whole blood was diluted 1:1 in PBS containing 2 mM EDTA. PBMCs were then isolated by Ficoll-paque Plus (GE Healthcare Bio-Sciences AB, Sweden) density gradient centrifugation after which the cells were washed first in PBS with 2 mM EDTA and second in lymphocyte culture media. Cell viability was assessed by exclusion of 0.02% Trypan Blue and was always above 95%. The cell suspension was counted in a haemocytometer. PBMCs were suspended in the culture medium without sera and the cell concentration adjusted to $1\times10^6$ lymphocytes/ml for proliferation assays and $6.4\times10^5$ for migration assays respectively. The lymphocyte culture medium RPMI 1640 (Invitrogen, Sweden) was complemented with 1% Penicillin/Streptomycin (Invitrogen, Sweden) and 4 mM Gluta-Max (Invitrogen, Sweden). For CD3 induced proliferation the plates were coated with purified anti-human CD3 antibodies (BD Pharmingen, Sweden). Therefore 50 µl of 2.5 µg/ml antibody PBS solution were pipetted into each well incubated for 1 hour. Cells were cultured for 4, 5 or 7 days in a humidified, 5% CO2-atmosphere at 37° C. Cell proliferation was assayed by the mitochondrial activity test CellTiter 96® AQueous Non-Radioactive Cell Proliferation Assay (MTS, Promega, Sweden) during the last 4 hours. To each well 10 µl of the MTS solution was added and measured after 4 hours of incubation at 37° C. The measured values of the reference dye were subtracted of each well. The peptide solutions were prepared by dissolving peptides 3028, SCF28R, 28209 and SCF27 (Schafer-N, Copenhagen, Denmark) in lymphocyte media to a concentration of 25 µg/ml. The final concentration in the cultures was 5 or 10 µg/ml.

Figure 8:
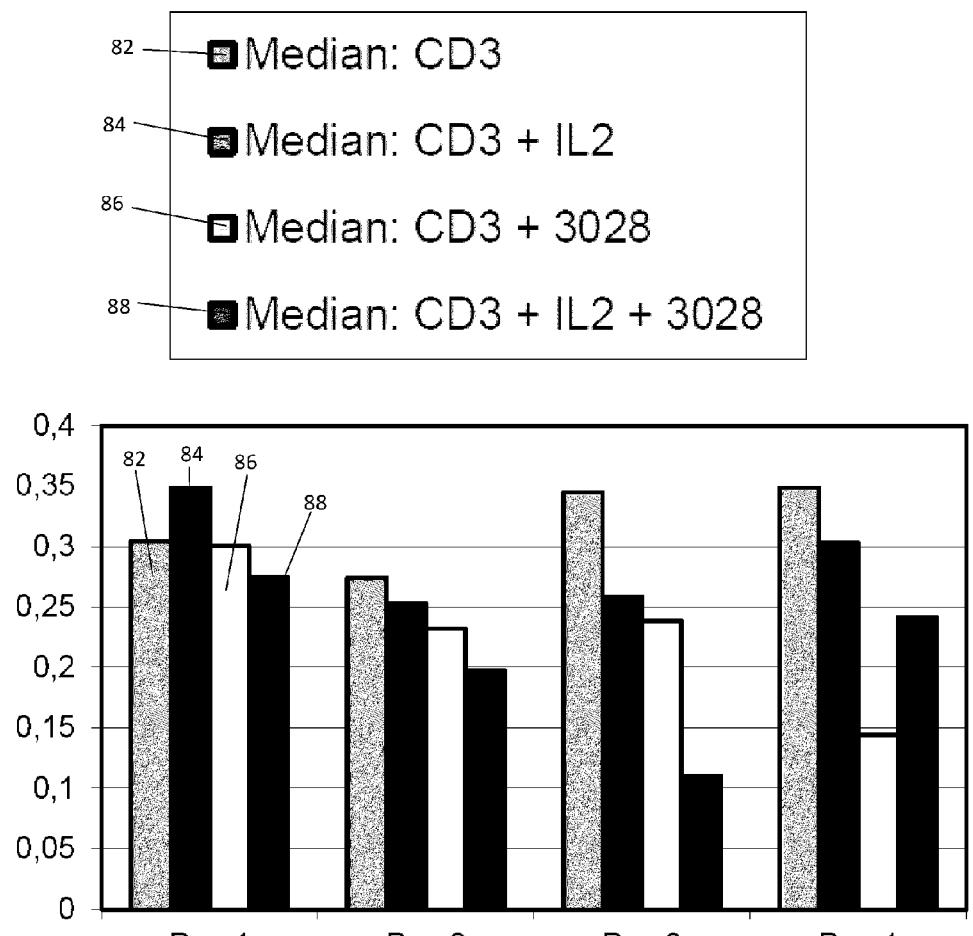
FIG. 8 illustrates effect of P3028 on TCR stimulated lymphocyte proliferation of PBMCs from four healthy persons.

T cells were stimulated in cultures on plates pre-coated with a monoclonal antibody directed against CD3 and the number of metabolically active cells (i.e., cell proliferation) was determined using MTS staining after 3 to 7 days of culture. Detection of solid phase CD3 monoclonal antibody was used as a measurement of T cell proliferation. FIG. 8 illustrates the effect of P3028 on TCR stimulated lymphocyte proliferation of PBMCs from four healthy persons. For each person, proliferation of lymphocytes was measured in the absence of stimulation 82, IL-2 stimulation 84, treatment with P3028 alone 86, and IL-2 stimulation plus P3028 88. Bars of the bar graph of FIG. 8 are in the same order for each person.

As can be seen in FIG. 8, P3028 had an inhibitory effect in at least three out of four experiments (p<0.001). It is unlikely that reduced MTS staining caused by P3028 was be due to a reduced cell metabolism. Taken together, the results from both models of lymphocyte proliferation, a reduced metabolism should reasonably reduce the endogenous thymidine pools and thereby result in an increased uptake of exogenous thymidine/specific activity of the thymidine pools, which then should be erroneously registered as an enhanced proliferation. The $^3$H-TdR was actually reduced in these experiments, indicating inhibition of proliferation.

Example 4

Effect of P3028 on NK-Cell Cytotoxicity

The NK-cell cytotoxic activity of blood mononuclear cells from four healthy donors was tested. Mononuclear cells were separated by standard Ficoll-paque Plus (Pharmacia AB, Sweden) density gradient centrifugation from heparinized blood obtained from healthy donors. NK cell cytotoxic activity of the mononuclear cells was then tested using a commercial kit (NKTEST, Orpegen Pharma GmbH, Heidelberg, Germany) following the manufacturers protocol. Briefly, the kit contains cryopreserved, NK-sensitive target cells (K562) labeled with a lipophilic green fluorescent membrane dye, which enables discrimination of effector and target cells. After incubation with effector cells, killed target cells are identified by a DNA-stain, which penetrates and specifically stain the nuclei of dead target cells. This way the percentage of killed targets can be determined by flow cytometry. The mononuclear cells were preincubated for 30 min at 37° C. with the indicated peptides (peptides have been described previously) at 10 ug/ml. Target cells were then added, giving an effector:target ratio of 40:1, and the cell mixture incubated at 37° C. for 3-4 hours. Samples were analysed on a FACSCalibur (BD Biosciences, San Jose, Calif.).

Figure 9A:
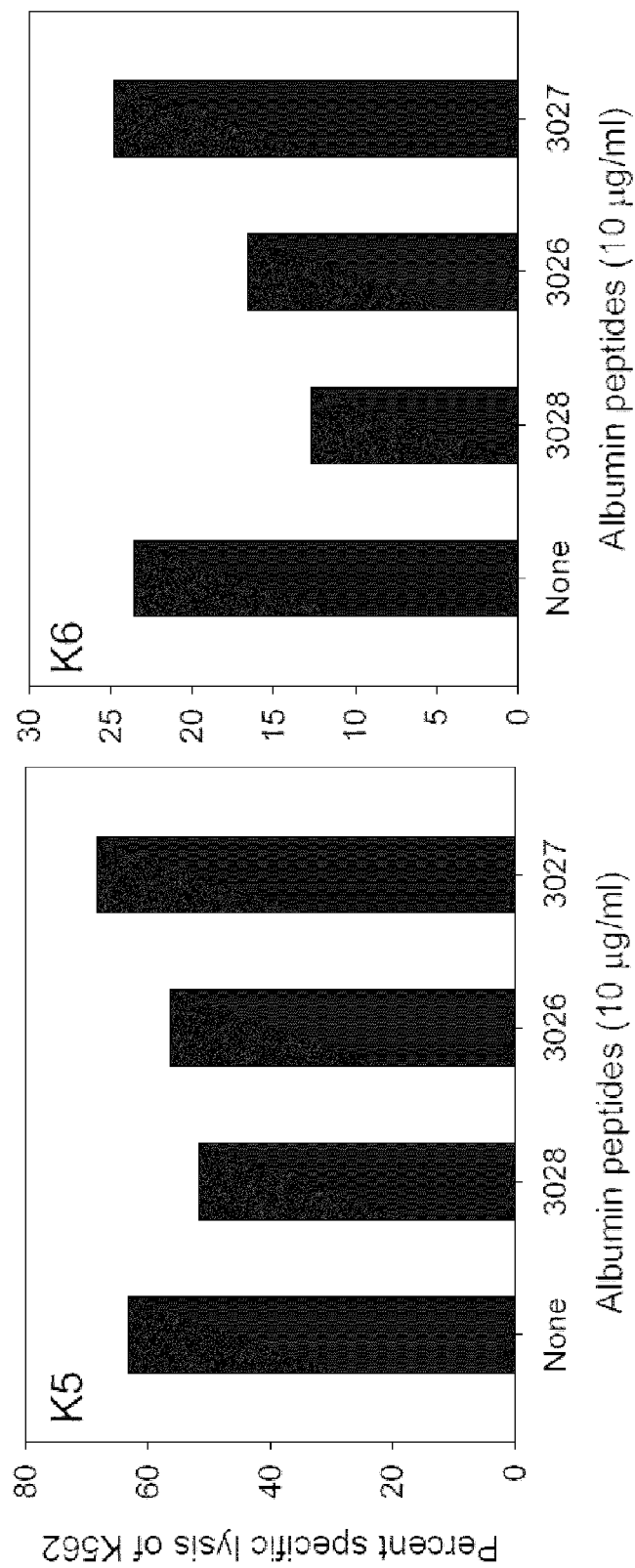
FIGS. 9A-9B illustrates effect of albumin peptides on NK-cell cytotoxicity.
Figure 9B:
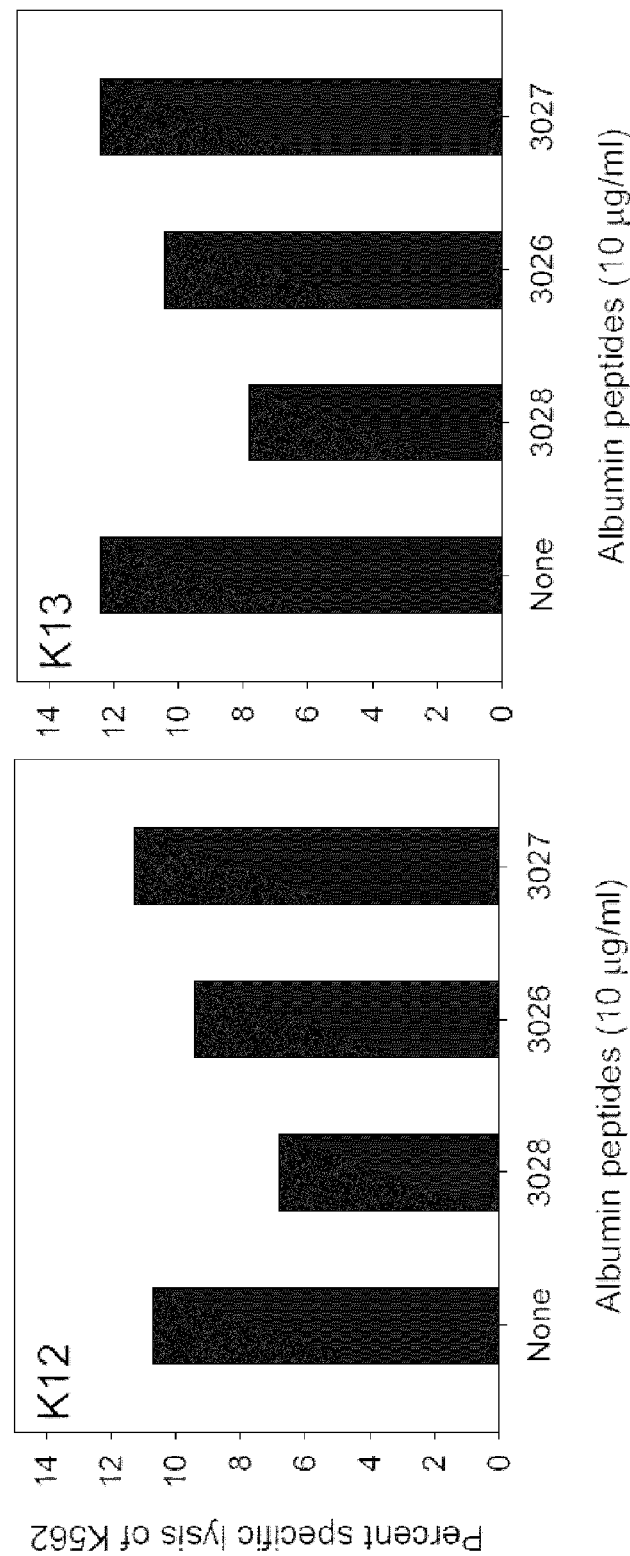

FIGS. 9A-B illustrate the effect of albumin peptides on NK-cell cytotoxicity (p=0.015, paired t-test, normal transformation log-values). As shown in FIG. 9A-B, the presence of P3028 and, to a lesser degree, peptide 3026 reduced the percent specific lysis of K562 target cells by all four donors. Inhibition was not seen in the presence of the control sample peptide 3027 with no structural relationship with P3028. Inhibition of NK-cell cytotoxicity, in this model, was not due to an effect of P3028 on the activity of IL-2 as no IL-2 was added to the short-term cultures.

Example 5

Effect of P3028 on Leukocyte Spreading and Immune Cell Migration

In properly functioning immune systems, immune cells are recruited to tissues, and migrate within tissues. The effect of P3028 in two functional tests, leukocyte spreading and immune cell migration was investigated.

Leukocyte Spreading

Figure 10:
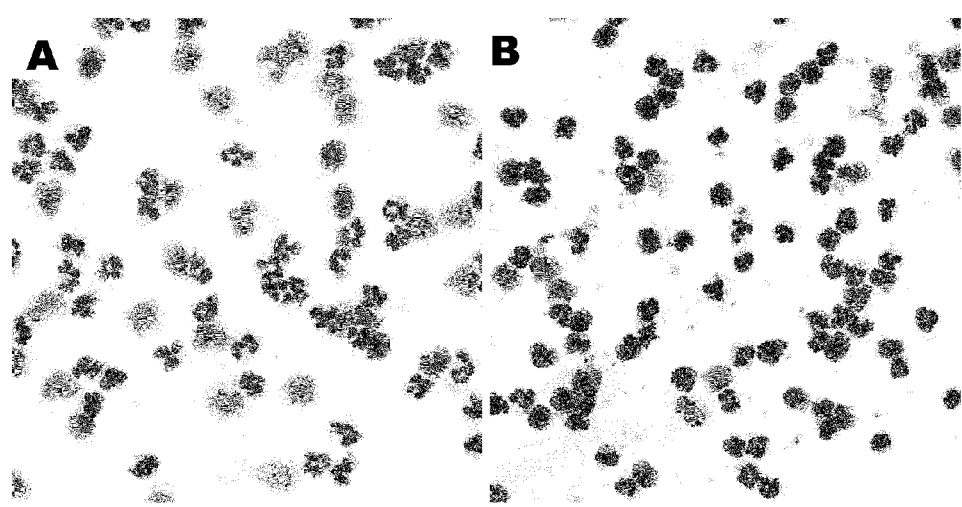
FIG. 10 illustrates effect of P3028 on the spreading on peripheral blood leukocytes.

To analyze the effect of P3028 on leukocyte spreading, buffy coat cells were prepared from heparinized blood by Dextran assisted sedimentation. These cells were then washed twice in PBS and transferred to slides washed in 70% and 96% ethanol. The cell suspension was dropped onto the slides and incubated for 15 min in a moist chamber with or without P3028, 10 µg/ml, the solution was carefully drained off, the slides were air dried and stained in May Grünewals Giemsa for 1 minute. As shown in FIG. 10A, the cells strongly adhered to the glass surface and spread out. Pre-treatment of these cells with P3028 efficiently inhibited the spreading (see FIG. 10B).

Immune Cell Migration

Blood for PBMC isolation was provided from healthy control samples in 50 ml transfusion bags with acid dextrose citrate solution A. Whole blood was diluted 1:1 in PBS containing 2 mM EDTA. PBMCs were then isolated by Ficoll-paque Plus (GE Healthcare Bio-Sciences AB, Sweden) density gradient centrifugation after which the cells were washed first in PBS with 2 mM EDTA and second in lymphocyte culture media. Cell viability was assessed by exclusion of 0.02% Trypan Blue and was always above 95%. The cell suspension was counted in a haemocytometer. PBMCs were suspended in the culture medium without sera and the cell concentration adjusted to $1 \times 10^6$ lymphocytes/ml for proliferation assays and $6.4 \times 10^5$ for migration assays respectively. The lymphocyte culture medium RPMI 1640 (Invitrogen, Sweden) was complemented with 1% Penicillin/Streptomycin (Invitrogen, Sweden) and 4 mM GlutaMax (Invitrogen, Sweden). For CD3 induced proliferation the plates were coated with purified anti-human CD3 antibodies (BD Pharmingen, Sweden). Therefore 50 µl of 2.5 µg/ml antibody PBS solution were pipetted into each well incubated for 1 hour. Cells were cultured for 4, 5 or 7 days in a humidified, 5% $CO_2$-atmosphere at 37° C. Cell proliferation was assayed by the mitochondrial activity test CellTiter 96® AQueous Non-Radioactive Cell Proliferation Assay (Promega, Sweden) during the last 4 hours. To each well 100 of the MTS solution was added and measured after 4 hours of incubation at 37° C. The measured values of the reference dye were subtracted of each well. The peptide solutions were prepared by dissolving peptides 3028, SCF28R, 28209 and SCF27 (Schafer-N, Copenhagen, Denmark) in lymphocyte media to a concentration of 25 µg/ml. The final concentration in the cultures was 5 or 10 µg/ml.

50 µl of the prepared $6.4 \times 10^5$ PBMC dilution were pipetted into Eppendorfs tubes and centrifuged for 5 minutes at 400 g, then the prepared dilutions of blank, P3028 and the inhibitors were added. The PBMCs were incubated at the 37° C. with the test substances for one hour. Meanwhile the Boyden Chamber was prepared by pipetting 25 µl of either media without fMLP or media containing 1×10-8M fMLP to the lower wells. Then 50 µl of the PBMCs final concentration, 3.2×104, were transferred to the upper wells of the chamber. The PBMCs were allowed to migrate for one hour at the 37° C. The filters were removed and stored in 70% ethanol overnight. Thereafter the filters were dehydrated in increasing alcohol concentration and finally placed in Xylene. Subsequently they were placed on slides, mounted and counted with a microscope, containing a µm scale. Each test was done in duplicates and migration was calculated as percentage of the mean of the blank duplicates without fMLP. As shown in FIG. 11, P3028 is a potent inhibitor of immune cell migration across the membrane of the Boyden chamber (p<0.002). Migration for healthy control samples (N=6) is illustrated in FIG. 11 using dark bars (left), while cancer patients (N=3) are shown as light bars (right). In FIG. 11, Error bars: 95% CI. P3028 reduced the migration of PBMCs of both healthy cells and cancer patients.

Example 6

Further Characterization of the Effect of P3028 on IL-2 Induced Proliferation

Figure 12:
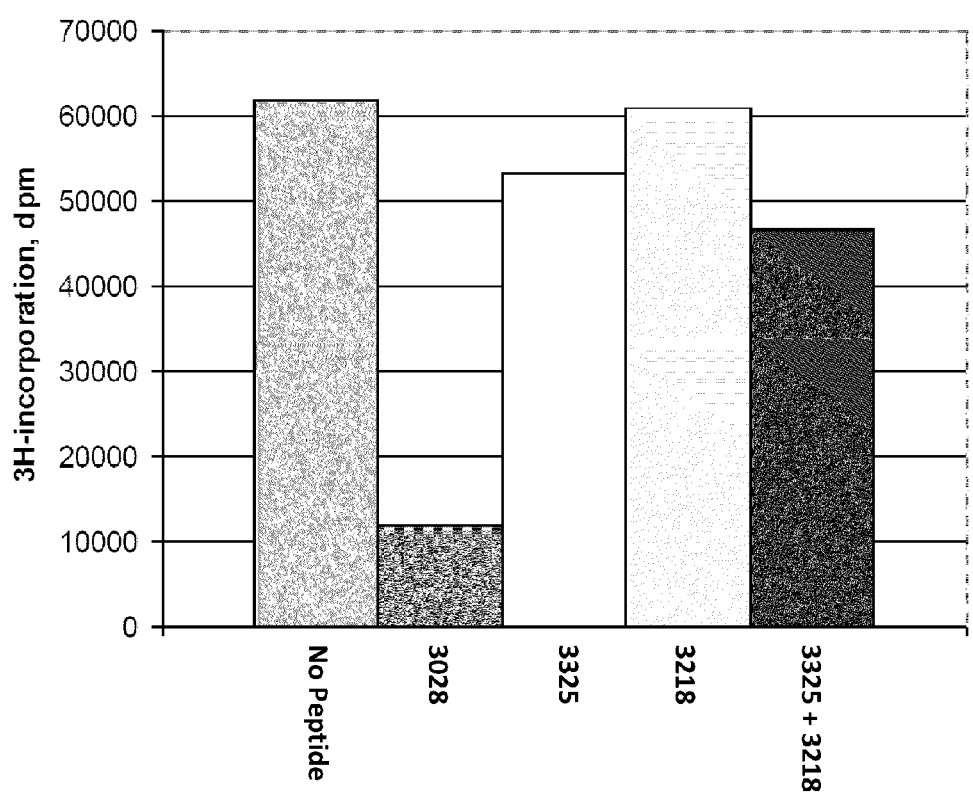
FIG. 12 illustrates effect of the C- (3218) and N-terminal (3325) parts of P3028 on 11-2 induced proliferation in comparison with the effect of the full length P3028.
Figure 13:
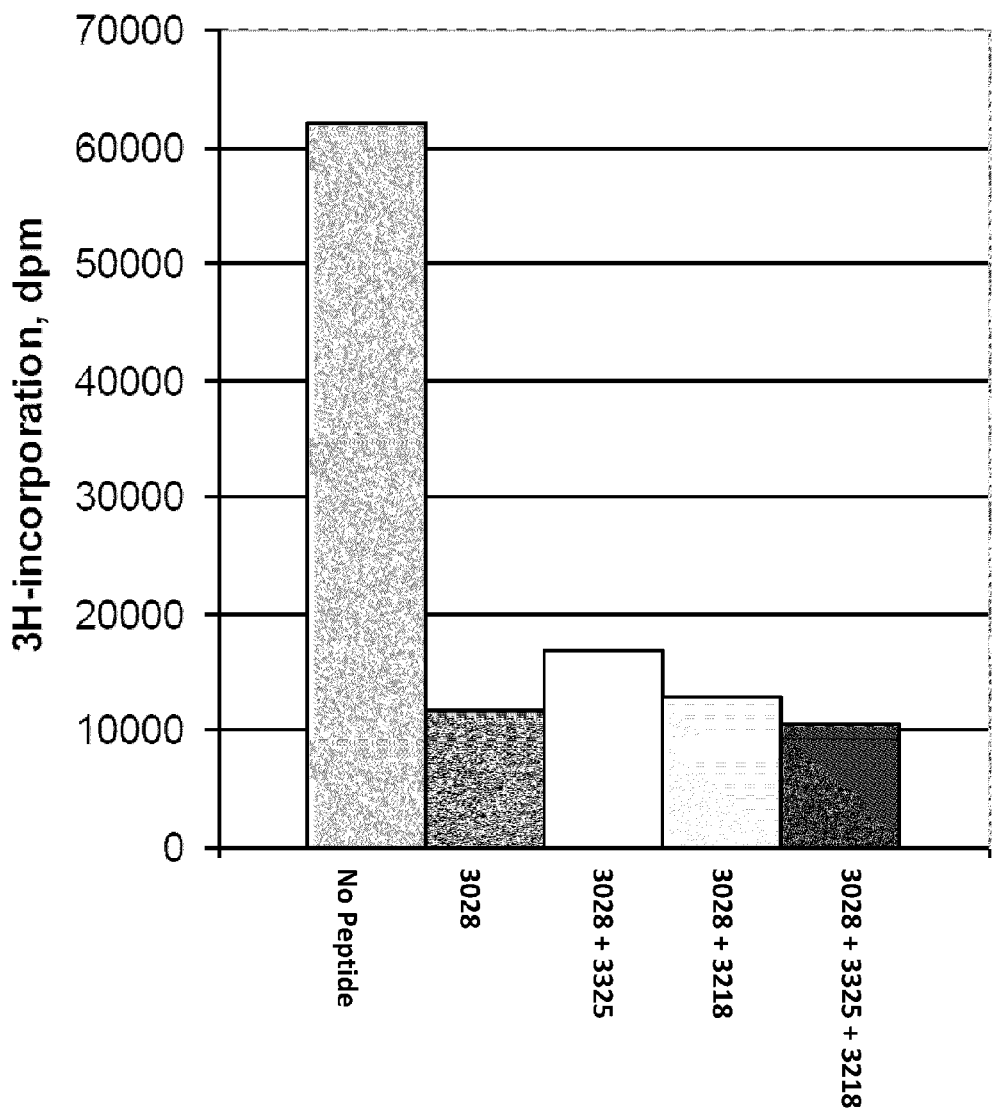
FIG. 13 illustrates the inhibitory effect of P3028 on IL-2 induced proliferation is not neutralized by the C- (3218) and N-terminal (3325) parts of P3028 alone or in combination.

The C and N-terminal parts of P3028 were synthesized and analyzed separately and in combination. The inhibitory activity of these two parts of P3028 alone or in combination is much weaker (see FIG. 12) and they do not inhibit the effect of P3028 on IL-2 induced proliferation (see FIG. 13) in the ex vivo human model. FIG. 12 illustrates effects of the C- (P3218) (SEQ ID NO: 187) and N-terminal (P3325) (SEQ ID NO: 186) parts of P3028 on 11-2 induced proliferation in comparison with the effect of the full length P3028. One representative experiment is shown. FIG. 13 illustrates that the inhibitory effect of P3028 on IL-2 induced proliferation is not neutralized by the C- (P3218) and N-terminal (P3325) parts of P3028 alone or in combination.

Example 7

Binding of P3028 to LFA-1

The presence of β2-integrins on PBMCs was demonstrated by immunocytochemical staining. The occurrence of factors interfering with the binding of monoclonal antibodies directed against β2-integrins in cancer patient sera was analysed by staining of β2-integrins on PBMCs. A standard immunohistochemical staining procedure using acetone fixation, 10% human AB-serum for blocking, incubation with anti-LFA-1 antibody. PBMCs were separated as described above and immediately spun down on pre-cleaned microscope slides in a Shandon Cytospin (Shandon Scientific Ltd, UK) at 1000 RPM for 7 min at 5×104 cells per slide. The slides were left to dry at room temperature over night, after which they were wrapped in parafilm and stored at 70° C. Immediately before use, the cytospins were thawed and fixed with acetone for 5 min at room temperature. The cytospins were first blocked with 10% normal human AB-serum with and without albumin peptides (40 µg/ml) or serum from cancer patients for 1 h before staining. Primary antibody, consisting of a monoclonal mouse anti-human CD11a (BD Biosciences) diluted in Tris buffered saline (TBS, pH 7.6) at 1 µg/ml (PBMC), was added. The slides were incubated for 30 min and then washed in TBS followed by Envision-Alkaline Phosphatase (Dako Norden A/S, Denmark) or, alternatively, Ultravision-Alkaline Phosphatase (Lab Vision Co) for 30 min. After additional washing in TBS, the slides were incubated in alkaline phosphatase substrate consisting of Fast Red TR salt (Sigma), naphtol AS-MX (Sigma) and 5 mM levamisol (Sigma) to block endogenous alkaline phosphatase activity, for 20 min followed by washing in TBS. They were then counterstained in Mayer's haematoxylin for 1 minute and mounted in Glycergel (Dako Norden A/S). Monoclonal mouse IgG1 against an irrelevant antigen (Aspergillus niger glukosoxidase, Dako Norden A/S) was used as a negative control sample. All incubations were performed at room temperature in a moist chamber.

Pre-incubation with peptides added to the AB serum was either no peptide added (see FIG. 15A), or P3028 added (see FIG. 15B). Notably, the anti-LFA-1 antibody used in these experiments was a potent inhibitor of IL-2 induced proliferation.

Figure 14:
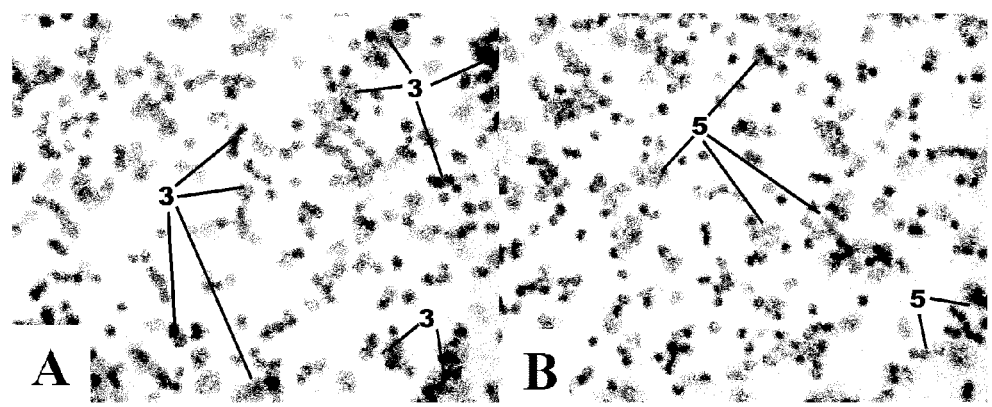
FIG. 14 illustrates inhibition of the binding of anti-LFA-1 antibody directed to CD11a by incubation of normal PBMCs with patient sera.

As shown in FIG. 14, the presence of β2-integrin blocking factors was then demonstrated as a reduced stainability 5 of these cells after incubation with cancer patient sera (see FIG. 14B), compared to preparations pre-incubated with control serum sample (see FIG. 14A) which showed strong staining 3 for LFA-1.

As shown in FIG. 15, similar to the results described for cancer patient sera, treatment with P3028 can modulate the binding of the LFA-1 antibody to LFA-1 of mononuclear blood cells, FIG. 15 illustrates inhibition of the binding of an anti-LFA-1, mAb, to mononuclear blood cells by P3028. Strong staining 3 for LFA-1 was observed in cells in which no peptide was added (see FIG. 15A), while weak staining 5 for LFA-1 was observed in cells in which P3028 was added (see FIG. 15B).

In order to further demonstrate the blockade of LFA-1 by the P3028 structure, the staining of this integrin on PBMCs from healthy control samples and cancer patients was compared. FIG. 16 illustrates staining of LFA-1 on PBMCs from a healthy control sample (see FIG. 16A), and a cancer patient before (see FIG. 16B) and after (see FIG. 16C) treatment with an antibody directed against P3028. As shown in FIG. 16A, a clear membrane staining 3 is found on PBMCs from healthy control samples in contrast to PBMCs from a patient with advanced cancer, which exhibited weak staining 5. However, when the PBMCs from this patient were incubated with an antibody directed towards the P3028 structure for 24 hours the membrane staining appeared 3, indicating that the antibody bound the P3028-structure and thereby unblocked LFA-1 (see FIG. 16C).

Figure 17:
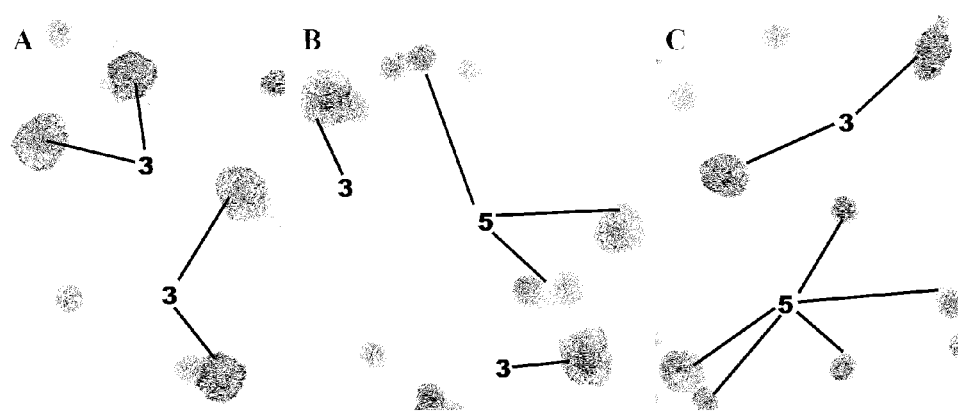
FIG. 17 illustrates staining of mononuclear blood cells by an anti-LFA-1 antibody (A) is blocked by P3028 (B) or cancer patient serum (C).

Similarly, as shown in FIG. 17, incubation of PBMCs from a healthy control sample with either P3028 or serum from a cancer patient blocked the membrane staining of LFA-1. FIG. 17 illustrates staining 3 of mononuclear blood cells by an anti-LFA-1 antibody (A) is blocked 5 by P3028 (B) or cancer patient serum (C).

Example 8

Binding of P3028 to the α-Chain (CD25) of the IL-2 Receptor

Figure 18B:
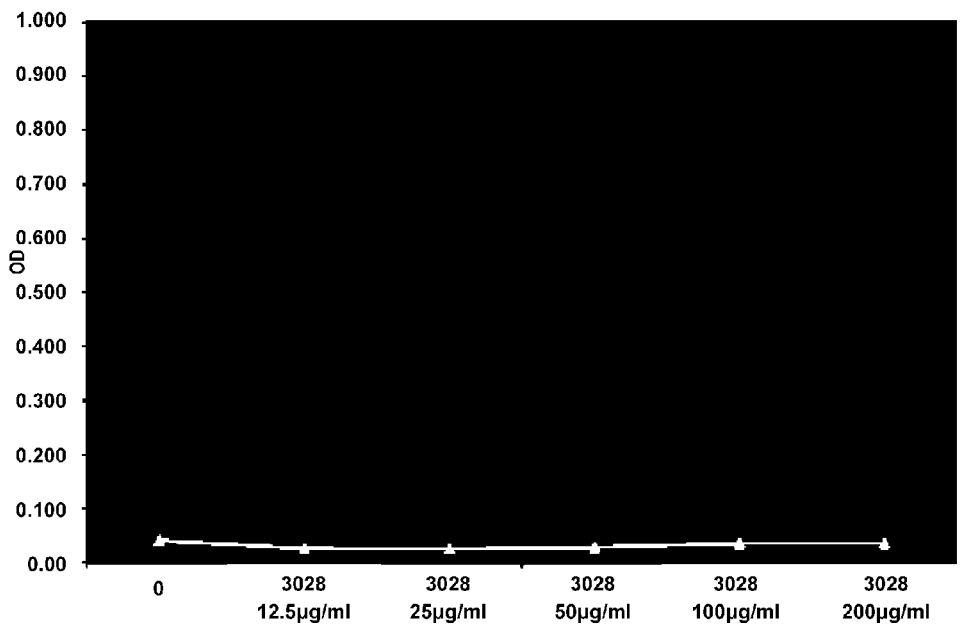

Because P3028 significantly inhibits the proliferative response to IL-2, the effect of P3028 on the binding of IL-2 to its receptor, CD25 was studied. The fusion protein of CD25 and the Fc-part of IgG was bound to protein G coated micro-plates/ELISA plates and the plates were incubated with biotinylated IL-2 with or without P3028 present. FIG. 18-B illustrate the results of this ELISA analysis for dilution of biotinylated IL-2 that were as follows: (diamond ♦) 1:300, (square ■) 1:600, (triangle ▲; see FIG. 18B) no biotinylated IL-2. The binding of biotinylated IL-2 to rhuIL-2R alpha was increased by increasing amounts of P3028. Surprisingly, the binding of IL-2 to CD25 was enhanced by P3028, indicating a three-part interaction between IL-2, CD25 and P3028 (see FIG. 18-B). Even if the binding of IL-2 to CD25 is enhanced the proper assembly of the high affinity receptor and/or signal transduction is blocked as P3028 is a potent inhibitor of IL-2 induced proliferation.

It was demonstrated using computer assisted molecular modeling that P3028 binds to CD25 at the IL-2 binding site (see FIG. 19). The crystal structure of the IL-2 receptor bound to IL-2 is known in the art (see Wang et al., Science 2005, 310(5751): 1159-1163, and Stauber et al, Proc. Natl. Acad. Sci. USA 2006, 103(8): 2788-2793, each of which is hereby incorporated by reference in its entirety), and binding of P3028 was modeled according. In FIG. 19, the α-chain 190 of the IL-2 receptor (CD25) binding P3028 192 (A) at the IL-2 binding site 194 (B) is depicted. IL-2 196 is also shown.

Example 9

Antibodies that Bind to P3028

Rabbit antisera directed against the albumin P3028 were generated. P3028 was synthesized with a cysteine added to the N-terminus end and then conjugated with keyhole limpet hemocyanin (KLH) as a carrier protein. Polyclonal antisera were generated by repeated immunizations of rabbits with KLH-conjugated P3028 and Freund's adjuvants. For some experiments, the antisera were affinity purified by chromatography on P3028-conjugated Ultralink Iodoacetyl gels (Pierce Biotechnology Inc.). For cell culture experiments, buffer exchange to RPMI 1640 Dutch's modification (Gibco, InVitrogen AB, Stockholm, Sweden) was performed by passage over PD-10 sephadex columns (Amersham Biosciences, Uppsala, Sweden) followed by filter sterilization on 0.22 µm Millex syringe filters (Millipore Co., MA, USA). Rabbit immunizations and purification of antisera were carried out by Agrisera AB, Sweden.

Figure 20:
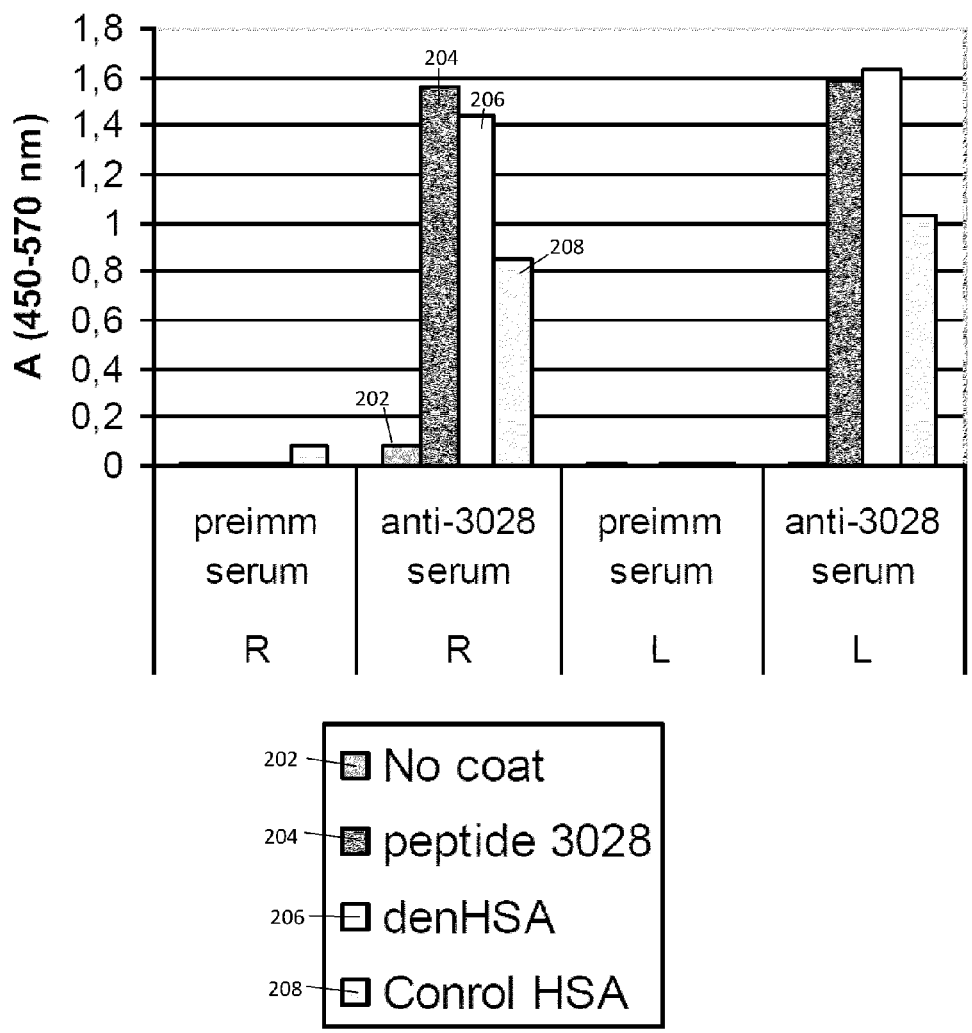
FIG. 20 illustrates antisera from rabbits immunized with P3028 binds to P3028.

Two antisera, R and L, from two different rabbits were tested for their ability to bind human serum and denatured Human Serum Albumin (dHSA). Human serum albumin commercially available for therapeutic purposes was tested, heated 10 times in order to be virus free. Wells were coated with the P3028, dHSA, or control sample treated (not denatured, but heated 10 times) HSA, which has been prepared just as the denatured HSA except for the denaturation procedure. As shown in FIG. 20, antisera, but not preimmune sera, from two rabbits immunized with the albumin P3028 bind to plates coated with the P3028 204, dHSA 206 and, to a lesser extent, to control sample treated HSA 208. No substantial binding was detected for wells with no coat 202. Thus, rabbit antisera directed against the albumin P3028 binds to dHSA and to a lesser extent to control sample HSA.

Figure 21:
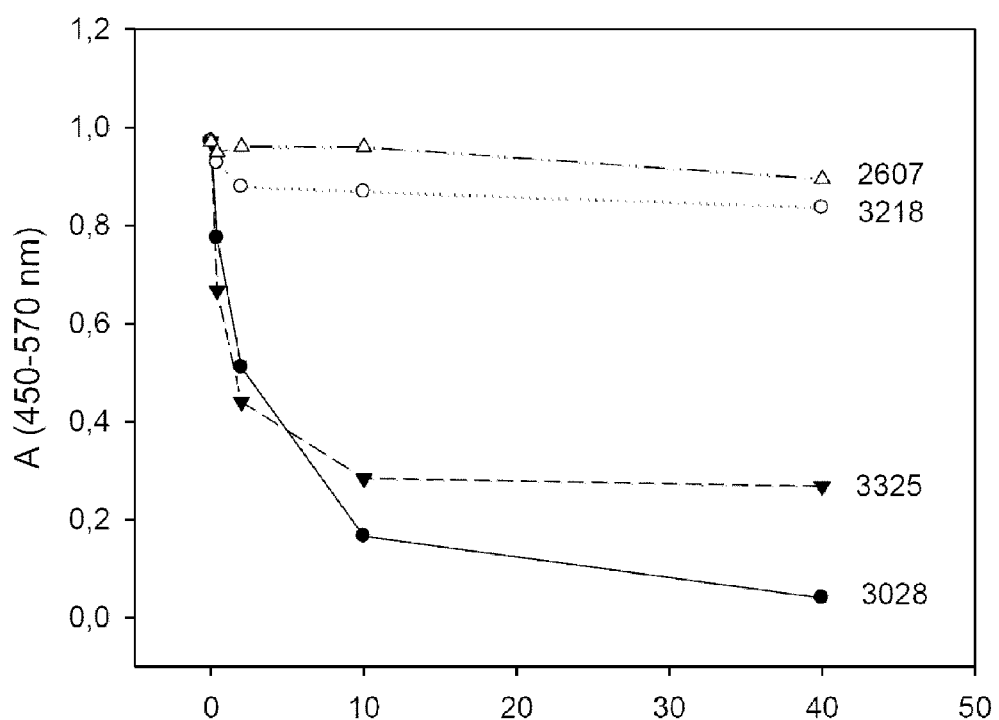
FIG. 21 illustrates inhibition of the binding of rabbit-anti 3028 serum L to wells coated with the P3028 in an ELISA by albumin peptides

The binding of the rabbit anti-P3028 serum to P3028 fragments was assayed using competition ELISA assay. Rabbit antisera, diluted 1/1000 000 in ELISA reagent diluent, was pre-incubated for 1 hr at room temperature with the indicated concentrations of the peptides. 100 μl of the monoclonal antibody alone, or, alternatively, the monoclonal antibody mixed with peptides, was then added to P3028 coated wells and the ELISA carried out. Inhibition of the binding of rabbit anti-P3028 serum L to wells coated with the P3028 was determined for albumin peptides 2607 (SEQ ID NO: 192), 3218 (C terminal of P3028) (SEQ ID NO: 187), 3325 (N terminal of P3028) (SEQ ID NO: 186), and full-length P3028 (SEQ ID NO: 185). Peptide 2607, containing the E5K structure, was used as a negative control sample. As shown in FIG. 21, these serum antibodies bound preferentially to the 3325 but not to the 3218 fragment of P3028. Similar results are also obtained with the affinity purified antibodies.

The effects of affinity purified antibodies directed against P3028 on the proliferative response to IL-2 were studied in the ex vivo model, using PBMCs from immunosuppressed cancer patients and normal control samples. Cultures to test the immunomodulatory effect of affinity purified rabbit antibodies specific for 3028 were performed as described above for IL-2 induced proliferation with the following exceptions; 2% HSA was omitted from the washing medium and from the PBMC suspension medium. Serum containing culture medium (100 μl/well) was pre-incubated with 20 μg/ml of rabbit antibodies for 30 min at room temperature before the addition of 100 μl PBMC suspension to the culture wells.

Figure 22A:
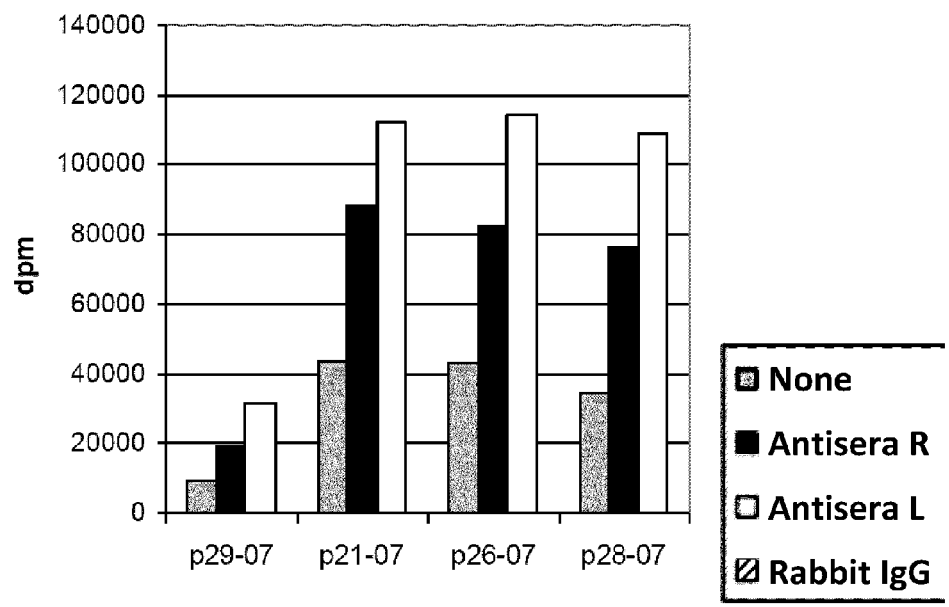
FIG. 22 illustrates effect of affinity purified antibodies directed against P3028 on the proliferative response to IL-2 of PBMCs from immunosuppressed cancer patients and normal control samples.
Figure 22B:
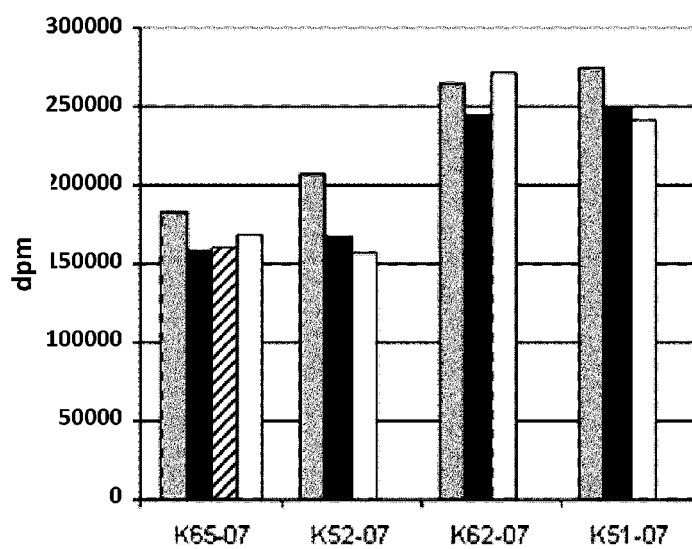

P21 had renal cell carcinoma and p26, p28 and p29 had malignant melanoma. As shown in FIG. 22, affinity-purified rabbit antibodies against P3028 overcame inhibition of the proliferative response to IL-2 in immunosuppressed cancer patients (FIG. 22A). In normal control samples with normal proliferative response to IL-2, no effect of addition of these antibodies was seen (see FIG. 22B) (antibody: R., cancer patients, p=0.0002, paired t-test, normal transformation log-values). In normal control samples with down-regulation of the immune reactivity having a proliferative rate of less than 100,000 dpm, the proliferative rate was stimulated similar to the situation in cultures from cancer patients.

Polyclonal rabbit IgG was added to control sample cultures in order to make sure that the effect of the affinity purified antibodies was not due to an unspecific activity of rabbit IgG in this model. Rabbit IgG had only minimal activity. The specificity of the anti-P3028 antibodies was further demonstrated as the stimulatory effect of these antibodies was neutralized by a small amount of P3028 having no inhibitory activity per se. Similar to the results in the autologous ex vivo model, the immunosuppressor activity of sera from persons with a low proliferative response to IL-2 was over-come by addition of the anti-P3028 antibodies to the cultures.

Example 10

Peptides that Bind to P3028

The information obtained by studying the effect of cancer patient sera and the synthetic peptide P3028, on staining of the α-chain, CD11a, of LFA-1 on PBMCs was used in order to design the structure of a potential binder/inhibitor of the immunomodulatory peptide P3028. The epitope of the particular monoclonal mouse antibody used, HI 111, was mapped to residues 249-300 of CD11a (Ma Q, et al., J Biol Chem. 2002; 277:10638-41). Based on complementarity of charged and hydrophobic amino acid sequences the first candidate binding to the P3028 peptide was designed. This sequence was then optimized by synthesizing and testing the binding efficacy of candidate peptides where each amino acid was substituted for all 19 L-amino acids.

Three candidate peptide inhibitors of P3028 sequences/structures were identified and their blocking capacity in solution was tested. Potential peptide inhibitors of P3028 were synthesized on a chip. The linear and/or CLIPS peptides were synthesized based on the amino acid sequence of the target protein using standard Fmoc-chemistry and deprotected using trifluoric acid with scavengers. The constrained peptides were synthesized on chemical scaffolds in order to reconstruct conformational epitopes, using Chemically Linked Peptides on Scaffolds (CLIPS) technology (Timmerman et al. (2007)). For example, the single looped peptides were synthesized containing a dicysteine, which was cyclized by treating with alpha, alpha'-dibromoxylene and the size of the loop is varied by introducing cysteine residues at variable spacing. If other cysteines besides the newly introduced cysteines are present, they were replaced by alanine. The side-chains of the multiple cysteines in the peptides are coupled to CLIPS templates by reacting onto credit-card format polypropylene PEPSCAN cards (455 peptide formats/card) with a 0.5 mM solution of CLIPS template such as 1,3-bis (bromomethyl) benzene in ammonium bicarbonate (20 mM, pH 7.9)/acetonitrile (1:1(v/v)). The cards were gently shaken in the solution for 30 to 60 minutes while completely covered in solution. Finally, the cards are washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes. The binding of His-tagged P3028 to each peptide was tested in a PEPSCAN-based ELISA. The 455-well credit card format polypropylene cards containing the covalently linked peptides are incubated with peptide solution for example consisting of 1 micrograms/mL diluted in blocking solution, for example 4% horse serum, 5% ovalbumin (w/v) in PBS/1% TWEEN reagent. After washing, the peptides were incubated with a monoclonal mouse anti-his tag antibody (1/1000, Novagen, 70796-3) and subsequently after washing with a rabbit-anti-mouse antibody peroxidase conjugate (1/1000, Southern Biotech, 6175-05) for one hour at 25° C. After washing, the peroxidase substrate 2,2'-azino-di-3-ethylbenzthiazoline sulfonate (ABTS) and 2 microliters of 3 percent $H_2O_2$ were added. After one hour, the color development was measured. The color development was quantified with a charge coupled device (CCD)—camera and an image processing system.

The raw data (Raw Data: Optical density, Arbitrary OD units) are optical values obtained by a CCD-camera. The values mostly range from 0 to 3000, a log scale similar to 1 to 3 of a standard 96-well plate ELISA-reader. First the CCD-camera makes a picture of the card before peroxidase coloring and then again a picture after the peroxidase coloring. These two pictures are subtracted from each other which results in the data which is called raw-data. This is copied into the Peplab™ database. Then the values are copied to excel and this file is labeled as raw-data file. One follow-up manipulation is allowed. Sometimes a well contains an air-bubble resulting in a false-positive value, the cards are manually inspected and any values caused by an air-bubble are scored as 0.

As shown in Position 17, 22 and 26 contained good binders of P3028 (PGE73=His-tag-P3028). As shown in the diagram, peptide SCF28 and SCF29 efficiently block the binding of P3028 (PGE73) but SCF27 does not. Peptide SCF28 (SEQ ID NO: 1), had a solubility good enough to allow testing in biological human ex vivo models. Based on this structure, peptide P28R (SEQ ID NO: 2) was developed. For each position, shown are data for no peptide added assay in PBS buffer 230, SCF027 assay in PBS buffer 232, SCF029 assay in PBS buffer+10% DMSO 234, no peptide added in PBS buffer+10% DMSO 236, and SCF028 assay in PBS buffer+10 DMSO 238. In the bar graph of FIG. 23, bars representing each assay were in the same left-to-right order for each position. Each peptide, when present in an assay, was at a concentration of 0.5 mg/mL.

Example 11

Peptide Interactions with P3028

The information obtained by studying the effect of cancer patient sera and the synthetic peptide P3028, on staining of the alpha-chain, CD11a (SEQ ID NO: 248), of LFA-1 on PBMCs was used in order to design the structure of a potential binder/inhibitor of the immunoinhibitory peptide P3028. The epitope of the particular monoclonal mouse antibody used, HIM, was mapped to residues 274-325 of CD11a, (SEQ ID NO: 248) (UniProt accession code P20701; Ma Q, et al., J Biol Chem. 2002; 277: 10638-41). Based on complementarity of charged and hydrophobic amino acid sequences (see FIG. 31) the first candidate binding to the P3028 peptide was designed using the sequence comprising 312-326 of CD11a. This resulted in the peptide KKL15 (SEQ ID NO: 1).

Peptide KKL15 (SEQ ID NO: 1), for example appears to be complementary to P3028. As shown in FIG. 31, positively charged amino acids interact with negatively charged amino acids of P3028 and hydrophobic amino acids make hydrophobic contacts enhancing the interaction.

Example 12

Peptides that Bind to P3028

Based on the structure of peptide P28R, additional peptides were identified that bind to P3028. The additional binders included deletions, truncations, and or amino acid substitutions of peptide P28R. Binding of peptides to P3028 was assayed using PEPSCAN technology. PEPSCAN technology, or "rampo" assays are biochemical binding assays, details of which are provided below:

A peptide microarray screening technology was used to measure binding of P28 (SEQ ID NO: 2) and variants of P28R to P3028 (SEQ ID NO: 185). In this technology libraries of synthetic peptides are synthesized and covalently linked onto polypropylene microarray chips. The linear peptides were synthesized onto credit-card format polypropylene cards (455 peptide formats/card) as described by (Timmerman et al., 2004) using standard Fmoc-chemistry using hexamethylenediamine (HMDA) as linker and deprotection using trifluoroacetic acid (TFA) with scavengers.

The binding of His-tagged P3028 to each peptide on the card was tested in an ELISA assay. The 455-well credit card format polypropylene cards containing the covalently linked peptides were incubated with His-tagged P3028 peptide (PGE73) solution consisting of 0.5 µg/mL diluted in blocking solution (4% horse serum, 5% ovalbumin (w/v) in PBS/1% TWEEN reagent). After washing, the peptides were incubated with a monoclonal mouse anti-His-tag antibody (Novagen, 70796-3, diluted 1/1000 in the incubation buffer) and subsequently after washing with a rabbit-anti-mouse antibody peroxidase (Rampo) conjugate (Southern Biotech, 6175-05, diluted 1/1000), for one hour at 25° C. After washing, the peroxidase substrate 2,2'-azine-di-3-ethylbenzthiazoline sulfonate (ABTS) and 2 µL of 3% H2O2 were added. The binding capacity of the mAb was measured as a color development at 405 nm (optical density, OD405). The color development was quantified with a charge-coupled device (CCD)—camera and an image processing system.

The OD405-values obtained by a CCD-camera was considered as raw data values ("rampo values," "rampo units," or "rampo scores"). The values mostly ranged from 0 to 3000, a log scale similar to 1 to 3 of a standard 96-well plate ELISA-reader. First the CCD-camera made a picture of the card before peroxidase coloring and then again a picture after the peroxidase coloring. These two pictures were subtracted from each other, which resulted in the data which was considered raw data. These values were copied into an excel file and labeled as a raw data file. One follow-up manipulation was allowed. Sometimes a well can contain an air-bubble resulting in a false-positive value. If manual inspection of the cards detect an air-bubble the value are set to 0 for that well.

A library of peptides tested for binding to peptide P3028 included all substitutions for each position of the peptide P28R (SEQ ID NO: 2) (i.e., 19 substitutions for each position). The results of the binding experiments are shown in FIGS. 27, 28, 29 and 30 and Table 5.1. Rampo scores ranged between 102 and 1190 for all substitutions in each of the 16 positions of P28R. P28R had rampo values ranging between 262 and 460 with a mean value of 370. As shown in FIG. 28, 31 single-amino acid substitutions of the peptide P28R (SEQ ID NO: 2) had a rampo score above 500. These 31 substituted peptides include SEQ ID NOs: 3-31, and are shown in Table 6.1. Significant higher values were observed for the substitutions M, Q, H, N in position 13 (SEQ ID NOs: 22 to 25, respectively), all with values above 800. In addition, M and S in position 7 (SEQ ID NOs: 9 and 10, respectively), and Q and M in position 11 (SEQ ID NOs: 15 and 16, respectively) all have rampo values over 700.

TABLE 6.1

Peptides that bind to P3028 with a rampo score above 500

| SEQ ID NO | Sequence |
| --- | --- |
| 3 | RKLDTFFVKLSLFTER |
| 4 | KKGDTFFVKLSLFTER |
| 5 | KKEDTFFVKLSLFTER |
| 6 | KKLDQFFVKLSLFTER |
| 7 | KKLDTAFVKLSLFTER |

TABLE 6.1-continued

Peptides that bind to P3028 with a rampo score above 500

| SEQ ID NO | Sequence |
|---|---|
| 8 | KKLDTVFVKLSLFTER |
| 9 | KKLDTFMVKLSLFTER |
| 10 | KKLDTFSVKLSLFTER |
| 11 | KKLDTFVVKLSLFTER |
| 12 | KKLDTFTVKLSLFTER |
| 13 | KKLDTFLVKLSLFTER |
| 14 | KKLDTFFVKVSLFTER |
| 15 | KKLDTFFVKLQLFTER |
| 16 | KKLDTFFVKLMLFTER |
| 17 | KKLDTFFVKLTLFTER |
| 18 | KKLDTFFVKLHLFTER |
| 19 | KKLDTFFVKLSQFTER |
| 20 | KKLDTFFVKLSVFTER |
| 21 | KKLDTFFVKLSMFTER |
| 22 | KKLDTFFVKLSLMTER |
| 23 | KKLDTFFVKLSLQTER |
| 24 | KKLDTFFVKLSLHTER |
| 25 | KKLDTFFVKLSLNTER |
| 26 | KKLDTFFVKLSLPTER |
| 27 | KKLDTFFVKLSLSTER |
| 28 | KKLDTFFVKLSLGTER |
| 29 | KKLDTFFVKLSLATER |
| 30 | KKLDTFFVKLSLRTER |
| 31 | KKLDTFFVKLSLFNER |
| 32 | KKLDTFFVKLSLFPER |
| 33 | KKLDTFFVKLSLFRER |

For each position of P28R, the rampo scores of the group of 19 different peptides containing an L-amino acid substitution were compared to the rampo score of a control sample P28R peptide (SEQ ID NO: 2) for that group. Single-amino acid substitutions having a rampo score greater than or substantially equivalent to P28R were identified. As used herein, a rampo score "substantially equivalent to P28R" is a rampo score that is at least 98% of the rampo score of P28R. Thus, variants of P28R having equivalent or better binding to P3028 were identified.

For example, at position 8 of P28R (SEQ ID NO: 2) is a V. The control sample P28R peptide had a rampo score of 308, and peptides having an F, G, L, P or R at position 8 (SEQ ID NOs: 326-330, respectively) each had a rampo score greater than or equal to 302 (98% of 308). The single amino acid substitutions of P28R having a score greater than or equal to that of the P28R control sample peptide for that group are shown in Table 6.2.

TABLE 6.2

Peptides that bind to a rampo score greater than or substantially equivalent to that of P28R

| SEQ ID NO | Position | Sequence | Rampo Score | Rampo score of P28R control sample |
|---|---|---|---|---|
| 268 | 1 | AKLDTFFVKLSLFTER | 466 | 308 |
| 269 | 1 | DKLDTFFVKLSLFTER | 373 | 308 |
| 270 | 1 | EKLDTFFVKLSLFTER | 396 | 308 |
| 271 | 1 | GKLDTFFVKLSLFTER | 367 | 308 |
| 272 | 1 | HKLDTFFVKLSLFTER | 428 | 308 |
| 273 | 1 | IKLDTFFVKLSLFTER | 483 | 308 |
| 274 | 1 | LKLDTFFVKLSLFTER | 449 | 308 |
| 275 | 1 | MKLDTFFVKLSLFTER | 457 | 308 |
| 276 | 1 | NKLDTFFVKLSLFTER | 445 | 308 |
| 277 | 1 | PKLDTFFVKLSLFTER | 387 | 308 |
| 278 | 1 | QKLDTFFVKLSLFTER | 455 | 308 |
| 279 | 1 | RKLDTFFVKLSLFTER | 523 | 308 |
| 280 | 1 | TKLDTFFVKLSLFTER | 493 | 308 |
| 281 | 1 | VKLDTFFVKLSLFTER | 442 | 308 |
| 282 | 3 | KKADTFFVKLSLFTER | 427 | 375 |
| 283 | 3 | KKCDTFFVKLSLFTER | 432 | 375 |
| 284 | 3 | KKDDTFFVKLSLFTER | 492 | 375 |
| 285 | 3 | KKEDTFFVKLSLFTER | 528 | 375 |
| 286 | 3 | KKFDTFFVKLSLFTER | 393 | 375 |
| 287 | 3 | KKGDTFFVKLSLFTER | 563 | 375 |
| 288 | 3 | KKHDTFFVKLSLFTER | 477 | 375 |
| 289 | 3 | KKIDTFFVKLSLFTER | 454 | 375 |
| 290 | 3 | KKKDTFFVKLSLFTER | 386 | 375 |
| 291 | 3 | KKMDTFFVKLSLFTER | 460 | 375 |
| 292 | 3 | KKNDTFFVKLSLFTER | 374 | 375 |
| 293 | 3 | KKQDTFFVKLSLFTER | 473 | 375 |
| 294 | 3 | KKRDTFFVKLSLFTER | 370 | 375 |
| 295 | 3 | KKSDTFFVKLSLFTER | 393 | 375 |
| 296 | 3 | KKTDTFFVKLSLFTER | 451 | 375 |
| 297 | 3 | KKVDTFFVKLSLFTER | 377 | 375 |
| 298 | 4 | KKLATFFVKLSLFTER | 494 | 414 |
| 299 | 4 | KKLETFFVKLSLFTER | 417 | 414 |
| 300 | 4 | KKLITFFVKLSLFTER | 430 | 414 |
| 301 | 4 | KKLVTFFVKLSLFTER | 424 | 414 |
| 302 | 4 | KKLWTFFVKLSLFTER | 443 | 414 |
| 303 | 4 | KKLYTFFVKLSLFTER | 422 | 414 |
| 304 | 5 | KKLDCFFVKLSLFTER | 449 | 424 |

TABLE 6.2-continued

Peptides that bind to a rampo score greater than or substantially equivalent to that of P28R

| SEQ ID NO | Position | Sequence | Rampo Score | Rampo score of P28R control sample |
|---|---|---|---|---|
| 305 | 5 | KKLDMFFVKLSLFTER | 475 | 424 |
| 306 | 5 | KKLDNFFVKLSLFTER | 436 | 424 |
| 307 | 5 | KKLDPFFVKLSLFTER | 427 | 424 |
| 308 | 5 | KKLDQFFVKLSLFTER | 535 | 424 |
| 309 | 5 | KKLDRFFVKLSLFTER | 430 | 424 |
| 310 | 5 | KKLDSFFVKLSLFTER | 458 | 424 |
| 311 | 5 | KKLDWFFVKLSLFTER | 418 | 424 |
| 312 | 5 | KKLDYFFVKLSLFTER | 425 | 424 |
| 313 | 6 | KKLDTAFVKLSLFTER | 575 | 437 |
| 314 | 6 | KKLDTIFVKLSLFTER | 466 | 437 |
| 315 | 6 | KKLDTMFVKLSLFTER | 467 | 437 |
| 316 | 6 | KKLDTNFVKLSLFTER | 446 | 437 |
| 317 | 6 | KKLDTPFVKLSLFTER | 497 | 437 |
| 318 | 6 | KKLDTTFVKLSLFTER | 481 | 437 |
| 319 | 6 | KKLDTVFVKLSLFTER | 547 | 437 |
| 320 | 7 | KKLDTFLVKLSLFTER | 517 | 460 |
| 321 | 7 | KKLDTFMVKLSLFTER | 712 | 460 |
| 322 | 7 | KKLDTFQVKLSLFTER | 511 | 460 |
| 323 | 7 | KKLDTFSVKLSLFTER | 700 | 460 |
| 324 | 7 | KKLDTFTVKLSLFTER | 517 | 460 |
| 325 | 7 | KKLDTFVVKLSLFTER | 527 | 460 |
| 326 | 8 | KKLDTFFFKLSLFTER | 358 | 308 |
| 327 | 8 | KKLDTFFGKLSLFTER | 379 | 308 |
| 328 | 8 | KKLDTFFLKLSLFTER | 411 | 308 |
| 329 | 8 | KKLDTFFPKLSLFTER | 456 | 308 |
| 330 | 8 | KKLDTFFRKLSLFTER | 365 | 308 |
| 331 | 9 | KKLDTFFVRLSLFTER | 374 | 377 |
| 332 | 10 | KKLDTFFVKASLFTER | 426 | 348 |
| 333 | 10 | KKLDTFFVKFSLFTER | 403 | 348 |
| 334 | 10 | KKLDTFFVKGSLFTER | 495 | 348 |
| 335 | 10 | KKLDTFFVKISLFTER | 415 | 348 |
| 336 | 10 | KKLDTFFVKMSLFTER | 460 | 348 |
| 337 | 10 | KKLDTFFVKNSLFTER | 365 | 348 |
| 338 | 10 | KKLDTFFVKPSLFTER | 436 | 348 |
| 339 | 10 | KKLDTFFVKQSLFTER | 470 | 348 |
| 340 | 10 | KKLDTFFVKRSLFTER | 439 | 348 |
| 341 | 10 | KKLDTFFVKSSLFTER | 351 | 348 |
| 342 | 10 | KKLDTFFVKTSLFTER | 399 | 348 |
| 343 | 10 | KKLDTFFVKVSLFTER | 658 | 348 |
| 344 | 10 | KKLDTFFVKYSLFTER | 382 | 348 |
| 345 | 11 | KKLDTFFVKLHLFTER | 535 | 442 |
| 346 | 11 | KKLDTFFVKLMLFTER | 744 | 442 |
| 347 | 11 | KKLDTFFVKLNLFTER | 451 | 442 |
| 348 | 11 | KKLDTFFVKLQLFTER | 768 | 442 |
| 349 | 11 | KKLDTFFVKLTLFTER | 520 | 442 |
| 350 | 12 | KKLDTFFVKLSAFTER | 462 | 428 |
| 351 | 12 | KKLDTFFVKLSHFTER | 460 | 428 |
| 352 | 12 | KKLDTFFVKLSIFTER | 456 | 428 |
| 353 | 12 | KKLDTFFVKLSMFTER | 499 | 428 |
| 354 | 12 | KKLDTFFVKLSNFTER | 462 | 428 |
| 355 | 12 | KKLDTFFVKLSQFTER | 651 | 428 |
| 356 | 12 | KKLDTFFVKLSRFTER | 483 | 428 |
| 357 | 12 | KKLDTFFVKLSSFTER | 478 | 428 |
| 358 | 12 | KKLDTFFVKLSTFTER | 437 | 428 |
| 359 | 12 | KKLDTFFVKLSVFTER | 545 | 428 |
| 360 | 12 | KKLDTFFVKLSWFTER | 409 | 428 |
| 361 | 13 | KKLDTFFVKLSLATER | 525 | 402 |
| 362 | 13 | KKLDTFFVKLSLCTER | 400 | 402 |
| 363 | 13 | KKLDTFFVKLSLGTER | 531 | 402 |
| 364 | 13 | KKLDTFFVKLSLHTER | 1046 | 402 |
| 365 | 13 | KKLDTFFVKLSLITER | 468 | 402 |
| 366 | 13 | KKLDTFFVKLSLLTER | 448 | 402 |
| 367 | 13 | KKLDTFFVKLSLMTER | 1190 | 402 |
| 368 | 13 | KKLDTFFVKLSLNTER | 862 | 402 |
| 369 | 13 | KKLDTFFVKLSLPTER | 696 | 402 |
| 370 | 13 | KKLDTFFVKLSLQTER | 1144 | 402 |
| 371 | 13 | KKLDTFFVKLSLRTER | 502 | 402 |
| 372 | 13 | KKLDTFFVKLSLSTER | 635 | 402 |
| 373 | 13 | KKLDTFEVKLSLTTER | 494 | 402 |
| 374 | 13 | KKLDTFFVKLSLVTER | 446 | 402 |
| 375 | 13 | KKLDTFFVKLSLWTER | 430 | 402 |
| 376 | 14 | KKLDTFFVKLSLFFER | 348 | 319 |
| 377 | 14 | KKLDTFFVKLSLFGER | 343 | 319 |

TABLE 6.2-continued

Peptides that bind to a rampo score greater than or substantially equivalent to that of P28R

| SEQ ID NO | Position | Sequence | Rampo Score | Rampo score of P28R control sample |
|---|---|---|---|---|
| 378 | 14 | KKLDTFFVKLSLFHER | 463 | 319 |
| 379 | 14 | KKLDTFFVKLSLFIER | 375 | 319 |
| 380 | 14 | KKLDTFFVKLSLFLER | 360 | 319 |
| 381 | 14 | KKLDTFFVKLSLFMER | 501 | 319 |
| 382 | 14 | KKLDTFFVKLSLFNER | 599 | 319 |
| 383 | 14 | KKLDTFFVKLSLFPER | 551 | 319 |
| 384 | 14 | KKLDTFFVKLSLFSER | 369 | 319 |
| 385 | 14 | KKLDTFFVKLSLFVER | 380 | 319 |
| 386 | 14 | KKLDTFFVKLSLFWER | 374 | 319 |
| 387 | 15 | KKLDTFFVKLSLFTDR | 404 | 371 |
| 388 | 16 | KKLDTFFVKLSLFTEF | 297 | 260 |
| 389 | 16 | KKLDTFFVKLSLFTEK | 291 | 260 |
| 390 | 16 | KKLDTFFVKLSLFTEN | 311 | 260 |
| 391 | 16 | KKLDTFFVKLSLFTER | 260 | 260 |
| 392 | 16 | KKLDTFFVKLSLFTET | 292 | 260 |
| 393 | 16 | KKLDTFFVKLSLFTEY | 311 | 260 |

The positional substitutions of P28R in Table 6.2, (SEQ ID NOs: 268-393) are summarized in FIG. 32. It is noted that positions 2 (K), 9 (K) and 15 (E) tolerate relatively few substitutions while still binding to P3028. Substitution of the residue at positions 2, 9, and/or 15 of P28R can result in binding to P3028 (as measured by rampo scores) substantially lower than unsubstituted P28R. Thus, it is contemplated herein that these 3 positions appear to modulate signal transduction. One skilled in the art will appreciate that signal transduction modulatory activity of these positions can be useful in designing inhibitors of immunomodulatory peptides.

PEPSCAN analysis was also performed on truncations and internal deletions of peptide P28R. Shown in FIG. 29 are rampo scores for peptides having the sequences KKLDTFFVKLSLFTER (SEQ ID NO: 2); KKLDTFFVKLSLFTE (SEQ ID NO 34); KKLDTFFVKLSLFT (SEQ ID NO: 35); KKLDTFFVKLSLF (SEQ ID NO 36); KKLDTFFVKLSL (SEQ ID NO: 37); KKLDTFFVKLS (SEQ ID NO: 38); KKLDTFFVKL (SEQ ID NO: 39); KKLDTFFVK (SEQ ID NO: 40); KKLDTFFV (SEQ ID NO: 41); KKLDTFF (SEQ ID NO: 42); KKLDTF (SEQ ID NO: 43); KKLDT (SEQ ID NO: 44); KKLD (SEQ ID NO: 45); KLDTFFVKLSLFTER (SEQ ID NO: 46); LDTFFVKLSLFTER (SEQ ID NO: 47); DTFFVKLSLFTER (SEQ ID NO: 48); TFFVKLSLFTER (SEQ ID NO: 49); FFVKLSLFTER (SEQ ID NO: 50); FVKLSLFTER (SEQ ID NO:51); VKLSLFTER (SEQ ID NO: 52); KLSLFTER (SEQ ID NO: 53); LSLFTER (SEQ ID NO: 54); SLFTER (SEQ ID NO: 55); LFTER (SEQ ID NO: 56); FTER (SEQ ID NO: 57); KLDTFFVKLSLFTE (SEQ ID NO: 58); LDTFFVKLSLFT (SEQ ID NO: 59); DTFFVKLSLF (SEQ ID NO: 60); TFFVKLSL (SEQ ID NO: 61); FFVKLS (SEQ ID NO: 62); FVKL (SEQ ID NO: 63).

Shown in FIG. 30 are rampo scores for peptides having the sequences KKLDTFFVKLSLFTER (SEQ ID NO: 2); KLDTFFVKLSLFTER (SEQ ID NO: 46); KKLTFFVKLSLFTER (SEQ ID NO: 64); KKLDT-FVKLSLFTER (SEQ ID NO: 65); KKLDTFFKLSLFTER (SEQ ID NO: 66); KKLDTFFVKSLFTER (SEQ ID NO: 67); KKLDTFFVKLSFTER (SEQ ID NO: 68); KLDTFFVKLSLFER (SEQ ID NO: 69); KLDTFFVKLSLFTE (SEQ ID NO: 58); LDTFFVKLSLFTER (SEQ ID NO: 47); KKTFFVKLSLFTER (SEQ ID NO: 70); KKLD-FVKLSLFTER (SEQ ID NO: 71); KKLDTEKLSLFTER (SEQ ID NO: 72); KKLDTFFVSLFTER (SEQ ID NO:73); KKLDTFFVKLFTER (SEQ ID NO: 74); KKLDTFFVKLSLER (SEQ ID NO: 75); LDTFFVKLSLFT (SEQ ID NO: 59); DTFFVKLSLFTER (SEQ ID NO: 48); KKFFVKLSLFTER (SEQ ID NO: 76); KKLDVKLSLFTER (SEQ ID NO: 77); KKLDT-FLSLFTER (SEQ ID NO: 78); KKLDTFFVLFTER (SEQ ID NO: 79); KKLDTFFVKLTER (SEQ ID NO: 80); KKLDTFFVKLSLR (SEQ ID NO: 81); KFFVKLSLFTER (SEQ ID NO: 82); KKLVKLSLFTER (SEQ ID NO: 83); KKLDTLSLFTER (SEQ ID NO: 84); KKLDTFFLFTER (SEQ ID NO: 85); KKLDTFFVKTER (SEQ ID NO: 86); KKLDTFFVKLSR (SEQ ID NO: 87); KFVKLSLFTER (SEQ ID NO: 88); KKLKLSLFTER (SEQ ID NO: 89); KKLDTSLFTER (SEQ ID NO:90); KKLDTFFFTER (SEQ ID NO: 91); KKLDTFFVKER (SEQ ID NO: 92); KKLDTFFVKLS (SEQ ID NO: 38); GKLDTFFVKLSLFTER (SEQ ID NO: 93); KKGDTFFVKLSLFTER (SEQ ID NO: 94); KKLDGFFVKLSLFTER (SEQ ID NO: 95); KKLDTF-GVKLSLFTER (SEQ ID NO: 96); KKLDTFFVGLSLFTER (SEQ ID NO: 97); KKLDTFFVGLSLFTER (SEQ ID NO: 98); KKLDTFFVKLGLFTER (SEQ ID NO: 99); KKLDTFFVKLSLGTER (SEQ ID NO: 100); KKLDTFFVKLSLFTGR (SEQ ID NO: 101).

As shown in FIG. 30, several deletions and truncations of peptide P28R have a rampo score comparable to, or higher than peptide P28R, including peptides of the sequences SEQ ID NOs: 64, 65, 68, and 76. Additionally several glycine substitutions had rampo scores comparable to P28R, including peptides of SEQ ID NOs: 94, 95, 96, 98, and 99. Deleting up to at least 8 amino acids from the N terminal of P28R (SEQ ID NOs: 46 to 53) retained a high affinity to P3028 as measured by rampo score. Deleting the C terminal R of P28R (SEQ ID NO: 34) retained a high affinity to P 3028.

Example 13

Effect of a Low Molecular Weight Inhibitor of P3028 on Lymphocyte Activation Analyses of the inhibitor of P3028, P28R, were performed in human ex vivo models. The stimulatory activity on PBMCs, measured using the MTS or CFSE techniques, were studied in 7 healthy control samples and 7 cancer patients of various diagnoses. Interestingly, even in the absence of other types of stimulation P28R has a significant stimulatory activity in 6 out of 7 cancer patients whereas PBMCs from control samples showed only a weak or no stimulation.

As shown in FIG. 24, stimulatory activity of P28R on suppressed proliferative response to IL-2. PBMCs were cultured for 7 days with IL-2 and the proliferative rate was determined as incorporation of BrdU. Each bar represents mean value of triplets. Similar to the studies on the efficacy of antibodies (see FIG. 22) directed against P3028 to reverse cancer related immunosuppression determined as a poor proliferative response of PBMCs from cancer patients to IL-2, the efficacy of the low molecular weight inhibitor P28R on reversal of suppressed IL-2 induced proliferation was investigated. The results of cultures of PBMCs from four different treatment naïve patients are shown in FIG. 24. For each quantity of added P28R, IL-2 stimulated cells 240 are shown in the left, and unstimulated 242 are shown on the right. PBMCs with a low initial proliferation (see FIGS. 24A and 24B) were markedly stimulated by P28R whereas a high initial proliferation was essentially unaffected by the drug (see FIGS. 24C and 24D). As expected, systemic immunosuppression was not present in all patients and only those with immunosuppression were stimulated.

Example 14

Binding of a Low Molecular Weight Inhibitor of P3028 to Tumor Cells

Figure 25:
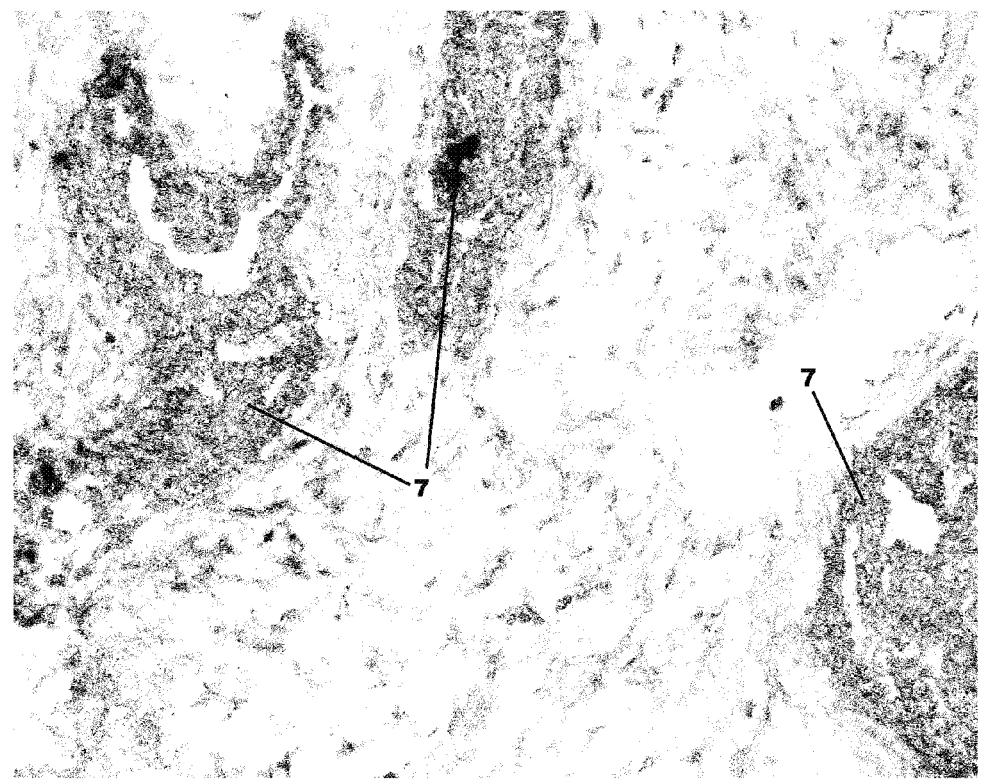
FIG. 25 illustrates binding of biotinylated P28R to a fresh frozen breast cancer tumor.

As demonstrated herein, P3028 structures are present in tumors. A biotinylated inhibitor of P3028, P28R, was used to further study the distribution of 3028 structures and the binding of the inhibitor in tumor tissue. Three breast cancers, two renal cell carcinomas and four malignant melanomas were analyzed. All investigated tumors bound the inhibitor. An example of a stained breast cancer is shown in FIG. 25, and a strong positive reaction 7 is seen indicating the presence of the inhibitory 3028-structure in this tumor. As the P3028-structure inhibits lymphocyte migration as well as cytotoxic activity (described above), an immune mediated attack against positively staining tumor areas can be efficiently suppressed as long as exposed P3028 is not blocked by binding P28R. However, lymphocytes were not stained by this procedure since the P3028 structure was blocked by binding to LFA-1 on these cells.

Example 15

Unblocking the LFA-1 Receptor by P28R

As described herein, β2-integrins play a role in the normal function of the immune system. Also described herein are immunosuppressor mechanisms based on the binding of an endogenous inhibitor, P3028, to the β2-integrin LFA-1. As described in Example 7, the membrane staining of PBMCs from cancer patients is markedly decreased compared to normal control samples. The exposure of LFA-1 could, however, be enhanced by incubating PBMCs from cancer patients with an antibody directed against the inhibitor P3028 (see Example 7 and FIG. 16). Staining for LFA-1 was performed using anti-LFA-1 antibody of Example 7 and a secondary antibody (Ultravision) followed by development with Fast Red. Fresh frozen tumor sections without any fixation were incubated for 4-20 hours with the drug candidate, P28R before staining for LFA-1 (see FIG. 26B). For comparison, control sample tumor sections were incubated with phosphate buffered saline only (see FIG. 26A).

As is shown in FIG. 26, P28R unblocked LFA-1, and thereby markedly enhanced the functional expression of LFA-1 enabling migration and cytotoxic activity of these cells. Strong LFA-1 staining 3 in P28R-treated cells is contrasted with weak LFA-1 staining 5 in untreated cells. These results show that LFA-1 was unblocked by removal of the P3028 structure by the P28R.

Example 16

Delivery of Immunoregulatory Peptide Inhibitors Via Nanodosing to Cancer Patients Cancer patients with immunosuppression due to the presence of P3028 structures and having subcutaneous melanoma metastases are selected. A micro-dialysis catheter is inserted into one of these metastases after the inflammatory infiltrate has been determined using a fine needle biopsy. The base line: inflammatory infiltrate, cytokine profile and concentration of P3028 structures are determined before infusion of the P3028-specific immunoregulatory peptide inhibitor. Changes of the cytokine profile and concentration of P3028 structures are then determined during and after the infusion. The infusion will continue for 24 or 48 hours and the area supplied by the micro-dialysis catheter will be excised immediately after the infusion and then after one and two weeks in order to study the inflammatory infiltrate and tumor regressive changes. It is expected that the administration of the immunoregulatory peptide inhibitor will reduce the immunosuppression of the cancer patient, as measured, for example, by de-blocking LFA-1, binding P3028 structures, and/or enhancing immune cell recruitment.

Example 17

Albumin Peptide Binders of Cell Surface Molecules

Albumin Fragments that Bind to Cell Surface Molecules
As taught in US Publication No: 2011/0262470 (hereby expressly incorporated by reference in its entirety) some albumin fragments can bind to cell surface molecules. U.S. Publication No: 2011/0262470 reports the identification of serum peptides that bind to Artificial Cell Surface (ACS) columns. The ACS columns were prepared as follows:

First, biotinylated cell surface proteins were prepared. Buffy coats generated from 450 ml blood each were collected from 4 healthy donors. Erythrocytes were removed by sedimentation on 2% dextran T500 solution (Amersham Pharmacia Biotech AB, Uppsala Sweden) in 0.9% NaCl. Mononuclear cells (PBMC) were then isolated by Ficoll-Paque Plus (GE Healthcare BioscienceAB Sweden) density gradient centrifugation. The PBMCs were then suspended in phosphate buffered saline (PBS) containing Ca and Mg (GIBCO) at a concentration of $10 \times 10^6$/ml. EZ Link Sulfo-NHS-biotin (Pierce USA) was added at a final concentration of 0.2 mg/ml and the mixture incubated on a shaker at room temperature for 10 min. Excess biotin was then removed by washing the PBMC in PBS. Biotinylated PBMC were then lysed by adding 1.0 ml ice-cold lysing buffer (50 mM Tris-HCL, pH 7.5, with 0.15 MNaCl, 5 mM MgCl2 containing 100 mM Octyl glucoside and 1 mM Phenylmethyl-sulfonyl fluoride) per 2×10$^7$ pelleted cells with gentle shaking, then incubated for 30 min. on ice. Debris was removed by centrifugation at 5000×g at 4° C. for 10 min and the supernatants were collected and pooled from all four donors. The lysate was then stored at −70° C. in polypropylene plastic tubes.

To study the absorptions by trypsin-fragment dHSA, affinity columns with biotinylated cell surface proteins from mononuclear cells coupled to streptavidin-sepharose were prepared as follows: 18 ml biotinylated cell lysate in lysate buffer was diluted 1/10 in binding buffer (20 mM NaH2PO4, 0.15 M NaCl, pH 7.5). This amount of lysate corresponds to 36×10$^7$ mononuclear cells. It was added to a 1 ml Hitrap Streptavidin HP affinity column (Amersham Biosciences). To block possible remaining free biotin, 5 ml of 0.1 M glycine (Sigma) was added to the column. Unsaturated streptavidin on the column was then reacted with 150 ug biotin (Sigma) in binding buffer. The column was carefully washed with PBS and stored in PBS with 0.1% NaN3 at 4° C. until use.

To study the absorptions by of ASP-N fragmented dHSA, affinity columns with biotinylated cell surface proteins from mononuclear cells coupled to streptavidin-sepharose were prepared as follows: Biotinylated cell lysate in lysate buffer underwent buffer exchange by dialysis with Spectrapore 4 dialysis tubing (Spectrum Europe, Breda, The Netherlands) in binding buffer (20 mM NaH2PO4, 0.15 MNaCl pH 7.5). 27 ml biotinylated cell lysate in binding buffer (corresponding to 54×10$^7$ mononuclear cells) was added to 1.5 ml washed Streptavidin Sepharose HP (Amersham Biosciences). To block possible remaining free biotin, 25 ml of 0.1 M glycine (Sigma) was added to the Streptavidin Sepharose. Unsaturated streptavidin was then reacted with 225 ug biotin (Sigma) in binding buffer. The Streptavidin Sepharose was carefully washed in PBS. One ml of the biotinylated cell lysate coupled Streptavidin Sepharose was then packed in an empty column (Tricorn Empty High Performance Column, Amersham Bioscience) and washed with phosphate buffered saline (PBS) containing Ca$^{2+}$ and Mg$^{2+}$ (GIBCO).

Digestion with trypsin or ASP-N was performed as follows. Freeze dried dHSA (0.5 mg) was reconstituted in 25 mM NH4HCO3, pH 8, containing 10 mg sequencing grade modified trypsin (Promega Corporation, WI) or 2 mg Endoproteinase ASP-N(Sigma) and incubated at 37° C. overnight. To remove unfragmented albumin and enzyme, the sample was ultra filtered through an Amicon Ultra 4 (mw cut-off of 5000) or a Centriplus (mw cut-off 10000) centrifugal filter (Millipore AB, Solna, Sweden). The filtrate, containing fragmented dHSA without enzymes, was collected and diluted with PBS with Ca and Mg (GIBCO).

dHSA was trypsinated, and the mixture of peptides obtained after trypsination was adsorbed by ACS. Two ml of enzyme-fragmented dHSA in PBS, corresponding to a total of 0.2 mg protein, was passaged over the ACS column. The flow-through was collected with consideration taken to void volume and dilution of adsorbed sample by collecting in small portions of 0.2 ml. Thirty microliters of each sample, including a control sample that has not been adsorbed, were dried in a Speed-Vac centrifuge. The binding peptides were identified by comparing adsorbed and unadsorbed peptide solutions using the MALDI TOF mass spectrometry technique. Dried samples were reconstituted in 10 ul of 0.1% TFA. Zip Tip pipette tips (Millipore, USA) containing C18 reversed-phase media were used for desalting reconstituted samples. For analysis of samples in the mass range 700-3600 Da, one μl of each Zip Tip eluted sample was mixed with 1 μl of a saturated solution of α-cyano-4-hydroxycinamic acid (0.02 mg/ml) in 70% acetonitrile/0.3% trifluoro acetic acid. For the analysis of samples in the mass range 1500-9000 Da, one μl of each Zip Tip eluted sample was mixed with 1 μl of sinapinic acid (3-methoxy-4-hydroxycinnamic acid). 1 μl of the mixture was spotted on the MALDI plate and analysed using MALDI-TOF MS (Voyager-DE PRO, Applied Biosystems, CA, US). Mass identity search of resulting spectra was performed in the SwissProt or NCBI databases using MS-Fit.

These peptides are shown in Table 7.

TABLE 7

Trypsin-generated albumin fragments that bind to ACS

| SEQ ID NO: | Percent Absorbed | Sequence | Albumin Positions |
|---|---|---|---|
| 194 | 71% | KYLYEIAR | 161-168 |
| 195 | 64% | KVPQVSTPTLVEVSR | 438-452 |
| 196 | 60% | VFDEFKPLVEEPQNLIK | 397-413 |
| 197 | 59% | VPQVSTPTLVEVSR | 439-452 |
| 198 | 42% | RPCFSALEVDETYVPK | 509-524 |
| 199 | 41% | FQNALLVR | 427-434 |
| 200 | 36% | SLHTLFGDK | 89-97 |
| 201 | 36% | LKECCEKPLLEK | 299-310 |
| 202 | 35% | LCTVATLR | 98-105 |
| 203 | 34% | YLYEIAR | 162-168 |
| 204 | 32% | CCAAADPHECYAK | 384-396 |
| 205 | 29% | AAFTECCQAADK | 187-198 |
| 206 | 26% | CCTESLVNR | 500-508 |
| 207 | 25% | QEPERNECFLQHK | 118-130 |
| 208 | 23% | AVMDDFAAFVEK | 570-581 |
| 209 | 77% | NECFLQHK | 123-130 |
| 210 | 20% | ONCELFEQLGEYK | 414-426 |
| 211 | 18% | QEPERNECFLQHK | 118-130 |
| 212 | 13% | VHTECCHGDLLECADDR | 265-281 |
| 213 | 8% | FKDLGEENFK | 35-44 |
| 214 | 3% | YICENQDSISSK | 287-298 |
| 215 | 2% | LDELRDEGK | 206-214 |
| 216 | 1% | DDNPNLPR | 131-138 |

Because the full peptide sequence of albumin is not recovered using the MALDI-TOF technique after trypsin degradation, and because some sequences with the capacity to bind to cell surface receptors of immune cells, might have been degraded by trypsin treatment, dHSA was also degraded by asparaginase (ASN-N), and the mixture of peptides obtained after degradation was adsorbed by ACS. The binding peptides were identified by comparing adsorbed and unadsorbed peptide solutions using the MALDI TOF ms technique. These peptides are shown in Table 8.

TABLE 8

Asp-N-generated albumin fragments that bind to ACS

| SEQ ID NO: | Percent Absorbed | Sequence | Albumin Positions |
|---|---|---|---|
| 217 | 100% | DHVKLVNEVTEFAKTCVA | 62-79 |
| 218 | 100% | DDKETCFAEEGKKLVAASQAALGL | 586-609 |
| 219 | 87% | DRVTKCCTESLVNRRPCFSALEV | 495-517 |
| 220 | 86% | DETYVPKEFNAETFTHA | 518-535 |
| 221 | 65% | DSISSKLKECCEKPLLEKSHCIAEVEN | 293-319 |
| 222 | 65% | DKLCTVATLRETYGEM | 96-112 |
| 223 | 100% | YSVVLLLRLAKTYETTLEKCCAAADPHECYAKVF | 364-398 |
| 224 | 100% | KLCTVATLRETYGEMADCCAKQEPERNECFLQHK | 96-130 |
| 225 | 100% | ICTLSEKERQIKKQTALVELVKHKPKATKEQLKAVM | 536-572 |
| 226 | 100% | LAKYICENQDSISSKLKECCEKPLLEKHCIAEVEN | 283-319 |
| 227 | 100% | VFLGMFLYEYARRHPDYSVVLLLRLAKTYETTLEKCCAAA | 348-388 |
| 228 | 100% | LGEENFKALVLIAFAQYLQQCPFEDHVKLVNEVTEFAKTCVA | 37-79 |
| 229 | 100% | RVTKCCTESLVNRRPCFSALEVDETYVPKEFNAETFTFHA | 495-535 |
| 230 | 37% | YLSVVLNQLCVLHEKTPVSDRVTKCCCTESLVNRRPFSALEV | 475-517 |

Additionally, nine synthetic albumin peptides were synthesized, as shown in Table 9.

TABLE 9

Synthetic albumin peptides

| SEQ ID NO: | Peptide Name | Sequence | Albumin Positions |
|---|---|---|---|
| 183 | 3026 | NEETFLKKYLYEIARRHPYFYAP | 153-176 |
| 184 | 3027 | ELFEQLGEYKFQNALLVR | 417-434 |
| 185 | 3028 | VFDEFKPLVEEPQNLIK | 397-413 |
| 188 | 3029 | KVPQVSTPTLVEVSR | 438-452 |
| 189 | 2604 | KLVNEVTEFAKT | 65-76 |
| 190 | 2605 | NEETFLKKYLYE | 153-168 |
| 191 | 2606 | LDELRDEGKAS | 205-217 |

TABLE 9-continued

Synthetic albumin peptides

| SEQ ID NO: | Peptide Name | Sequence | Albumin Positions |
|---|---|---|---|
| 192 | 2607 | EMADCCAKQEPE | 110-122 |
| 193 | 2608 | ELFEQLGEYKF | 417-427 |

Example 18

Albumin Peptide Binders of Cell Surface Molecules

Monoclonal antibody mAb A was shown to have immunomodulatory activity. Structures of the epitope bound by mAb A were further investigated. Briefly, albumin fragments were incubated with antibody, and Matrix-Assisted Laser Desorption/Ionisation Time-of-Flight mass spectrometry (MALDI-TOF ms) were used in order to define the possible site or sites on human serum albumin to which a mouse monoclonal antibody specific for denatured albumin binds. One approach took advantage of the fact that some tryptic peptides to which an antibody is bound will not generate characteristic mass spectra in MALDI as they are "hidden" from the analysis. Another approach takes advantage of the fact that sites on a protein where an antibody has bound are protected from proteolysis.

Purified human serum albumin (HSA) was denatured with urea, reduced with DTT and alkylated. The denatured HSA was then subjected to trypsin treatment with a low concentration (0.02-2 ng/ml) of trypsin. However, the spectra obtained with MALDI were unsatisfactory, as the peptides masses typical for albumin were not found. Based on gel electrophoresis this preparation (digested by 0.02 ng/ml of trypsin) was found to contain substantial amounts of undigested albumin. Therefore, trypsin digestion was continued, at a higher concentration (5 ug/ml) in order to obtain the mass spectra usually used for identification of proteins by MALDI.

To identify albumin fragments bound by mAb A, some of the now completely cleaved albumin solution was incubated with the mAb A. MALDI-TOF ms was performed and spectra of enzyme-treated denatured albumin obtained in the presence or absence of mAb A were compared. Fourteen albumin (SEQ ID NOs: 231-244) massed were absent or reduced after incubation with mAb A. The amino acid sequence of these peptides is shown in Table 10. The spectra represent multiple areas encompassing residues 66 to 508 of the albumin molecule.

In order to further confirm these results the monoclonal antibody mAb A was allowed to bind to the denatured albumin (previously digested by trypsin at a concentration of 0.02 ng/ml) in order to protect the peptide sequences of the epitope. The complex was then again treated with trypsin. MALDI-TOF ms was then performed and the peptide mass spectra generated from albumin were compared with spectra generated from denatured albumin trypsin-treated in the absence of antibody. The same fourteen masses out of 39 albumin masses disappeared completely or were significantly reduced in the sample were the mAb was present during trypsin treatment (see Table 10, Column 6). Multiple readings were taken to verify the results.

TABLE 10

Albumin peptides that bind to monoclonal antibody mAb A

| SEQ ID NO: | Sequence | Albumin Positions | Peak area before Ab incub. (2 spectra) | Peak area after Ab incub. (5 spectra) | Peak area trypsiniated Albumin + Ab (6 spectra) |
|---|---|---|---|---|---|
| 231 | LVNEVTEFAK | 066-075 | 1970, 4092 | 0, 0, 0, 0, 0, | 0, 0, 0, 0, 0, 0, |
| 232 | SLHTLFGDK | 089-097 | 1695, 5089 | 0, 0, 0, 0, 0, | 0, 0, 0, 0, 0, 0, |
| 233 | LCTVATLR | 098-105 | 1862, 4869 | 0, 0, 132, 0, 0 | 0, 0, 0, 0, 0, 0, |
| 234 | ETYGEMADCCAK | 106-117 | 809, 1010 | 0, 0, 0, 0, 0, | 0, 0, 0, 0, 0, 0, |
| 235 | YLYEIAR | 162-168 | 6036, 13066 | 504, 118, 473, 281, 288 | 448, 895, 216, 724, 2346, 1571 |
| 236 | LDELRDEGK | 206-214 | 3064, 7917 | 0, 0, 0, 0, 0 | 0, 0, 0, 0, 0, 0 |
| 237 | YICENQDSISSK | 287-298 | 583, 1394 | 0, 0, 0, 0, 0, | 0, 0, 53, 0, 0, 0, |
| 238 | LKECCEKPLLEK | 299-310 | 2283, 4675 | 0, 0, 0, 0, 0, | 0, 0, 0, 0, 0, 0, |
| 239 | HPDYSWLLLR | 362-372 | 1036, 1482 | 0, 0, 0, 0, 0, | 0, 0, 51, 0, 407 (1312), 226(1312) |
| 240 | CCAAADPHECYAK | 384-396 | 2186, 3327 | 0, 0, 0, 0, 0, | 0, 0, 0, 0, 0, 0, |
| 241 | QNCELFEQLGEYK | 414-426 | 2519, 2978 | 0, 0, 0, 0, 0, | 0, 0, 0, 0, 0, 212(1656.64) |
| 242 | FQNALLVR | 427-434 | 15276, 32846 | 267, 315, 931, 494, 309 | 591, 1284, 199, 1015, 2963, 1998 |
| 243 | CCTESLVNR | 500-508 | 1360, 4659 | 0, 0, 0, 0, 0, | 0, 258, 0, 0, 0, 204(1139) |
| 244 | AVMDDFAAFVEK | 570-581 | 2720, 3758 | 0, 0, 0, 0, 0 | 0, 0, 0, 0, 0, 0 |

Some peptide fragments of albumin might not be identified by binding an antibody to trypsinated fragments of albumin because of the possibility that the mAb binding epitope of albumin is cleaved by trypsin, resulting in fragments of the epitope with too low binding affinity to bind to the mAb. Therefore, an additional method was used to identify fragments bound by the antibody. MALDI epitope mapping of mAb A based on antibody protection of proteolysis was repeated. This time a slightly different approach was used. Denatured HSA was incubated with mAb A. Albumin not bound by the antibody, was removed from the sample by size exclusion on an ultra filter. The remaining free mAbs and the complexes of mAb-albumin was then digested with trypsin (sequences of the albumin molecule to which mAb is bound should resist the trypsin digestion). Small cleaved fragments of mAb and unprotected albumin was then removed from the sample by ultrafiltration (30 kD). The complexes of mAb and bound albumin fragments were dissociated by lowering the pH to 2.7. Again ultrafiltration at 30 kD was performed to separate whole mAb from albumin fragments smaller than 30 kD. MALDI TOF analysis of these fragments did not identify spectra typical for albumin. Reasonably, because the fragments containing the epitope of mAb A were still too large. This filtrate (<30 kD) was then further digested with trypsin (for cleavage of sites previously protected by the mAb) in order to generate peptide masses suitable for analysis with MALDI TOF ms.

After this second trypsin treatment, eight of 32 masses detected by MALDI TOF ms matched to albumin (see Table 11). Thus, these new amino acid sequences represent a part of the epitope, which also contains sequences on the other side of the trypsin cleavage point. Six of the eight peptide masses ((SEQ ID NOs: 231, 233, 235, 236, 242, and 243) were peptide masses that also disappeared when analysed previously when completely cleaved albumin was incubated with the mAb A before the MALDI-TOF analysis (see Table 10). Two of the eight peptides (SEQ ID NOs: 245 and 346) had not been identified in the binding assays with completely cleaved albumin. The epitope/s of this antibody was thus established. It is important to note that multiple such structures are present in the albumin molecule, which can then cause cross-linking of the receptors to which they are bound. However, multiple epitope sites for mAb A can indeed exist on albumin.

TABLE 11

Albumin peptides that bind to monoclonal antibody mAb A

| SEQ ID NO: | Sequence | Albumin Positions |
|---|---|---|
| 245 | LSQRFPK | 243-249 |
| 246 | DDNPNLPR | 131-138 |
| 235 | YLYEIAR | 162-168 |
| 233 | LCTVATLR | 98-105 |
| 242 | FQNALLVR | 427-434 |

TABLE 11-continued

Albumin peptides that bind to monoclonal antibody mAb A

| SEQ ID NO: | Sequence | Albumin Positions |
|---|---|---|
| 236 | LDELRDEGK | 206-214 |
| 243 | CCTESLVNR | 500-508 |
| 231 | LVNEVTEFAK | 66-75 |

Example 19

Cyclic Peptides that Bind P3028

In order to identify cyclic peptides that bind to P3028, all possible variants of di- and tripeptides were synthesized on chips and the binding of the His-tag labeled P 3028 was analyzed using the ELISA-technique. Based on the identified binding motifs, looped 6-meres were produced and tested. These results together enable the construction of a lead cyclic peptide CLALNVMCG (SEQ ID NO: 264). Positional scans were performed in each position of the lead cyclic peptide was replaced with each of the other 19 L-amino acids. Binding of each of the substituted peptides was tested, and peptide sequences with even better binding capacity than that of the lead peptide were identified. The two peptides with the highest affinity were CLRLNVFCG (SEQ ID NO: 265) and CLRLIVMCG (SEQ ID NO: 266). The two best looped peptides that bind to P3028 based on the positional scan binding assay are summarized in Table 12.

TABLE 12

Cyclic peptides that bind to P3028

| SEQ ID NO: | SEQUENCE |
|---|---|
| 264 | CLALNVMCC |
| 265 | CLRLNVFCG |
| 266 | CLRLIVMCG |

Substitutable amino acid residues in the lead looped peptide that were identified in the positional scans as providing improved binding to P3028 (SEQ ID NO: 185) are summarized in FIG. 33 (i.e., SEQ ID NOs: 264 to 266). Positional substitutions of P28R that result in equivalent or better binding to P28R to P3028 that were identified as providing higher or substantially equal binding to P3028 (see Tables 6.1 and 6.2) are also summarized in FIG. 33. It was observed that there was very good homology between looped peptide sequences that bind to P3028 based on the scan data (SEQ ID NOs: 264-266), and sequences of linear peptides that identified as binding to P3028 (SEQ ID NOs: 2-31 and 268-393) (see FIG. 33). It is noted that the N-terminal C residues and C-terminal CG residues of the cyclic peptides are involved in cyclization of the peptide. Thus, as shown by shaded boxes in FIG. 33, there is strong homology between 6-mere cyclic peptides identified as binders of P3028 (SEQ ID NOs: 264-266) and either the N terminus of C-terminus of P28R-related peptide (SEQ ID NOs: 2-31 and 268-393). It is contemplated that additional cyclic peptides that bind to and inhibit albumin-derived immunoregulatory peptides can be identified.

Example 20

Effect of Albumin Peptides on IL-2 Induced Proliferation

The effect of albumin peptides including at least one of SEQ ID NOs: 183-185 or 188-246 is determined using the ex vivo human model as described in Example 2.

PBMCs are isolated from venous blood samples from healthy blood donors (control samples) or cancer patients. One hundred pl of culture medium (RPMI 1640 Dutch's modification (Gibco, InVitrogenAB, Stockholm, Sweden) supplemented with 200 IV/ml penicillin, 200 ul/ml streptomycin, 4 mM L-glutamine (all from Sigma Chemical Co. MO, US) and 20% heat-inactivated human serum) is added to roundbottomed, 96-well tissue culture plates (Costar, Corning Inc. NY, US). For experimental cultures, the culture medium of each well is supplemented with a peptide of SEQ ID NOs: 183-185 or 188-246. One hundred pl of PBMCs in RPMI/2% HAS ($5 \times 10^4$ lymphocytes) is then added per well followed by IL-2 (Proleukin, Chiron, NL) at a final concentration of 120 IU/well. Control wells without IL-2 are set up in parallel. Cells are cultured for 7 days in a humidified, 5% CO2-atmosphere at 37° C. Cell proliferation is assayed by incorporation of 1.6 pCi/well of [$^3$H]-thymidine (Amersham Int., UK) during the last 18-24 h hrs. Mean values of dpm (disintegrations per minute) of triplicate wells are used for the calculations.

Thus, albumin peptides that inhibit IL-2 stimulation of PBMC's are identified.

Example 21

Effect of Albumin Peptides on T Cell Receptor Stimulation

The effect of albumin peptides including at least one of SEQ ID NOs: 183-185 or 188-246 on T Cell receptor stimulation is determined as in Example 3. Cells are stimulated in cultures on plates pre-coated with a monoclonal antibody directed against CD3 and the number of metabolically active cells (i.e., cell proliferation) is determined using MTS staining after 3 to 7 days of culture. Detection of solid phase CD3 monoclonal antibody is used as a measurement of T cell proliferation.

Thus, albumin peptides that inhibit T cell receptor stimulation are identified.

Example 22

Effect of Albumin Peptides on NK Cell Cytotoxicity

The effect of albumin peptides including at least one of SEQ ID NOs: 183-185 or 188-246 on NK cell cytotoxicity is determined as in Example 4.

Mononuclear cells are separated by standard Ficoll-paque Plus (Pharmacia AB, Sweden) density gradient centrifugation from heparinized blood obtained from healthy donors. NK cell cytotoxic activity of the mononuclear cells is then tested using a commercial kit (NKTEST, Orpegen Pharma GmbII, Heidelberg, Germany) following the manufacturers protocol. Briefly, the kit contains cryopreserved, NK-sensitive target cells (K562) labeled with a lipophilic green fluorescent membrane dye, which enables discrimination of effector and target cells. After incubation with effector cells, killed target cells are identified by a DNA-stain, which penetrates and specifically stain the nuclei of dead target cells. This way the percentage of killed targets can be determined by flow cytometry. The mononuclear cells were preincubated for 30 min at 37° C. with the indicated peptides (peptides have been described previously) at 10 ug/ml. Target cells were then added, giving an effector:target ratio of 40:1, and the cell mixture incubated at 37° C. for 3-4 hours. Samples are analysed on a FACSCalibur (BD Biosciences, San Jose, Calif.).

Thus, albumin peptides that inhibit NK cell cytotoxicity are identified.

Example 23

Effect of Albumin Peptides on Leukocyte Spreading

The effect of albumin peptides including at least one SEQ ID NOs: 183-185 or 188-246 on leukocyte spreading is determined as in Example 5. Buffy coat cells are prepared from heparinized blood by Dextran assisted sedimentation. To test the effects of each peptide, a samples of cells are treated with of one of the peptides of (SEQ ID NOs: 183-185 or 188-246 at a concentration of 10 µg/ml for 15 minutes efficiently inhibited the spreading. These cells are then washed twice in PBS and transferred to clean slides. Cells adherence to the glass surface and spreading is detected.

Thus, albumin peptides that inhibit leukocyte spreading are identified.

Example 24

Effect of Albumin Peptides on Immune Cell Migration

The effect of albumin peptides including at least one of SEQ ID NOs: 183-185 or 188-246 on immune cell migration is determined as in Example 5. PBMC migration is studied using the Boyden chamber technique. Migration for PBMCs of healthy control samples and cancer patients is assessed in both the presence and absence of each of the peptides of SEQ ID NOs: 183-185 or 188-246. Thus, albumin peptides that inhibit immune cells migration are identified.

Example 25

Binding of Albumin Peptides to LFA-1

The binding of albumin peptides including at least one of SEQ ID NOs: 183-185 or 188-246 to LFA-1 is determined as in Example 7. A standard immunohistochemical staining procedure is performed using acetone fixation, 10% human AB-serum for blocking, incubation with anti-LFA-1 antibody and a secondary antibody (Ultravision) followed by development with Fast Red. Pre-incubation with peptides added to the AB serum is either no peptide added, or a peptide of SEQ ID NOs: 183-185 or 188-246 is added.

Peptides that bind to LFA-1 prevent the binding of the antibody, thus decreasing the amount of Fast Red staining in antibody-treated cells as compared to untreated control samples.

Example 26

Antibodies that Bind Albumin Peptides

Antibodies that specifically bind to peptides including at least one of SEQ ID NOs: 183-185 or 188-246 are generated as in Example 9. Rabbit antisera directed against each of the peptides of SEQ ID NOs: 183-185 or 188-246 are generated. Each peptide of SEQ ID NOs: 183-185 or 188-246 is synthesized with a cysteine added to the N-terminus end and then conjugated with keyhole limpet hemocyanin (KLH) as a carrier protein. Polyclonal antisera is generated by repeated immunizations of rabbits with KLH-conjugated P3028 and Freund's adjuvants. The antisera are affinity purified by chromatography on P3028-conjugated Ultralink Iodoacetyl gels (Pierce Biotechnology Inc.).

The antisera are tested for their ability to bind human serum and dHSA. Human serum commercially available for therapeutic purposes is tested, heated 10 times in order to be virus free. Thus, rabbit antisera that specifically binds the albumin peptide binds to dHSA and/or control sample HSA.

The binding of the rabbit antiserum to peptides of SEQ ID NOs: 183-185 or 188-246 is assayed using competition ELISA assay.

Effects of affinity purified antibodies directed against of SEQ ID NOs: 183-185 or 188-246 on the proliferative response to IL-2 are examined the ex vivo model, using PBMCs from immunosuppressed cancer patients and normal control samples.

Thus, antibodies that bind peptides of SEQ ID NOs: 183-185 or 188-246 are identified.

Example 27

Peptides that Bind to Albumin-Derived Peptides

Peptides that bind to peptides including at least one of SEQ ID NOs: 183-185 or 188-246 are identified as in Example 10. Potential binders of the peptides are synthesized. For each peptide of SEQ ID NOs: 183-185 or 188-246 a His-tagged peptide is contacted with the potential binders in solution, and then isolated from solution using the His tag. Binders of each peptide are isolated along with the peptide, and subsequently identified.

Additionally, substitutions, truncations, and deletions of peptides that bind to each of the albumin peptides are identified as in Example 12. Substitutions, truncations, and deletions are synthesized on a chip, and contacted with the albumin peptide of one of SEQ ID NOs: 183-185 or 188-246 to determine binding. The amount of bound peptide is quantified using a rampo assay as in Example 12. The binders with the highest rampo scores are isolated.

The highest-score binders of each peptide are assessed for their ability to reduce immunosuppression, as in Examples 13 and 15. Each binder is assessed for its ability to induce lymphocyte activation, and unblock the LFA-1 receptor. Additionally, each binder is assessed to bind to tumor cells, as in Example 14.

Example 28

Effect of P28R on Mitochondrial Metabolism and Conversion of MTS

PBMCs from eight healthy control samples and nine cancer patients with various diagnoses (including renal cell cancer, malignant melanoma, rectal cancer, small cell lung cancer, non-small cell lung cancer (adenocarcinoma), squamous cell carcinoma, bladder cancer, osteosarcoma, pancreatic cancer, or bronchial cancer) were cultured in a modified version of the ex vivo model of Example 2 for seven days in the presence of various quantities of P28R (SEQ ID NO: 2), and control samples were untreated with P28R. As shown in FIGS. 33A and 33B, the cells were cultured in either no P28R 322, 5 µg/mL 324, 10 µg/ml 326, or 20 µg/ml 328 of P28R. A dose dependent stimulation of the mitochondrial metabolism measured as conversion of MTS was observed in 5/8 (see FIG. 33A) control samples and 9/9 cancer patients (see FIG. 33B). Similar results were obtained when the PBMCs were cultured for only three days.

Example 29

Effects of Inhibitors of Immunoregulatory Peptides on Mitochondrial Metabolism and Conversion of MTS The effect of P28R (SEQ ID NO: 2) on mitochondrial metabolism based on MTS conversion was compared to the effect of a closely related peptide P27. P27 (aka "SCF 27") has the sequence KKLDTFFKKLSLFTER (SEQ ID NO: 264), and is a variant of P28R that differs in that V8 of P28R is substituted to K8 in P27. P28R binds to P3028 more efficiently than P27 (P27 binds P3028 with a rampo score of 253, while a P28R control sample binds P3028 with a rampo score of 308; see Example 12).

PBMCs from cancer patients with various diagnoses were cultured in a modified version of the ex vivo model of Example 2 with various concentrations of P28R or P27 (N=9 for P28R: N=8 for P27). The concentrations were either untreated control samples, 5 µg/mL ("SCF28-R5" and "SCF275"), 10 µg/ml ("SCF28-R10" and "SCF2710"), 20 µg/ml ("SCF28-R20" and "SCF2720"), or 40 µg/ml ("SCF28-R40" and "SCF2740"). The results are shown in FIG. 34. While P28R stimulated the cells of cancer patients in a dose-dependent manner, P27 had no effect.

Example 30

Effect of P28R on IL-2 Induced Proliferation (BrdU Incorporation)

The effect of P28R (SEQ ID NO: 2) on IL-2 induced proliferation was measured in a BrdU incorporation assay. PBMCs from six healthy control samples and ten cancer patients (including renal cell cancer, malignant melanoma, rectal cancer, small cell lung cancer, non-small cell lung cancer (adenocarcinoma), squamous cell carcinoma, bladder cancer, osteosarcoma, pancreatic cancer, or bronchial cancer) were harvested in a modified version of the ex vivo model of Example 2. One hundred pI of culture medium (RPMI 1640 Dutch's modification (Gibco, InVitrogenAB, Stockholm, Sweden) supplemented with 200 IV/ml penicillin, 200 ul/rnl streptomycin, 4 mM L-glutamine (all from Sigma Chemical Co. MO, US) and 20% heat-inactivated human serum) were added to roundbottomed, 96-well tissue culture plates (Costar, Corning Inc. NY, US). One hundred pI of PBMCs in RPMI/2% HAS (5×104 lymphocytes) was then added per well followed by IL-2 (Proleukin, Chiron, NL) at a final concentration of 120 IU/well. Control sample wells without IL-2 was set up in parallel. Cells were cultured for 7 days in a humidified, 5% CO2-atmosphere at 37° C. Cell proliferation was assayed by incorporation of BrdU.

As shown in FIG. 35, four out of six control samples had a high proliferative response to IL-2 compared to four out of ten cancer patients. These differences in proliferative response to IL-2 in PBMCs demonstrated the difference existence of high and low responders to IL-2.

The response of high responders and low responders to various doses of P28R was compared. Cells from either high responders or low responders were cultured for 7 days with either no P28R, 5 µg/mL, 10 µg/ml, or 20 µg/ml of P28R. IL-2-induced proliferation was measured as BrdU incorporation, as in the above example, and the results are shown for high responders in FIG. 36A, and low responders in FIG. 36B. While P28R had no stimulatory effect in cells from patients with a high response to IL-2 (N=4) (see FIG. 36A), P28R had a stimulatory effect on cells from patients with a low response to IL-2 (N=6) (see FIG. 36B).

Example 31

Effects of Inhibitors of Immunoregulatory Peptides on IL-2 Induced Proliferation (BrdU Incorporation and MTS Conversion)

The effect of P27, a peptide related to P28R was compared to the effect of P28R on Il-2 induced proliferation as measured by BrdU Incorporation. P27 (aka "SCF 27") has the sequence KKLDTFFKKLSLFTER (SEQ ID NO: 264), and is a variant of P28R that differs in that V8 of P28R is substituted to K8 in P27. P28R binds to P3028 more efficiently than P27 (P27 binds P3028 with a rampo score of 253, while a P28R control sample binds P3028 with a rampo score of 308; see Example 12).

PBMCs from low responder cancer patients of Example 30 were cultured as in Example 30, except that some samples were cultured with various concentrations P28R (aka "SCF28-R"), and others were cultured with various concentrations of P27 (aka "SCF27"). The concentrations were either no peptide ("untreated cells"), 5 µg/mL, 10 µg/ml, or 20 µg/ml. BrdU incorporation was measured as in Example 30. As shown in FIG. 37, both P28R and P27 enhanced the proliferative rate of PBMC's induced by IL-2. A comparison can be drawn to the data of Example 29 and FIG. 34, in which P28R, but not P27 enhanced IL-2 stimulation of mitochondrial metabolism, as measured by MTS conversion. P27 was observed to enhance IL-2 stimulation of cell proliferation as measured by BrdU incorporation, but not mitochondrial metabolism as measured by MTS conversion. On the other hand, P28R was observed to enhance both parameters. The inhibitory peptide P3028 binds to different receptors, including CD25 (see Example 8 and FIGS. 18-19) and LFA-1 (see Example 7 and FIGS. 15-16), as described herein. It is contemplated that the more efficient binder of P3028, P28R, is capable of removing P3028 from LFA-1 and/or unblocking CD25. However, it is contemplated that P27 with a lower/weaker binding to P3028, does not have the capacity to unblock LFA-1 but can unblock CD25. Thus, it is contemplated that different populations of patients may be affected in different ways by immunoregulatory peptides such as P3028. Moreover, it is contemplated that different inhibitors of immunoregulatory peptides can modulate the activity of different receptors, and/or different signal transduction pathways.

Example 32

Comparison of MTS and BrdU Assays

The two cell proliferation assays in this study are both widely used in order to measure cell proliferation. Peptide P28R had a stimulatory activity of MTS conversion in seven day cultures of PBMCs in 9/9 patients and in 5/8 healthy control samples. In contrast, P28R stimulated incorporation of BrdU in seven day cultures of PBMCs from only 1/6 and 2/10 patients.

IL-2 induced proliferation, measured as incorporation of BrdU, was stimulated by P28R in PBMC cultures from cancer patients with a low proliferative response to IL-2 (experimental conditions were as described in Example 30). PBMCs from 2/3 healthy control samples and 2/4 cancer patients were not stimulated by IL-2 when the effect was measured as MTS conversion (experimental conditions were as described in Example 28). However, PBMCs from all these persons ("non-responders") who did not respond when measured with MTS were significantly stimulated by IL-2 when the effect was measured as incorporation of BrdU.

The above results are illustrated in FIG. 38. PBMC cultures from two different patients (A, B) and (C, D), with IL-2 382 (bars on left) or without IL-2 384 (bars on right). The effect of IL-2 and the peptides P28R (aka "SCR28R") and P27 (aka "SCF27") were measured at concentrations of either no peptide ("untreated cells"), 5 µg/mL, 10 µg/ml, or 20 µg/ml of peptide.

In two patients, the response to IL-2, measured as BrdU incorporation, was enhanced by P28R (see FIGS. 38A and 38C), but this effect of P28R was only observed in one of these patients when MTS conversion was used (see FIG. 38B). Thus, while in one patient (see FIGS. 38A and 38B) the stimulatory activity of IL-2 was registered using both BrdU and MTS, in the other patient, the stimulatory activity of IL-2 was registered using BrdU only (see FIG. 38C). Based on these observations, it is concluded that effects on the metabolic activity measured as MTS conversion does not always correlate with DNA synthesis measured as incorporation of BrdU.

Additionally, P28R enhanced the effect of IL-2 measured both with BrdU and MTS, but the stimulatory effect of SCF27 was observed only when BrdU incorporation is measured. In the patient shown in C the results are very similar to those shown in A, but in D no stimulatory effect is seen when the effect is determined using MTS conversion.

These results indicate that albumin-derived immunomodulatory structures such as P3028 appear to modulate signal transduction through different mechanisms. Thus, different patient populations can respond differently to inhibitors of immunomodulatory peptides. It is contemplated that in vitro diagnostic assays can be helpful in identifying which patients have albumin-derived immunomodulatory structures, and can be further helpful in identifying which patients will respond to certain inhibitors (or combinations of inhibitors) of immunomodulatory structures.

Example 33

Effects of Binders of Immunoregulatory Peptides on Lymphocyte Activation

Binders of immunoregulatory peptides, for example the peptides of Tables 5.1, 6.1, 6.2, or 12 (SEQ ID NOs: 1-32, 265-393), or SEQ ID NOs: 34, 46-53, 64-66, 68, 76, 94-96, 98, or 264, are assayed for effects on lymphocyte activation, as in Example 13. Analyses of these peptides are performed in human ex vivo models. The stimulatory activity on PBMCs, measured using the MTS or CFSE techniques, are studied in 7 healthy control samples and 7 cancer patients of various diagnoses. The peptides are assayed for stimulatory activity even in the absence of other types of stimulation, and are compared to untreated control samples.

Stimulatory activity of the peptides of Tables 5.1, 6.1, 6.2, or 12 (SEQ ID NOs: 1-32, 265-393), or SEQ ID NOs: 34, 46-53, 64-66, 68, 76, 94-96, 98, or 264 on a proliferative response to IL-2 suppressed by a P3028 sequence or structure. PBMCs are cultured for 7 days with IL-2 and the proliferative rate is determined as incorporation of BrdU. Each set of conditions is assayed in triplicate. Initial proliferation of PBMCs is compared to proliferation of PBMCs from the same donor after treatment with each peptide.

Example 34

Binding of Inhibitors of Immunoregulatory Peptides to Tumor Cells

A biotinylated version of each of the P28R peptides of Tables 5.1, 6.1, 6.2, or 12 (SEQ ID NOs: 1-32, 265-393), or SEQ ID NOs: 34, 46-53, 64-66, 68, 76, 94-96, 98, or 264, each of which has been shown to bind to P3028, is used to assay binding of the peptide to tumor cells. Five breast cancers, two renal cell carcinomas and four malignant melanomas are analyzed, as in Example 14.

Example 35

Unblocking the LFA-1 Receptor by Inhibitors of Immunoregulatory Peptides

As described herein, β2-integrins play a role in the normal function of the immune system. Also described herein are immunosuppressor mechanisms based on the binding of an endogenous inhibitor, P3028, to the β2-integrin LFA-1. As described in Example 7, the membrane staining of PBMCs from cancer patients is markedly decreased compared to normal control samples. The exposure of LFA-1 could, however, be enhanced by incubating PBMCs from cancer patients with an antibody directed against the inhibitor P3028 (see Example 7 and FIG. 16).

Staining for LFA-1 is performed with the anti-LFA-1 antibody of Example 7 and a secondary antibody (Ultravision) followed by development with Fast Red. Fresh frozen tumor sections without any fixation are incubated for 4-20 hours with each of the P28R peptides of Tables 5.1, 6.1, 6.2, or 12 (SEQ ID NOs: 1-32, 265-393), or SEQ ID NOs: 34, 46-53, 64-66, 68, 76, 94-96, 98, or 264, each of which has been shown to bind to P3028, before staining for LFA-1. For comparison, control sample tumor sections were incubated with phosphate buffered saline only. The amount of anti-LFA-1 antibody staining is observed, and used to determine the amount of blocking, if any, of the LFA-1 receptor. Migration and cytotoxic activity of treated cells is also ongoing.

Example 36

Positional Scans of Amino Acid Residues in SEQ ID NO: 2

Positional scan data was used to study the influence of substitution of different types of amino acids in each position of P28R (SEQ ID NO: 2) on the binding of P3028 (SEQ ID NO: 185). Each amino acid in the peptide sequence of P28R (SEQ ID NO: 2) was exchanged with all of the naturally occurring amino acids, and immobilized on a solid phase chip. The binding of P3028 to these "mutated" P28 R peptides synthesized on a chip was determined using the ELISA technique. The results are summarized in Table 13.

In view of the results, Table 13 includes a column identifying optional substitutions at each position that can maintain binding to P3028.

TABLE 13

Analysis of P3028 Binding to Solid Phase P28R Variants

| Position | Substitution Category | ELISA signal | | | | Avg | Optional Substitutions that maintain 3028 binding |
|---|---|---|---|---|---|---|---|
| K1 | RHK | 523 | 428 | 366 | | 439 | any type of amino acid possible |
| | DE | 373 | 396 | | | 385 | |
| | AVIL (SEQ ID NO: 813) | 466 | 442 | 483 | 449 | 460 | |
| | M | 457 | | | | 457 | |
| | FYW | 332 | 315 | 284 | | 310 | |
| | STNQ (SEQ ID NO: 814) | 344 | 493 | 445 | 455 | 434 | |
| K2 | RHK | 417 | 394 | 445 | | 419 | positively charged amino acids preferable, F and N possible* |
| | DE | 335 | 349 | | | 342 | |
| | AVIL (SEQ ID NO: 813) | 309 | 317 | 331 | 343 | 325 | |
| | M | 400 | | | | 400 | |
| | FYW | 390 | 301 | 304 | | 332 | |
| | STNQ (SEQ ID NO: 814) | 281 | 331 | 432 | 350 | 349 | |
| L3 | RHK | 370 | 477 | 386 | | 411 | any type of amino acid possible |
| | DE | 492 | 528 | | | 510 | |
| | AVIL (SEQ ID NO: 813) | 427 | | 454 | 375 | 408 | |
| | M | 460 | | | | 460 | |
| | FYW | 393 | 344 | 341 | | 359 | |
| | STNQ (SEQ ID NO: 814) | 393 | 451 | 374 | 473 | 423 | |
| D4 | RHK | 317 | 317 | 274 | | 303 | any type of amino acid possible |
| | DE | 414 | 417 | | | 416 | |
| | AVIL (SEQ ID NO: 813) | 494 | 424 | 430 | 303 | 413 | |
| | M | 384 | | | | 384 | |
| | FYW | 380 | 422 | 443 | | 415 | |
| | STNQ (SEQ ID NO: 814) | 344 | 405 | 296 | 345 | 348 | |
| T5 | RHK | 430 | 391 | 237 | | 353 | polar uncharged amino acids preferable, R, Y and W are possible* |
| | DE | 295 | 341 | | | 318 | |
| | AVIL (SEQ ID NO: 813) | 346 | 374 | 293 | 311 | 331 | |
| | M | 475 | | | | 475 | |
| | FYW | 290 | 425 | 418 | | 378 | |
| | STNQ (SEQ ID NO: 814) | 458 | 424 | 436 | 535 | 463 | |
| F6 | RHK | 309 | 332 | 309 | | 317 | hydrophobic and uncharged polar amino acids are preferable; avoid positively and negatively charged |
| | DE | 193 | 229 | | | 211 | |
| | AVIL (SEQ ID NO: 813) | 575 | 547 | 466 | 408 | 499 | |
| | M | 467 | | | | 467 | |
| | FYW | 437 | 364 | 348 | | 383 | |
| | STNQ (SEQ ID NO: 814) | 432 | 481 | 446 | 410 | 442 | |
| F7 | RHK | 369 | 364 | 232 | | 322 | hydrophobic and uncharged polar amino acids are preferable; avoid positively and negatively charged |
| | DE | 301 | 381 | | | 341 | |
| | AVIL (SEQ ID NO: 813) | 426 | 527 | 446 | 517 | 479 | |
| | M | 712 | | | | 712 | |
| | FYW | 460 | 334 | 380 | | 391 | |
| | STNQ (SEQ ID NO: 814) | 700 | 517 | 348 | 511 | 519 | |
| V8 | RHK | 365 | 213 | 253 | | 277 | hydrophobic nonaromatic carbon chain amino acids are preferable, F possible, avoid negatively charged |
| | DE | 122 | 139 | | | 131 | |
| | AVIL (SEQ ID NO: 813) | 299 | 308 | 401 | 411 | 355 | |
| | M | 221 | | | | 221 | |
| | FYW | 358 | 211 | 228 | | 266 | |
| | STNQ (SEQ ID NO: 814) | 216 | 298 | 203 | 271 | 247 | |
| K9 | RHK | 374 | 306 | 377 | | 352 | positively charged amino acids preferable, polar uncharged T and Q possible |
| | DE | 149 | 240 | | | 195 | |
| | AVIL (SEQ ID NO: 813) | 191 | 248 | 190 | 166 | 199 | |
| | M | 283 | | | | 283 | |
| | FYW | 174 | 198 | 245 | | 206 | |
| | STNQ (SEQ ID NO: 814) | 274 | 347 | 256 | 330 | 302 | |
| L10 | RHK | 439 | 293 | 285 | | 339 | any type of amino acid except negatively charged are possible |
| | DE | 102 | 81 | | | 92 | |
| | AVIL (SEQ ID NO: 813) | 426 | 658 | 415 | 348 | 462 | |
| | M | 460 | | | | 460 | |
| | FYW | 403 | 382 | 316 | | 367 | |
| | STNQ (SEQ ID NO: 814) | 351 | 399 | 365 | 470 | 396 | |
| S11 | RHK | 333 | 535 | 323 | | 397 | polar uncharged amino acids are preferable, H is possible* |
| | DE | | 234 | | | 278 | |
| | AVIL (SEQ ID NO: 813) | 318 | 392 | 289 | 213 | 303 | |
| | M | 744 | | | | 744 | |
| | FYW | 250 | 402 | 324 | | 325 | |
| | STNQ (SEQ ID NO: 814) | 442 | 520 | 451 | 768 | 545 | |
| L12 | RHK | 483 | 460 | 355 | | 433 | any type of amino acid except negatively charged |
| | DE | 89 | 82 | | | 86 | |
| | AVIL (SEQ ID NO: 813) | 462 | 545 | 456 | 428 | 473 | |
| | M | 499 | | | | 499 | |
| | FYW | 389 | 320 | 409 | | 373 | |
| | STNQ (SEQ ID NO: 814) | 478 | 437 | 462 | 651 | 507 | |
| F13 | RHK | 502 | 1046 | 220 | | 589 | any type of amino acid except negatively charged* |
| | DE | 112 | 98 | | | 105 | |
| | AVIL (SEQ ID NO: 813) | 525 | 446 | 468 | 448 | 472 | |
| | M | 1190 | | | | 1190 | |
| | FYW | 402 | 291 | 430 | | 374 | |
| | STNQ (SEQ ID NO: 814) | 635 | 494 | 862 | 1144 | 784 | |
| T14 | RHK | 264 | 463 | 259 | | 329 | any type of amino acid except negatively charged |
| | DE | 159 | 110 | | | 135 | |
| | AVIL (SEQ ID NO: 813) | 305 | 380 | 375 | 360 | 355 | |
| | M | 501 | | | | 501 | |
| | FYW | 348 | 270 | 374 | | 331 | |
| | STNQ (SEQ ID NO: 814) | 369 | 319 | 599 | 301 | 397 | |

TABLE 13-continued

Analysis of P3028 Binding to Solid Phase P28R Variants

| Position | Substitution Category | ELISA signal | | | | Avg | Optional Substitutions that maintain 3028 binding |
|---|---|---|---|---|---|---|---|
| E15 | RHK | 237 | 318 | 324 | | 293 | negatively |
| | DE | 404 | 371 | | | 388 | charged amino |
| | AVIL (SEQ ID NO: 813) | 174 | 163 | 163 | 246 | 187 | acids preferable, possibly Y or Q |
| | M | 247 | | | | 247 | |
| | FYW | 137 | 340 | 226 | | 234 | |
| | STNQ (SEQ ID NO: 814) | 165 | 152 | 161 | 344 | 206 | |
| R16 | RHK | 260 | 239 | 291 | | 263 | any type |
| | DE | 133 | 107 | | | 120

("P28 core") (FFVKLS) (SEQ ID NO: 62) did not activate healthy PBMC's in this model.

However, in PBMC cultures where normal human AB-serum in the culture medium was substituted for by sera from dogs with cancer or human patients with cancer, P28R (SEQ ID NO: 2) and P28 core (peptide 32230(FFVKLS) (SEQ ID NO: 62) each activated PBMCs, measured as enhanced expression of CD69 (see FIG. 43). FIG. 43 shows a comparison between the full length peptide P28R (SEQ ID NO: 2) and the 6 amino acid P28 core sequence (peptide 32230) (FFVKLS) (SEQ ID NO: 62) in culture medium containing sera from two different cancer patients (human ca serum 1 430 and human ca serum 2 432). Both P28R (SEQ ID NO: 2) and P28 core (SEQ ID NO: 62) activated PBMCs in the presence of cancer serum.

In addition, biotinylated P28R has been shown to bind directly to PBMCs as demonstrated by immunocytochemistry or rosetting of P28R coated beads (binding of beads to the cells).

Taken together, these results show that P28R (SEQ ID NO: 2) can bind to P3028 and de-block cellular receptors and can also have a direct stimulatory activity on immune cells. Additionally, P28 core (SEQ ID NO: 62) can bind to P3028 and de-block cellular receptors.

Example 39

Cytotoxic Activity of P28R

The effect of P28R (SEQ ID NO:2) was further studied in in vivo models in nude and immunocompetent mice. Injection of P28R intra-tumorally into human pancreas cancer in a xenograft model in nude mice demonstrated a capacity to induce tumor cell apoptosis after one day. FIGS. 44A and 44B shows immunohistochemical staining for Caspase 3 (440), indicating an ongoing apoptosis) with a significantly enhanced activation of this enzyme in P28R treated tumors (FIG. 44A) compared to tumors which were treated with the drug solvent only (FIG. 44B). An absence of staining is also indicated 442. It is noted that the results shown were obtained only one day after administration of P28R in animals with no capacity to form an immune reactivity to the tumor.

As such, intra-tumoral administration of P28R a can have a cytotoxic action on tumor cells in accordance with some embodiments herein. In some embodiments, P28R has a direct cytotoxic action on tumor cells.

Example 40

Therapeutic Activity of P28R

The capacity of P28R (SEQ ID NO: 2) to activate the immune system and thereby induce tumor cell-lysis was studied in immunocompetent mice, C57Bl, with inoculated B16 melanoma. P28R, 40 microgram in 100 microliter, was injected intra-tumorally and the tumors were taken out after 3 days. As shown in FIG. 45, the dominating cells in the tumors after this treatment are inflammatory cells, which were identified by immunohistochemical staining 450 using a polyclonal rabbit anti-CD45 antibody (FIG. 45A). For comparison a control tumor section was incubated with rabbit IgG at the same concentration (FIG. 45B). An absence of staining is also indicated 452.

Accordingly, it was demonstrated that P28R can induce infiltration of a B16 melanoma tumor by inflammatory cells. In accordance with some embodiments herein, P28R can induce infiltration of tumors, for example melanomas, by immune cells.

Example 41

Effects of Modified Peptides on Immune Cell Stimulation

The influence of various amino acid substitutions and additions on the immunostimulatory effect was studied. Effects of modified peptides on activation of PBMCs from healthy control person were assessed. Activation was determined as percentage of cells with enhanced marker CD69 or CD71 using flow cytometry. PBMCs were incubated with the peptides (40 µg/mL) for 48 hours in RPMI plus 10% human AB serum. Two experiments (460 and 462 in FIG. 46A; 464 and 466 in FIG. 46B, respectively) were performed for each peptide. Peptides P28R (SEQ ID NO: 2), P28 core (peptide 32230) (SEQ ID NO: 62), 32251 (KKLDTFFPKLSLFTER) (SEQ ID NO: 592), 32814 (RKLDTFFVKLSLFTERRR) (SEQ ID NO: 591), 32815 (KKLDQFFVKLSQHNER) (SEQ ID NO: 595), 32665 (SEQ ID NO: 593), and 32819 (SEQ ID NO: 594) were tested.

As shown in FIG. 46, peptide 32814 (SEQ ID NO: 591), had a stimulatory effect in short term cultures similar to that of P28R (SEQ ID NO: 2) (batch CS8040). Accordingly, peptide 32814 (SEQ ID NO: 591) activated healthy PBMCs as indicated by enhanced CD69 (FIG. 46A) and also by enhanced CD71 (FIG. 46B).

Example 42

Diagnostic Uses

In addition to therapeutic applications, diagnostic applications of P28R and truncations and modifications thereof were also contemplated. For example, information about patients systemic and local (intra-tumoural) immune status can be obtained using reagents comprising P28R, or a truncation or modification thereof.

It is contemplated that the occurrence of immunoinhibitory 3028-structures in tumors can be identified by immunohistochemical staining using either an antibody directed against P3028 or using labeled P28R (SEQ ID NO: 2) or P28 core (SEQ ID NO: 62), for example biotinylated P28R or P28 core. FIG. 47 shows two areas of a human breast cancer stained using biotinylated P28R. Staining 470 is observed in FIG. 47B. Staining is not observed in FIG. 47A. An absence of staining is indicated 472.

As such, areas of tumors comprising P3028 structures (as well as areas not comprising these structures) can be identified using labeled peptides in accordance with embodiments herein.

Example 43

Treatment of a Tumor Using a P28 Peptide Inhibitor

A patient having a melanoma is identified. A pharmaceutical composition comprising 40 µg/100 ml of a peptide consisting of the amino acid sequence SEQ ID NO: 2 and a PBS buffer formulated as a gel-like substance is injected peri-tumorally in the patient once a week for three weeks. Tumor cytotoxicity is observed. Immune cell invasion of the tumor is observed.

Example 44

Treatment of a Tumor Using a P28 Core Peptide Inhibitor

A patient having breast cancer is identified. A pharmaceutical composition comprising a 80 μg/100 ml of a peptide consisting the amino acid sequence SEQ ID NO: 62 and a tris buffer formulated as a gel-like substance is injected peri-tumorally in the patient. Immune cell invasion of the tumor is observed.

Example 45

Treatment of a Tumor Using a P28R-Modification Peptide Inhibitor

A patient having prostate cancer is identified. A pharmaceutical composition comprising 1 mg/kg of a peptide consisting of the amino acid sequence SEQ ID NO: 586 dissolved in an aqueous buffer is administered systemically to the patient once every two days for five total administrations. Tumor cytotoxicity is observed. Immune cell invasion of the tumor is observed.

The invention claimed is:

1. An isolated peptide comprising the amino acid sequence KKLDTFFVKLSLFTER (SEQ ID NO: 2), wherein the isolated peptide comprises no more than 100 amino acid residues, and wherein the isolated peptide binds specifically to a second peptide consisting of the amino acid sequence VFDEFKPLVEEPQNLIK (SEQ ID NO: 185).

2. The isolated peptide of claim 1, wherein the isolated peptide comprises no more than 30 amino acid residues.

3. The isolated peptide of claim 1, wherein the isolated peptide comprises no more than 20 amino acid residues.

4. The isolated peptide of claim 1, wherein the isolated peptide comprises a modification selected from the group consisting of a D amino acid, an N-terminal acetyl group, a C-terminal amide group, glycosylation, nitrosylation, carbonylation, oxidation, a linked pharmacokinetic modifier, and a linked polyethylene glycol or any combination thereof.

5. The isolated peptide of claim 1, wherein the isolated peptide is bound to a support.

6. A method of making the isolated peptide of claim 1, the method comprising synthesizing the peptide by solid phase chemical synthesis, thereby making the peptide of claim 1.

7. An isolated peptide comprising the amino acid sequence KKLDTFFVKLSLFTER (SEQ ID NO: 2).

8. The isolated peptide of claim 7, wherein the isolated peptide comprises no more than 100 amino acid residues.

9. The isolated peptide of claim 7, wherein the isolated peptide comprises no more than 30 amino acid residues.

10. The isolated peptide of claim 7, wherein the isolated peptide consists of the amino acid sequence of SEQ ID NO: 2.

11. The isolated peptide of claim 7, wherein the isolated peptide is bound to a support.

12. The isolated peptide of claim 7, wherein the isolated peptide comprises a modification selected from the group consisting of a D amino acid, an N-terminal acetyl group, a C-terminal amide group, glycosylation, nitrosylation, carbonylation, oxidation, a linked pharmacokinetic modifier, and a linked polyethylene glycol or any combination thereof.

13. The isolated peptide of claim 7, wherein the isolated peptide specifically binds to a second peptide consisting of the amino acid sequence VFDEFKPLVEEPQNLIK (SEQ ID NO: 185).

14. A method of making the isolated peptide of claim 7, the method comprising synthesizing the peptide by solid phase chemical synthesis, thereby making the peptide of claim 7.

15. An isolated peptide comprising the amino acid sequence RKLDTFFVKLSLFTERRR (SEQ ID NO: 586).

16. The isolated peptide of claim 15, wherein the isolated peptide comprises no more than 100 amino acid residues.

17. The isolated peptide of claim 15, wherein the isolated peptide comprises no more than 30 amino acid residues.

18. The isolated peptide of claim 15, wherein the isolated peptide consists of the amino acid sequence of SEQ ID NO: 586.

19. The isolated peptide of claim 15, wherein the isolated peptide is bound to a support.

20. The isolated peptide of claim 15, wherein the isolated peptide comprises a modification selected from the group consisting of a D amino acid, an N-terminal acetyl group, a C-terminal amide group, glycosylation, nitrosylation, carbonylation, oxidation, a linked pharmacokinetic modifier, and a linked polyethylene glycol or any combination thereof.

21. A method of making the isolated peptide of claim 15, the method comprising synthesizing the peptide by solid phase chemical synthesis, thereby making the peptide of claim 15.

* * * * *